US007309487B2

(12) United States Patent
Inana et al.

(10) Patent No.: US 7,309,487 B2
(45) Date of Patent: Dec. 18, 2007

(54) METHODS AND COMPOSITIONS FOR DETECTING AND TREATING RETINAL DISEASES

(76) Inventors: George Inana, 6500 SW. 133 Dr., Miami, FL (US) 33156; Margaret McLaren, 6500 SW. 133 Dr., Miami, FL (US) 33156

( * ) Notice: Subject to any disclaimer, the term of this patent is extended or adjusted under 35 U.S.C. 154(b) by 0 days.

(21) Appl. No.: 10/773,446

(22) Filed: Feb. 9, 2004

(65) Prior Publication Data

US 2005/0176662 A1 Aug. 11, 2005

(51) Int. Cl.
*A61K 39/395* (2006.01)

(52) U.S. Cl. .................................................. 424/130.1

(58) Field of Classification Search ..................... None
See application file for complete search history.

(56) References Cited

U.S. PATENT DOCUMENTS

2003/0199440 A1* 10/2003 Dack et al. .................. 514/12
2005/0059595 A1* 3/2005 Lasko et al. .................. 514/12

OTHER PUBLICATIONS

Sivak et al. 2002, Progress in Retinal and Eye Research, vol. 21: 1-14.*
Smine et al., 1997, Curr. Eye. Res. vol. 16: 925-929.*
Rando Allikmets et al, Mutation of the Stargardt Disease Gene (ABCR) in Age-Related Macular Degeneration, Science, vol. 277, Sep. 19, 1997, pp. 1805-1807.
J. Ambati et al, An Animal Model of Age-Related Macular Degeneration in Senescent CCL-2-OR CCR-2-Deficient Mice, Nature Medicine, vol. 9, No. 11, Nov. 2003, pp. 1390-1397.
S.S. Apte et al, The Matrix Metalloproteinase-14 (MMP-14) Gene is Structurally Distinct From Other MMP Genes and is Co-Expressed With the TIMP-2 Gene During Mouse Embryogenesis, The Journal of Biological Chemistry, vol. 272, No. 41, Oct. 10, 1997, pp. 25522-25517.
J. Cao et al, The C-Terminal Region of Membrane Type Matrix Metalloproteinase is a Functional Transmembrane Domain Required for Pro-Gelatinase A Activation, The Journal of Biological Chemistry, vol. 270, No. 2, Jan. 13, 1995, pp. 801-805.
T. Ikeda, M.D. et al, Paraoxonase Gene Polymorphisms and Plasma Oxidized Low-Density Lipoprotein Level as Possible Risks Factors for Exudative Age-Related Macular Degeneration, Elsevier Science, Inc., American Journal of Ophthalmology, vol. 132, No. 2, Mar. 5, 2001, pp. 191-195.
K. Kimura, M.D., Genetic Association of Manganese Superoxide Dismutase With Exudative Age-Related Macular Degeneration, Elsevier Science, Inc., American Journal of Ophthaamology, vol. 130, No. 6, Dec. 2000, pp. 769-773.
C.C.W. Klaver et al, Genetic Association of Apolipoprotein E with Age-Related Macular Degeneration, American Journal of Human Genetics, No. 63, 1998, pp. 200-206.
J. Lohi et al, Structural Analysis and Promoter Characterization of the Human Membrane-Type Matrix Metalloproteinase-1 (MT1-MMP) Gene, Elsevier Science B.V., Gene 242, 2000, pp. 75-86.
M.J. McLaren et al, Spontaneously Arising Immortal Cell Line of Rat Retinal Pigmented Epithelial Cells, Experimental Cell Research 204, 1993, pp. 311-320.
M.J. McLaren, Kinetics of Rod Outer Segment Phagocytosis by Cultured Retinal Pigment Epithelial Cells, Investigative Ophthalmology & Visual Science, Jun. 1996, vol. 37, No. 7, pp. 1213-1224.
M.J. McLaren et al., Double Fluorescent Vital Assay of Phagocytosis by Cultured Retinal Pigment Epithelial Cells, Investigative Ophthalmology & Visual Science, Feb. 1993, vol. 34, No. 2, pp. 317-326.
N. Oku et al, Inhibitory Effect of Green Tea Polyphenols on Membrane-Type 1 Matrix Metalloproteinase, MT1-MMP[1] , Biol. Pharm. Bull. vol. 26, No. 9, Sep. 2003, pp. 1235-1238.
D. Pei et al, Transmembrane-Deletion Mutants of the Membrane-Type Matrix Metalloproteinase-1 Process Progelatinase A and Express Intrinsic Matrix-Degrading Activity, The Journal of Biological Chemistry, vol. 271, No. 15, Apr. 13, 1996, pp. 9135-9140.
J.J. Plantner et al, Increase in Interphotoreceptor Matrix Gelatinase A (MMP-2) Associated With Age-Related Macular Degeneration, Exp. Eye Res. No. 67, 1998,pp. 637-645.
D.W. Schultz et al, Analysis of the ARMD1 Locus: Evidence That a Mutation in Hemicentin-1 is Associated With Age-Related Macular Degeneration in a Large Family, Human Molecular Genetics, 2003, vol. 12, No. 24, pp. 3315-3323.
F. Simonelli et al, Apolipoprotein E Polymorphisms in Age-Related Macular Degeneration in an Italian Population, Ophthalmic Research, 2001, 33, pp. 325-328.
H. Sato et al, A Matrix Metalloproteinase Expressed on the Surface of Invasive Tumour Cells, Nature, vol. 370, Jul. 7, 1994, pp. 61-65.
J. Zurdel et al, CST3 Genotype Associated With Exudative Age Related Macular Degeneration, Clinical Science, Br J. Ophthalmol. 2002, 86, pp. 214-219.

* cited by examiner

*Primary Examiner*—G. R. Ewoldt
*Assistant Examiner*—Amy Juedes
(74) *Attorney, Agent, or Firm*—Margaret J. McLaren, Esq.; Carey Rodriguez Greenberg & Paul LLP

(57) ABSTRACT

The invention discloses multiple genes related to age-related macular degeneration (AMD) and/or phagocytosis by RPE cells of the eye, and methods and compositions for detecting and treating AMD and other retinal degenerative conditions based on these phagocytosis-related and/or AMD-related genes. Also provided are animal models useful for testing therapeutic compounds and treatment protocols for AMD, and gene arrays including polymorphic variants of phagocytosis-related and/or AMD-related genes, useful for genetic screening of nucleic acid samples from subjects to obtain profiles of polymorphic variant sequences in a plurality of genes associated with AMD.

7 Claims, 15 Drawing Sheets

PHASE

SR STAIN

BOUND ROS

INGESTED ROS

BPEI-1 CELLS SHOWING ROS BINDING (5-9 hr) AND INGESTION (11 -22 hr)

| SEVERITY |
|---|
| +3 - +4 |

| SEVERITY |
|---|
| +2 - +3 |

| SEVERITY |
|---|
| 0 - +1 |

+ X-arrestin Ab

CONTROL

+MT1-MMP Ab

O.S. MT1-MMP Ab

O.D. UNINJECTED

O.S. X-arrestin Ab

MT1-MMP Exon 5 PCR PRODUCT (SEQ ID NO: 59)

```
1    GGGAGGCTGA GGGAAGGGAC TCAGGCTGCT ATCGTCACTG TCCCCATCCTT

51   CCAGGAAATG ACATCTTCCT GGTGGCTGTG CACGAGCTGG GCCATGCCCT

101  GGGGCTCGAG CATTCCAGTG ACCCCTCGGC CATCATGGCA CCCTTTTACC
                                                codon 259
151  AGTGGATGGA CACGGAGAAT TTTGTGCTGC CCGATGATGA CCGCCGGGGC
                                      codon 273
201  ATCCAGCAAC TTTATGGCGA GTAGTCTACA CCCACGCCTG CTCCCTCCTC

251  TGCTGCTTGT TCCCTCCTGG TCTACGCATT TCCCC
```

FIG. 14

1 MONTH AFTER INJECTION

UNINJECTED

SEQUENCE LISTING

```
<160> NUMBER OF SEQ ID NOS: 131

<210> SEQ ID NO 1
<211> LENGTH: 2110
<212> TYPE: DNA
<213> ORGANISM: Homo sapiens

<400> SEQUENCE: 1

gggatcgttc gatttaagcc atcatcagct taatttaagt ttgtagtttt tgctgaagga      60

ttatatgtat taatacttac ggttttaaat gtgttgcttt ggatacacac atagtttctt     120

ttttaataga atatactgtc ttgtctcact ttggactggg acagtggatg cccatctaaa     180

agttaagtgt catttctttt agatgtttac cttcagccat agcttgattg ctcagagaaa     240

tatgcagaag gcaggatcaa agacacacag gagtcctttc ttttgaaatg ccacgtgcca     300

ttgtctttcc tcccttcttt gcttcttttt cttaccctct ctttcaattg cagatgccaa     360

aaaagatgcc aacagacact acattaccct aatggctgct acccagaacc tttttatagg     420

ttgttcttaa tttttttgtt gttgttgttc aagcttttcc tttctttttt ttcttggtgt     480

ttgggccacg attttaaaat gacttttatt atgggtatgt gttgccaaag ctggcttttt     540

gtcaaataaa atgaatacga acttaaaaaa taaaagctgg tatcttaaaa tgtaagagag     600

taagactgtg aagcctaaaa tgactggctg agaatgaacc agaaatgcca tttgccaaac     660

agttgtaact agaaatttga ttctcacggt ccattctttt ctttgtcctt aagatgacat     720

tgttagtgtt cacgtcccat gttcagtgtc caaaccggca atgtaaaaag tatcctgtgt     780

ggtttaacag gaaatctgtt tatgtctctt tatttgaaac cagttttact ctcagtggtt     840

ctttaagttc aatgaagtct gccaggaaca ttggttggta gtattattcc gacaccttta     900

atttccaaaa tctgaagttc ctgctagttt accaccttca tgatcttctt gaactggtaa     960

ctgattaggt tgaacttatg gaagatttgt ggacttaact caaaagtaac ctctcagtgt    1020

tctatagaac atgtatttgt gtaactgaac ctaccaggag aaatgtttgg aattctatat    1080
```

-continued

```
gtgcaatttt tcaacaaatg caaaaaaaat acagcacatg tattgacaag cttctgtcaa   1140

gcagcttgag ttgaaatttg atttaagaaa ataaatcatg attgttcaaa gctgctggga   1200

cgttagaatt aggccatgat actggtctca ttttaactac agtggtattt ggcactagtg   1260

taaacttcca tataaatcac tcttttggaa caacaaaggg ggagggagaa aaatcacggc   1320

ctgttaaatg agtaccaaag ccgcccaaca gtaatgagat gttctcatcc ttgattctcc   1380

cagcctcaaa caacacagct tacttttttt ttcccttgct cagaaagtac ctgtaattta   1440

acaaacagac tgcctgtagg tatagtgcaa ttacaaatgc tctaatcatt gtacatacat   1500

ctctcttgat attgcagcat ccatactggc tttgtaatca ttaatttttt ggcagattga   1560

atgtgctgta ttgatatgta tctatgtaat tgtattgtat gtctatagct aattcacgtt   1620

ttgaataatg ttattttatt tacttttta agagaggaga atgtaaattt gtcagtttat   1680

ttctgactag ggatattttc tttccattta gaaaagaaga aaaaaaaaaa accttactgt   1740

catacagagc ggtactagcg tcgtgctgta taaaatcatt tgcacattcc tgagtagagg   1800

tatactgatt ataagaccca aaggtaattt catagcaaaa tacataaaat cagtcggagc   1860

ttttatacaa acatggaaac caactttgta gaacttttgc catttgatct aggattggaa   1920

tatgagcttt tatacaattc atattcttat ttggcaaatg cacagtttag tattacctct   1980

ctgatggcct ttactagaaa ggcagtttta gaagctattg tgatccacta aggaaatgtt   2040

ttaacagcta gagaccactg cttgcctgaa agggcgttct taaatttggt gcagcaaaaa   2100

aaagaaaaaa                                                          2110
```

<210> SEQ ID NO 2
<211> LENGTH: 775
<212> TYPE: DNA
<213> ORGANISM: Homo sapiens

<400> SEQUENCE: 2

```
tgcaggagaa tggctactca tcacacgctg tggatgggac tggccctgct gggggtgctg     60

ggcgacctgc aggcagcacc ggaggcccag gtctccgtgc agcccaactt ccagcaggac    120

aagttcctgg ggcgctggtt cagcgcgggc ctcgcctcca actcgagctg gctccgggag    180

aagaaggcgg cgttgtccat gtgcaagtct gtggtggccc ctgccacgga tggtggcctc    240

aacctgacct ccaccttcct caggaaaaac cagtgtgaga cccgaaccat gctgctgcag    300

cccgcggggt ccctcggctc ctacagctac cggagtcccc actggggcag cacctactcc    360

gtgtcagtgg tggagaccga ctacgaccag tacgcgctgc tgtacagcca gggcagcaag    420

ggccctggcg aggacttccg catggccacc ctctacagcc gaacccagac ccccagggct    480

gagttaaagg agaaattcac cgccttctgc aaggcccagg gcttcacaga ggataccatt    540

gtcttcctgc cccaaaccga taagtgcatg acggaacaat aggactcccc agggctgaag    600

ctgggatccc ggccagccag gtgacccccca cgctctggat gtctctgctc tgttccttcc    660

ccgagcccct gccccggctc cccgccaaag cacccctgcc cactcgggct tcatcctgca    720

caataaactc cggaagcaag tcagttaaaa aaaaaaaaaa aaaaaaaaaa aaaaa         775
```

<210> SEQ ID NO 3
<211> LENGTH: 2139
<212> TYPE: DNA
<213> ORGANISM: Homo sapiens

<400> SEQUENCE: 3

```
gaaaacagtg cagccacctc cgagagcctg gatgtgatgg cgtcacagaa gagaccctcc     60
```

-continued

```
cagaggcacg gatccaagta cctggccaca gcaagtacca tggaccatgc caggcatggc    120
ttcctcccaa ggcacagaga cacgggcatc cttgactcca tcgggcgctt ctttggcggt    180
gacaggggtg cgccaaagcg gggctctggc aaggactcac accacccggc aagaactgct    240
cactatggct ccctgcccca gaagtcacac ggccggaccc aagatgaaaa ccccgtagtc    300
cacttcttca agaacattgt gacgcctcgc acaccacccc cgtcgcaggg aaaggggaga    360
ggactgtccc tgagcagatt tagctggggg gccgaaggcc agagaccagg atttggctac    420
ggaggcagag cgtccgacta taaatcggct cacaagggat tcaagggagt cgatgcccag    480
ggcacgcttt ccaaaatttt taagctggga ggaagagata gtcgctctgg atcacccatg    540
gctagacgct gaaaacccac ctggttccgg aatcctgtcc tcagcttctt aatataactg    600
ccttaaaact ttaatcccac ttgcccctgt tacctaatta gagcagatga cccctcccct    660
aatgcctgcg gagttgtgca cgtagtaggg tcaggccacg gcagcctacc ggcaatttcc    720
ggccaacagt taaatgagaa catgaaaaca gaaaacggtt aaaactgtcc ctttctgtgt    780
gaagatcacg ttccttcccc cgcaatgtgc ccccagacgc acgtgggtct tcagggggcc    840
aggtgcacag acgtccctcc acgttcaccc ctccaccctt ggactttctt ttcgccgtgg    900
ctcggcaccc ttgcgctttt gctggtcact gccatggagg cacacagctg cagagacaga    960
gaggacgtgg gcggcagaga ggactgttga catccaagct tcctttgttt tttttcctg    1020
tccttctctc acctcctaaa gtagacttca tttttcctaa caggattaga cagtcaagga   1080
gtggcttact acatgtggga gctttttggt atgtgacatg cgggctgggc agctgttaga   1140
gtccaacgtg gggcagcaca gagaggggc cacctcccca ggccgtggct gcccacacac    1200
cccaattagc tgaattcgcg tgtggcagag ggaggaaaag gaggcaaacg tgggctgggc   1260
aatggcctca cataggaaac agggtcttcc tggagatttg gtgatggaga tgtcaagcag   1320
gtggcctctg gacgtcaccg ttgccctgca tggtggcccc agagcagcct ctatgaacaa   1380
cctcgtttcc aaaccacagc ccacagccgg agagtccagg aagacttgcg cactcagagc   1440
agaagggtag gagtcctcta gacagcctcg cagccgcgcc agtcgcccat agacactggc   1500
tgtgaccggg cgtgctggca gcggcagtgc acagtggcca gcactaaccc tccctgagaa   1560
gataaccggc tcattcactt cctcccagaa gacgcgtggt agcgagtagg cacaggcgtg   1620
cacctgctcc cgaattactc accgagacac acgggctgag cagacggccc ctgtgatgga   1680
gacaaagagc tcttctgacc atatccttct taacacccgc tggcatctcc tttcgcgcct   1740
ccctccctaa cctactgacc caccttttga ttttagcgca cctgtgattg ataggccttc   1800
caaagagtcc cacgctggca tcaccctccc cgaggacgga gatgaggagt agtcagcgtg   1860
atgccaaaac gcgtcttctt aatccaattc taattctgaa tgtttcgtgt gggcttaata   1920
ccatgtctat taatatatag cctcgatgat gagagagtta caaagaacaa aactccagac   1980
acaaacctcc aaatttttca gcagaagcac tctgcgtcgc tgagctgagg tcggctctgc   2040
gatccatacg tggccgcacc cacacagcac gtgctgtgac gatggctgaa cggaaagtgt   2100
acactgttcc tgaatattga aataaaacaa taaactttt                          2139
```

<210> SEQ ID NO 4
<211> LENGTH: 166
<212> TYPE: DNA
<213> ORGANISM: Homo sapiens

<400> SEQUENCE: 4

-continued

```
ttcatataca aaaagataaa acttgaaata gttctagatt tttcctccta ttgttggggt     60

gtaactgctt cttcacacag ggggaaaaaa ctacattcac atcggtttat ttgaggaccc    120

agtgcagagt tcaagcagca aaaccccaac ttagcagatc taattt                   166
```

<210> SEQ ID NO 5
<211> LENGTH: 1618
<212> TYPE: DNA
<213> ORGANISM: Homo sapiens

<400> SEQUENCE: 5

```
ggcttggtca ccgcattaag gcattcccgc tctccgcgga actgctctgc cgtctcggcg     60

gtgaaagtgt gagagggtcc gtagttgggt caactttgac tcctctcgcc tgcccggatc    120

cttaagggcc tcctcgtcct cccggtctcc ggtcgctgcc gggtctgtgc gccggtccgc    180

gcccgccctc gctctgccat gggcgcttcc agctcctccg cgctggcccg cctcggcctc    240

ccagcccggc cctggcccag gtggctcggg gtcgccgcgc taggactggc cgccgtggcc    300

ctggggactg tcgcctggcg ccgcgcatgg cccaggcggc gccggcggct gcagcaggtg    360

ggcaccgtgg cgaagctctg gatctacccg gtgaaatcct gcaaaggggt gccggtgagc    420

gaggctgagt gcacggccat ggggctgcgc agcggcaacc tgcgggacag gttttggctg    480

gtgattaagg aagatggaca catggtcact gcccgacagg agcctcgcct cgtgctcatc    540

tccatcattt atgagaataa ctgcctgatc ttcagggctc cagacatgga ccagctggtt    600

ttgcctagca agcagccttc ctcaaacaaa ctccacaact gcaggatatt tggccttgac    660

attaaaggca gagactgtgg caatgaggca gctaagtggt tcaccaactt cttgaaaact    720

gaagcgtata gattggttca atttgagaca aacatgaagg gaagaacatc aagaaaactt    780

ctccccactc ttgatcagaa tttccaggtg gcctacccag actactgccc gctcctgatc    840

atgacagatg cctccctggt agatttgaat accaggatgg agaagaaaat gaaaatggag    900

aatttcaggc caaatattgt ggtgaccggc tgtgatgctt ttgaggagga tacctgggat    960

gaactcctaa ttggtagtgt agaagtgaaa aaggtaatgg catgccccag gtgtattttg   1020

acaacggtgg acccagacac tggagtcata gacaggaaac agccactgga caccctgaag   1080

agctaccgcc tgtgtgatcc ttctgagagg gaattgtaca agttgtctcc actttttggg   1140

atctattatt cagtggaaaa aattggaagc ctgagagttg gtgaccctgt gtatcggatg   1200

gtgtagtgat gagtgatgga tccactaggg tgatatggct tcagcaacca ggagggattg   1260

actgagatct taacaacagc agcaacgata catcagcaaa tccttattat ccagccttca   1320

actatcttta ccctggaaaa caatctcgat ttttgacttt tcaaagttgt gtatgctcca   1380

ggttaatgca aggaaagtat tagagggggg aatatgaaag tatatatata aattttaggt   1440

actgaaggct ttaaaaataa ttaagatcat caaaaatgct attttgaatg ttatcatggc   1500

tattacactt ttacttcctg actttaatat tgatgaataa agcaagttta atgaatcaac   1560

taaaaagctg caaaaaaaaa aaaaaaaaaa aaaaaaaaaa aaaaaaaaaa aaaaaaaa     1618
```

<210> SEQ ID NO 6
<211> LENGTH: 1669
<212> TYPE: DNA
<213> ORGANISM: Homo sapiens

<400> SEQUENCE: 6

```
cggcggtgct gcgaggtcgg cgcgcagctc cgccgcgggt cgctcgggcg ctgtccaggc     60

ggagccggcc ccgcccgggc tgcagccatg atcaagcgtt tcctggagga caccacggat    120
```

-continued

```
gatggagaac tgagcaagtt cgtgaaggat ttctcaggaa atgcgagctg ccacccacca    180
gaggctaaga cctgggcatc caggccccaa gtcccggagc caaggcccca ggccccggac    240
ctctatgatg atgacctgga gttcagaccc ccctcgcggc cccagtcctc tgacaaccag    300
cagtacttct gtgccccagc ccctctcagc ccatctgcca ggccccgcag cccatggggc    360
aagcttgatc cctatgattc ctctgaggat gacaaggagt atgtgggctt tgcaaccctc    420
cccaaccaag tccaccgaaa gtccgtgaag aaaggctttg actttaccct catggtggca    480
ggagagtctg gcctgggcaa atccacactt gtcaatagcc tcttcctcac tgatctgtac    540
cgggaccgga aacttcttgg tgctgaagag aggatcatgc aaactgtgga gatcactaag    600
catgcagtgg acatagaaga gaagggtgtg aggctgcggc tcaccattgt ggacacacca    660
ggttttgggg atgcagtcaa caacacagag tgctggaagc ctgtggcaga atacattgat    720
cagcagtttg agcagtattt ccgagacgag agtggcctga accgaaagaa catccaagac    780
aacagggtgc actgctgcct gtacttcatc tcacccttcg gccatgggct ccggccattg    840
gatgttgaat tcatgaaggc cctgcatcag cgggtcaaca tcgtgcctat cctggctaag    900
gcagacacac tgacacctcc cgaagtggac cacaagaaac gcaaaatccg ggaggagatt    960
gagcattttg gaatcaagat ctatcaattc ccagactgtg actctgatga ggatgaggac   1020
ttcaaattgc aggaccaagc cctaaaggaa agcatcccat ttgcagtaat tggcagcaac   1080
actgtagtag aggccagagg gcggcgagtt cggggtcgac tctacccctg gggcatcgtg   1140
gaagtggaaa acccagggca ctgcgacttt gtgaagctga ggacaatgct ggtacgtacc   1200
cacatgcagg acctgaagga tgtgacgcgg gagacacatt atgagaacta ccgggcacag   1260
tgcatccaga gcatgacccg cctggtggtg aaggaacgga atcgcaacaa actgactcgg   1320
gaaagtggta ccgacttccc catccctgct gtcccaccag ggacagatcc agaaactgag   1380
aagcttatcc gagagaaaga tgaggagctg cggcggatgc aggagatgct acacaaaata   1440
caaaaacaga tgaaggagaa ctattaactg gctttcagcc ctggatattt aaatctcctc   1500
ctcttcttcc tgtccatgcc ggcccctccc agcaccagct ctgctcaggc cccttcagct   1560
actgccactt cgccttacat ccctgctgac tgcccagaga ctcagaggaa ataaagttta   1620
ataaatctgt aggtggctaa aaaaaaaaaa aaaaaaaaaa aaaaaaaaa              1669
```

<210> SEQ ID NO 7
<211> LENGTH: 1850
<212> TYPE: DNA
<213> ORGANISM: Homo sapiens

<400> SEQUENCE: 7

```
cgcgctcgca gctcgcaggc gccgcgtagc cgtcgccacc gccgccagcc cgtgcgccct     60
cggcgcgtac ccgccgcgct cccatccccg ccgccggcca ggggcgcgct cggccgcccc    120
ggacagtgtc ccgctgcggc tccgcggcga tggccaccaa gatcgacaaa gaggcttgcc    180
gggcggcgta caacctggtg cgcgacgacg gctcggccgt catctgggtg acttttaaat    240
atgacggctc caccatcgtc cccggcgagc agggagcgga gtaccagcac ttcatccagc    300
agtgcacaga tgacgtccgg ttgtttgcct tcgtgcgctt caccaccggg gatgccatga    360
gcaagaggtc caagtttgcc ctcatcacgt ggatcggtga gaacgtcagc gggctgcagc    420
gcgccaaaac cgggacggac aagaccctgg tgaaggaggt cgtacagaat ttcgctaagg    480
agtttgtgat cagtgatcgg aaggagctgg aggaagattt catcaagagc gagctgaaga    540
```

-continued

```
aggcgggggg agccaattac gacgcccaga cggagtaacc ccagcccccg ccacaccacc    600

ccttgccaaa gtcatctgcc tgctccccgg gggagaggac cgccggcctc agctactagc    660

ccaccagccc accagggaga aaagaagcca tgagaggcag cgcccgccac cctgtgtcca    720

cagcccccac cttcccgctt cccttagaac cctgccgtgt cctatctcat gacgctcatg    780

gaacctcttt ctttgatctt ctttttcttt tctccccctc ttttttgttc taaagaaaag    840

tcattttgat gcaaggtcct gcctgccatc agatccgagg tgcctcctgc agtgacccct    900

tttcctggca tttctcttcc acgcgacgag gtctgcctag tgagatctgc atgacctcac    960

gttgctttcc agagcccggg cctattttgc catctcagtt ttcctggacc ctgcttcctg   1020

tgtaccactg aggggcagct gggccaggag ctgtgcccgg tgcctgcagc cttcataagc   1080

acacacgtcc attccctact aaggcccaga cctcctggta tctgccccgg gctccctcat   1140

cccacctcca tccggagttg cctaagatgc atgtccagca taggcaggat tgctcggtgg   1200

tgagaaggtt aggtccggct cagactgaat aagaagagat aaaatttgcc ttaaaactta   1260

cctggcagtg gctttgctgc acggtctgaa accacctgtt cccaccctct tgaccgaaat   1320

ttccttgtga cacagagaag ggcaaaggtc tgagcccaga gttgacggag ggagtatttc   1380

agggttcact tcaggggctc ccaaagcgac aagatcgtta gggagagagg cccagggtgg   1440

ggactgggaa tttaaggaga gctgggaacg gatcccttag gttcaggaag cttctgtgta   1500

agctgcgagg atggcttggg ccgaagggtt gctctgcccg ccgcgctagc tgtgagctga   1560

gcaaagccct gggctcacag caccccaaaa gcctgtggct tcagtcctgc gtctgcacca   1620

cacattcaaa aggatcgttt tgttttgttt ttaaagaaag gtgagattgg cttggttctt   1680

catgagcaca tttgatatag ctctttttct gtttttcctt gctcatttcg ttttggggaa   1740

gaaatctgta ctgtattggg attgtaaaga acatctctgc actcagacag tttacagaaa   1800

taaatgtttt ttttgttttt cagaaaaaaa aaaaaaaaaa aaaaaaaaaa              1850
```

<210> SEQ ID NO 8
<211> LENGTH: 1646
<212> TYPE: DNA
<213> ORGANISM: Homo sapiens

<400> SEQUENCE: 8

```
ctgaccgagg cgtgcaaaga ctccagaatt ggaggcatga tgaagactct gctgctgttt     60

gtggggctgc tgctgacctg ggagagtggg caggtcctgg gggaccagac ggtctcagac    120

aatgagctcc aggaaatgtc caatcaggga agtaagtacg tcaataagga aattcaaaat    180

gctgtcaacg gggtgaaaca gataaagact ctcatagaaa aaacaaacga agagcgcaag    240

acactgctca gcaacctaga agaagccaag aagaagaaag aggatgccct aaatgagacc    300

agggaatcag agacaaagct gaaggagctc ccaggagtgt gcaatgagac catgatggcc    360

ctctgggaag agtgtaagcc ctgcctgaaa cagacctgca tgaagttcta cgcacgcgtc    420

tgcagaagtg gctcaggcct ggttggccgc cagcttgagg agttcctgaa ccagagctcg    480

cccttctact tctggatgaa tggtgaccgc atcgactccc tgctggagaa cgaccggcag    540

cagacgcaca tgctggatgt catgcaggac cacttcagcc gcgcgtccag catcatagac    600

gagctcttcc aggacaggtt cttcacccgg gagccccagg atacctacca ctacctgccc    660

ttcagcctgc cccaccggag gcctcacttc ttctttccca agtcccgcat cgtccgcagc    720

ttgatgccct tctctccgta cgagcccctg aacttccacg ccatgttcca gcccttcctt    780

gagatgatac acgaggctca gcaggccatg gacatccact tccacagccc ggccttccag    840
```

-continued

```
cacccgccaa cagaattcat acgagaaggc gacgatgacc ggactgtgtg ccgggagatc    900

cgccacaact ccacgggctg cctgcggatg aaggaccagt gtgacaagtg ccgggagatc    960

ttgtctgtgg actgttccac caacaacccc tcccaggcta agctgcggcg ggagctcgac   1020

gaatccctcc aggtcgctga gaggttgacc aggaaataca acgagctgct aaagtcctac   1080

cagtggaaga tgctcaacac ctcctccttg ctggagcagc tgaacgagca gtttaactgg   1140

gtgtcccggc tggcaaacct cacgcaaggc gaagaccagt actatctgcg ggtcaccacg   1200

gtggcttccc acacttctga ctcggacgtt ccttccggtg tcactgaggt ggtcgtgaag   1260

ctctttgact ctgatcccat cactgtgacg gtccctgtag aagtctccag gaagaaccct   1320

aaatttatgg agaccgtggc ggagaaagcg ctgcaggaat accgcaaaaa gcaccgggag   1380

gagtgagatg tggatgttgc ttttgcacct acgggggcat ctgagtccag ctcccccca   1440

gatgagctgc agccccccag agagagctct gcacgtcacc aagtaaccag gccccagcct   1500

ccaggccccc aactccgccc agcctctccc cgctctggat cctgcactct aacactcgac   1560

tctgctgctc atgggaagaa cagaattgct cctgcatgca actaattcaa taaaactgtc   1620

ttgtgagctg aaaaaaaaaa aaaaaa                                        1646
```

<210> SEQ ID NO 9
<211> LENGTH: 1559
<212> TYPE: DNA
<213> ORGANISM: Homo sapiens

<400> SEQUENCE: 9

```
gggaggcggc ggcggcggcg gcggcggcgg cgagagccca gagccagagc ccggccgggg     60

ccgagcggag cgcggcggcg gcggcggcgg cggcggctgg gccgggagag gctggcgcgc    120

cgggcggctc cgcgaatcct ccggcatccg ccccggcggg ccgcccccgc ccgcggcagc    180

cccccgagca gtggcccggc atcggcgcct tcccggcggg caagagtgag ccatggagct    240

acgtgtgggg aacaagtacc gcctgggacg gaagatcggg agcgggtcct tcggagatat    300

ctacctgggt gccaacatcg cctctggtga ggaagtcgcc atcaagctgg agtgtgtgaa    360

gacaaagcac cccccagctgc acatcgagag caagttctac aagatgatgc agggtggcgt    420

ggggatcccg tccatcaagt ggtgcggagc tgagggcgac tacaacgtga tggtcatgga    480

gctgctgggg cctagcctcg aggacctgtt caacttctgt tcccgcaaat tcagcctcaa    540

gacggtgctg ctcttggccg accagatgat cagccgcatc gagtatatcc actccaagaa    600

cttcatccac cgggacgtca agcccgacaa cttcctcatg ggctgggga agaagggcaa    660

cctggtctac atcatcgact tcggcctggc caagaagtac cgggacgccc gcacccacca    720

gcacattccc taccgggaaa acaagaacct gaccggcacg gcccgctacg cttccatcaa    780

cacgcacctg ggcattgagc aaagccgtcg agatgacctg gagagcctgg gctacgtgct    840

catgtacttc aacctgggct ccctgccctg gcaggggctc aaagcagcca ccaagcgcca    900

gaagtatgaa cggatcagcg agaagaagat gtcaacgccc atcgaggtcc tctgcaaagg    960

ctatccctcc gaattctcaa catacctcaa cttctgccgc tccctgcggt ttgacgacaa   1020

gcccgactac tcttacctac gtcagctctt ccgcaacctc ttccaccggc agggcttctc   1080

ctatgactac gtctttgact ggaacatgct gaaattcggt gcagcccgga atcccgagga   1140

tgtggaccgg gagcggcgag aacacgaacg cgaggagagg atggggcagc tacgggggtc   1200

cgcgacccga gccctgcccc ctggcccacc cacgggggcc actgccaacc ggctccgcag   1260
```

-continued

```
tgccgccgag cccgtggctt ccacgccagc ctcccgcatc cagccggctg gcaatacttc   1320

tcccagagcg atctcgcggg tcgaccggga gaggaaggtg agtatgaggc tgcacagggg   1380

tgcgcccgcc aacgtctcct cctcagacct cactgggcgg caagaggtct cccggatccc   1440

agcctcacag acaagtgtgc catttgacca tctcgggaag tgaggagagc cccattgga   1500

ccagtgtttg cttagtgtct tcactgtatt ttctttaaaa aaaaaaaaaa aaaaaaaaa    1559
```

<210> SEQ ID NO 10
<211> LENGTH: 910
<212> TYPE: DNA
<213> ORGANISM: Homo sapiens

<400> SEQUENCE: 10

```
cctgcttcaa cagtgcttgg acggaacccg gcgctcgttc cccaccccgg ccggccgccc     60

atagccagcc ctccgtcacc tcttcaccgc accctcggac tgccccaagg cccccgccgc    120

cgctccagcg ccgcgcagcc accgccgccg ccgccgcctc tccttagtcg ccgccatgac    180

gaccgcgtcc acctcgcagg tgcgccagaa ctaccaccag gactcagagg ccgccatcaa    240

ccgccagatc aacctggagc tctacgcctc ctacgtttac ctgtccatgt cttactactt    300

tgaccgcgat gatgtggctt tgaagaactt tgccaaatac tttcttcacc aatctcatga    360

ggagagggaa catgctgaga aactgatgaa gctgcagaac caacgaggtg gccgaatctt    420

ccttcaggat atcaagaaac cagactgtga tgactgggag agcgggctga atgcaatgga    480

gtgtgcatta catttggaaa aaatgtgaat cagtcactac tggaactgca caaactggcc    540

actgacaaaa atgaccccca tttgtgtgac ttcattgaga cacattacct gaatgagcag    600

gtgaaagcca tcaaagaatt gggtgaccac gtgaccaact tgcgcaagat gggagcgccc    660

gaatctggct tggcggaata tctctttgac aagcacaccc tgggagacag tgataatgaa    720

agctaagcct cgggctaatt tccccatagc cgtggggtga cttccctggt caccaaggca    780

gtgcatgcat gttggggttt cctttacctt ttctataagt tgtaccaaaa catccactta    840

agttctttga tttgtaccat tccttcaaat aaagaaattt ggtacccaaa aaaaaaaaaa    900

aaaaaaaaaa                                                           910
```

<210> SEQ ID NO 11
<211> LENGTH: 2740
<212> TYPE: DNA
<213> ORGANISM: Homo sapiens

<400> SEQUENCE: 11

```
cgctgccatg cggctggcgc tgctctgggc cctggggctc ctgggcgcgg gcagccctct     60

gccttcctgg ccgctcccaa atataggtgg cactgaggag cagcaggcag agtcagagaa    120

ggccccgagg gagcccttgg agccccaggt ccttcaggac gatctcccaa ttagcctcaa    180

aaaggtgctt cagaccagtc tgcctgagcc cctgaggatc aagttggagc tggacggtga    240

cagtcatatc ctggagctgc tacagaatag ggagttggtc ccaggccgcc caaccctggt    300

gtggtaccag cccgatggca ctcgggtggt cagtgaggga cacactttgg agaactgctg    360

ctaccaggga agagtgcggg gatatgcagg ctcctgggtg tccatctgca cctgctctgg    420

gctcagaggc ttggtggtcc tgaccccaga gagaagctat accctggagc aggggcctgg    480

ggaccttcag ggtcctccca ttatttcgcg aatccaagat ctccacctgc caggccacac    540

ctgtgccctg agctggcggg aatctgtaca cactcagacg ccaccagagc acccccctggg    600

acagcgccac attcgccgga ggcgggatgt ggtaacagag accaagactg tggagttggt    660
```

-continued

```
gattgtggct gatcactcgg aggcccagaa ataccgggac ttccagcacc tgctaaaccg    720
cacactggaa gtggccctct tgctggacac attcttccgg cccctgaatg tacgagtggc    780
actagtgggc ctggaggcct ggacccagcg tgacctggtg gagatcagcc caaacccagc    840
tgtcaccctc gaaaacttcc tccactggcg cagggcacat ttgctgcctc gattgcccca    900
tgacagtgcc cagctggtga ctggtacttc attctctggg cctacggtgg gcatggccat    960
tcagaactcc atctgttctc ctgacttctc aggaggtgtg aacatggacc actccaccag   1020
catcctggga gtcgcctcct ccatagccca tgagttgggc cacagcctgg gcctggacca   1080
tgatttgcct gggaatagct gcccctgtcc aggtccagcc ccagccaaga cctgcatcat   1140
ggaggcctcc acagacttcc taccaggcct gaacttcagc aactgcagcc gacgggccct   1200
ggagaaagcc ctcctggatg gaatgggcag ctgcctcttc gaacggctgc ctagcctacc   1260
ccctatggct gctttctgcg gaaatatgtt tgtggagccg ggcgagcagt gtgactgtgg   1320
cttcctggat gactgcgtcg atccctgctg tgattctttg acctgccagc tgaggccagg   1380
tgcacagtgt gcatctgacg gaccctgttg tcaaaattgc cagctgcgcc cgtctggctg   1440
gcagtgtcgt cctaccagag ggattgtga cttgcctgaa ttctgcccag gagacagctc    1500
ccagtgtccc cctgatgtca gcctagggga tggcgagccc tgcgctggcg ggcaagctgt   1560
gtgcatgcac gggcgttgtg cctcctatgc ccagcagtgc cagtcacttt ggggacctgg   1620
agcccagccc gctgcgccac tttgcctcca gacagctaat actcggggaa atgcttttgg   1680
gagctgtggg cgcaacccca gtggcagtta tgtgtcctgc acccctagag atgccatttg   1740
tgggcagctc cagtgccaga caggtaggac ccagcctctg ctgggctcca tccgggatct   1800
actctgggag acaatagatg tgaatgggac tgagctgaac tgcagctggg tgcacctgga   1860
cctgggcagt gatgtggccc agcccctcct gactctgcct ggcacagcct gtggccctgg   1920
cctggtgtgt atagaccatc gatgccagcg tgtggatctc ctgggggcac aggaatgtcg   1980
aagcaaatgc catggacatg ggtctgtga cagcaacagg cactgctact gtgaggaggg    2040
ctgggcaccc cctgactgca ccactcagct caaagcaacc agctccctga ccacagggct   2100
gctcctcagc ctcctggtct tattggtcct ggtgatgctt ggtgccggct actggtaccg   2160
tgcccgcctg caccagcgac tctgccagct caagggaccc acctgccagt acagggcagc   2220
ccaatctggt ccctctgaac ggccaggacc tccgcagagg gccctgctgg cacgaggcac   2280
taagtctcag gggccagcca agcccccacc cccaaggaag ccactgcctg ccgaccccca   2340
gggccggtgc ccatcgggtg acctgcccgg cccaggggct ggaatcccgc ccctagtggt   2400
accctccaga ccagcgccac cgcctccgac agtgtcctcg ctctacctct gacctctccg   2460
gaggttccgc tgcctccaag ccggacttag ggcttcaaga ggcgggcgtg ccctctggag   2520
tcccctacca tgactgaagg cgccagagac tggcggtgtc ttaagactcc gggcaccgcc   2580
acgcgctgtc aagcaacact ctgcggacct gccggcgtag ttgcagcggg ggcttgggga   2640
ggggctgggg gttggacggg attgaggaag gtccgcacag cctgtctctg ctcagttgca   2700
ataaacgtga catcttggga gcgttaaaaa aaaaaaaaaa                          2740
```

<210> SEQ ID NO 12
<211> LENGTH: 1476
<212> TYPE: DNA
<213> ORGANISM: Homo sapiens

<400> SEQUENCE: 12

-continued

```
gtttaatagc ttgaggaagg gagactttaa aaggacgtgt gtgagtgaaa taggatatag      60
ccattaccac ggtgccagga cctgacagcg ttccaattct ttttgcagca tggggaatca     120
aaggtggcat gccaagttca actcagggct gaggtatcca cattgtccac atcaggcaag     180
ccctgcactg acggttgagc ctcatggaga ggagcatgtg ttggaaagag atccctttgt     240
taactgtttt gtggtgttct cttcaatgaa ttagagctca tgcccctttt ctggctttgc     300
tgttgatttt ggatggtaga gaatattcct gagagccttc cttttggccc ccagcttatg     360
ccacccactc tcttctcttg gttgaattct ctgaaggaaa ggttcatgtg ctattgtcct     420
gttagtcaat agtcttcata tataattgtg ttacatatat tgctgtagac tctcagaaat     480
cagggtagag cttttccttt gagcagttta atgagtgaat tcagcagcaa agtcgcaaga     540
aatggttctc cagccaggag aggttatgtt tatcctctga ttgcccgttt tctctgcaca     600
cagtgatatc gtattcagtg agaggtgctg ttggcaccca gcagcaccct gggcacacag     660
catttcatgt catgtcacag tgtacaagct accctctaat tcagaaagaa gagcattttg     720
cacagagaaa aataaaaaga tccatgaatg tcatctttta tcttttattt tcagttggct     780
gatgttggaa tttttgttct tgtcatgaac ttgtaaacca atcttgccaa gatacaagtt     840
gttttggttt ttcactacaa tgacctcttg ttcctcctgt cttgactgct gacgttcctc     900
aatgattcta ttgtctattt tatgggaagc agccttccca taggtttcct tttacacact     960
gcagggctat ctttatactt taaaaaaaaa aaaaaaaaaa aaaaggacaa gaactgtcac    1020
taacctcatg gaggggtttg cgtaaaacca tttagcccac cttgagcaaa gggtagattc    1080
cgtgttgttt ttttaagctc actgtaataa aatagatcta attcagcatt attgtgctac    1140
ctcaaaggta aaaaatgttt taaggtcttc ttttggtcct gagttctata tacagtgttt    1200
gaaatgtctt tcatttggaa ttattttta aattcttgga gtgaatttta ttttaatctg    1260
ttttaatctt gtattttaat ctcagaagaa taagtgattg aaacgtgatc aattcttgct    1320
ctgtggtgtt aaacatataa tgaacagtca ttaagaatta agtcactgtt tgccataaac    1380
aaggttgatg ttctttttgt tgttgttaag gaaaccctag ggctcggctt tactcttgat    1440
taataaaggc tgacaaatca aaaaaaaaaa aaaaaa                              1476
```

<210> SEQ ID NO 13
<211> LENGTH: 1679
<212> TYPE: DNA
<213> ORGANISM: Homo sapiens

<400> SEQUENCE: 13

```
ggcacgaggt agagctccag gacattcagg taccaggtag ccccaaggag gagctgccga      60
cctggcaggg aacaaccaag actggggtta aatctcacag cctgcaagtg gaagagaaga     120
acttgaaccc aggtccaact tttgcgccac agcaggctgc ctcttggtcc tgacaggaag     180
tcacaacttg gccctgactt cctatcctag ggaaggggcc ggctggagag gccaggacag     240
agaaagcaga tcccttcttt ttccaaggac tctgtgtctt ccataggcaa catgtcagaa     300
ggggtgggca cgttccgcat ggtacctgaa gaggaacagg agctccgtgc ccaactggag     360
cagctcacaa ccaaggacca tggacctgtc tttggcccgt gcagccagct gccccgccac     420
accttgcaga aggccaagga tgagctgaac gagagagagg agacccggga ggaggcagtg     480
cgagagctgc aggagatggt gcaggcgcag gcggcctcgg gggaggagct ggcggtggcc     540
gtggcggaga gggtgcaaga gaaggacagc ggcttcttcc tgcgcttcat ccgcgcacgg     600
aagttcaacg tgggccgtgc ctatgagctg ctcagaggct atgtgaattt ccggctgcag     660
```

-continued

```
taccctgagc tctttgacag cctgtcccca gaggctgtcc gctgcaccat tgaagctggc    720

taccctggtg tcctctctag tcgggacaag tatggccgag tggtcatgct cttcaacatt    780

gagaactggc aaagtcaaga aatcaccttt gatgagatct tgcaggcata ttgcttcatc    840

ctggagaagc tgctggagaa tgaggaaact caaatcaatg gcttctgcat cattgagaac    900

ttcaagggct ttaccatgca gcaggctgct agtctccgga cttcagatct caggaagatg    960

gtggacatgc tccaggattc cttcccagcc cggttcaaag ccatccactt catccaccag   1020

ccatggtact tcaccacgac ctacaatgtg gtcaagccct tcttgaagag caagctgctt   1080

gagagggtct ttgtccacgg ggatgacctt tctggtttct accaggagat cgatgagaac   1140

atcctgccct ctgacttcgg gggcacgctg cccaagtatg atggcaaggc cgttgctgag   1200

cagctctttg gcccccaggc ccaagctgag aacacagcct tctgaaaaca tctcctgcca   1260

gctgaactgt agttagaatc tctgggcctc tcctcaactg tcctggaccc aaggctagga   1320

aagggctgct tgagatgact gtggtccccc cttagactcc ctaagcccga gtgagctcag   1380

gtgtcaccct gttctcaagt tgggggatgg ggaataaagg agggggaatt cccttgaaca   1440

agaagaactg ggatagttta tatttccacc tgcccttgaa gctttaagac agtgattttt   1500

gtgtaaggtt gtatttcaaa gactcgaatt cattttctca atcatttcct ttgtaacaga   1560

gttttacgac ttagagtctg tgaaaacagg caaggagccc gggttaaaat atccccctat   1620

tcgcccccaa aatgcaataa aagaagataa aagagagagg aaaaaaaaaa aaaaaaaaa    1679
```

<210> SEQ ID NO 14
<211> LENGTH: 1962
<212> TYPE: DNA
<213> ORGANISM: Homo sapiens

<400> SEQUENCE: 14

```
agctctcgca ctctgttctt ccgccgctcc gccgtcgcgt ttctctgccg gtcgcaatgg     60

aagaagagat cgccgcgctg gtcattgaca atggctccgg catgtgcaaa gctggttttg    120

ctggggacga cgctccccga gccgtgtttc cttccatcgt cgggcgcccc agacaccagg    180

gcgtcatggt gggcatgggc cagaaggact cctacgtggg cgacgaggcc cagagcaagc    240

gtggcatcct gaccctgaag taccccattg agcatggcat cgtcaccaac tgggacgaca    300

tggagaagat ctggcaccac accttctaca acgagctgcg cgtggccccg gaggagcacc    360

cagtgctgct gaccgaggcc cccctgaacc ccaaggccaa cagagagaag atgactcaga    420

ttatgtttga gaccttcaac accccggcca tgtacgtggc catccaggcc gtgctgtccc    480

tctacgcctc tgggcgcacc actggcattg tcatggactc tggagacggg gtcacccaca    540

cggtgcccat ctacgagggc tacgccctcc cccacgccat cctgcgtctg gacctggctg    600

gccgggacct gaccgactac ctcatgaaga tcctcactga gcgaggctac agcttcacca    660

ccacggccga gcgggaaatc gtgcgcgaca tcaaggagaa gctgtgctac gtcgccctgg    720

acttcgagca ggagatggcc accgccgcat cctcctcttc tctggagaag agctacgagc    780

tgcccgatgg ccaggtcatc accattggca atgagcggtt ccggtgtccg gaggcgctgt    840

tccagccttc cttcctgggt atggaatctt gcggcatcca cgagaccacc ttcaactcca    900

tcatgaagtg tgacgtggac atccgcaaag acctgtacgc caacacggtg ctgtcgggcg    960

gcaccaccat gtacccgggc attgccgaca ggatgcagaa ggagatcacc gccctggcgc   1020

ccagcaccat gaagatcaag atcatcgcac ccccagagcg caagtactcg gtgtggatcg   1080
```

-continued

```
gtggctccat cctggcctca ctgtccacct tccagcagat gtggattagc aagcaggagt   1140

acgacgagtc gggcccctcc atcgtccacc gcaaatgctt ctaaacggac tcagcagatg   1200

cgtagcattt gctgcatggg ttaattgaga atagaaattt gcccctggca aatgcacaca   1260

cctcatgcta gcctcacgaa actggaataa gccttcgaaa agaaattgtc cttgaagctt   1320

gtatctgata tcagcactgg attgtagaac ttgttgctga ttttgacctt gtattgaagt   1380

taactgttcc ccttggtatt tgtttaatac cctgtacata tctttgagtt caacctttag   1440

tacgtgtggc ttggtcactt cgtggctaag gtaagaacgt gcttgtggaa gacaagtctg   1500

tggcttggtg agtctgtgtg gccagcagcc tctgatctgt gcagggtatt aacgtgtcag   1560

ggctgagtgt tctgggattt ctctagaggc tggcaagaac cagttgtttt gtcttgcggg   1620

tctgtcaggg ttggaaagtc caagccgtag gacccagttt cctttcttag ctgatgtctt   1680

tggccagaac accgtgggct gttacttgct ttgagttgga agcggtttgc atttacgcct   1740

gtaaatgtat tcattcttaa tttatgtaag gtttttttg tacgcaattc tcgattcttt   1800

gaagagatga caacaaattt tggttttcta ctgttatgtg agaacattag gccccagcaa   1860

cacgtcattg tgtaaggaaa aataaaagtg ctgccgtaac caaaaaaaaa aaaaaaaaaa   1920

aaaaaaaaaa aaaaaaaaaa aaaaaaaaaa aaaaaaaaaa aa                      1962
```

<210> SEQ ID NO 15
<211> LENGTH: 2365
<212> TYPE: DNA
<213> ORGANISM: Homo sapiens

<400> SEQUENCE: 15

```
gaattcaagt tcagtgccta ccgaagacaa aggcgccccg agggagtggc ggtgcgaccc     60

cagggcgtgg gcccggccgc ggagcccaca ctgcccggct gacccggtgg tctcggacca    120

tgtctcccgc cccaagaccc tcccgttgtc tcctgctccc cctgctcacg ctcggcaccg    180

cgctcgcctc cctcggctcg gcccaaagca gcagcttcag ccccgaagcc tggctacagc    240

aatatggcta cctgcctccc ggggacctac gtacccacac acagcgctca ccccagtcac    300

tctcagcggc catcgctgcc atgcagaagt tttacggctt gcaagtaaca ggcaaagctg    360

atgcagacac catgaaggcc atgaggcgcc cccgatgtgg tgttccagac aagtttgggg    420

ctgagatcaa ggccaatgtt cgaaggaagc gctacgccat ccagggtctc aaatggcaac    480

ataatgaaat cactttctgc atccagaatt acacccccaa ggtgggcgag tatgccacat    540

acgaggccat tcgcaaggcg ttccgcgtgt gggagagtgc cacaccactg cgcttccgcg    600

aggtgcccta tgcctacatc cgtgagggcc atgagaagca ggccgacatc atgatcttct    660

ttgccgaggg cttccatggc gacagcacgc ccttcgatgg tgagggcggc ttcctggccc    720

atgcctactt cccaggcccc aacattggag gagacaccca ctttgactct gccgagcctt    780

ggactgtcag gaatgaggat ctgaatggaa atgacatctt cctggtggct gtgcacgagc    840

tgggccatgc cctggggctc gagcattcca gtgacccctc ggccatcatg gcaccctttt    900

accagtggat ggacacggag aattttgtgc tgcccgatga tgaccgccgg ggcatccagc    960

aactttatgg gggtgagtca gggttcccca ccaagatgcc ccctcaaccc aggactacct   1020

cccggccttc tgttcctgat aaacccaaaa accccaccta tgggcccaac atctgtgacg   1080

ggaactttga caccgtggcc atgctccgag ggagatgtt tgtcttcaag gagcgctggt    1140

tctggcgggt gaggaataac caagtgatgg atggataccc aatgcccatt ggccagttct   1200

ggcggggcct gcctgcgtcc atcaacactg cctacgagag gaaggatggc aaattcgtct   1260
```

-continued

```
tcttcaaagg agacaagcat tgggtgtttg atgaggcgtc cctggaacct ggctacccca   1320
agcacattaa ggagctgggc cgagggctgc ctaccgacaa gattgatgct gctctcttct   1380
ggatgcccaa tggaaagacc tacttcttcc gtggaaacaa gtactaccgt ttcaacgaag   1440
agctcagggc agtggatagc gagtacccca agaacatcaa agtctgggaa gggatccctg   1500
agtctcccag agggtcattc atgggcagcg atgaagtctt cacttacttc tacaagggga   1560
acaaatactg gaaattcaac aaccagaagc tgaaggtaga accgggctac cccaagtcag   1620
ccctgaggga ctggatgggc tgcccatcgg gaggccggcc cgatgagggg actgaggagg   1680
agacggaggt gatcatcatt gaggtggacg aggagggcgg cggggcggtg agcgctgctg   1740
ccgtggtgct gcccgtgctg ctgctgctcc tggtgctggc ggtgggacta gcagtcttct   1800
tcttcagacg ccatgggacc cccaggcgac tgctctactg ccagcgttcc ctgctggaca   1860
aggtctgacg cccaccgccg gcccgcccac tcctaccaca aggactttgc ctctgaagac   1920
cagtgtcagc aaggtggtgg tgggtgggct gctcccatcc gtccggagcc ccctccccgc   1980
agcctccttg cttctctcag tcccctggct ggcctccttc accctcaccg cctgtagctt   2040
gtgtctgtcc agccccatct gaatgtgttg ggggctctgc acttgaaggc aggaccctca   2100
gacctcgctg gtaaaggtca aatggggtca tctgctcctt ttccatcccc tgacatacct   2160
taacctctga actctgacct caggaggctc tgggcactcc agccctgaaa gccccaagtg   2220
tacccagttg gcagcctccc gtcactctga ctaaaaagaa tcttcagagt gcatatttgg   2280
aggtggaaag attgttcagt taccctaaag actttgaaag aaagaaagaa agaaagaaaa   2340
aaaaaaaaaa aaaaaaaaaa aaaaa                                         2365
```

<210> SEQ ID NO 16
<211> LENGTH: 8595
<212> TYPE: DNA
<213> ORGANISM: Homo sapiens

<400> SEQUENCE: 16

```
aaagcggaga gtcacagcgg ggccaggccc tggggagcgg agcctccacc gcccccctca     60
ttcccaggca agggcttggg gggaatgagc cgggagagcc gggtcccgag cctacagagc    120
cgggagcagc tgagccgccg gcgcctcggc cgccgccgcc gcctcctcct cctccgccgc    180
cgccagcccg gagcctgagc cggcggggcg ggggggagag gagcgagcgc agcgcagcag    240
cggagccccg cgaggcccgc ccgggcgggt ggggagggca gcccggggga ctgggccccg    300
gggcggggtg ggaggggggg agaagacgaa gacagggccg ggtctctccg cggacgagac    360
agcggggatc atggccgcgc aggtcgcccc cgccgccgcc agcagcctgg gcaacccgcc    420
gccgccgccg ccctcggagc tgaagaaagc cgagcagcag cagcgggagg aggcgggggg    480
cgaggcggcg gcggcggcag cggccgagcg cggggaaatg aaggcagccg ccgggcagga    540
aagcgagggc cccgccgtgg ggccgccgca gccgctggga aaggagctgc aggacggggc    600
cgagagcaat gggggtggcg gcggcggcgg agccggcagc ggcggcgggc ccggcgcgga    660
gccggacctg aagaactcga acgggaacgc gggccctagg cccgccctga acaataacct    720
cacggagccg cccggcggcg gcggtggcgg cagcagcgat ggggtggggg cgcctcctca    780
ctcagccgcg gccgccttgc cgcccccagc ctacggcttc gggcaaccct acggccggag    840
cccgtctgcc gtcgccgccg ccgcggccgc cgtcttccac caacaacatg gcggacaaca    900
aagccctggc ctggcagcgc tgcagagcgg cggcggcggg ggcctggagc cctacgcggg    960
```

-continued

```
gccccagcag aactctcacg accacggctt ccccaaccac cagtacaact cctactaccc   1020
caaccgcagc gcctaccccc cgcccgcccc ggcctacgcg ctgagctccc cgagaggtgg   1080
cactccgggc tccggcgcgg cggcggctgc cggctccaag ccgcctccct cctccagcgc   1140
ctccgcctcc tcgtcgtctt cgtccttcgc tcagcagcgc ttcggggcca tgggggggagg   1200
cggcccctcc gcggccggcg ggggaactcc ccagcccacc gccaccccca ccctcaacca   1260
actgctcacg tcgcccagct cggcccgggg ctaccagggc taccccgggg gcgactacag   1320
tggcgggccc caggacgggg gcgccggcaa gggcccggcg gacatggcct cgcagtgttg   1380
gggggctgcg gcggcggcag ctgcggcggc ggccgcctcg ggagggggccc aacaaaggag   1440
ccaccacgcg cccatgagcc ccgggagcag cggcggcggg gggcagccgc tcgcccggac   1500
ccctcagcca tccagtccaa tggatcagat gggcaagatg agacctcagc catatggcgg   1560
gactaaccca tactcgcagc aacagggacc tccgtcagga ccgcagcaag gacatgggta   1620
cccagggcag ccatacgggt cccagacccc gcagcggtac ccgatgacca tgcagggccg   1680
ggcgcagagt gccatgggcg gcctctctta tacacagcag attcctcctt atggacaaca   1740
aggccccagc gggtatggtc aacagggcca gactccatat tacaaccagc aaagtcctca   1800
ccctcagcag cagcagccac cctactccca gcaaccaccg tcccagaccc ctcatgccca   1860
accttcgtat cagcagcagc cacagtctca accaccacag ctccagtcct ctcagcctcc   1920
atactcccag cagccatccc agcctccaca tcagcagtcc ccggctccat acccctccca   1980
gcagtcgacg acacagcagc acccccagag ccagcccccc tactcacagc cacaggctca   2040
gtctccttac cagcagcagc aacctcagca gccagcaccc tcgacgctct cccagcaggc   2100
tgcgtatcct cagccccagt ctcagcagtc ccagcaaact gcctattccc agcagcgctt   2160
ccctccaccg caggagctat ctcaagattc atttgggtct caggcatcct cagccccctc   2220
aatgacctcc agtaagggag ggcaagaaga tatgaacctg agccttcagt caagaccctc   2280
cagcttgcct gatctatctg gttcaataga tgacctcccc atggggacag aaggagctct   2340
gagtcctgga gtgagcacat cagggatttc cagcagccaa ggagagcaga gtaatccagc   2400
tcagtctcct ttctctcctc atacctcccc tcacctgcct ggcatccgag gcccttcccc   2460
gtcccctgtt ggctctcccg ccagtgttgc tcagtctcgc tcaggaccac tctcgcctgc   2520
tgcagtgcca ggcaaccaga tgccacctcg gccacccagt ggccagtcgg acagcatcat   2580
gcatccttcc atgaaccaat caagcattgc ccaagatcga ggttatatgc agaggaaccc   2640
ccagatgccc cagtacagtt ccccccagcc cggctcagcc ttatctccgc gtcagccttc   2700
cggaggacag atacacacag gcatgggctc ctaccagcag aactccatgg ggagctatgg   2760
tccccagggg ggtcagtatg gcccacaagg tggctaccccc aggcagccaa actataatgc   2820
cttgcccaat gccaactacc ccagtgcagg catggctgga ggcataaacc ccatgggtgc   2880
cggaggtcaa atgcatggac agcctggcat cccaccttat ggcacactcc ctccagggag   2940
gatgagtcac gcctccatgg gcaaccggcc ttatggccct aacatggcca atatgccacc   3000
tcaggttggg tcagggatgt gtcccccacc agggggcatg aaccggaaaa cccaagaaac   3060
tgctgtcgcc atgcatgttg ctgccaactc tatccaaaac aggccgccag gctaccccaa   3120
tatgaatcaa gggggcatga tgggaactgg acctccttat ggacaaggga ttaatagtat   3180
ggctggcatg atcaaccctc agggaccccc atattccatg ggtggaacca tggccaacaa   3240
ttctgcaggg atggcagcca gcccagagat gatgggcctt ggggatgtaa agttaactcc   3300
agccaccaaa atgaacaaca aggcagatgg gacacccaag acagaatcca aatccaagaa   3360
```

-continued

```
atccagttct tctactacaa ccaatgagaa gatcaccaag ttgtatgagc tgggtggtga   3420
gcctgagagg aagatgtggg tggaccgtta tctggccttc actgaggaga aggccatggg   3480
catgacaaat ctgcctgctg tgggtaggaa acctctggac ctctatcgcc tctatgtgtc   3540
tgtgaaggag attggtggat tgactcaggt caacaagaac aaaaaatggc gggaacttgc   3600
aaccaacctc aatgtgggca catcaagcag tgctgccagc tccttgaaaa agcagtatat   3660
ccagtgtctc tatgcctttg aatgcaagat tgaacgggga gaagaccctc cccagacat    3720
ctttgcagct gctgattcca agaagtccca gcccaagatc cagcctccct ctcctgcggg   3780
atcaggatct atgcaggggc cccagactcc ccagtcaacc agcagttcca tggcagaagg   3840
aggagactta aagccaccaa ctccagcatc cacaccacac agtcagatcc ccccattgcc   3900
aggcatgagc aggagcaatt cagttgggat ccaggatgcc tttaatgatg gaagtgactc   3960
cacattccag aagcggaatt ccatgactcc aaaccctggg tatcagccca gtatgaatac   4020
ctctgacatg atggggcgca tgtcctatga gccaaataag gatccttatg gcagcatgag   4080
gaaagctcca gggagtgatc ccttcatgtc ctcagggcag ggccccaacg gcgggatggg   4140
tgacccctac agtcgtgctg ccggccctgg gctaggaaat gtggcgatgg gaccacgaca   4200
gcactatccc tatggaggtc cttatgacag agtgaggacg gagcctggaa tagggcctga   4260
gggaaacatg agcactgggg ccccacagcc gaatctcatg ccttccaacc cagactcggg   4320
gatgtattct cctagccgct accccccgca gcagcagcag cagcagcagc aacgacatga   4380
ttcctatggc aatcagttct ccacccaagg caccccttct ggcagcccct tccccagcca   4440
gcagactaca atgtatcaac agcaacagca gaattacaag cggccaatgg atggcacata   4500
tggccctcct gccaagcggc acgaagggga gatgtacagc gtgccataca gcactgggca   4560
ggggcagcct cagcagcagc agttgccccc agcccagccc cagcctgcca gccagcaaca   4620
agctgcccag ccttcccctc agcaagatgt atacaaccag tatggcaatg cctatcctgc   4680
cactgccaca gctgctactg agcgccgacc agcaggcggc cccagaacc aatttccatt    4740
ccagtttggc cgagaccgtg tctctgcacc ccctggcacc aatgcccagc aaaacatgcc   4800
accacaaatg atgggcggcc ccatacaggc atcagctgag gttgctcagc aaggcaccat   4860
gtggcagggg cgtaatgaca tgacctataa ttatgccaac aggcagagca cgggctctgc   4920
cccccagggc cccgcctatc atggcgtgaa ccgaacagat gaaatgctgc acacagatca   4980
gagggccaac cacgaaggct cgtggccttc ccatggcaca cgccagcccc catatggtcc   5040
ctctgcccct gtgcccccca tgacaaggcc ccctccatct aactaccagc ccccaccaag   5100
catgcagaat cacattcctc aggtatccag ccctgctccc ctgccccggc caatggagaa   5160
ccgcacctct cctagcaagt ctccattcct gcactctggg atgaaaatgc agaaggcagg   5220
tcccccagta cctgcctcgc acatagcacc tgcccctgtg cagcccccca tgattcggcg   5280
ggatatcacc ttcccacctg gctctgttga agccacacag cctgtgttga agcagaggag   5340
gcggctcaca atgaaagaca ttggaacccc ggaggcatgg cgggtaatga tgtccctcaa   5400
gtctggtctc ctggcagaga gcacatgggc attagatacc atcaacatcc tgctgtatga   5460
tgacaacagc atcatgacct tcaacctcag tcagctccca gggttgctag agctccttgt   5520
agaatatttc cgacgatgcc tgattgagat ctttggcatt ttaaaggagt atgaggtggg   5580
tgacccagga cagagaacgc tactggatcc tgggaggttc agcaaggtgt ctagtccagc   5640
tcccatggag ggtggggaag aagaagaaga acttctaggt cctaaactag aagaggaaga   5700
```

-continued

```
agaagaggaa gtagttgaaa atgatgagga gatagccttt tcaggcaagg acaagccagc   5760
ttcagagaat agtgaggaga agctgatcag taagtttgac aagcttccag taaagatcgt   5820
acagaagaat gatccatttg tggtggactg ctcagataag cttgggcgtg tgcaggagtt   5880
tgacagtggc ctgctgcact ggcggattgg tggggggac accactgagc atatccagac   5940
ccacttcgag agcaagacag agctgctgcc ttcccggcct cacgcaccct gcccaccagc   6000
ccctcggaag catgtgacaa cagcagaggg tacaccaggg acaacagacc aggaggggcc   6060
cccacctgat ggacctccag aaaaacggat cacagccact atggatgaca tgttgtctac   6120
tcggtctagc accttgaccg aggatggagc taagagttca gaggccatca aggagagcag   6180
caagtttcca tttggcatta gcccagcaca gagccaccgg aacatcaaga tcctagagga   6240
cgaaccccac agtaaggatg agacccact gtgtaccctt ctggactggc aggattctct   6300
tgccaagcgc tgcgtctgtg tgtccaatac cattcgaagc ctgtcatttg tgccaggcaa   6360
tgactttgag atgtccaaac acccaggct gctgctcatc ctgggcaagc tgatcctgct   6420
gcaccacaag cacccagaac ggaagcaggc accactaact tatgaaaagg aggaggaaca   6480
ggaccaaggg gtgagctgca acaaagtgga gtggtggtgg gactgcttgg agatgctccg   6540
ggaaaacacc ttggttacac tcgccaacat ctcggggcag ttggacctat ctccataccc   6600
cgagagcatt tgcctgcctg tcctggacgg actcctacac tgggcagttt gcccttcagc   6660
tgaagcccag gacccctttt ccaccctggg ccccaatgcc gtcctttccc cgcagagact   6720
ggtcttggaa accctcagca aactcagcat ccaggacaac aatgtggacc tgattctggc   6780
cacaccccc ttcagccgcc tggagaagtt gtatagcact atggtgcgct tcctcagtga   6840
ccgaaagaac ccggtgtgcc gggagatggc tgtggtactg ctggccaacc tggctcaggg   6900
ggacagcctg gcagctcgtg ccattgcagt gcagaagggc agtatcggca acctcctggg   6960
cttcctagag gacagccttg ccgccacaca gttccagcag agccaggcca gcctcctcca   7020
catgcagaac ccaccctttg agccaactag tgtggacatg atgcggcggg ctgcccgcgc   7080
gctgcttgcc ttggccaagg tggacgagaa ccactcagag tttactctgt acgaatcacg   7140
gctgttggac atctcggtat caccgttgat gaactcattg gtttcacaag tcatttgtga   7200
tgtactgttt ttgattggcc agtcatgaca gccgtgggac acctcccccc cccgtgtgtg   7260
tgtgcgtgtg tggagaactt agaaactgac tgttgccctt tatttatgca aaaccacctc   7320
agaatccagt ttaccctgtg ctgtccagct tctcccttgg gaaaaagtct ctcctgtttc   7380
tctctcctcc ttccacctcc cctccctcca tcacctcacg cctttctgtt ccttgtcctc   7440
accttactcc cctcaggacc ctaccccacc ctctttgaaa agacaaagct ctgcctacat   7500
agaagacttt ttttatttta accaaagtta ctgttgttta cagtgagttt ggggaaaaaa   7560
aataaaataa aaatggcttt cccagtcctt gctggctttc ccagtccttg catcaacggg   7620
atgccacatt tcataactgt ttttaatggt aaaaaaaaaa aaaaaaaata caaaaaaaaa   7680
ttctgaagga caaaaaaggt gactgctgaa ctgtgtgtgg tttattgttg tacattcaca   7740
atcttgcagg agccaagaag ttcgcagttg tgaacagacc ctgttcactg gagaggcctg   7800
tgcagtagag tgtagaccct ttcatgtact gtactgtaca cctgatactg taaacatact   7860
gtaataataa tgtctcacat ggaaacagaa aacgctgggt cagcagcaag ctgtagtttt   7920
taaaaatgtt tttagttaaa cgttgaggag aaaaaaaaaa aaggcttttc ccccaaagta   7980
tcatgtgtga acctacaaca ccctgacctc tttctctcct ccttgattgt atgaataacc   8040
ctgagatcac ctcttagaac tggttttaac ctttagctgc agcggctacg ctgccacgtg   8100
```

-continued

```
tgtatatata tgacgttgta cattgcacat acccttggat ccccacagtt tggtcctcct   8160

cccagctacc cctttatagt atgacgagtt aacaagttgg tgacctgcac aaagcgagac   8220

acagctattt aatctcttgc cagatatcgc ccctcttggt gcgatgctgt acaggtctct   8280

gtaaaaagtc cttgctgtct cagcagccaa tcaacttata gtttattttt ttctgggttt   8340

ttgttttgtt ttgttttctt tctaatcgag gtgtgaaaaa gttctaggtt cagttgaagt   8400

tctgatgaag aaacacaatt gagatttttt cagtgataaa atctgcatat ttgtatttca   8460

acaatgtagc taaaacttga tgtaaattcc tcctttttttt ccttttttgg cttaatgaat   8520

atcatttatt cagtatgaaa tctttatact atatgttcca cgtgttaaga ataaatgtac   8580

attaaatctt ggtaa                                                     8595
```

<210> SEQ ID NO 17
<211> LENGTH: 3488
<212> TYPE: DNA
<213> ORGANISM: Homo sapiens

<400> SEQUENCE: 17

```
taaaaagcat taggcatata aatgtataaa tatattttat catgtacagt acaaaaatgg     60

aaccttatgc atgggcctta ggaatacagg ctagtatttc agcacagact tccctgcttg    120

agttcttgct gatgcttgca ccgtgacagt gggcaccaac acagacgtgc cacccaaccc    180

cctgcacaca ccaccggcca ccaggggccc ccttgtgcgc cttggcttta taactcctct    240

gggggtgata ttggtggtga tcacagctcc tagcataatg agagttccat ttggtattgt    300

cacacgtctc ctgcctcgct tgggttgcca tgtttgagcg atggccctgt tgatttcacc    360

ctgcctttta ctgaatctgt aaattgttgt gcaattgtgg ttatagtaga ctgtagcaca    420

ttgccttttc taaactgcta catgtttata atcttcattt ttaaagtatg tgtaattttt    480

ttaagtatgt attctattca tatggtctgc ttgtcagtga gccagacttg cttactatat    540

tcctttataa taatgctagc cacttcctgg attctttagt aatgtgctgc atgcaagaac    600

tttccagtag cagtgaagga gggctgcctc tccaagcttc ctaagggatg ctgccctgtg    660

tggggatgca ttgcagaggc actagtagca tgggggctag agtggggagc gagatgtaaa    720

agggtggggg gataggagaa ttccagagtg cttccagcat tagggtcctg agaacttctg    780

agttcagaga aacatgcaaa gtgactaaca aaatagctac ttacctttgc agttctacag    840

accctgggag ctgctttggg agtgagaaag gcaaccctcc aatgtgtttc aactttaaaa    900

tgttgaattc ttttcagaca tggtatctca tttattctcc ttttctagcg tttgttgaat    960

ttcaggcaga atgtcttaca gactgtccta gaaccagatt atcatttaat ctgaaacagc   1020

tgaggaaggg acagagaagg tacaagggca aggcagcaca aaacagatca ggagaatgaa   1080

gagggaatgc tttggttttt tgttttgttt tgttttttct ttttcaagta actaaaacaa   1140

catctacatg tagagtgttg tggagagctg agaccagggt aaagtcaagt gcagcatcag   1200

tactgcgaga cccaccagcc cctggagagg gtcagccgag aatctggtag tgaagcctgt   1260

ctagggtccc ggcaccctca ccctcagcca cctgcagaga ggccagggcc ccagagacta   1320

gcctggttct gaagtgggca ggggtgctgc cagagccctc tgccccttat gttgagaccc   1380

tgctttcagg acaggccagc cgttggccac catgtcacat tctgagtgag tgtcacaggt   1440

ccctaacaat aattttctga tctggagcat atcagcagaa tgcttagcct caaggggcct   1500

ggaagctgta atgtttgatt tatgatgaga actatccgag gccacccttg gcctctaaat   1560
```

-continued

```
aagctgctct agggagccgc ctactttttg atgagaaatt agaagagtac ctaatgttga   1620

aaacatgaca tgcgctcttg ggatctgctg ttctctccag ggctccagaa cctgatacct   1680

gttaccaaag ctaggaaaga gctttatcac aagccttcac tgtcctggca tgagaactgg   1740

ctgccaggct cagtgtaccc cattaactgt gaatgaatct gagcttggtt tcctttattg   1800

cttcctctgc aatatgattg ctgaaacaca ttttaaaaat tcagaagctt gtcactcctg   1860

ttaatgggag gatcagtcac acatgtgtag tacaaggcgg actttgtgtt tgtttttggt   1920

gttaattttt agcattgtgt gtgttgcttc cccaccctga ggagaggaca ccatggctta   1980

ctactcagga caagtatgcc ccgctcaggg tgtgatttca ggtggcttcc aaacttgtac   2040

gcagtttaaa gatggtgggg acagactttg cctctaccta gtgaacccca cttaaagaat   2100

aaggagcatt tgaatctctt ggaaaaggcc atgaagaata aagcagtcaa aaagaagtcc   2160

tccatgttgg tgccaaggac ttgcgagggg aaataaaaat gttatccagc ctgaccaaca   2220

tggagaaacc ccgtctccat taaaaataca aaattagcct ggcatggtgg cgcatgcctg   2280

taatcccagc tactctggag gctgaggcag gagaatcgct tgaacccagg aggcggaggt   2340

cgcagtgagc cgagatcatg ccagtgcact ccagcctggg taacaagagt gaaactccgt   2400

gtcaaaaaaa aaaaaaaaaa atgttactca tcctctctga aagcaaaaag gaaaccctaa   2460

cagctctgaa ctctggtttt atttttcttg ctgtatttgg gtgaacattg tatgattagg   2520

cataatgtta aaaaaaaaaa attttttttt ggtagaaatg caatcaccag taaagaggta   2580

cgaaaaagct agcctctctc agagaccggg gaggcagagt actactagag gaagtgaagt   2640

tctgatggaa tcatgcctgt caaatgaggt cttgaagcgg atgcccaaat aaaagagtat   2700

attttatcta aatcttaagt gggtaacatt ttatgcagtt taaatgaatg gaatattttc   2760

ctcttgttta gttgtatctg tttgtatttt tctttgatga atgattggtc atgaggcctc   2820

ttgccacact ccagaaatac gtgtgcggct gcttttaaga actatgtgtc tggtcactta   2880

tttctctaaa attatctcat tgcctggcaa tcagtcttct cttgtatact tgtcctagca   2940

cattatgtac atgggaaatg taaacaaatg tgaaggagga ccagaaaaat tagttaatat   3000

ttaaaaaaat gtattgtgca ttttggcttc acatgtttaa cttttttttaa gaaaaaagtt   3060

gcatgaatgg aaaaaaaaat ctgtatacag tatctgtaaa aactatctta tctgtttcaa   3120

ttccttgctc atatcccata taatctagaa ctaaatatgg tgtgtggcca tatttaaaca   3180

cctgagagtc aagcagttga gactttgatt tgaagcacct catccttctt tcaatgcgaa   3240

cactatcata tggcattctt actgaggatt ttgtctaacc atatgttgcc atgaattaac   3300

tctgccgcct ttcttaagga tcaaaaccag tttgatttgg gaatcttccc ctttccaaat   3360

gaaatagaga tgcagtactt aactttcctt ggtgtttgta gatattgcct tgtgtattcc   3420

acttaaaacc gtaatctagt ttgtaaaaga gatggtgacg catgtaaata aagcatcagt   3480

gacactct                                                             3488
```

<210> SEQ ID NO 18
<211> LENGTH: 20
<212> TYPE: DNA
<213> ORGANISM: Homo sapiens

<400> SEQUENCE: 18

```
gcctaccgaa gacaaaggcg                                                  20
```

<210> SEQ ID NO 19
<211> LENGTH: 20

-continued

<212> TYPE: DNA
<213> ORGANISM: Homo sapiens

<400> SEQUENCE: 19
tagaggctgt cccctaggag 20

<210> SEQ ID NO 20
<211> LENGTH: 20
<212> TYPE: DNA
<213> ORGANISM: Homo sapiens

<400> SEQUENCE: 20
agaggcaccc tatgggccag 20

<210> SEQ ID NO 21
<211> LENGTH: 20
<212> TYPE: DNA
<213> ORGANISM: Homo sapiens

<400> SEQUENCE: 21
catctctggc gctggcattg 20

<210> SEQ ID NO 22
<211> LENGTH: 20
<212> TYPE: DNA
<213> ORGANISM: Homo sapiens

<400> SEQUENCE: 22
gcactgatcc caatcctcgc 20

<210> SEQ ID NO 23
<211> LENGTH: 20
<212> TYPE: DNA
<213> ORGANISM: Homo sapiens

<400> SEQUENCE: 23
ccctgcataa gcacaatggg 20

<210> SEQ ID NO 24
<211> LENGTH: 20
<212> TYPE: DNA
<213> ORGANISM: Homo sapiens

<400> SEQUENCE: 24
gggaaggaga atgttgcccc 20

<210> SEQ ID NO 25
<211> LENGTH: 20
<212> TYPE: DNA
<213> ORGANISM: Homo sapiens

<400> SEQUENCE: 25
gaggagggaa ccacccctac 20

<210> SEQ ID NO 26
<211> LENGTH: 20
<212> TYPE: DNA
<213> ORGANISM: Homo sapiens

<400> SEQUENCE: 26
gggaggctga gggaagggac 20

<210> SEQ ID NO 27

-continued

<211> LENGTH: 20
<212> TYPE: DNA
<213> ORGANISM: Homo sapiens

<400> SEQUENCE: 27
ggggaaatgc gtagaccagg 20

<210> SEQ ID NO 28
<211> LENGTH: 20
<212> TYPE: DNA
<213> ORGANISM: Homo sapiens

<400> SEQUENCE: 28
cccgcctcct cctaagtctg 20

<210> SEQ ID NO 29
<211> LENGTH: 20
<212> TYPE: DNA
<213> ORGANISM: Homo sapiens

<400> SEQUENCE: 29
cagcatgagc caccatgccc 20

<210> SEQ ID NO 30
<211> LENGTH: 20
<212> TYPE: DNA
<213> ORGANISM: Homo sapiens

<400> SEQUENCE: 30
gaaccagaga cctaggccgc 20

<210> SEQ ID NO 31
<211> LENGTH: 20
<212> TYPE: DNA
<213> ORGANISM: Homo sapiens

<400> SEQUENCE: 31
cagctcctct agggagaccc 20

<210> SEQ ID NO 32
<211> LENGTH: 20
<212> TYPE: DNA
<213> ORGANISM: Homo sapiens

<400> SEQUENCE: 32
ctagagccta agttgaaccc 20

<210> SEQ ID NO 33
<211> LENGTH: 20
<212> TYPE: DNA
<213> ORGANISM: Homo sapiens

<400> SEQUENCE: 33
gtggtggtgg tttatgaggg 20

<210> SEQ ID NO 34
<211> LENGTH: 20
<212> TYPE: DNA
<213> ORGANISM: Homo sapiens

<400> SEQUENCE: 34
taggacatgc ccatgtccgc 20

-continued

<210> SEQ ID NO 35
<211> LENGTH: 20
<212> TYPE: DNA
<213> ORGANISM: Homo sapiens

<400> SEQUENCE: 35
tccgctcttc ctcaactccc 20

<210> SEQ ID NO 36
<211> LENGTH: 20
<212> TYPE: DNA
<213> ORGANISM: Homo sapiens

<400> SEQUENCE: 36
ctctttgggt cttcccttcc 20

<210> SEQ ID NO 37
<211> LENGTH: 20
<212> TYPE: DNA
<213> ORGANISM: Homo sapiens

<400> SEQUENCE: 37
cttcagaggc aaagtccttg 20

<210> SEQ ID NO 38
<211> LENGTH: 20
<212> TYPE: DNA
<213> ORGANISM: Homo sapiens

<400> SEQUENCE: 38
ctcggctcgg cccaaagcag 20

<210> SEQ ID NO 39
<211> LENGTH: 20
<212> TYPE: DNA
<213> ORGANISM: Homo sapiens

<400> SEQUENCE: 39
gtaggtcccc gggaggcagg 20

<210> SEQ ID NO 40
<211> LENGTH: 21
<212> TYPE: DNA
<213> ORGANISM: Homo sapiens

<400> SEQUENCE: 40
gttttacggc ttgcaagtaa c 21

<210> SEQ ID NO 41
<211> LENGTH: 20
<212> TYPE: DNA
<213> ORGANISM: Homo sapiens

<400> SEQUENCE: 41
ccaaacttgt ctggaacacc 20

<210> SEQ ID NO 42
<211> LENGTH: 20
<212> TYPE: DNA
<213> ORGANISM: Homo sapiens

<400> SEQUENCE: 42
ccagggtctc aaatggcaac 20

-continued

<210> SEQ ID NO 43
<211> LENGTH: 20
<212> TYPE: DNA
<213> ORGANISM: Homo sapiens

<400> SEQUENCE: 43
atgtggcata ctcgcccacc 20

<210> SEQ ID NO 44
<211> LENGTH: 20
<212> TYPE: DNA
<213> ORGANISM: Homo sapiens

<400> SEQUENCE: 44
ctctgccgag ccttggactg 20

<210> SEQ ID NO 45
<211> LENGTH: 20
<212> TYPE: DNA
<213> ORGANISM: Homo sapiens

<400> SEQUENCE: 45
gcatggccca gctcgtgcac 20

<210> SEQ ID NO 46
<211> LENGTH: 20
<212> TYPE: DNA
<213> ORGANISM: Homo sapiens

<400> SEQUENCE: 46
tgcccgatga tgaccgccgg 20

<210> SEQ ID NO 47
<211> LENGTH: 20
<212> TYPE: DNA
<213> ORGANISM: Homo sapiens

<400> SEQUENCE: 47
gggttgaggg ggcatcttgg 20

<210> SEQ ID NO 48
<211> LENGTH: 20
<212> TYPE: DNA
<213> ORGANISM: Homo sapiens

<400> SEQUENCE: 48
caccgtggcc atgctccgag 20

<210> SEQ ID NO 49
<211> LENGTH: 20
<212> TYPE: DNA
<213> ORGANISM: Homo sapiens

<400> SEQUENCE: 49
ccatcacttg gttattcctc 20

<210> SEQ ID NO 50
<211> LENGTH: 20
<212> TYPE: DNA
<213> ORGANISM: Homo sapiens

<400> SEQUENCE: 50
cctacgagag gaaggatggc 20

-continued

<210> SEQ ID NO 51
<211> LENGTH: 20
<212> TYPE: DNA
<213> ORGANISM: Homo sapiens

<400> SEQUENCE: 51
ggttccaggg acgcctcatc 20

<210> SEQ ID NO 52
<211> LENGTH: 20
<212> TYPE: DNA
<213> ORGANISM: Homo sapiens

<400> SEQUENCE: 52
ggatgcccaa tggaaagacc 20

<210> SEQ ID NO 53
<211> LENGTH: 20
<212> TYPE: DNA
<213> ORGANISM: Homo sapiens

<400> SEQUENCE: 53
cgctatccac tgccctgagc 20

<210> SEQ ID NO 54
<211> LENGTH: 20
<212> TYPE: DNA
<213> ORGANISM: Homo sapiens

<400> SEQUENCE: 54
gggatccctg agtctcccag 20

<210> SEQ ID NO 55
<211> LENGTH: 20
<212> TYPE: DNA
<213> ORGANISM: Homo sapiens

<400> SEQUENCE: 55
tgttgaattt ccagtatttg 20

<210> SEQ ID NO 56
<211> LENGTH: 20
<212> TYPE: DNA
<213> ORGANISM: Homo sapiens

<400> SEQUENCE: 56
tattagtaaa ctggcccttc 20

<210> SEQ ID NO 57
<211> LENGTH: 20
<212> TYPE: DNA
<213> ORGANISM: Homo sapiens

<400> SEQUENCE: 57
atctttcttc tgcttagtcg 20

<210> SEQ ID NO 58
<211> LENGTH: 20
<212> TYPE: DNA
<213> ORGANISM: Homo sapiens

<400> SEQUENCE: 58

-continued

```
tagaggtgga actaaacccc                                                  20


<210> SEQ ID NO 59
<211> LENGTH: 286
<212> TYPE: DNA
<213> ORGANISM: Homo sapiens

<400> SEQUENCE: 59

gggaggctga gggaagggac tcaggctgct atcgtcactg tccccatcct tccaggaaat      60

gacatcttcc tggtggctgt gcacgagctg ggccatgccc tggggctcga gcattccagt     120

gacccctcgg ccatcatggc acccttttac cagtggatgg acacggagaa ttttgtgctg     180

cccgatgatg accgccgggg catccagcaa ctttatggcg agtagtctac acccacgcct     240

gctccctcct ctgctgcttg ttccctcctg gtctacgcat ttcccc                    286


<210> SEQ ID NO 60
<211> LENGTH: 286
<212> TYPE: DNA
<213> ORGANISM: Homo sapiens

<400> SEQUENCE: 60

gggaggctga gggaagggac tcaggctgct atcgtcactg tccccatcct tccaggaaat      60

gacatcttcc tggtggctgt gcacgagctg ggccatgccc tggggctcga gcattccagt     120

gacccctcgg ccatcatggc accgttttac cagtggatgg acacggagaa ttttgtgctg     180

cccgatgatg accgccgggg catccagcaa ctttatggcg agtagtctac acccacgcct     240

gctccctcct ctgctgcttg ttccctcctg gtctacgcat ttcccc                    286


<210> SEQ ID NO 61
<211> LENGTH: 286
<212> TYPE: DNA
<213> ORGANISM: Homo sapiens

<400> SEQUENCE: 61

gggaggctga gggaagggac tcaggctgct atcgtcactg tccccatcct tccaggaaat      60

gacatcttcc tggtggctgt gcacgagctg ggccatgccc tggggctcga gcattccagt     120

gacccctcgg ccatcatggc accgttttac cagtggatgg acacggagaa ttttgtgctg     180

cccaatgatg accgccgggg catccagcaa ctttatggcg agtagtctac acccacgcct     240

gctccctcct ctgctgcttg ttccctcctg gtctacgcat ttcccc                    286


<210> SEQ ID NO 62
<211> LENGTH: 7318
<212> TYPE: DNA
<213> ORGANISM: Homo sapiens

<400> SEQUENCE: 62

ctggctctta acggcgttta tgtcctttgc tgtctgaggg gcctcagctc tgaccaatct      60

ggtcttcgtg tggtcattag catgggcttc gtgagacaga tacagctttt gctctggaag     120

aactggaccc tgcggaaaag gcaaaagatt cgctttgtgg tggaactcgt gtggccttta     180

tctttatttc tggtcttgat ctggttaagg aatgccaacc cgctctacag ccatcatgaa     240

tgccatttcc ccaacaaggc gatgccctca gcaggaatgc tgccgtggct ccaggggatc     300

ttctgcaatg tgaacaatcc ctgttttcaa agccccaccc caggagaatc tcctggaatt     360

gtgtcaaact ataacaactc catcttggca agggtatatc gagattttca agaactcctc     420

atgaatgcac cagagagcca gcaccttggc cgtatttgga cagagctaca catcttgtcc     480
```

-continued

```
caattcatgg acaccctccg gactcacccg gagagaattg caggaagagg aatacgaata    540
agggatatct tgaaagatga agaaacactg acactatttc tcattaaaaa catcggcctg    600
tctgactcag tggtctacct tctgatcaac tctcaagtcc gtccagagca gttcgctcat    660
ggagtcccgg acctggcgct gaaggacatc gcctgcagcg aggccctcct ggagcgcttc    720
atcatcttca gccagagacg cggggcaaag acggtgcgct atgccctgtg ctccctctcc    780
cagggcaccc tacagtggat agaagacact ctgtatgcca acgtggactt cttcaagctc    840
ttccgtgtgc ttcccacact cctagacagc cgttctcaag gtatcaatct gagatcttgg    900
ggaggaatat tatctgatat gtcaccaaga attcaagagt ttatccatcg gccgagtatg    960
caggacttgc tgtgggtgac caggcccctc atgcagaatg gtggtccaga gacctttaca   1020
aagctgatgg gcatcctgtc tgacctcctg tgtggctacc ccgagggagg tggctctcgg   1080
gtgctctcct tcaactggta tgaagacaat aactataagg cctttctggg gattgactcc   1140
acaaggaagg atcctatcta ttcttatgac agaagaacaa catccttttg taatgcattg   1200
atccagagcc tggagtcaaa tcctttaacc aaaatcgctt ggagggcggc aaagcctttg   1260
ctgatgggaa aaatcctgta cactcctgat tcacctgcag cacgaaggat actgaagaat   1320
gccaactcaa cttttgaaga actggaacac gttaggaagt tggtcaaagc ctgggaagaa   1380
gtagggcccc agatctggta cttctttgac aacagcacac agatgaacat gatcagagat   1440
accctgggga acccaacagt aaaagacttt ttgaataggc agcttggtga agaaggtatt   1500
actgctgaag ccatcctaaa cttcctctac aagggccctc gggaaagcca ggctgacgac   1560
atggccaact tcgactggag ggacatattt aacatcactg atcgcaccct ccgcctggtc   1620
aatcaatacc tggagtgctt ggtcctggat aagtttgaaa gctacaatga tgaaactcag   1680
ctcacccaac gtgccctctc tctactggag gaaaacatgt tctgggccgg agtggtattc   1740
cctgacatgt atccctggac cagctctcta ccacccccacg tgaagtataa gatccgaatg   1800
gacatagacg tggtggagaa aaccaataag attaaagaca ggtattggga ttctggtccc   1860
agagctgatc ccgtggaaga tttccggtac atctggggcg ggtttgccta tctgcaggac   1920
atggttgaac aggggatcac aaggagccag gtgcaggcgg aggctccagt tggaatctac   1980
ctccagcaga tgccctaccc ctgcttcgtg gacgattctt tcatgatcat cctgaaccgc   2040
tgtttcccta tcttcatggt gctggcatgg atctactctg tctccatgac tgtgaagagc   2100
atcgtcttgg agaaggagtt gcgactgaag gagaccttga aaaatcaggg tgtctccaat   2160
gcagtgattt ggtgtacctg gttcctggac agcttctcca tcatgtcgat gagcatcttc   2220
ctcctgacga tattcatcat gcatggaaga atcctacatt acagcgaccc attcatcctc   2280
ttcctgttct tgttggcttt ctccactgcc accatcatgc tgtgctttct gctcagcacc   2340
ttcttctcca aggccagtct ggcagcagcc tgtagtggtg tcatctattt caccctctac   2400
ctgccacaca tcctgtgctt cgcctggcag gaccgcatga ccgctgagct gaagaaggct   2460
gtgagcttac tgtctccggt ggcatttgga tttggcactg agtacctggt tcgctttgaa   2520
gagcaaggcc tggggctgca gtggagcaac atcgggaaca gtcccacgga aggggacgaa   2580
ttcagcttcc tgctgtccat gcagatgatg ctccttgatg ctgcgtgcta tggcttactc   2640
gcttggtacc ttgatcaggt gtttccagga gactatggaa ccccacttcc ttggtacttt   2700
cttctacaag agtcgtattg gcttagcggt gaagggtgtt caaccagaga agaaagagcc   2760
ctggaaaaga ccgagcccct aacagaggaa acggaggatc cagagcaccc agaaggaata   2820
```

-continued

```
cacgactcct tctttgaacg tgagcatcca gggtgggttc ctggggtatg cgtgaagaat   2880
ctggtaaaga tttttgagcc ctgtggccgg ccagctgtgg accgtctgaa catcaccttc   2940
tacgagaacc agatcaccgc attcctgggc cacaatggag ctgggaaaac caccaccttg   3000
tccatcctga cgggtctgtt gccaccaacc tctgggactg tgctcgttgg gggaagggac   3060
attgaaacca gcctggatgc agtccggcag agccttggca tgtgtccaca gcacaacatc   3120
ctgttccacc acctcacggt ggctgagcac atgctgttct atgcccagct gaaaggaaag   3180
tcccaggagg aggcccagct ggagatggaa gccatgttgg aggacacagg cctccaccac   3240
aagcggaatg aagaggctca ggacctatca ggtggcatgc agagaaagct gtcggttgcc   3300
attgcctttg tgggagatgc caaggtggtg attctggacg aacccacctc tggggtggac   3360
ccttactcga gacgctcaat ctgggatctg ctcctgaagt atcgctcagg cagaaccatc   3420
atcatgccca ctcaccacat ggacgaggcc gaccaccaag gggaccgcat tgccatcatt   3480
gcccagggaa ggctctactg ctcaggcacc ccactcttcc tgaagaactg ctttggcaca   3540
ggcttgtact taaccttggt gcgcaagatg aaaaacatcc agagccaaag gaaaggcagt   3600
gaggggacct gcagctgctc gtctaagggt ttctccacca cgtgtccagc ccacgtcgat   3660
gacctaactc cagaacaagt cctggatggg gatgtaaatg agctgatgga tgtagttctc   3720
caccatgttc cagaggcaaa gctggtggag tgcattggtc aagaacttat cttccttctt   3780
ccaaataaga acttcaagca cagagcatat gccagccttt tcagagagct ggaggagacg   3840
ctggctgacc ttggtctcag cagttttgga atttctgaca ctcccctgga agagattttt   3900
ctgaaggtca cggaggattc tgattcagga cctctgtttg cgggtggcgc tcagcagaaa   3960
agagaaaacg tcaacccccg acacccctgc ttgggtccca gagagaaggc tggacagaca   4020
ccccaggact ccaatgtctg ctccccaggg gcgccggctg ctcacccaga gggccagcct   4080
cccccagagc cagagtgccc aggcccgcag ctcaacacgg ggacacagct ggtcctccag   4140
catgtgcagg cgctgctggt caagagattc caacacacca tccgcagcca caaggacttc   4200
ctggcgcaga tcgtgctccc ggctaccttt gtgtttttgg ctctgatgct ttctattgtt   4260
atccttcctt ttggcgaata ccccgctttg acccttcacc cctggatata tgggcagcag   4320
tacaccttct tcagcatgga tgaaccaggc agtgagcagt tcacggtact tgcagacgtc   4380
ctcctgaata agccaggctt tggcaaccgc tgcctgaagg aagggtggct tccggagtac   4440
ccctgtggca actcaacacc ctggaagact ccttctgtgt ccccaaacat cacccagctg   4500
ttccagaagc agaaatggac acaggtcaac ccttcaccat cctgcaggtg cagcaccagg   4560
gagaagctca ccatgctgcc agagtgcccc gagggtgccg gggcctccc gcccccccag   4620
agaacacagc gcagcacgga aattctacaa gacctgacgg acaggaacat ctccgacttc   4680
ttggtaaaaa cgtatcctgc tcttataaga agcagcttaa agagcaaatt ctgggtcaat   4740
gaacagaggt atggaggaat ttccattgga ggaaagctcc cagtcgtccc catcacgggg   4800
gaagcacttg ttgggttttt aagcgacctt ggccggatca tgaatgtgag cgggggccct   4860
atcactagag aggcctctaa agaaatacct gatttcctta aacatctaga aactgaagac   4920
aacattaagg tgtggtttaa taacaaaggc tggcatgccc tggtcagctt tctcaatgtg   4980
gcccacaacg ccatcttacg ggccagcctg cctaaggaca ggagccccga ggagtatgga   5040
atcaccgtca ttagccaacc cctgaacctg accaaggagc agctctcaga gattacagtg   5100
ctgaccactt cagtggatgc tgtggttgcc atctgcgtga ttttctccat gtccttcgtc   5160
ccagccagct ttgtccttta tttgatccag gagcgggtga acaaatccaa gcacctccag   5220
```

-continued

```
tttatcagtg gagtgagccc caccacctac tgggtgacca acttcctctg ggacatcatg   5280
aattattccg tgagtgctgg gctggtggtg ggcatcttca tcgggtttca gaagaaagcc   5340
tacacttctc cagaaaacct tcctgccctt gtggcactgc tcctgctgta tggatgggcg   5400
gtcattccca tgatgtaccc agcatccttc ctgtttgatg tccccagcac agcctatgtg   5460
gctttatctt gtgctaatct gttcatcggc atcaacagca gtgctattac cttcatcttg   5520
gaattatttg ataataaccg gacgctgctc aggttcaacg ccgtgctgag gaagctgctc   5580
attgtcttcc cccacttctg cctgggccgg ggcctcattg accttgcact gagccaggct   5640
gtgacagatg tctatgcccg gtttggtgag gagcactctg caaatccgtt ccactgggac   5700
ctgattggga agaacctgtt tgccatggtg gtggaagggg tggtgtactt cctcctgacc   5760
ctgctggtcc agcgccactt cttcctctcc caatggattg ccgagcccac taaggagccc   5820
attgttgatg aagatgatga tgtggctgaa gaaagacaaa gaattattac tggtggaaat   5880
aaaactgaca tcttaaggct acatgaacta accaagattt atctgggcac ctccagccca   5940
gcagtggaca ggctgtgtgt cggagttcgc cctggagagt gctttggcct cctgggagtg   6000
aatggtgccg gcaaaacaac cacattcaag atgctcactg gggacaccac agtgacctca   6060
ggggatgcca ccgtagcagg caagagtatt ttaaccaata tttctgaagt ccatcaaaat   6120
atgggctact gtcctcagtt tgatgcaatc gatgagctgc tcacaggacg agaacatctt   6180
tacctttatg cccggcttcg aggtgtacca gcagaagaaa tcgaaaaggt tgcaaactgg   6240
agtattaaga gcctgggcct gactgtctac gccgactgcc tggctggcac gtacagtggg   6300
ggcaacaagc ggaaactctc cacagccatc gcactcattg gctgcccacc gctggtgctg   6360
ctggatgagc ccaccacagg gatggacccc caggcacgcc gcatgctgtg gaacgtcatc   6420
gtgagcatca tcagaaaagg gagggctgtg gtcctcacat cccacagcat ggaagaatgt   6480
gaggcactgt gtacccggct ggccatcatg gtaaagggcg cctttcgatg tatgggcacc   6540
attcagcatc tcaagtccaa atttggagat ggctatatcg tcacaatgaa gatcaaatcc   6600
ccgaaggacg acctgcttcc tgacctgaac cctgtggagc agttcttcca ggggaacttc   6660
ccaggcagtg tgcagaggga gaggcactac aacatgctcc agttccaggt ctcctcctcc   6720
tccctggcga ggatcttcca gctcctcctc tcccacaagg acagcctgct catcgaggag   6780
tactcagtca cacagaccac actggaccag gtgtttgtaa attttgctaa acagcagact   6840
gaaagtcatg acctccctct gcaccctcga gctgctggag ccagtcgaca agcccaggac   6900
tgatctttca caccgctcgt tcctgcagcc agaaaggaac tctgggcagc tggaggcgca   6960
ggagcctgtg cccatatggt catccaaatg gactggccca gcgtaaatga ccccactgca   7020
gcagaaaaca aacacacgag gagcatgcag cgaattcaga aagaggtctt tcagaaggaa   7080
accgaaactg acttgctcac ctggaacacc tgatggtgaa accaaacaaa tacaaaatcc   7140
ttctccagac cccagaacta gaaaccccgg gccatcccac tagcagcttt ggcctccata   7200
ttgctctcat ttcaagcaga tctgcttttc tgcatgtttg tctgtgtgtc tgcgttgtgt   7260
gtgattttca tggaaaaata aaatgcaaat gcactcatca caaaaaaaaa aaaaaaa      7318
```

<210> SEQ ID NO 63
<211> LENGTH: 1156
<212> TYPE: DNA
<213> ORGANISM: Homo sapiens

<400> SEQUENCE: 63

-continued cgcagcggag gtgaaggacg tccttcccca ggagccgact ggccaatcac aggcaggaag 60
atgaaggttc tgtgggctgc gttgctggtc acattcctgg caggatgcca ggccaaggtg 120
gagcaagcgg tggagacaga gccggagccc gagctgcgcc agcagaccga gtggcagagc 180
ggccagcgct gggaactggc actgggtcgc ttttgggatt acctgcgctg ggtgcagaca 240
ctgtctgagc aggtgcagga ggagctgctc agctcccagg tcacccagga actgagggcg 300
ctgatggacg agaccatgaa ggagttgaag gcctacaaat cggaactgga ggaacaactg 360
accccggtgg cggaggagac gcgggcacgg ctgtccaagg agctgcaggc ggcgcaggcc 420
cggctgggcg cggacatgga ggacgtgtgc ggccgcctgg tgcagtaccg cggcgaggtg 480
caggccatgc tcggccagag caccgaggag ctgcgggtgc gcctcgcctc ccacctgcgc 540
aagctgcgta agcggctcct ccgcgatgcc gatgacctgc agaagcgcct ggcagtgtac 600
caggccgggg cccgcgaggg cgccgagcgc ggcctcagcg ccatccgcga gcgcctgggg 660
cccctggtgg aacagggccg cgtgcgggcc gccactgtgg gctccctggc cggccagccg 720
ctacaggagc gggcccaggc ctggggcgag cggctgcgcg cgcggatgga ggagatgggc 780
agccggaccc gcgaccgcct ggacgaggtg aaggagcagg tggcggaggt gcgcgccaag 840
ctggaggagc aggcccagca gatacgcctg caggccgagg ccttccaggc ccgcctcaag 900
agctggttcg agcccctggt ggaagacatg cagcgccagt gggccgggct ggtggagaag 960
gtgcaggctg ccgtgggcac cagcgccgcc cctgtgccca gcgacaatca ctgaacgccg 1020
aagcctgcag ccatgcgacc ccacgccacc ccgtgcctcc tgcctccgcg cagcctgcag 1080
cgggagaccc tgtccccgcc ccagccgtcc tcctggggtg gaccctagtt taataaagat 1140
tcaccaagtt tcacgc 1156

<210> SEQ ID NO 64
<211> LENGTH: 2273
<212> TYPE: DNA
<213> ORGANISM: Homo sapiens

<400> SEQUENCE: 64
caggactgcc tgagacaagc cacaagctga acagagaaag tggattgaac aaggacgcat 60
ttccccagta catccacaac atgctgtcca catctcgttc tcggtttatc agaaatacca 120
acgagagcgg tgaagaagtc accacctttt ttgattatga ttacggtgct ccctgtcata 180
aatttgacgt gaagcaaatt ggggcccaac tcctgcctcc gctctactcg ctggtgttca 240
tctttggttt tgtgggcaac atgctggtcg tcctcatctt aataaactgc aaaaagctga 300
agtgcttgac tgacatttac ctgctcaacc tggccatctc tgatctgctt tttcttatta 360
ctctcccatt gtgggctcac tctgctgcaa atgagtgggt ctttgggaat gcaatgtgca 420
aattattcac agggctgtat cacatcggtt attttggcgg aatcttcttc atcatcctcc 480
tgacaatcga tagatacctg gctattgtcc atgctgtgtt tgctttaaaa gccaggacgg 540
tcacctttgg ggtggtgaca agtgtgatca cctggttggt ggctgtgttt gcttctgtcc 600
caggaatcat ctttactaaa tgccagaaag aagattctgt ttatgtctgt ggcccttatt 660
ttccacgagg atggaataat ttccacacaa taatgaggaa cattttgggg ctggtcctgc 720
cgctgctcat catggtcatc tgctactcgg gaatcctgaa aaccctgctt cggtgtcgaa 780
acgagaagaa gaggcatagg gcagtgagag tcatcttcac catcatgatt gtttactttc 840
tcttctggac tccctataac attgtcattc tcctgaacac cttccaggaa ttcttcggcc 900
tgagtaactg tgaaagcacc agtcaactgg accaagccac gcaggtgaca gagactcttg 960

-continued

```
ggatgactca ctgctgcatc aatcccatca tctatgcctt cgttggggag aagttcagaa   1020
gcctttttca catagctctt ggctgtagga ttgccccact ccaaaaacca gtgtgtggag   1080
gtccaggagt gagaccagga aagaatgtga aagtgactac acaaggactc ctcgatggtc   1140
gtggaaaagg aaagtcaatt ggcagagccc ctgaagccag tcttcaggac aaagaaggag   1200
cctagagaca gaaatgacag atctctgctt tggaaatcac acgtctggct tcacagatgt   1260
gtgattcaca gtgtgaatct tggtgtctac gttaccaggc aggaaggctg agaggagaga   1320
gactccagct gggttggaaa acagtatttt ccaaactacc ttccagttcc tcatttttga   1380
atacaggcat agagttcaga ctttttttaa atagtaaaaa taaaattaaa gctgaaaact   1440
gcaacttgta aatgtggtaa agagttagtt tgagttgcta tcatgtcaaa cgtgaaaatg   1500
ctgtattagt cacagagata attctagctt tgagcttaag aattttgagc aggtggtatg   1560
tttgggagac tgctgagtca acccaatagt tgttgattgg caggagttgg aagtgtgtga   1620
tctgtgggca cattagccta tgtgcatgca gcatctaagt aatgatgtcg tttgaatcac   1680
agtatacgct ccatcgctgt catctcagct ggatctccat tctctcaggc ttgctgccaa   1740
aagccttttg tgttttgttt tgtatcatta tgaagtcatg cgtttaatca cattcgagtg   1800
tttcagtgct tcgcagatgt ccttgatgct catattgttc cctaatttgc cagtgggaac   1860
tcctaaatca aattggcttc taatcaaagc ttttaaaccc tattggtaaa gaatggaagg   1920
tggagaagct ccctgaagta agcaaagact ttcctcttag tcgagccaag ttaagaatgt   1980
tcttatgttg cccagtgtgt ttctgatctg atgcaagcaa gaaacactgg gcttctagaa   2040
ccaggcaact tgggaactag actcccaagc tggactatgg ctctactttc aggccacatg   2100
gctaaagaag gtttcagaaa gaagtgggga cagagcagaa ctttcacctt catatatttg   2160
tatgatccta atgaatgcat aaaatgttaa gttgatggtg atgaaatgta aatactgttt   2220
ttaacaacta tgatttggaa aataaatcaa tgctataact atgttgataa aag          2273
```

<210> SEQ ID NO 65
<211> LENGTH: 818
<212> TYPE: DNA
<213> ORGANISM: Homo sapiens

<400> SEQUENCE: 65

```
cgcagcgggt cctctctatc tagctccagc ctctcgcctg cgccccactc cccgcgtccc     60
gcgtcctagc cgaccatggc cgggcccctg cgcgccccgc tgctcctgct ggccatcctg    120
gccgtggccc tggccgtgag ccccgcggcc ggctccagtc ccggcaagcc gccgcgcctg    180
gtgggaggcc ccatggacgc cagcgtggag gaggagggtg tgcggcgtgc actggacttt    240
gccgtcggcg agtacaacaa agccagcaac gacatgtacc acagccgcgc gctgcaggtg    300
gtgcgcgccc gcaagcagat cgtagctggg gtgaactact tcttggacgt ggagctgggc    360
cgaaccacgt gtaccaagac ccagcccaac ttggacaact gccccttcca tgaccagcca    420
catctgaaaa ggaaagcatt ctgctctttc cagatctacg ctgtgccttg gcagggcaca    480
atgaccttgt cgaaatccac ctgtcaggac gcctaggggt ctgtaccggg ctggcctgtg    540
cctatcacct cttatgcaca cctcccaccc cctgtattcc cacccctgga ctggtggccc    600
ctgccttggg gaaggtctcc ccatgtgcct gcaccaggag acagacagag aaggcagcag    660
gcggcctttg ttgctcagca aggggctctg ccctccctcc ttccttcttg cttctcatag    720
ccccggtgtg cggtgcatac acccccacct cctgcaataa aatagtagca tcggcaaaaa    780
```

-continued aaaaaaaaaa aaaaaaaaaa aaaaaaaaaa aaaaaaaa 818

<210> SEQ ID NO 66
<211> LENGTH: 18209
<212> TYPE: DNA
<213> ORGANISM: Homo sapiens

<400> SEQUENCE: 66
gaagccgcat ccagacaaaa gctgccgcat ccctgccctg cccaacccct ggagggattc 60
gagtttggtg cttgtccccg tctgattctc agcgccaaac tttttgctag ttcagagatt 120
ccaagagtct gatgagttac tctgagagga aaccctctgc ctgttgttga ggaggactga 180
gcacagtgct taggcgctga gggggaaaaa gagggggaaa aaaaagaaaa tgatttcctg 240
ggaagttgtc catacagtat tcctgtttgc tcttctttat tcttccctag ctcaagatgc 300
gagcccccag tcagagatca gagctgagga aattcccgag ggggcctcca cgttggcttt 360
tgtgtttgat gtgactggtt ctatgtatga tgatttagtt caggtgattg aaggggcttc 420
caaaattttg gagacgtctt tgaaaagacc taaaagacct cttttcaact ttgcgttggt 480
gcctttccat gatccagaaa ttggcccagt gacaattacc acagatccca agaaatttca 540
atatgaactc agagaactgt atgttcaggg tggtggtgat tgcccagaaa tgagtattgg 600
agctataaaa attgccttgg aaatttctct tcctggttct ttcatctatg ttttcactga 660
tgctcggtcc aaagattacc ggctcaccca tgaggtgctg caacttatcc aacagaaaca 720
gtcacaagtc gtatttgttc tgactggaga ttgtgatgac aggacccata ttggatataa 780
agtctatgaa gaaattgcct ctacaagttc tggtcaagtg ttccatctgg acaaaaaaca 840
agttaatgag gtattaaaat gggtagaaga agcagtacag gcctccaaag ttcacctttt 900
atccacagat catttggaac aggctgtaaa tacttggaga attcctttttg atcccagcct 960 gaaagaggtc actgtgtctt tgagtgggcc ttctccaatg attgaaattc gcaatccttt 1020
agggaagctg ataaaaaagg gatttggcct gcatgagcta ttaaatatcc ataactctgc 1080
caaagtagtg aatgtgaaag agccagaggc tggaatgtgg acagtgaaga cctcaagcag 1140
tggaaggcac tctgttcgca ttactggcct cagtactatt gatttccgag ctggcttttc 1200
tcgaaagccc accctggact tcaaaaaaac agtcagcaga ccagtgcaag gaatacctac 1260
ctatgtactg ctcaatactt ctggaatttc cactccagct agaatagatc ttcttgaact 1320
tttgagtatc tcaggaagtt ctcttaagac tattcctgtt aaatattacc cacatcgaaa 1380
accttatggc atatggaata tttctgactt tgtaccacca aatgaagctt tctttctcaa 1440
agtaacaggc tatgataaag atgattacct cttccagaga gtatcaagtg tttccttttc 1500
tagtattgtc ccagatgctc ccaaagttac gatgcctgag aaaaccccag gatactatct 1560
gcagccgggc caaattccct gctctgttga cagtcttttg ccctttacct tgagctttgt 1620
cagaaatgga gttacacttg gagtagacca gtatttgaaa gaatctgcca gtgtgaactt 1680
agatattgca aaggtcactt tgtctgacga aggtttctat gaatgcattg ctgtcagcag 1740
tgcaggtact ggacgggcac agacattttt tgacgtatca gagcccccctc cggtcatcca 1800 agtgcctaac aatgttacag tcactcctgg agagagagca gttttaacat gtctcatcat 1860
cagtgcggtg gattacaatc taacctggca gaggaatgac agagatgtca gactggcaga 1920
gccagcgaga attaggacct tggctaatct gtcattggag ctaaagagtg tgaaattcaa 1980
cgatgctgga gagtatcatt gtatggtttc tagtgaaggt ggatcatcag ccgcttcagt 2040
tttcctcaca gtgcaagaac cacccaaagt cactgtgatg cccaagaatc agtctttcac 2100

-continued

```
aggagggtct gaggtctcca tcatgtgttc tgcaacaggt tatcccaaac caaagattgc   2160
ctggaccgtt aacgatatgt ttatcgtggg ttcacacagg tataggatga cctcagatgg   2220
taccttattt atcaaaaatg cagctcccaa agatgcaggg atctatggtt gcctagcaag   2280
taattcagct ggaacagata aacagaattc tactctcaga tacattgaag cccctaagtt   2340
gatggtagtt cagagtgagc tcttggttgc ccttggggat ataaccgtta tggaatgcaa   2400
aacctctggt attcctccac ctcaagttaa atggttcaaa ggagatcttg agttgaggcc   2460
ctcaacattc ctcattattg accctctctt gggacttttg aagattcaag aaacacaaga   2520
tctggatgct ggcgattata cctgtgtagc catcaatgag gctggaagag caactggcaa   2580
gataactctg gatgttggct cacctccagt tttcatacaa gaacctgctg atgtgtctat   2640
ggaaattggc tcaaatgtga cattaccttg ttatgttcag ggttatccag aaccaacaat   2700
caaatggcga agattagaca acatgccaat tttctcaaga cctttttcag ttagttccat   2760
cagccaacta agaacaggag ctctctttat tttaaactta tgggcaagtg ataaaggaac   2820
ctatatttgt gaagctgaaa accagtttgg aaagatccag tcagagacaa cagtaacagt   2880
gaccggactt gttgctccac ttattggaat cagcccttca gtggccaatg ttattgaagg   2940
acagcagctt actttgccct gtactctgtt agctggaaat cccattccag aacgtcggtg   3000
gattaagaat tcagctatgt tgctccaaaa tccttacatc actgtgcgca gtgatgggag   3060
cctccatatt gaaagagttc agcttcagga tggtggtgaa tatacttgtg tggccagtaa   3120
cgttgctggg accaataaca aaactacctc tgtggttgtg catgttctgc caaccattca   3180
gcatgggcag cagatactca gtacaattga aggcattcca gtaactttac catgcaaagc   3240
aagtggaaat cccaaaccgt ctgtcatctg gtccaagaaa ggagagctga tttcaaccag   3300
cagtgctaag ttttcagcag gagctgatgg tagtctgtat gtggtatcac ctggaggaga   3360
ggagagtggg gagtatgtct gcactgccac caatacagcc ggctacgcca aaaggaaagt   3420
gcagctaaca gtctatgtaa ggcccagagt gtttggagat caacgaggac tgtcccagga   3480
taagcctgtt gagatctccg tccttgcagg ggaagaggta acacttccat gtgaagtgaa   3540
gagcttacct ccacccataa ttacttgggc caaagaaacc cagctcatct caccgttctc   3600
tccaagacac acattcctcc cttctggttc aatgaagatc actgaaaccc gcacttcaga   3660
tagtgggatg tatctttgtg ttgccacaaa tattgctggg aatgtgactc aggctgtcaa   3720
attaaatgtc catgttcctc caaagataca gcgtggacct aaacatctca aagtccaagt   3780
tggtcaaaga gtggatattc catgtaatgc tcaagggact cctcttcctg taatcacctg   3840
gtccaaaggt ggaagcacta tgctggttga tggagagcac catgttagca atccagacgg   3900
aactttaagc atcgaccaag ccacgccctc agatgctggc atatatacat gtgttgctac   3960
taacatagca ggcactgatg aaacagagat aacgctacat gtccaagaac cacccacagt   4020
ggaagatcta gaacctccat ataacactac tttccaagaa agagtggcca atcaacgcat   4080
tgaatttcca tgtcctgcaa aaggtacccc taaaccaacc atcaaatggt tacacaatgg   4140
tagagagttg acaggcagag agcctggcat ttctatcttg gaagatggca cattgctggt   4200
tattgcttct gttacaccct atgacaatgg ggagtacatc tgtgtggcag tcaatgaagc   4260
tggaaccaca gaaagaaaat ataacctcaa agtccatgtt cctccagtaa ttaaagataa   4320
agaacaagtt acaaatgtgt cggtgttgtt aaatcagctg accaatctct tctgtgaagt   4380
ggaaggcact ccatctccca tcattatgtg gtataaagat aatgtccagg tgactgaaag   4440
```

-continued

```
cagcactatt cagactgtga acaatgggaa gatactgaag ctcttcagag ccactccaga   4500
ggatgcagga agatattcct gcaaagcaat taatattgca ggcacttctc agaagtactt   4560
taacattgat gtgctagttc cacccaccat aataggtacc aacttcccaa atgaagtctc   4620
agttgtcctc aaccgtgacg tcgcccttga atgccaggtc aaaggcactc cctttcctga   4680
tattcattgg ttcaaagatg gcaagccttt atttttgggc gatcctaatg ttgaacttct   4740
agacagagga caagtcttac atttaaagaa tgcacggaga aatgacaagg ggcgctacca   4800
atgtactgtg tctaatgcag ctggcaaaca agccaaggat ataaaactga ctatctatat   4860
tccacctagt attaaaggag gaaatgtcac cacagacata tcagtattga tcaacagcct   4920
tattaaactg gaatgtgaaa cacggggact tccaatgcct gccattactt ggtataagga   4980
cgggcagcca atcatgtcca gctcacaagc actttatatt gataaaggac aatatcttca   5040
tattcctcga gcacaggtct ctgattcagc aacatatacg tgtcacgtag ccaatgttgc   5100
tggaactgct gaaaaatcat tccatgtgga tgtctatgtt cctccaatga ttgaaggcaa   5160
cttggccacg cctttgaata agcaagtagt tattgctcat tctctgacac tggagtgcaa   5220
agctgctgga aacccttctc ccattctcac ctggttgaaa gatggtgtac ctgtgaaagc   5280
taatgacaat atccgcatag aagctggtgg gaagaaactc gaaatcatga gtgcccaaga   5340
aattgatcga ggacagtaca tatgcgtggc taccagtgtg gcaggagaaa aggaaatcaa   5400
atatgaagtt gatgtcttgg tgccaccagc tatagaagga ggagatgaaa catcttactt   5460
cattgtgatg gttaataact tactggagct agattgtcat gtgacaggct ctcccccacc   5520
aactatcatg tggctgaagg atggccagtt aattgatgaa agggatggat tcaagatttt   5580
attaaatgga cgcaaactgg ttattgctca ggctcaagtg tcaaacacag gcctttatcg   5640
gtgcatggca gcaaatactg ctggagacca caagaaggaa tttgaagtga ctgttcatgt   5700
tcctccaaca atcaagtcct caggcctttc tgagagagtt gtggtaaaat acaagcctgt   5760
cgccttgcag tgcatagcca atgggattcc aaatccttcc attacatggt taaaagatga   5820
ccagcctgtg aacactgccc aaggaaacct taaaatacag tcttctggtc gagttctaca   5880
aattgccaaa accctgttgg aagatgctgg cagatacaca tgtgtggcta ccaacgcagc   5940
tggagaaaca caacagcaca ttcaactgca tgttcatgaa ccacctagtc tggaagatgc   6000
tggaaaaatg ctgaatgaga ctgtgttggt gagcaaccct gtacagctgg agtgtaaggc   6060
agctggaaat cctgtgcctg ttattacatg gtacaaagat aatcgtctac tctcaggttc   6120
caccagcatg actttcttga acagaggaca gatcattgat attgaaagtg cccagatctc   6180
agatgctggc atatataaat gcgtggccat caactcagct ggagctacag agttatttta   6240
cagtctgcaa gttcatgtgg ccccatcaat ttctggcagc aataacatgg tggcagtggt   6300
ggttaataac ccggtgaggt tagaatgtga agccagaggt attcctgccc caagtctgac   6360
ctggttgaaa gatgggagtc ctgtttctag tttttctaat ggattacagg ttctctctgg   6420
tggtcgaatc ctagcattga ccagtgcaca aatcagcgac acaggaaggt acacctgcgt   6480
ggcagtgaat gctgctggag aaaagcaaag ggacattgac ctccgagtat atgttccgcc   6540
aaatattatg ggagaagaac agaatgtctc tgtcctcatt agccaagctg tggaattact   6600
atgtcaaagt gatgctattc ccccacctac tcttacttgg ttaaaagacg gccacccctt   6660
gctgaagaaa ccaggcctca gtatatctga aaatagaagt gtgttaaaga ttgaagatgc   6720
tcaggttcaa gacactggtc gttacacttg tgaagcaaca aatgttgctg gaaaaactga   6780
aaaaaaaaac tacaatgtca acatttgggt ccccccaaat attggtggtt ctgatgaact   6840
```

-continued tactcaactt acagtcattg aagggaatct cattagtctg ttgtgtgaat caagtggtat 6900
tccaccccca aatctcatct ggaagaagaa aggctctcca gtgctgactg attccatggg 6960
gcgagttaga attttatctg gggcaggca attacaaatt tcaattgctg aaaagtctga 7020
tgcagcactc tattcatgtg tggcgtcgaa tgttgctggg actgcaaaga aagaatacaa 7080
tctgcaagtt tacattagac caaccataac caacagtggc agccacccta ctgaaattat 7140
tgtgacccga gggaagagta tctccttgga gtgtgaggtg cagggtattc caccaccaac 7200
agtgacctgg atgaaagatg gccacccctt gatcaaggca aagggagtag aaatactgga 7260
tgaaggtcac atccttcagc tgaagaacat tcatgtatct gacacaggcc gttatgtgtg 7320
tgttgctgtg aatgtagcag gaatgactga caaaaaatat gacttaagtg tccatgctcc 7380
tccaagcatc ataggaaacc acaggtcacc tgaaaatatt agtgtggtag aaaagaactc 7440
agtatctttg acttgtgaag cttctggaat tcccctgcct tccataacct ggttcaaaga 7500
tgggtggcct gtcagcctta gcaattctgt gaggattctt tcaggaggca ggatgctacg 7560
gctgatgcag accacaatgg aagatgctgg ccaatatact tgcgttgtaa ggaatgcagc 7620
tggtgaagaa agaaaaatct ttgggctttc agtattagta ccacctcata ttgtgggtga 7680
aaatacattg gaagatgtga aggtaaaaga gaaacagagt gttacgctga cttgtgaagt 7740
gacagggaat ccagtgccag aaattacatg gcacaaagat gggcagcccc tccaagaaga 7800
tgaagcccat cacattatat ctggtggccg ttttcttcaa attaccaatg tccaggtgcc 7860
acacactgga agatatacat gtttggcttc cagtccagct ggccacaaga gcaggagctt 7920
cagtcttaat gtatttgtat ctcctacaat tgctggtgta ggtagtgatg gcaaccctga 7980
agatgtcact gtcatcctta acagccctac atctttggtc tgtgaagctt attcatatcc 8040
tccagctacc atcacctggt ttaaggatgg cactccttta gaatctaacc gaaatattcg 8100
tattcttcca ggaggcagaa ctctgcagat cctcaatgca caggaggaca atgctggaag 8160
atactcttgt gtagccacga atgaggctgg agaaatgata aagcactatg aagtgaaggt 8220
gtacattcca cccataatca ataaagggga cctttggggg ccaggtcttt cccctaaaga 8280
agtgaagatc aaagtaaaca acactctgac cttggaatgt gaagcgtatg caattccttc 8340
tgcctccctc agctggtaca aggatggaca gccccttaaa tccgatgatc atgttaatat 8400
tgctgcgaat ggacacacac ttcaaataaa ggaggctcaa atatcagaca ccggacgata 8460
tacttgtgta gcatctaaca ttgcaggtga agatgagttg gattttgatg tgaatattca 8520
agttcctcca agttttcaga aactctggga aataggaaac atgctagata ctggcaggaa 8580
tggtgaagcc aaagatgtga tcatcaacaa tcccatttct ctttactgtg agacaaatgc 8640
tgctcccccct cctacactga catggtacaa agatggccac cctctgacct caagtgataa 8700
agtattgatt ttgccaggag ggcgagtgtt gcagattcct cgggctaaag tagaagatgc 8760
tgggagatac acatgtgtgg ctgtgaatga ggctggagaa gattcccttc aatatgatgt 8820
ccgtgtactc gtgccgccaa ttatcaaggg agcaaatagt gatctccctg aagaggtcac 8880
cgtgctggtg aacaagagtg cactgataga gtgtttatcc agtggcagcc cagcaccaag 8940
gaattcctgg cagaaagatg gacagccctt gctagaagat gaccatcata aatttctatc 9000
taatggacga attctgcaga ttctgaatac tcaaataaca gatatcggca ggtatgtgtg 9060
tgttgctgag aacacagctg ggagtgccaa aaaatatttt aacctcaatg ttcatgttcc 9120
tccaagtgtc attggtccta aatctgaaaa tcttaccgtc gtggtgaaca atttcatctc 9180

-continued

```
tttgacctgt gaggtctctg gttttccacc tcctgacctc agctggctca agaatgaaca   9240
gcccatcaaa ctgaacacaa atactctcat tgtgcctggt ggtcgaactc tacagattat   9300
tcgggccaag gtatcagatg gtggtgaata cacttgtata gctatcaatc aagctggcga   9360
aagcaagaaa aagttttccc tgactgttta tgtgccccca agcattaaag accatgacag   9420
tgaatctctt tctgtagtta atgtaagaga gggaacttct gtgtctttgg agtgtgagtc   9480
gaacgctgtg ccacctccag tcatcacttg gtataagaat gggcggatga taacagagtc   9540
tactcatgtg gagattttag ctgatggaca aatgctacac attaagaaag ctgaggtatc   9600
tgacacaggc cagtatgtat gtagagctat aaatgtagca ggacgggatg ataaaaattt   9660
ccacctcaat gtatatgtgc cacccagtat tgaaggacct gaaagagaag tgattgtgga   9720
gacgatcagc aatcctgtga cattaacatg tgatgccact gggatcccac ctcccacgat   9780
agcatggtta aagaaccaca agcgcataga aaattctgac tcactggaag ttcgtatttt   9840
gtctggaggt agcaaactcc agattgcccg gtctcagcat tcagatagtg gaaactatac   9900
atgtattgct tcaaatatgg agggaaaagc ccagaaatat tactttcttt caattcaagt   9960
tcctccaagt gttgctggtg ctgaaattcc aagtgatgtc agtgtccttc taggagaaaa  10020
tgttgagctg gtctgcaatg caaatggcat tcctactcca cttattcaat ggcttaaaga  10080
tggaaagccc atagctagtg gtgaaacaga aagaatccga gtgagtgcaa atggcagcac  10140
attaaacatt tatggagctc ttacatctga cacggggaaa tacacatgtg ttgctactaa  10200
tcccgctgga gaagaagacc gaatttttaa cttgaatgtc tatgttacac ctacaattag  10260
gggtaataaa gatgaagcag agaaactaat gactttagtg gatacttcaa taaatattga  10320
atgcagagcc acagggacgc ctccaccaca gataaactgg ctgaagaatg gacttcctct  10380
gcctctctcc tcccatatcc ggttactggc agcaggacaa gttatcagga ttgtgagagc  10440
tcaggtgtct gatgtcgctg tgtatacttg tgtggcctcc aacagagctg gggtggataa  10500
taagcattac aatcttcaag tgtttgcacc accaaatatg gacaattcaa tggggacaga  10560
ggaaatcaca gttctcaaag gtagttccac ctctatggca tgcattactg atggaacccc  10620
agctcccagt atggcctggc ttagagatgg ccagcctctg ggcttgatg cccatctgac  10680
agtcagcacc catggaatgg tcctgcagct cctcaaagca gagactgaag attcgggaaa  10740
gtacacctgc attgcctcaa atgaagctgg agaagtcagc aagcacttta tcctcaaggt  10800
cctagaacca cctcacatta atggatctga agaacatgaa gagatatcag taattgttaa  10860
taacccactt gaacttacct gcattgcttc tggaatccca gcccctaaaa tgacctggat  10920
gaaagatggc cggccccttc cacagacgga tcaagtgcaa actctaggag gaggagaggt  10980
tcttcgaatt tctactgctc aggtggagga tacaggaaga tatacatgtc tggcatccag  11040
tcctgcagga gatgatgata aggaatatct agtgagagtg catgtacctc ctaatattgc  11100
tggaactgat gagccccggg atatcactgt gttacggaac agacaagtga cattggaatg  11160
caagtcagat gcagtgcccc cacctgtaat tacttggctc agaaatggag aacggttaca  11220
ggcaacacct cgagtgcgaa tcctatctgg agggagatac ttgcaaatca acaatgctga  11280
cctaggtgat acagccaatt atacctgtgt tgccagcaac attgcaggaa agactacaag  11340
agaatttatt ctcactgtaa atgttcctcc aaacataaag gggggccccc agagccttgt  11400
aattctttta aataagtcaa ctgtattgga atgcatcgct gaaggtgtgc caactccaag  11460
gataacatgg agaaaggatg gagctgttct agctgggaat catgcaagat attccatctt  11520
ggaaaatgga ttccttcata ttcaatcagc acatgtcact gacactggac ggtatttgtg  11580
```

-continued

```
tatggccacc aatgctgctg gaacagatcg caggcgaata gatttacagg tccatgttcc  11640
tccatctatt gctccgggtc ctaccaacat gactgtaata gtaaatgttc aaactactct  11700
ggcttgtgag gctactggga taccaaaacc atcaatcaat tggagaaaaa atgggcatct  11760
tcttaatgtg gatcaaaatc agaactcata caggctcctt tcttcaggtt cactagtaat  11820
tatttcccct tctgtggatg acactgcaac ctatgaatgt actgtgacaa acggtgctgg  11880
agatgataaa agaactgtgg atctcactgt ccaagttcca ccttccatag ctgatgagcc  11940
tacagatttc ctagtaacca aacatgcccc agcagtaatt acctgcactg cttcgggagt  12000
tccatttccc tcaattcact ggaccaaaaa tggtataaga ctgcttccca ggggagatgg  12060
ctatagaatt ctgtcctcag gagcaattga aatacttgcc acccaattaa accatgctgg  12120
aagatacact tgtgtcgcta ggaatgcggc tggctctgca catcgacacg tgacccttca  12180
tgttcatgag cctccagtca ttcagcccca accaagtgaa ctacacgtca ttctgaacaa  12240
tcctatttta ttaccatgtg aagcaacagg gacacccagt cctttcatta cttggcaaaa  12300
agaaggcatc aatgttaaca cttcaggcag aaaccatgca gttcttccta gtggcggctt  12360
acagatctcc agagctgtcc gagaggatgc tggcacttac atgtgtgtgg cccagaaccc  12420
ggctggtaca gccttgggca aaatcaagtt aaatgtccaa gttcctccag tcattagccc  12480
tcatctaaag gaatatgtta ttgctgtgga caagcccatc acgttatcct gtgaagcaga  12540
tggcctccct ccgcctgaca ttacatggca taaagatggg cgtgcaattg tggaatctat  12600
ccgccagcgc gtcctcagct ctggctctct gcaaatagca tttgtccagc ctggtgatgc  12660
tggccattac acgtgcatgg cagccaatgt agcaggatca agcagcacaa gcaccaagct  12720
caccgtccat gtaccaccca ggatcagaag tacagaagga cactacacgg tcaatgagaa  12780
ttcacaagcc attcttccat gcgtagctga tggaatcccc acaccagcaa ttaactggaa  12840
aaaagacaat gttcttttag ctaacttgtt aggaaaatac actgctgaac catatggaga  12900
actcatttta gaaaatgttg tgctggagga ttctggcttc tatacctgtg ttgctaacaa  12960
tgctgcaggt gaagatacac acactgtcag cctgactgtg catgttctcc ccactttac  13020
tgaacttcct ggagacgtgt cattaaataa aggagaacag ctacgattaa gctgtaaagc  13080
tactggtatt ccattgccca aattaacatg gaccttcaat aacaatatta ttccagccca  13140
ctttgacagt gtgaatggac acagtgaact tgttattgaa agagtgtcaa aagaggattc  13200
aggtacttat gtgtgcaccg cagagaacag cgttggcttt gtgaaggcaa ttggatttgt  13260
ttatgtgaaa gaacctccag tcttcaaagg tgattatcct tctaactgga ttgaaccact  13320
tggtgggaat gcaatcctga attgtgaggt gaaaggagac ccccaccccaa ccatccagtg  13380
gaacagaaag ggagtggata ttgaaattag ccacagaatc cggcaactgg gcaatggctc  13440
cctggccatc tatggcactg ttaatgaaga tgccggtgac tatacatgtg tagctaccaa  13500
tgaagctggg gtggtggagc gcagcatgag tctgactctg caaagtcctc ctattatcac  13560
tcttgagcca gtggaaactg ttattaatgc tggtggcaaa atcatattga attgtcaggc  13620
aactggagag cctcaaccaa ccattacatg gtcccgtcaa gggcactcta tttcctggga  13680
tgaccgggtt aacgtgttgt ccaacaactc attatatatt gctgatgctc agaaagaaga  13740
tacctctgaa tttgaatgtg ttgctcgaaa cttaatgggt tctgtccttg tcagagtgcc  13800
agtcatagtc caggttcatg gtggattttc ccagtggtct gcatggagag cctgcagtgt  13860
cacctgtgga aaaggcatcc aaaagaggag tcgtctgtgc aaccagcccc ttccagccaa  13920
```

-continued

```
tggtgggaag ccctgccaag gttcagattt ggaaatgcga aactgtcaaa ataagccttg  13980
tccagtggat ggtagctggt cggaatggag tctttgggaa gaatgcacaa ggagctgtgg  14040
acgcggcaac caaaccagga ccaggacttg caataatcca tcagttcagc atggtgggcg  14100
gccatgtgaa gggaatgctg tggaaataat tatgtgcaac attaggcctt gcccagttca  14160
tggagcatgg agcgcttggc agccttgggg aacatgcagc gaaagttgtg ggaaaggtac  14220
tcagacaaga gcaagacttt gtaataaccc accaccagcg tttggtgggt cctactgtga  14280
tggagcagaa acacagatgc aagtttgcaa tgaaagaaat tgtccaattc atggcaagtg  14340
ggcgacttgg gccagttgga gtgcctgttc tgtgtcatgt ggaggaggtg ccagacagag  14400
aacaaggggc tgctccgacc ctgtgcccca gtatggagga aggaaatgcg aagggagtga  14460
tgtccagagt gatttttgca acagtgaccc ttgcccaacc catggtaact ggagtccttg  14520
gagtggctgg ggaacatgca gccggacgtg taacggaggg cagatgcggc ggtaccgcac  14580
atgtgataac cctcctccct ccaatggggg aagagcttgt gggggaccag actcccagat  14640
ccagaggtgc aacactgaca tgtgtcctgt ggatggaagt tggggaagct ggcatagttg  14700
gagccagtgc tctgcctcct gtggaggagg tgaaaagact cggaagcggc tgtgcgacca  14760
tcctgtgcca gttaaaggtg gccgtccctg tcccggagac actactcagg tgaccaggtg  14820
caatgtacaa gcatgtccag gtgggcccca gcgagccaga ggaagtgtta ttggaaatat  14880
taatgatgtt gaatttggaa ttgctttcct taatgccaca ataactgata gccctaactc  14940
tgatactaga ataatacgtg ccaaaattac caatgtacct cgtagtcttg gttcagcaat  15000
gagaaagata gtttctattc taaatcccat ttattggaca acagcaaagg aaataggaga  15060
agcagtcaat ggctttaccc tcaccaatgc agtcttcaaa agagaaactc aagtggaatt  15120
tgcaactgga gaaatcttgc agatgagtca tattgcccgg ggcttggatt ccgatggttc  15180
tttgctgcta gatatcgttg tgagtggcta tgtcctacag cttcagtcac ctgctgaagt  15240
cactgtaaag gattacacag aggactacat tcaaacaggt cctgggcagc tgtacgccta  15300
ctcaacccgg ctgttcacca ttgatggcat cagcatccca tacacatgga accacaccgt  15360
tttctatgat caggcacagg gaagaatgcc tttcttggtt gaaacacttc atgcatcctc  15420
tgtggaatct gactataacc agatagaaga gacactgggt tttaaaattc atgcttcaat  15480
atccaaagga gatcgcagta atcagtgccc ctccgggttt accttagact cagttggacc  15540
tttttgtgct gatgaggatg aatgtgcagc agggaatccc tgctcccata gctgccacaa  15600
tgccatgggg acttactact gctcctgccc taaaggcctc accatagctg cagatggaag  15660
aacttgtcaa gatattgatg agtgtgcttt gggtaggcat acctgccacg ctggtcagga  15720
ctgtgacaat acgattggat cttatcgctg tgtggtccgt tgtggaagtg gctttcgaag  15780
aacctctgat gggctgagtt gtcaagatat taatgaatgt caagaatcca gcccctgtca  15840
ccagcgctgt ttcaatgcca taggaagttt ccattgtgga tgtgaacctg ggtatcagct  15900
caaaggcaga aaatgcatgg atgtgaacga gtgtagacaa aatgtatgca gaccagatca  15960
gcactgtaag aacacccgtg gtggctataa gtgcattgat ctttgtccaa atggaatgac  16020
caaggcagaa aatggaacct gtattgatat tgatgaatgt aaagatggga cccatcagtg  16080
cagatataac cagatatgtg agaatacaag aggcagctat cgttgtgtat gcccaagagg  16140
ttatcggtct caaggagttg gaagaccctg catggacatt aatgaatgtg aacaagtgcc  16200
taaaccttgt gcacatcagt gctccaacac ccccggcagc ttcaagtgta tctgtccacc  16260
aggacaacat ttattagggg acgggaaatc ttgcgctgga ttggagaggc tgccaaatta  16320
```

-continued tggcactcaa tacagtagct ataaccttgc acggttctcc cctgtgagaa acaactatca 16380
acctcaacag cattacagac agtactcaca tctctacagc tcctactcag agtatagaaa 16440
cagcagaaca tctctctcca ggactagaag gactattagg aaaacttgcc ctgaaggctc 16500
tgaggcaagc catgacacat gtgtagatat tgatgaatgt gaaaatacag atgcctgcca 16560
gcatgagtgt aagaatacct ttggaagtta tcagtgcatc tgcccacctg gctatcaact 16620
cacacacaat ggaaagacat gccaagatat cgatgaatgt ctggagcaga atgtgcactg 16680
tggacccaat cgcatgtgct tcaacatgag aggaagctac cagtgcatcg atacaccctg 16740
tccacccaac taccaacggg atcctgtttc agggttctgc ctcaagaact gtccacccaa 16800
tgatttggaa tgtgccttga gcccatatgc cttggaatac aaactcgtct ccctcccatt 16860
tggaatagcc accaatcaag atttaatccg gctggttgca tacacacagg atggagtgat 16920
gcatcccagg acaactttcc tcatggtaga tgaggaacag actgttcctt ttgccttgag 16980
ggatgaaaac ctgaaaggag tggtgtatac aacacgacca ctacgagaag cagagaccta 17040
ccgcatgagg gtccgagcct catcctacag tgccaatggg accattgaat atcagaccac 17100
attcatagtt tatatagctg tgtccgccta tccatactaa ggaactctcc aaagcctatt 17160
ccacatattt aaaccgcatt aatcatggca atcaagcccc cttccagatt actgtctctt 17220
gaacagttgc aatcttggca gcttgaaaat ggtgctacac tctgttttgt gtgccttcct 17280
tggtacttct gaggtatttt catgatccca ccatggtcat atcttgaagt atggtctaga 17340
aaagtccctt attattttat ttattacact ggagcagtta cttcccaaag attattctga 17400
acatctaaca ggacatatca gtgatggttt acagtagtgt agtacctaag atcattttcc 17460
tgaaagccaa accaaacaac gaaaaacaag aacaactaat tcagaatcaa atagagtttt 17520
tgagcatttg actattttta gaatcataaa attagttact aagtattttg atcaaagctt 17580
ataaaataac ttacggagat ttttgtaagt attgatacat tataatagga cttgcctatt 17640
ttcattttta agaagaaaaa caccactcat tttataaaat atagtacagc tactataagg 17700
cttgtttgat cccaaatggt gcttatcttg attgaacatt cagaacaagg atattatttt 17760
cagtgatttt gtgagatcag ctgaaccact tatgataata ataataaaaa agactgcttt 17820
gccctcacgt cagttgtaca tggcatggaa ctttaaaaat tttaatataa actttcatcc 17880
agttagcttc ataactttta cgttccagaa ttttgtttat tttcctgtca atgaaagcaa 17940
tttttaaaga taccagtggg acaggtttgg ttttttaaaa atctcatgtg ttcaaattaa 18000
cataaatatt acacgtcaat acactgtaca tggtggtaat agactctaag caattgccaa 18060
gatgtattct atttttatga agtgtatata tattacctta gtgtgcattt tctatataat 18120
atcttgatgg actcttttat aaaattattt tataaaaaac aatgttacac taaaatcagc 18180
ctaaataaat tttcacaact ttttttcat 18209

<210> SEQ ID NO 67
<211> LENGTH: 1026
<212> TYPE: DNA
<213> ORGANISM: Homo sapiens

<400> SEQUENCE: 67
cagcatgttg agccgggcag tgtgcggcac cagcaggcag ctgcctccgg ttttggggta 60
tctgggctcc aggcagaagc acagcctccc cgacctgccc tacgactacg gcgccctgga 120
acctcacatc aacgcgcaga tcatgcagct gcaccacagc aagcaccacg cggcctacgt 180

-continued gaacaacctg aacgtcaccg aggagaagta ccaggaggcg ttggccaagg gagatgttac 240
agcccagata gctcttcagc ctgcactgaa gttcaatggt ggtggtcata tcaatcatag 300
cattttctgg acaaacctca gccctaacgg tggtggagaa cccaaagggg agttgctgga 360
agccatcaaa ctggactttg gttcctttga caagtttaag gagaagctga cggctgcatc 420
tgttggtgtc caaggctcag gttggggttg gcttggtttc aataaggaac ggggacactt 480
acaaattgct gcttgtccaa atcaggatcc actgcaagga acaacaggcc ttattccact 540
gctggggatt gatgtgtggg agcacgctta ctaccttcag tataaaaatg tcaggcctga 600
ttatctaaaa gctatttgga atgtaatcaa ctgggagaat gtaactgaaa gatacatggc 660
ttgcaaaaag taaaccacga tcgttatgct gagtatgtta agctctttat gactgttttt 720
gtagtggtat agagtactgc agaatacagt aagctgctct attgtagcat ttcttgatgt 780
tgcttagtca cttatttcat aaacaactta atgttctgaa taatttctta ctaaacattt 840
tgttattggg caagtgattg aaaatagtaa atgctttgtg tgattgaatc tgattggaca 900
ttttcttcag agagctaaat tacaattgtc atttataaaa ccatcaaaaa tattccatcc 960
atatactttg ggacttgta gggatgcctt tctagtccta ttctattgca gttatagaaa 1020
atctag 1026

<210> SEQ ID NO 68
<211> LENGTH: 757
<212> TYPE: DNA
<213> ORGANISM: Homo sapiens

<400> SEQUENCE: 68
ggaaccgaga ggctgagact aacccagaaa catccaattc tcaaactgaa gctcgcactc 60
tcgcctccag catgaaagtc tctgccgccc ttctgtgcct gctgctcata gcagccacct 120
tcattcccca agggctcgct cagccagatg caatcaatgc cccagtcacc tgctgttata 180
acttcaccaa taggaagatc tcagtgcaga ggctcgcgag ctatagaaga atcaccagca 240
gcaagtgtcc caaagaagct gtgatcttca agaccattgt ggccaaggag atctgtgctg 300
accccaagca gaagtgggtt caggattcca tggaccacct ggacaagcaa acccaaactc 360
cgaagacttg aacactcact ccacaaccca agaatctgca gctaacttat tttcccctag 420
ctttccccag acaccctgtt ttattttatt ataatgaatt ttgtttgttg atgtgaaaca 480
ttatgcctta agtaatgtta attcttattt aagttattga tgttttaagt ttatctttca 540
tggtactagt gttttttaga tacagagact tggggaaatt gcttttcctc ttgaaccaca 600
gttctacccc tgggatgttt tgagggtctt tgcaagaatc attaatacaa agaatttttt 660
ttaacattcc aatgcattgc taaaatatta ttgtggaaat gaatattttg taactattac 720
accaaataaa tatatttttg tacaaaaaaa aaaaaaa 757

<210> SEQ ID NO 69
<211> LENGTH: 2395
<212> TYPE: DNA
<213> ORGANISM: Homo sapiens

<400> SEQUENCE: 69
agagcctcct agcccgtcgg tgtctgcgcc catcgatccc tttgtctatc cccgaccatg 60
gcgaagctga ttgcgctcac cctcttgggg atgggactgg cactcttcag gaaccaccag 120
tcttcttacc aaacacgact taatgctctc cgagaggtac aacccgtaga acttcctaac 180
tgtaatttag ttaaaggaat cgaaactggc tctgaagact tggagatact gcctaatgga 240

-continued

```
ctggctttca ttagctctgg attaaagtat cctggaataa agagcttcaa ccccaacagt    300
cctggaaaaa tacttctgat ggacctgaat gaagaagatc caacagtgtt ggaattgggg    360
atcactggaa gtaaatttga tgtatcttca tttaaccctc atgggattag cacattcaca    420
gatgaagata atgccatgta cctcctggtg gtgaaccatc cagatgccaa gtccacagtg    480
gagttgttta aatttcaaga agaagaaaaa tcgcttttgc atctaaaaac catcagacat    540
aaacttctgc ctaatttgaa tgatattgtt gctgtgggac ctgagcactt ttatggcaca    600
aatgatcact attttcttga cccctactta caatcctggg agatgtattt gggtttagcg    660
tggtcgtatg ttgtctacta tagtccaagt gaagttcgag tggtggcaga aggatttgat    720
tttgctaatg gaatcaacat ttcacccgat ggcaagtatg tctatatagc tgagttgctg    780
gctcataaga ttcatgtgta tgaaaagcat gctaattgga ctttaactcc attgaagtcc    840
cttgacttta ataccctcgt ggataacata tctgtggatc ctgagacagg agacctttgg    900
gttggatgcc atcccaatgg catgaaaatc ttcttctatg actcagagaa tcctcctgca    960
tcagaggtgc ttcgaatcca gaacattcta acagaagaac ctaaagtgac acaggtttat   1020
gcagaaaatg gcacagtgtt gcaaggcagt acagttgcct ctgtgtacaa agggaaactg   1080
ctgattggca cagtgtttca caaagctctt tactgtgagc tctaacagac cgatttgcac   1140
ccatgccata gaaactgagg ccattatttc aaccgcttgc catattccga ggacccagtg   1200
ttcttagctg aacaatgaat gctgacccta aatgtggaca tcatgaagca tcaaagcact   1260
gtttaactgg gagtgatatg atgtgtaggg cttttttttg agaatacact atcaaatcag   1320
tcttggaata cttgaaaacc tcatttacca taaaaatcct tctcactaaa atggataaat   1380
cagttatgtc aattgtcaga tattaaataa cagtgtgtga ccccaaaagt acttacccta   1440
aaacatgtgt tgcctgaaag cacatgtgtg tatcgctgcc ttgccatgtc ttgttcagaa   1500
gacacagggg agcagggtta gctcacgtgt ctttagaact ccagtactca cccagggact   1560
ccagttcaca ggccagaaaa catatgcatt atgaagttcc cctctactcc atgcacatag   1620
taagtctgac tatggcagtc agacttactt actcccattt tcccttcgat atatgacttt   1680
ttctcagtaa atattaacct gaactattcc aactcccctt gtactcttgc tttttcaatt   1740
ctcctgttgc aatgacacat aggaaaatct taaaattctt gggagtgttg tcacacctga   1800
aaattatgag tctctatgat cttggcacaa attgtacatt tgagtgtctt tgacttggtt   1860
aaaggaagtt tgttcacttc gatgactgga tacagaatga atcccataat tgacatgggc   1920
gacagtaaaa gtgtccccaa agactacact gttgttgagg tggtggtagt gctggtgggt   1980
ttttgtttaa tatttaaact tcttgttgtg gaggctgaaa agaaaaaaaa taatagaaag   2040
gtaaacaaac aaataaatag aaaagatcaa caaccccttt ggctatctac tgagacatga   2100
ctaggaagaa aacatgactt tatcattttg ttatagaagc tgatatataa ggttacacat   2160
tttcatttat ttgtttttct gatttgaagg tataaccttc atgatgaatt acttcttcag   2220
ggtgttaagg cagtgacttt agaaacaaat ttttttcttg cttttgtttt gtttttgaga   2280
ccgaatctca ctctgttgcc caggctggag tgcagtggtg cgatcttggc tcactgcaac   2340
ttctacctcc gaggttcaag agattcttgt gcctcagcct cccggatagc tgccg        2395
```

<210> SEQ ID NO 70
<211> LENGTH: 74
<212> TYPE: PRT
<213> ORGANISM: Homo sapiens -continued

<400> SEQUENCE: 70

```
Met Ala Phe Leu Val His Ser Gln Pro Val Ile Leu Gly Phe Thr Val
1               5                   10                  15

Leu Leu Ser Tyr Ile Leu Arg Tyr Gln Leu Leu Phe Phe Lys Phe Val
            20                  25                  30

Phe Ile Leu Phe Asp Lys Lys Pro Ala Leu Ala Thr His Thr His Asn
        35                  40                  45

Lys Ser His Phe Lys Ile Val Ala Gln Thr Pro Arg Lys Lys Arg Lys
    50                  55                  60

Glu Lys Leu Glu Gln Gln Gln Gln Lys Asn
65                  70
```

<210> SEQ ID NO 71
<211> LENGTH: 55
<212> TYPE: PRT
<213> ORGANISM: Homo sapiens

<400> SEQUENCE: 71

```
Met Thr Leu Leu Val Phe Thr Ser His Val Gln Cys Pro Asn Arg Gln
1               5                   10                  15

Cys Lys Lys Tyr Pro Val Trp Phe Asn Arg Lys Ser Val Tyr Val Ser
            20                  25                  30

Leu Phe Glu Thr Ser Phe Thr Leu Ser Gly Ser Leu Ser Ser Met Lys
        35                  40                  45

Ser Ala Arg Asn Ile Gly Trp
    50                  55
```

<210> SEQ ID NO 72
<211> LENGTH: 52
<212> TYPE: PRT
<213> ORGANISM: Homo sapiens

<400> SEQUENCE: 72

```
Met Glu Thr Asn Phe Val Glu Leu Leu Pro Phe Asp Leu Gly Leu Glu
1               5                   10                  15

Tyr Glu Leu Leu Tyr Asn Ser Tyr Ser Tyr Leu Ala Asn Ala Gln Phe
            20                  25                  30

Ser Ile Thr Ser Leu Met Ala Phe Thr Arg Lys Ala Val Leu Glu Ala
        35                  40                  45

Ile Val Ile His
    50
```

<210> SEQ ID NO 73
<211> LENGTH: 45
<212> TYPE: PRT
<213> ORGANISM: Homo sapiens

<400> SEQUENCE: 73

```
Met Tyr Phe Ala Met Lys Leu Pro Leu Gly Leu Ile Ile Ser Ile Pro
1               5                   10                  15

Leu Leu Arg Asn Val Gln Met Ile Leu Tyr Ser Thr Thr Leu Val Pro
            20                  25                  30

Leu Cys Met Thr Val Arg Phe Phe Phe Phe Leu Leu Phe
        35                  40                  45
```

<210> SEQ ID NO 74
<211> LENGTH: 43
<212> TYPE: PRT
<213> ORGANISM: Homo sapiens -continued

<400> SEQUENCE: 74

Met Asp Arg Glu Asn Gln Ile Ser Ser Tyr Asn Cys Leu Ala Asn Gly
1               5                   10                  15

Ile Ser Gly Ser Phe Ser Ala Ser His Phe Arg Leu His Ser Leu Thr
            20                  25                  30

Leu Leu His Phe Lys Ile Pro Ala Phe Ile Phe
        35                  40

<210> SEQ ID NO 75
<211> LENGTH: 37
<212> TYPE: PRT
<213> ORGANISM: Homo sapiens

<400> SEQUENCE: 75

Met Cys Cys Phe Gly Tyr Thr His Ser Phe Phe Phe Asn Arg Ile Tyr
1               5                   10                  15

Cys Leu Val Ser Leu Trp Thr Gly Thr Val Asp Ala His Leu Lys Val
            20                  25                  30

Lys Cys His Phe Phe
        35

<210> SEQ ID NO 76
<211> LENGTH: 35
<212> TYPE: PRT
<213> ORGANISM: Homo sapiens

<400> SEQUENCE: 76

Met Phe Ser Val Gln Thr Gly Asn Val Lys Ser Ile Leu Cys Gly Leu
1               5                   10                  15

Thr Gly Asn Leu Phe Met Ser Leu Tyr Leu Lys Pro Val Leu Leu Ser
            20                  25                  30

Val Val Leu
        35

<210> SEQ ID NO 77
<211> LENGTH: 34
<212> TYPE: PRT
<213> ORGANISM: Homo sapiens

<400> SEQUENCE: 77

Met Ile Tyr Phe Leu Lys Ser Asn Phe Asn Ser Ser Cys Leu Thr Glu
1               5                   10                  15

Ala Cys Gln Tyr Met Cys Cys Ile Phe Phe Ala Phe Val Glu Lys Leu
            20                  25                  30

His Ile

<210> SEQ ID NO 78
<211> LENGTH: 34
<212> TYPE: PRT
<213> ORGANISM: Homo sapiens

<400> SEQUENCE: 78

Met Pro Arg Ala Ile Val Phe Pro Pro Phe Phe Ala Ser Phe Ser Tyr
1               5                   10                  15

Pro Leu Phe Gln Leu Gln Met Pro Lys Lys Met Pro Thr Asp Thr Thr
            20                  25                  30

Leu Pro

-continued

<210> SEQ ID NO 79
<211> LENGTH: 190
<212> TYPE: PRT
<213> ORGANISM: Homo sapiens

<400> SEQUENCE: 79

```
Met Ala Thr His His Thr Leu Trp Met Gly Leu Ala Leu Leu Gly Val
1               5                   10                  15

Leu Gly Asp Leu Gln Ala Ala Pro Glu Ala Gln Val Ser Val Gln Pro
            20                  25                  30

Asn Phe Gln Gln Asp Lys Phe Leu Gly Arg Trp Phe Ser Ala Gly Leu
        35                  40                  45

Ala Ser Asn Ser Ser Trp Leu Arg Glu Lys Lys Ala Ala Leu Ser Met
    50                  55                  60

Cys Lys Ser Val Val Ala Pro Ala Thr Asp Gly Gly Leu Asn Leu Thr
65                  70                  75                  80

Ser Thr Phe Leu Arg Lys Asn Gln Cys Glu Thr Arg Thr Met Leu Leu
                85                  90                  95

Gln Pro Ala Gly Ser Leu Gly Ser Tyr Ser Tyr Arg Ser Pro His Trp
            100                 105                 110

Gly Ser Thr Tyr Ser Val Ser Val Val Glu Thr Asp Tyr Asp Gln Tyr
        115                 120                 125

Ala Leu Leu Tyr Ser Gln Gly Ser Lys Gly Pro Gly Glu Asp Phe Arg
    130                 135                 140

Met Ala Thr Leu Tyr Ser Arg Thr Gln Thr Pro Arg Ala Glu Leu Lys
145                 150                 155                 160

Glu Lys Phe Thr Ala Phe Cys Lys Ala Gln Gly Phe Thr Glu Asp Thr
                165                 170                 175

Ile Val Phe Leu Pro Gln Thr Asp Lys Cys Met Thr Glu Gln
            180                 185                 190
```

<210> SEQ ID NO 80
<211> LENGTH: 170
<212> TYPE: PRT
<213> ORGANISM: Homo sapiens

<400> SEQUENCE: 80

```
Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Gly Gly Asp
        35                  40                  45

Arg Gly Ala Pro Lys Arg Gly Ser Gly Lys Asp Ser His His Pro Ala
    50                  55                  60

Arg Thr Ala His Tyr Gly Ser Leu Pro Gln Lys Ser His Gly Arg Thr
65                  70                  75                  80

Gln Asp Glu Asn Pro Val Val His Phe Phe Lys Asn Ile Val Thr Pro
                85                  90                  95

Arg Thr Pro Pro Pro Ser Gln Gly Lys Gly Arg Gly Leu Ser Leu Ser
            100                 105                 110

Arg Phe Ser Trp Gly Ala Glu Gly Gln Arg Pro Gly Phe Gly Tyr Gly
        115                 120                 125

Gly Arg Ala Ser Asp Tyr Lys Ser Ala His Lys Gly Phe Lys Gly Val
    130                 135                 140

Asp Ala Gln Gly Thr Leu Ser Lys Ile Phe Lys Leu Gly Gly Arg Asp
```

-continued

```
145                 150                 155                 160

Ser Arg Ser Gly Ser Pro Met Ala Arg Arg
                165                 170


<210> SEQ ID NO 81
<211> LENGTH: 38
<212> TYPE: PRT
<213> ORGANISM: Homo sapiens

<400> SEQUENCE: 81

Ile Arg Ser Ala Lys Leu Gly Phe Cys Cys Leu Asn Ser Ala Leu Gly
1               5                   10                  15

Pro Gln Ile Asn Arg Cys Glu Cys Ser Phe Phe Pro Leu Cys Glu Glu
            20                  25                  30

Ala Val Thr Pro Gln Gln
        35


<210> SEQ ID NO 82
<211> LENGTH: 38
<212> TYPE: PRT
<213> ORGANISM: Homo sapiens

<400> SEQUENCE: 82

Leu Leu Gly Cys Asn Cys Phe Phe Thr Gln Gly Glu Lys Thr Thr Phe
1               5                   10                  15

Thr Ser Val Tyr Leu Arg Thr Gln Cys Arg Val Gln Ala Ala Lys Pro
            20                  25                  30

Gln Leu Ser Arg Ser Asn
        35


<210> SEQ ID NO 83
<211> LENGTH: 37
<212> TYPE: PRT
<213> ORGANISM: Homo sapiens

<400> SEQUENCE: 83

Phe Ile Tyr Lys Lys Ile Lys Leu Glu Ile Val Leu Asp Phe Ser Ser
1               5                   10                  15

Tyr Cys Trp Gly Val Thr Ala Ser Ser His Arg Gly Lys Lys Leu His
            20                  25                  30

Ser His Arg Phe Ile
        35


<210> SEQ ID NO 84
<211> LENGTH: 335
<212> TYPE: PRT
<213> ORGANISM: Homo sapiens

<400> SEQUENCE: 84

Met Gly Ala Ser Ser Ser Ser Ala Leu Ala Arg Leu Gly Leu Pro Ala
1               5                   10                  15

Arg Pro Trp Pro Arg Trp Leu Gly Val Ala Ala Leu Gly Leu Ala Ala
            20                  25                  30

Val Ala Leu Gly Thr Val Ala Trp Arg Arg Ala Trp Pro Arg Arg Arg
        35                  40                  45

Arg Arg Leu Gln Gln Val Gly Thr Val Ala Lys Leu Trp Ile Tyr Pro
    50                  55                  60

Val Lys Ser Cys Lys Gly Val Pro Val Ser Glu Ala Glu Cys Thr Ala
65                  70                  75                  80
```

-continued

```
Met Gly Leu Arg Ser Gly Asn Leu Arg Asp Arg Phe Trp Leu Val Ile
                85                  90                  95

Lys Glu Asp Gly His Met Val Thr Ala Arg Gln Glu Pro Arg Leu Val
            100                 105                 110

Leu Ile Ser Ile Ile Tyr Glu Asn Asn Cys Leu Ile Phe Arg Ala Pro
        115                 120                 125

Asp Met Asp Gln Leu Val Leu Pro Ser Lys Gln Pro Ser Ser Asn Lys
    130                 135                 140

Leu His Asn Cys Arg Ile Phe Gly Leu Asp Ile Lys Gly Arg Asp Cys
145                 150                 155                 160

Gly Asn Glu Ala Ala Lys Trp Phe Thr Asn Phe Leu Lys Thr Glu Ala
                165                 170                 175

Tyr Arg Leu Val Gln Phe Glu Thr Asn Met Lys Gly Arg Thr Ser Arg
            180                 185                 190

Lys Leu Leu Pro Thr Leu Asp Gln Asn Phe Gln Val Ala Tyr Pro Asp
        195                 200                 205

Tyr Cys Pro Leu Leu Ile Met Thr Asp Ala Ser Leu Val Asp Leu Asn
    210                 215                 220

Thr Arg Met Glu Lys Lys Met Lys Met Glu Asn Phe Arg Pro Asn Ile
225                 230                 235                 240

Val Val Thr Gly Cys Asp Ala Phe Glu Glu Asp Thr Trp Asp Glu Leu
                245                 250                 255

Leu Ile Gly Ser Val Glu Val Lys Lys Val Met Ala Cys Pro Arg Cys
            260                 265                 270

Ile Leu Thr Thr Val Asp Pro Asp Thr Gly Val Ile Asp Arg Lys Gln
        275                 280                 285

Pro Leu Asp Thr Leu Lys Ser Tyr Arg Leu Cys Asp Pro Ser Glu Arg
    290                 295                 300

Glu Leu Tyr Lys Leu Ser Pro Leu Phe Gly Ile Tyr Tyr Ser Val Glu
305                 310                 315                 320

Lys Ile Gly Ser Leu Arg Val Gly Asp Pro Val Tyr Arg Met Val
                325                 330                 335


<210> SEQ ID NO 85
<211> LENGTH: 459
<212> TYPE: PRT
<213> ORGANISM: Homo sapiens

<400> SEQUENCE: 85

Met Ile Lys Arg Phe Leu Glu Asp Thr Thr Asp Asp Gly Glu Leu Ser
1               5                   10                  15

Lys Phe Val Lys Asp Phe Ser Gly Asn Ala Ser Cys His Pro Pro Glu
            20                  25                  30

Ala Lys Thr Trp Ala Ser Arg Pro Gln Val Pro Glu Pro Arg Pro Gln
        35                  40                  45

Ala Pro Asp Leu Tyr Asp Asp Asp Leu Glu Phe Arg Pro Pro Ser Arg
    50                  55                  60

Pro Gln Ser Ser Asp Asn Gln Gln Tyr Phe Cys Ala Pro Ala Pro Leu
65                  70                  75                  80

Ser Pro Ser Ala Arg Pro Arg Ser Pro Trp Gly Lys Leu Asp Pro Tyr
                85                  90                  95

Asp Ser Ser Glu Asp Asp Lys Glu Tyr Val Gly Phe Ala Thr Leu Pro
            100                 105                 110

Asn Gln Val His Arg Lys Ser Val Lys Lys Gly Phe Asp Phe Thr Leu
        115                 120                 125
```

-continued

```
Met Val Ala Gly Glu Ser Gly Leu Gly Lys Ser Thr Leu Val Asn Ser
    130                 135                 140

Leu Phe Leu Thr Asp Leu Tyr Arg Asp Arg Lys Leu Leu Gly Ala Glu
145                 150                 155                 160

Glu Arg Ile Met Gln Thr Val Glu Ile Thr Lys His Ala Val Asp Ile
                165                 170                 175

Glu Glu Lys Gly Val Arg Leu Arg Leu Thr Ile Val Asp Thr Pro Gly
            180                 185                 190

Phe Gly Asp Ala Val Asn Asn Thr Glu Cys Trp Lys Pro Val Ala Glu
        195                 200                 205

Tyr Ile Asp Gln Gln Phe Glu Gln Tyr Phe Arg Asp Glu Ser Gly Leu
    210                 215                 220

Asn Arg Lys Asn Ile Gln Asp Asn Arg Val His Cys Cys Leu Tyr Phe
225                 230                 235                 240

Ile Ser Pro Phe Gly His Gly Leu Arg Pro Leu Asp Val Glu Phe Met
                245                 250                 255

Lys Ala Leu His Gln Arg Val Asn Ile Val Pro Ile Leu Ala Lys Ala
            260                 265                 270

Asp Thr Leu Thr Pro Pro Glu Val Asp His Lys Lys Arg Lys Ile Arg
        275                 280                 285

Glu Glu Ile Glu His Phe Gly Ile Lys Ile Tyr Gln Phe Pro Asp Cys
    290                 295                 300

Asp Ser Asp Glu Asp Glu Asp Phe Lys Leu Gln Asp Gln Ala Leu Lys
305                 310                 315                 320

Glu Ser Ile Pro Phe Ala Val Ile Gly Ser Asn Thr Val Val Glu Ala
                325                 330                 335

Arg Gly Arg Arg Val Arg Gly Arg Leu Tyr Pro Trp Gly Ile Val Glu
            340                 345                 350

Val Glu Asn Pro Gly His Cys Asp Phe Val Lys Leu Arg Thr Met Leu
        355                 360                 365

Val Arg Thr His Met Gln Asp Leu Lys Asp Val Thr Arg Glu Thr His
    370                 375                 380

Tyr Glu Asn Tyr Arg Ala Gln Cys Ile Gln Ser Met Thr Arg Leu Val
385                 390                 395                 400

Val Lys Glu Arg Asn Arg Asn Lys Leu Thr Arg Glu Ser Gly Thr Asp
                405                 410                 415

Phe Pro Ile Pro Ala Val Pro Pro Gly Thr Asp Pro Glu Thr Glu Lys
            420                 425                 430

Leu Ile Arg Glu Lys Asp Glu Glu Leu Arg Arg Met Gln Glu Met Leu
        435                 440                 445

His Lys Ile Gln Lys Gln Met Lys Glu Asn Tyr
    450                 455


<210> SEQ ID NO 86
<211> LENGTH: 142
<212> TYPE: PRT
<213> ORGANISM: Homo sapiens

<400> SEQUENCE: 86

Met Ala Thr Lys Ile Asp Lys Glu Ala Cys Arg Ala Ala Tyr Asn Leu
1               5                   10                  15

Val Arg Asp Asp Gly Ser Ala Val Ile Trp Val Thr Phe Lys Tyr Asp
            20                  25                  30

Gly Ser Thr Ile Val Pro Gly Glu Gln Gly Ala Glu Tyr Gln His Phe
```

-continued

```
        35                  40                  45

Ile Gln Gln Cys Thr Asp Asp Val Arg Leu Phe Ala Phe Val Arg Phe
    50                  55                  60

Thr Thr Gly Asp Ala Met Ser Lys Arg Ser Lys Phe Ala Leu Ile Thr
65                  70                  75                  80

Trp Ile Gly Glu Asn Val Ser Gly Leu Gln Arg Ala Lys Thr Gly Thr
                85                  90                  95

Asp Lys Thr Leu Val Lys Glu Val Val Gln Asn Phe Ala Lys Glu Phe
            100                 105                 110

Val Ile Ser Asp Arg Lys Glu Leu Glu Glu Asp Phe Ile Lys Ser Glu
        115                 120                 125

Leu Lys Lys Ala Gly Gly Ala Asn Tyr Asp Ala Gln Thr Glu
    130                 135                 140


<210> SEQ ID NO 87
<211> LENGTH: 449
<212> TYPE: PRT
<213> ORGANISM: Homo sapiens

<400> SEQUENCE: 87

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270
```

-continued

```
Glu Phe Ile Arg Glu Gly Asp Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
    370                 375                 380

Arg Val Thr Thr Val Ala Ser His Thr Ser Asp Ser Asp Val Pro Ser
385                 390                 395                 400

Gly Val Thr Glu Val Val Val Lys Leu Phe Asp Ser Asp Pro Ile Thr
                405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
        435                 440                 445

Glu
```

<210> SEQ ID NO 88
<211> LENGTH: 416
<212> TYPE: PRT
<213> ORGANISM: Homo sapiens

<400> SEQUENCE: 88

```
Met Glu Leu Arg Val Gly Asn Lys Tyr Arg Leu Gly Arg Lys Ile Gly
1               5                   10                  15

Ser Gly Ser Phe Gly Asp Ile Tyr Leu Gly Ala Asn Ile Ala Ser Gly
            20                  25                  30

Glu Glu Val Ala Ile Lys Leu Glu Cys Val Lys Thr Lys His Pro Gln
        35                  40                  45

Leu His Ile Glu Ser Lys Phe Tyr Lys Met Met Gln Gly Gly Val Gly
    50                  55                  60

Ile Pro Ser Ile Lys Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190
```

-continued

```
Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
    210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ser Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
        275                 280                 285

Asp Trp Asn Met Leu Lys Phe Gly Ala Ala Arg Asn Pro Glu Asp Val
    290                 295                 300

Asp Arg Glu Arg Arg Glu His Glu Arg Glu Glu Arg Met Gly Gln Leu
305                 310                 315                 320

Arg Gly Ser Ala Thr Arg Ala Leu Pro Pro Gly Pro Pro Thr Gly Ala
                325                 330                 335

Thr Ala Asn Arg Leu Arg Ser Ala Ala Glu Pro Val Ala Ser Thr Pro
            340                 345                 350

Ala Ser Arg Ile Gln Pro Ala Gly Asn Thr Ser Pro Arg Ala Ile Ser
        355                 360                 365

Arg Val Asp Arg Glu Arg Lys Val Ser Met Arg Leu His Arg Gly Ala
    370                 375                 380

Pro Ala Asn Val Ser Ser Ser Asp Leu Thr Gly Arg Gln Glu Val Ser
385                 390                 395                 400

Arg Ile Pro Ala Ser Gln Thr Ser Val Pro Phe Asp His Leu Gly Lys
                405                 410                 415


<210> SEQ ID NO 89
<211> LENGTH: 110
<212> TYPE: PRT
<213> ORGANISM: Homo sapiens

<400> SEQUENCE: 89

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Met
            100                 105                 110


<210> SEQ ID NO 90
<211> LENGTH: 814
<212> TYPE: PRT
<213> ORGANISM: Homo sapiens

<400> SEQUENCE: 90
```

-continued

```
Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45

Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Thr Pro
            180                 185                 190

Pro Glu His Pro Leu Gly Gln Arg His Ile Arg Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
    370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
```

-continued

```
            420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
    450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
        515                 520                 525

Gln Gln Cys Gln Ser Leu Trp Gly Pro Gly Ala Gln Pro Ala Ala Pro
    530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
                565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
    610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
    690                 695                 700

Leu Leu Val Leu Val Met Leu Gly Ala Gly Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Ser Gln Gly Pro Ala Lys Pro Pro Pro
        755                 760                 765

Pro Arg Lys Pro Leu Pro Ala Asp Pro Gln Gly Arg Cys Pro Ser Gly
    770                 775                 780

Asp Leu Pro Gly Pro Gly Ala Gly Ile Pro Pro Leu Val Val Pro Ser
785                 790                 795                 800

Arg Pro Ala Pro Pro Pro Pro Thr Val Ser Ser Leu Tyr Leu
                805                 810
```

<210> SEQ ID NO 91
<211> LENGTH: 55
<212> TYPE: PRT
<213> ORGANISM: Homo sapiens -continued

<400> SEQUENCE: 91

```
Met Asn Leu Ser Phe Arg Glu Phe Asn Gln Glu Lys Arg Val Gly Gly
1               5                   10                  15

Ile Ser Trp Gly Pro Lys Gly Arg Leu Ser Gly Ile Phe Ser Thr Ile
            20                  25                  30

Gln Asn Gln Gln Gln Ser Gln Lys Arg Gly Met Ser Ser Asn Ser Leu
        35                  40                  45

Lys Arg Thr Pro Gln Asn Ser
    50                  55
```

<210> SEQ ID NO 92
<211> LENGTH: 54
<212> TYPE: PRT
<213> ORGANISM: Homo sapiens

<400> SEQUENCE: 92

```
Met Gly Asn Gln Arg Trp His Ala Lys Phe Asn Ser Gly Leu Arg Tyr
1               5                   10                  15

Pro His Cys Pro His Gln Ala Ser Pro Ala Leu Thr Val Glu Pro His
            20                  25                  30

Gly Glu Glu His Val Leu Glu Arg Asp Pro Phe Val Asn Cys Phe Val
        35                  40                  45

Val Phe Ser Ser Met Asn
    50
```

<210> SEQ ID NO 93
<211> LENGTH: 51
<212> TYPE: PRT
<213> ORGANISM: Homo sapiens

<400> SEQUENCE: 93

```
Met Leu Cys Ala Gln Gly Ala Ala Gly Cys Gln Gln His Leu Ser Leu
1               5                   10                  15

Asn Thr Ile Ser Leu Cys Ala Glu Lys Thr Gly Asn Gln Arg Ile Asn
            20                  25                  30

Ile Thr Ser Pro Gly Trp Arg Thr Ile Ser Cys Asp Phe Ala Ala Glu
        35                  40                  45

Phe Thr His
    50
```

<210> SEQ ID NO 94
<211> LENGTH: 43
<212> TYPE: PRT
<213> ORGANISM: Homo sapiens

<400> SEQUENCE: 94

```
Met Pro Pro Leu Ile Pro His Ala Ala Lys Arg Ile Gly Thr Leu Ser
1               5                   10                  15

Gly Pro Gly Thr Val Val Met Ala Ile Ser Tyr Phe Thr His Thr Arg
            20                  25                  30

Pro Phe Lys Val Ser Leu Pro Gln Ala Ile Lys
        35                  40
```

<210> SEQ ID NO 95
<211> LENGTH: 39
<212> TYPE: PRT
<213> ORGANISM: Homo sapiens

<400> SEQUENCE: 95

```
Met Val Glu Asn Ile Pro Glu Ser Leu Pro Phe Gly Pro Gln Leu Met
1               5                   10                  15

Pro Pro Thr Leu Phe Ser Trp Leu Asn Ser Leu Lys Glu Arg Phe Met
            20                  25                  30

Cys Tyr Cys Pro Val Ser Gln
        35


<210> SEQ ID NO 96
<211> LENGTH: 36
<212> TYPE: PRT
<213> ORGANISM: Homo sapiens

<400> SEQUENCE: 96

Met Ser Gln Cys Thr Ser Tyr Pro Leu Ile Gln Lys Glu Glu His Phe
1               5                   10                  15

Ala Gln Arg Lys Ile Lys Arg Ser Met Asn Val Ile Phe Tyr Leu Leu
            20                  25                  30

Phe Ser Val Gly
        35


<210> SEQ ID NO 97
<211> LENGTH: 33
<212> TYPE: PRT
<213> ORGANISM: Homo sapiens

<400> SEQUENCE: 97

Met Gly Ser Ser Leu Pro Ile Gly Phe Leu Leu His Thr Ala Gly Leu
1               5                   10                  15

Ser Leu Tyr Phe Lys Lys Lys Lys Lys Lys Lys Lys Asp Lys Asn Cys
            20                  25                  30

His


<210> SEQ ID NO 98
<211> LENGTH: 317
<212> TYPE: PRT
<213> ORGANISM: Homo sapiens

<400> SEQUENCE: 98

Met Ser Glu Gly Val Gly Thr Phe Arg Met Val Pro Glu Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Glu Glu Ala Val Arg
    50                  55                  60

Glu Leu Gln Glu Met Val Gln Ala Gln Ala Ala Ser Gly Glu Glu Leu
65                  70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Ile Glu Ala Gly Tyr
    130                 135                 140

Pro Gly Val Leu Ser Ser Arg Asp Lys Tyr Gly Arg Val Val Met Leu
```

-continued 145 150 155 160

Phe Asn Ile Glu Asn Trp Gln Ser Gln Glu Ile Thr Phe Asp Glu Ile
165 170 175

Leu Gln Ala Tyr Cys Phe Ile Leu Glu Lys Leu Leu Glu Asn Glu Glu
180 185 190

Thr Gln Ile Asn Gly Phe Cys Ile Ile Glu Asn Phe Lys Gly Phe Thr
195 200 205

Met Gln Gln Ala Ala Ser Leu Arg Thr Ser Asp Leu Arg Lys Met Val
210 215 220

Asp Met Leu Gln Asp Ser Phe Pro Ala Arg Phe Lys Ala Ile His Phe
225 230 235 240

Ile His Gln Pro Trp Tyr Phe Thr Thr Thr Tyr Asn Val Val Lys Pro
245 250 255

Phe Leu Lys Ser Lys Leu Leu Glu Arg Val Phe Val His Gly Asp Asp
260 265 270

Leu Ser Gly Phe Tyr Gln Glu Ile Asp Glu Asn Ile Leu Pro Ser Asp
275 280 285

Phe Gly Gly Thr Leu Pro Lys Tyr Asp Gly Lys Ala Val Ala Glu Gln
290 295 300

Leu Phe Gly Pro Gln Ala Gln Ala Glu Asn Thr Ala Phe
305 310 315

<210> SEQ ID NO 99
<211> LENGTH: 375
<212> TYPE: PRT
<213> ORGANISM: Homo sapiens

<400> SEQUENCE: 99

Met Glu Glu Glu Ile Ala Ala Leu Val Ile Asp Asn Gly Ser Gly Met
1 5 10 15

Cys Lys Ala Gly Phe Ala Gly Asp Asp Ala Pro Arg Ala Val Phe Pro
20 25 30

Ser Ile Val Gly Arg Pro Arg His Gln Gly Val Met Val Gly Met Gly
35 40 45

Gln Lys Asp Ser Tyr Val Gly Asp Glu Ala Gln Ser Lys Arg Gly Ile
50 55 60

Leu Thr Leu Lys Tyr Pro Ile Glu His Gly Ile Val Thr Asn Trp Asp
65 70 75 80

Asp Met Glu Lys Ile Trp His His Thr Phe Tyr Asn Glu Leu Arg Val
85 90 95

Ala Pro Glu Glu His Pro Val Leu Leu Thr Glu Ala Pro Leu Asn Pro
100 105 110

Lys Ala Asn Arg Glu Lys Met Thr Gln Ile Met Phe Glu Thr Phe Asn
115 120 125

Thr Pro Ala Met Tyr Val Ala Ile Gln Ala Val Leu Ser Leu Tyr Ala
130 135 140

Ser Gly Arg Thr Thr Gly Ile Val Met Asp Ser Gly Asp Gly Val Thr
145 150 155 160

His Thr Val Pro Ile Tyr Glu Gly Tyr Ala Leu Pro His Ala Ile Leu
165 170 175

Arg Leu Asp Leu Ala Gly Arg Asp Leu Thr Asp Tyr Leu Met Lys Ile
180 185 190

Leu Thr Glu Arg Gly Tyr Ser Phe Thr Thr Thr Ala Glu Arg Glu Ile
195 200 205

-continued

```
Val Arg Asp Ile Lys Glu Lys Leu Cys Tyr Val Ala Leu Asp Phe Glu
    210                 215                 220

Gln Glu Met Ala Thr Ala Ala Ser Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375


<210> SEQ ID NO 100
<211> LENGTH: 582
<212> TYPE: PRT
<213> ORGANISM: Homo sapiens

<400> SEQUENCE: 100

Met Ser Pro Ala Pro Arg Pro Ser Arg Cys Leu Leu Leu Pro Leu Leu
1               5                   10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205
```

-continued

```
Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
        435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Glu Thr Glu Val Ile Ile Ile Glu
        515                 520                 525

Val Asp Glu Glu Gly Gly Gly Ala Val Ser Ala Ala Ala Val Val Leu
    530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
            580
```

<210> SEQ ID NO 101
<211> LENGTH: 2285
<212> TYPE: PRT
<213> ORGANISM: Homo sapiens -continued

<400> SEQUENCE: 101

```
Met Ala Ala Gln Val Ala Pro Ala Ala Ala Ser Ser Leu Gly Asn Pro
1               5                   10                  15

Pro Pro Pro Pro Pro Ser Glu Leu Lys Lys Ala Glu Gln Gln Gln Arg
            20                  25                  30

Glu Glu Ala Gly Gly Glu Ala Ala Ala Ala Ala Ala Ala Glu Arg Gly
        35                  40                  45

Glu Met Lys Ala Ala Ala Gly Gln Glu Ser Glu Gly Pro Ala Val Gly
    50                  55                  60

Pro Pro Gln Pro Leu Gly Lys Glu Leu Gln Asp Gly Ala Glu Ser Asn
65                  70                  75                  80

Gly Gly Gly Gly Gly Gly Gly Ala Gly Ser Gly Gly Gly Pro Gly Ala
                85                  90                  95

Glu Pro Asp Leu Lys Asn Ser Asn Gly Asn Ala Gly Pro Arg Pro Ala
            100                 105                 110

Leu Asn Asn Asn Leu Thr Glu Pro Pro Gly Gly Gly Gly Gly Gly Ser
        115                 120                 125

Ser Asp Gly Val Gly Ala Pro Pro His Ser Ala Ala Ala Ala Leu Pro
    130                 135                 140

Pro Pro Ala Tyr Gly Phe Gly Gln Pro Tyr Gly Arg Ser Pro Ser Ala
145                 150                 155                 160

Val Ala Ala Ala Ala Ala Ala Val Phe His Gln Gln His Gly Gly Gln
                165                 170                 175

Gln Ser Pro Gly Leu Ala Ala Leu Gln Ser Gly Gly Gly Gly Gly Leu
            180                 185                 190

Glu Pro Tyr Ala Gly Pro Gln Gln Asn Ser His Asp His Gly Phe Pro
        195                 200                 205

Asn His Gln Tyr Asn Ser Tyr Tyr Pro Asn Arg Ser Ala Tyr Pro Pro
    210                 215                 220

Pro Ala Pro Ala Tyr Ala Leu Ser Ser Pro Arg Gly Gly Thr Pro Gly
225                 230                 235                 240

Ser Gly Ala Ala Ala Ala Ala Gly Ser Lys Pro Pro Pro Ser Ser Ser
                245                 250                 255

Ala Ser Ala Ser Ser Ser Ser Ser Ser Phe Ala Gln Gln Arg Phe Gly
            260                 265                 270

Ala Met Gly Gly Gly Gly Pro Ser Ala Ala Gly Gly Gly Thr Pro Gln
        275                 280                 285

Pro Thr Ala Thr Pro Thr Leu Asn Gln Leu Leu Thr Ser Pro Ser Ser
    290                 295                 300

Ala Arg Gly Tyr Gln Gly Tyr Pro Gly Gly Asp Tyr Ser Gly Gly Pro
305                 310                 315                 320

Gln Asp Gly Gly Ala Gly Lys Gly Pro Ala Asp Met Ala Ser Gln Cys
                325                 330                 335

Trp Gly Ala Ala Ala Ala Ala Ala Ala Ala Ala Ala Ala Ser Gly Gly
            340                 345                 350

Ala Gln Gln Arg Ser His His Ala Pro Met Ser Pro Gly Ser Ser Gly
        355                 360                 365

Gly Gly Gly Gln Pro Leu Ala Arg Thr Pro Gln Pro Ser Ser Pro Met
    370                 375                 380

Asp Gln Met Gly Lys Met Arg Pro Gln Pro Tyr Gly Gly Thr Asn Pro
385                 390                 395                 400

Tyr Ser Gln Gln Gln Gly Pro Pro Ser Gly Pro Gln Gln Gly His Gly
                405                 410                 415
```

-continued

```
Tyr Pro Gly Gln Pro Tyr Gly Ser Gln Thr Pro Gln Arg Tyr Pro Met
            420                 425                 430

Thr Met Gln Gly Arg Ala Gln Ser Ala Met Gly Gly Leu Ser Tyr Thr
        435                 440                 445

Gln Gln Ile Pro Pro Tyr Gly Gln Gln Gly Pro Ser Gly Tyr Gly Gln
    450                 455                 460

Gln Gly Gln Thr Pro Tyr Tyr Asn Gln Gln Ser Pro His Pro Gln Gln
465                 470                 475                 480

Gln Gln Pro Pro Tyr Ser Gln Gln Pro Pro Ser Gln Thr Pro His Ala
                485                 490                 495

Gln Pro Ser Tyr Gln Gln Gln Pro Gln Ser Gln Pro Pro Gln Leu Gln
            500                 505                 510

Ser Ser Gln Pro Pro Tyr Ser Gln Gln Pro Ser Gln Pro Pro His Gln
        515                 520                 525

Gln Ser Pro Ala Pro Tyr Pro Ser Gln Gln Ser Thr Thr Gln Gln His
    530                 535                 540

Pro Gln Ser Gln Pro Pro Tyr Ser Gln Pro Gln Ala Gln Ser Pro Tyr
545                 550                 555                 560

Gln Gln Gln Gln Pro Gln Gln Pro Ala Pro Ser Thr Leu Ser Gln Gln
                565                 570                 575

Ala Ala Tyr Pro Gln Pro Gln Ser Gln Gln Ser Gln Gln Thr Ala Tyr
            580                 585                 590

Ser Gln Gln Arg Phe Pro Pro Pro Gln Glu Leu Ser Gln Asp Ser Phe
        595                 600                 605

Gly Ser Gln Ala Ser Ser Ala Pro Ser Met Thr Ser Ser Lys Gly Gly
    610                 615                 620

Gln Glu Asp Met Asn Leu Ser Leu Gln Ser Arg Pro Ser Ser Leu Pro
625                 630                 635                 640

Asp Leu Ser Gly Ser Ile Asp Asp Leu Pro Met Gly Thr Glu Gly Ala
                645                 650                 655

Leu Ser Pro Gly Val Ser Thr Ser Gly Ile Ser Ser Ser Gln Gly Glu
            660                 665                 670

Gln Ser Asn Pro Ala Gln Ser Pro Phe Ser Pro His Thr Ser Pro His
        675                 680                 685

Leu Pro Gly Ile Arg Gly Pro Ser Pro Ser Pro Val Gly Ser Pro Ala
    690                 695                 700

Ser Val Ala Gln Ser Arg Ser Gly Pro Leu Ser Pro Ala Ala Val Pro
705                 710                 715                 720

Gly Asn Gln Met Pro Pro Arg Pro Pro Ser Gly Gln Ser Asp Ser Ile
                725                 730                 735

Met His Pro Ser Met Asn Gln Ser Ser Ile Ala Gln Asp Arg Gly Tyr
            740                 745                 750

Met Gln Arg Asn Pro Gln Met Pro Gln Tyr Ser Ser Pro Gln Pro Gly
        755                 760                 765

Ser Ala Leu Ser Pro Arg Gln Pro Ser Gly Gly Gln Ile His Thr Gly
    770                 775                 780

Met Gly Ser Tyr Gln Gln Asn Ser Met Gly Ser Tyr Gly Pro Gln Gly
785                 790                 795                 800

Gly Gln Tyr Gly Pro Gln Gly Gly Tyr Pro Arg Gln Pro Asn Tyr Asn
                805                 810                 815

Ala Leu Pro Asn Ala Asn Tyr Pro Ser Ala Gly Met Ala Gly Gly Ile
            820                 825                 830
```

-continued

```
Asn Pro Met Gly Ala Gly Gly Gln Met His Gly Gln Pro Gly Ile Pro
        835                 840                 845

Pro Tyr Gly Thr Leu Pro Pro Gly Arg Met Ser His Ala Ser Met Gly
    850                 855                 860

Asn Arg Pro Tyr Gly Pro Asn Met Ala Asn Met Pro Pro Gln Val Gly
865                 870                 875                 880

Ser Gly Met Cys Pro Pro Pro Gly Gly Met Asn Arg Lys Thr Gln Glu
                885                 890                 895

Thr Ala Val Ala Met His Val Ala Ala Asn Ser Ile Gln Asn Arg Pro
            900                 905                 910

Pro Gly Tyr Pro Asn Met Asn Gln Gly Gly Met Met Gly Thr Gly Pro
        915                 920                 925

Pro Tyr Gly Gln Gly Ile Asn Ser Met Ala Gly Met Ile Asn Pro Gln
    930                 935                 940

Gly Pro Pro Tyr Ser Met Gly Gly Thr Met Ala Asn Asn Ser Ala Gly
945                 950                 955                 960

Met Ala Ala Ser Pro Glu Met Met Gly Leu Gly Asp Val Lys Leu Thr
                965                 970                 975

Pro Ala Thr Lys Met Asn Asn Lys Ala Asp Gly Thr Pro Lys Thr Glu
            980                 985                 990

Ser Lys Ser Lys Lys Ser Ser Ser  Ser Thr Thr Thr Asn  Glu Lys Ile
        995                 1000                1005

Thr Lys  Leu Tyr Glu Leu Gly  Gly Glu Pro Glu Arg  Lys Met Trp
    1010                 1015                 1020

Val Asp  Arg Tyr Leu Ala Phe  Thr Glu Glu Lys Ala  Met Gly Met
    1025                 1030                 1035

Thr Asn  Leu Pro Ala Val Gly  Arg Lys Pro Leu Asp  Leu Tyr Arg
    1040                 1045                 1050

Leu Tyr  Val Ser Val Lys Glu  Ile Gly Gly Leu Thr  Gln Val Asn
    1055                 1060                 1065

Lys Asn  Lys Lys Trp Arg Glu  Leu Ala Thr Asn Leu  Asn Val Gly
    1070                 1075                 1080

Thr Ser  Ser Ser Ala Ala Ser  Ser Leu Lys Lys Gln  Tyr Ile Gln
    1085                 1090                 1095

Cys Leu  Tyr Ala Phe Glu Cys  Lys Ile Glu Arg Gly  Glu Asp Pro
    1100                 1105                 1110

Pro Pro  Asp Ile Phe Ala Ala  Ala Asp Ser Lys Lys  Ser Gln Pro
    1115                 1120                 1125

Lys Ile  Gln Pro Pro Ser Pro  Ala Gly Ser Gly Ser  Met Gln Gly
    1130                 1135                 1140

Pro Gln  Thr Pro Gln Ser Thr  Ser Ser Ser Met Ala  Glu Gly Gly
    1145                 1150                 1155

Asp Leu  Lys Pro Pro Thr Pro  Ala Ser Thr Pro His  Ser Gln Ile
    1160                 1165                 1170

Pro Pro  Leu Pro Gly Met Ser  Arg Ser Asn Ser Val  Gly Ile Gln
    1175                 1180                 1185

Asp Ala  Phe Asn Asp Gly Ser  Asp Ser Thr Phe Gln  Lys Arg Asn
    1190                 1195                 1200

Ser Met  Thr Pro Asn Pro Gly  Tyr Gln Pro Ser Met  Asn Thr Ser
    1205                 1210                 1215

Asp Met  Met Gly Arg Met Ser  Tyr Glu Pro Asn Lys  Asp Pro Tyr
    1220                 1225                 1230

Gly Ser  Met Arg Lys Ala Pro  Gly Ser Asp Pro Phe  Met Ser Ser
```

-continued

```
    1235                1240                1245

Gly Gln  Gly Pro Asn Gly Gly  Met Gly Asp Pro Tyr  Ser Arg Ala
    1250                1255                1260

Ala Gly  Pro Gly Leu Gly Asn  Val Ala Met Gly Pro  Arg Gln His
    1265                1270                1275

Tyr Pro  Tyr Gly Gly Pro Tyr  Asp Arg Val Arg Thr  Glu Pro Gly
    1280                1285                1290

Ile Gly  Pro Glu Gly Asn Met  Ser Thr Gly Ala Pro  Gln Pro Asn
    1295                1300                1305

Leu Met  Pro Ser Asn Pro Asp  Ser Gly Met Tyr Ser  Pro Ser Arg
    1310                1315                1320

Tyr Pro  Pro Gln Gln Gln Gln  Gln Gln Gln Gln Arg  His Asp Ser
    1325                1330                1335

Tyr Gly  Asn Gln Phe Ser Thr  Gln Gly Thr Pro Ser  Gly Ser Pro
    1340                1345                1350

Phe Pro  Ser Gln Gln Thr Thr  Met Tyr Gln Gln Gln  Gln Gln Asn
    1355                1360                1365

Tyr Lys  Arg Pro Met Asp Gly  Thr Tyr Gly Pro Pro  Ala Lys Arg
    1370                1375                1380

His Glu  Gly Glu Met Tyr Ser  Val Pro Tyr Ser Thr  Gly Gln Gly
    1385                1390                1395

Gln Pro  Gln Gln Gln Gln Leu  Pro Pro Ala Gln Pro  Gln Pro Ala
    1400                1405                1410

Ser Gln  Gln Gln Ala Ala Gln  Pro Ser Pro Gln Gln  Asp Val Tyr
    1415                1420                1425

Asn Gln  Tyr Gly Asn Ala Tyr  Pro Ala Thr Ala Thr  Ala Ala Thr
    1430                1435                1440

Glu Arg  Arg Pro Ala Gly Gly  Pro Gln Asn Gln Phe  Pro Phe Gln
    1445                1450                1455

Phe Gly  Arg Asp Arg Val Ser  Ala Pro Pro Gly Thr  Asn Ala Gln
    1460                1465                1470

Gln Asn  Met Pro Pro Gln Met  Met Gly Gly Pro Ile  Gln Ala Ser
    1475                1480                1485

Ala Glu  Val Ala Gln Gln Gly  Thr Met Trp Gln Gly  Arg Asn Asp
    1490                1495                1500

Met Thr  Tyr Asn Tyr Ala Asn  Arg Gln Ser Thr Gly  Ser Ala Pro
    1505                1510                1515

Gln Gly  Pro Ala Tyr His Gly  Val Asn Arg Thr Asp  Glu Met Leu
    1520                1525                1530

His Thr  Asp Gln Arg Ala Asn  His Glu Gly Ser Trp  Pro Ser His
    1535                1540                1545

Gly Thr  Arg Gln Pro Pro Tyr  Gly Pro Ser Ala Pro  Val Pro Pro
    1550                1555                1560

Met Thr  Arg Pro Pro Pro Ser  Asn Tyr Gln Pro Pro  Pro Ser Met
    1565                1570                1575

Gln Asn  His Ile Pro Gln Val  Ser Ser Pro Ala Pro  Leu Pro Arg
    1580                1585                1590

Pro Met  Glu Asn Arg Thr Ser  Pro Ser Lys Ser Pro  Phe Leu His
    1595                1600                1605

Ser Gly  Met Lys Met Gln Lys  Ala Gly Pro Pro Val  Pro Ala Ser
    1610                1615                1620

His Ile  Ala Pro Ala Pro Val  Gln Pro Pro Met Ile  Arg Arg Asp
    1625                1630                1635
```

-continued

Ile Thr Phe Pro Pro Gly Ser Val Glu Ala Thr Gln Pro Val Leu
1640 1645 1650

Lys Gln Arg Arg Arg Leu Thr Met Lys Asp Ile Gly Thr Pro Glu
1655 1660 1665

Ala Trp Arg Val Met Met Ser Leu Lys Ser Gly Leu Leu Ala Glu
1670 1675 1680

Ser Thr Trp Ala Leu Asp Thr Ile Asn Ile Leu Leu Tyr Asp Asp
1685 1690 1695

Asn Ser Ile Met Thr Phe Asn Leu Ser Gln Leu Pro Gly Leu Leu
1700 1705 1710

Glu Leu Leu Val Glu Tyr Phe Arg Arg Cys Leu Ile Glu Ile Phe
1715 1720 1725

Gly Ile Leu Lys Glu Tyr Glu Val Gly Asp Pro Gly Gln Arg Thr
1730 1735 1740

Leu Leu Asp Pro Gly Arg Phe Ser Lys Val Ser Ser Pro Ala Pro
1745 1750 1755

Met Glu Gly Gly Glu Glu Glu Glu Glu Leu Leu Gly Pro Lys Leu
1760 1765 1770

Glu Glu Glu Glu Glu Glu Glu Val Val Glu Asn Asp Glu Glu Ile
1775 1780 1785

Ala Phe Ser Gly Lys Asp Lys Pro Ala Ser Glu Asn Ser Glu Glu
1790 1795 1800

Lys Leu Ile Ser Lys Phe Asp Lys Leu Pro Val Lys Ile Val Gln
1805 1810 1815

Lys Asn Asp Pro Phe Val Val Asp Cys Ser Asp Lys Leu Gly Arg
1820 1825 1830

Val Gln Glu Phe Asp Ser Gly Leu Leu His Trp Arg Ile Gly Gly
1835 1840 1845

Gly Asp Thr Thr Glu His Ile Gln Thr His Phe Glu Ser Lys Thr
1850 1855 1860

Glu Leu Leu Pro Ser Arg Pro His Ala Pro Cys Pro Pro Ala Pro
1865 1870 1875

Arg Lys His Val Thr Thr Ala Glu Gly Thr Pro Gly Thr Thr Asp
1880 1885 1890

Gln Glu Gly Pro Pro Pro Asp Gly Pro Pro Glu Lys Arg Ile Thr
1895 1900 1905

Ala Thr Met Asp Asp Met Leu Ser Thr Arg Ser Ser Thr Leu Thr
1910 1915 1920

Glu Asp Gly Ala Lys Ser Ser Glu Ala Ile Lys Glu Ser Ser Lys
1925 1930 1935

Phe Pro Phe Gly Ile Ser Pro Ala Gln Ser His Arg Asn Ile Lys
1940 1945 1950

Ile Leu Glu Asp Glu Pro His Ser Lys Asp Glu Thr Pro Leu Cys
1955 1960 1965

Thr Leu Leu Asp Trp Gln Asp Ser Leu Ala Lys Arg Cys Val Cys
1970 1975 1980

Val Ser Asn Thr Ile Arg Ser Leu Ser Phe Val Pro Gly Asn Asp
1985 1990 1995

Phe Glu Met Ser Lys His Pro Gly Leu Leu Leu Ile Leu Gly Lys
2000 2005 2010

Leu Ile Leu Leu His His Lys His Pro Glu Arg Lys Gln Ala Pro
2015 2020 2025

-continued

```
Leu Thr  Tyr Glu Lys Glu Glu  Glu Gln Asp Gln Gly  Val Ser Cys
    2030                 2035                 2040

Asn Lys  Val Glu Trp Trp Trp  Asp Cys Leu Glu Met  Leu Arg Glu
    2045                 2050                 2055

Asn Thr  Leu Val Thr Leu Ala  Asn Ile Ser Gly Gln  Leu Asp Leu
    2060                 2065                 2070

Ser Pro  Tyr Pro Glu Ser Ile  Cys Leu Pro Val Leu  Asp Gly Leu
    2075                 2080                 2085

Leu His  Trp Ala Val Cys Pro  Ser Ala Glu Ala Gln  Asp Pro Phe
    2090                 2095                 2100

Ser Thr  Leu Gly Pro Asn Ala  Val Leu Ser Pro Gln  Arg Leu Val
    2105                 2110                 2115

Leu Glu  Thr Leu Ser Lys Leu  Ser Ile Gln Asp Asn  Asn Val Asp
    2120                 2125                 2130

Leu Ile  Leu Ala Thr Pro Pro  Phe Ser Arg Leu Glu  Lys Leu Tyr
    2135                 2140                 2145

Ser Thr  Met Val Arg Phe Leu  Ser Asp Arg Lys Asn  Pro Val Cys
    2150                 2155                 2160

Arg Glu  Met Ala Val Val Leu  Leu Ala Asn Leu Ala  Gln Gly Asp
    2165                 2170                 2175

Ser Leu  Ala Ala Arg Ala Ile  Ala Val Gln Lys Gly  Ser Ile Gly
    2180                 2185                 2190

Asn Leu  Leu Gly Phe Leu Glu  Asp Ser Leu Ala Ala  Thr Gln Phe
    2195                 2200                 2205

Gln Gln  Ser Gln Ala Ser Leu  Leu His Met Gln Asn  Pro Pro Phe
    2210                 2215                 2220

Glu Pro  Thr Ser Val Asp Met  Met Arg Arg Ala Ala  Arg Ala Leu
    2225                 2230                 2235

Leu Ala  Leu Ala Lys Val Asp  Glu Asn His Ser Glu  Phe Thr Leu
    2240                 2245                 2250

Tyr Glu  Ser Arg Leu Leu Asp  Ile Ser Val Ser Pro  Leu Met Asn
    2255                 2260                 2265

Ser Leu  Val Ser Gln Val Ile  Cys Asp Val Leu Phe  Leu Ile Gly
    2270                 2275                 2280

Gln Ser
    2285


<210> SEQ ID NO 102
<211> LENGTH: 88
<212> TYPE: PRT
<213> ORGANISM: Homo sapiens

<400> SEQUENCE: 102

Met Ala Thr Gln Ala Arg Gln Glu Thr Cys Asp Asn Thr Lys Trp Asn
1               5                   10                  15

Ser His Tyr Ala Arg Ser Cys Asp His His Gln Tyr His Pro Gln Arg
            20                  25                  30

Ser Tyr Lys Ala Lys Ala His Lys Gly Ala Pro Gly Gly Arg Trp Cys
        35                  40                  45

Val Gln Gly Val Gly Trp His Val Cys Val Gly Ala His Cys His Gly
    50                  55                  60

Ala Ser Ile Ser Lys Asn Ser Ser Arg Glu Val Cys Ala Glu Ile Leu
65                  70                  75                  80

Ala Cys Ile Pro Lys Ala His Ala
                85
```

-continued

<210> SEQ ID NO 103
<211> LENGTH: 69
<212> TYPE: PRT
<213> ORGANISM: Homo sapiens

<400> SEQUENCE: 103

```
Met Pro Tyr Asp Ser Val Arg Ile Glu Arg Arg Met Arg Cys Phe Lys
1               5                   10                  15

Ser Lys Ser Gln Leu Leu Asp Ser Gln Val Phe Lys Tyr Gly His Thr
            20                  25                  30

Pro Tyr Leu Val Leu Asp Tyr Met Gly Tyr Glu Gln Gly Ile Glu Thr
        35                  40                  45

Asp Lys Ile Val Phe Thr Asp Thr Val Tyr Arg Phe Phe Phe Pro Phe
    50                  55                  60

Met Gln Leu Phe Ser
65
```

<210> SEQ ID NO 104
<211> LENGTH: 65
<212> TYPE: PRT
<213> ORGANISM: Homo sapiens

<400> SEQUENCE: 104

```
Met Cys Phe Asn Phe Lys Met Leu Asn Ser Phe Gln Thr Trp Tyr Leu
1               5                   10                  15

Ile Tyr Ser Pro Phe Leu Ala Phe Val Glu Phe Gln Ala Glu Cys Leu
            20                  25                  30

Thr Asp Cys Pro Arg Thr Arg Leu Ser Phe Asn Leu Lys Gln Leu Arg
        35                  40                  45

Lys Gly Gln Arg Arg Tyr Lys Gly Lys Ala Ala Gln Asn Arg Ser Gly
    50                  55                  60

Glu
65
```

<210> SEQ ID NO 105
<211> LENGTH: 61
<212> TYPE: PRT
<213> ORGANISM: Homo sapiens

<400> SEQUENCE: 105

```
Met Leu Gly Ala Val Ile Thr Thr Asn Ile Thr Pro Arg Gly Val Ile
1               5                   10                  15

Lys Pro Arg Arg Thr Arg Gly Pro Leu Val Ala Gly Gly Val Cys Arg
            20                  25                  30

Gly Leu Gly Gly Thr Ser Val Leu Val Pro Thr Val Thr Val Gln Ala
        35                  40                  45

Ser Ala Arg Thr Gln Ala Gly Lys Ser Val Leu Lys Tyr
    50                  55                  60
```

<210> SEQ ID NO 106
<211> LENGTH: 58
<212> TYPE: PRT
<213> ORGANISM: Homo sapiens

<400> SEQUENCE: 106

```
Met Cys Asn Phe Phe Lys Tyr Val Phe Tyr Ser Tyr Gly Leu Leu Val
1               5                   10                  15

Ser Glu Pro Asp Leu Leu Thr Ile Phe Leu Tyr Asn Asn Ala Ser His
```

-continued

```
            20                  25                  30

Phe Leu Asp Ser Leu Val Met Cys Cys Met Gln Glu Leu Ser Ser Ser
        35                  40                  45

Ser Glu Gly Gly Leu Pro Leu Gln Ala Ser
    50                  55


<210> SEQ ID NO 107
<211> LENGTH: 55
<212> TYPE: PRT
<213> ORGANISM: Homo sapiens

<400> SEQUENCE: 107

Met Leu Lys Lys Lys Asn Phe Phe Leu Val Glu Met Gln Ser Pro Val
1               5                   10                  15

Lys Arg Tyr Glu Lys Ala Ser Leu Ser Gln Arg Pro Gly Arg Gln Ser
            20                  25                  30

Thr Thr Arg Gly Ser Glu Val Leu Met Glu Ser Cys Leu Ser Asn Glu
        35                  40                  45

Val Leu Lys Arg Met Pro Lys
    50                  55


<210> SEQ ID NO 108
<211> LENGTH: 50
<212> TYPE: PRT
<213> ORGANISM: Homo sapiens

<400> SEQUENCE: 108

Met Leu Gln Ile Arg Lys Leu Leu Leu Gly Thr Cys Asp Thr His Ser
1               5                   10                  15

Glu Cys Asp Met Val Ala Asn Gly Trp Pro Val Leu Lys Ala Gly Ser
            20                  25                  30

Gln His Lys Gly Gln Arg Ala Leu Ala Ala Pro Leu Pro Thr Ser Glu
        35                  40                  45

Pro Gly
    50


<210> SEQ ID NO 109
<211> LENGTH: 49
<212> TYPE: PRT
<213> ORGANISM: Homo sapiens

<400> SEQUENCE: 109

Met Arg His His Leu Phe Tyr Lys Leu Asp Tyr Gly Phe Lys Trp Asn
1               5                   10                  15

Thr Gln Gly Asn Ile Tyr Lys His Gln Gly Lys Leu Ser Thr Ala Ser
            20                  25                  30

Leu Phe His Leu Glu Arg Gly Arg Phe Pro Asn Gln Thr Gly Phe Asp
        35                  40                  45

Pro


<210> SEQ ID NO 110
<211> LENGTH: 48
<212> TYPE: PRT
<213> ORGANISM: Homo sapiens

<400> SEQUENCE: 110

Met Pro Val His Ser Ser Leu Gly Asn Lys Ser Glu Thr Pro Cys Gln
1               5                   10                  15

Lys Lys Lys Lys Lys Met Leu Leu Ile Leu Ser Glu Ser Lys Lys Glu
```

-continued

```
            20                  25                  30

Thr Leu Thr Ala Leu Asn Ser Gly Phe Ile Phe Leu Ala Val Phe Gly
        35                  40                  45


<210> SEQ ID NO 111
<211> LENGTH: 48
<212> TYPE: PRT
<213> ORGANISM: Homo sapiens

<400> SEQUENCE: 111

Met Arg Ser Trp Asp Leu Leu Phe Ser Pro Gly Leu Gln Asn Leu Ile
1               5                   10                  15

Pro Val Thr Lys Ala Arg Lys Glu Leu Tyr His Lys Pro Ser Leu Ser
            20                  25                  30

Trp His Glu Asn Trp Leu Pro Gly Ser Val Tyr Pro Ile Asn Cys Glu
        35                  40                  45


<210> SEQ ID NO 112
<211> LENGTH: 45
<212> TYPE: PRT
<213> ORGANISM: Homo sapiens

<400> SEQUENCE: 112

Met Ile Gly His Glu Ala Ser Cys His Thr Pro Glu Ile Arg Val Arg
1               5                   10                  15

Leu Leu Leu Arg Thr Met Cys Leu Val Thr Tyr Phe Ser Lys Ile Ile
            20                  25                  30

Ser Leu Pro Gly Asn Gln Ser Ser Leu Val Tyr Leu Ser
        35                  40                  45


<210> SEQ ID NO 113
<211> LENGTH: 45
<212> TYPE: PRT
<213> ORGANISM: Homo sapiens

<400> SEQUENCE: 113

Met Phe Ile Ile Phe Ile Phe Lys Val Cys Val Ile Phe Leu Ser Met
1               5                   10                  15

Tyr Ser Ile His Met Val Cys Leu Ser Val Ser Gln Thr Cys Leu Leu
            20                  25                  30

Tyr Ser Phe Ile Ile Met Leu Ala Thr Ser Trp Ile Leu
        35                  40                  45


<210> SEQ ID NO 114
<211> LENGTH: 44
<212> TYPE: PRT
<213> ORGANISM: Homo sapiens

<400> SEQUENCE: 114

Met Arg Thr Gly Cys Gln Ala Gln Cys Thr Pro Leu Thr Val Asn Glu
1               5                   10                  15

Ser Glu Leu Gly Phe Leu Tyr Cys Phe Leu Cys Asn Met Ile Ala Glu
            20                  25                  30

Thr His Phe Lys Asn Ser Glu Ala Cys His Ser Cys
        35                  40


<210> SEQ ID NO 115
<211> LENGTH: 41
<212> TYPE: PRT
<213> ORGANISM: Homo sapiens
```

-continued

<400> SEQUENCE: 115

```
Val Met Ala Tyr Tyr Ser Gly Gln Val Cys Pro Ala Gln Gly Val Ile
1               5                   10                  15

Ser Gly Gly Phe Gln Thr Cys Thr Gln Phe Lys Asp Gly Gly Asp Arg
            20                  25                  30

Leu Cys Leu Tyr Leu Val Asn Pro Thr
        35                  40
```

<210> SEQ ID NO 116
<211> LENGTH: 39
<212> TYPE: PRT
<213> ORGANISM: Homo sapiens

<400> SEQUENCE: 116

```
Met Ile Ser Ala His Cys Asp Leu Arg Leu Leu Gly Ser Ser Asp Ser
1               5                   10                  15

Pro Ala Ser Ala Ser Arg Val Ala Gly Ile Thr Gly Met Arg His His
            20                  25                  30

Ala Arg Leu Ile Leu Tyr Phe
        35
```

<210> SEQ ID NO 117
<211> LENGTH: 39
<212> TYPE: PRT
<213> ORGANISM: Homo sapiens

<400> SEQUENCE: 117

```
Met Glu Asp Phe Phe Leu Thr Ala Leu Phe Phe Met Ala Phe Ser Lys
1               5                   10                  15

Arg Phe Lys Cys Ser Leu Phe Phe Lys Trp Gly Ser Leu Gly Arg Gly
            20                  25                  30

Lys Val Cys Pro His His Leu
        35
```

<210> SEQ ID NO 118
<211> LENGTH: 39
<212> TYPE: PRT
<213> ORGANISM: Homo sapiens

<400> SEQUENCE: 118

```
Met Leu Glu Ala Leu Trp Asn Ser Pro Ile Pro Pro Pro Phe Tyr Ile
1               5                   10                  15

Ser Leu Pro Thr Leu Ala Pro Met Leu Leu Val Pro Leu Gln Cys Ile
            20                  25                  30

Pro Thr Gln Gly Ser Ile Pro
        35
```

<210> SEQ ID NO 119
<211> LENGTH: 34
<212> TYPE: PRT
<213> ORGANISM: Homo sapiens

<400> SEQUENCE: 119

```
Met Tyr Ser Thr Lys Met Glu Pro Tyr Ala Trp Ala Leu Gly Ile Gln
1               5                   10                  15

Ala Ser Ile Ser Ala Gln Thr Ser Leu Leu Glu Phe Leu Leu Met Leu
            20                  25                  30

Ala Pro
```

-continued

<210> SEQ ID NO 120
<211> LENGTH: 33
<212> TYPE: PRT
<213> ORGANISM: Homo sapiens

<400> SEQUENCE: 120

```
Met Val Ser Ser Pro Gln Gly Gly Glu Ala Thr His Thr Met Leu Lys
1               5                   10                  15

Ile Asn Thr Lys Asn Lys His Lys Val Arg Leu Val Leu His Met Cys
            20                  25                  30

Asp
```

<210> SEQ ID NO 121
<211> LENGTH: 53
<212> TYPE: PRT
<213> ORGANISM: Homo sapiens

<400> SEQUENCE: 121

```
Asn Asp Ile Phe Leu Val Ala Val His Glu Leu Gly His Ala Leu Gly
1               5                   10                  15

Leu Glu His Ser Ser Asp Pro Ser Ala Ile Met Ala Pro Phe Tyr Gln
            20                  25                  30

Trp Met Asp Thr Glu Asn Phe Val Leu Pro Asp Asp Asp Arg Arg Gly
        35                  40                  45

Ile Gln Gln Leu Tyr
    50
```

<210> SEQ ID NO 122
<211> LENGTH: 260
<212> TYPE: PRT
<213> ORGANISM: Homo sapiens

<400> SEQUENCE: 122

```
Met Ser Pro Ala Pro Arg Pro Ser Arg Cys Leu Leu Leu Pro Leu Leu
1               5                   10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190
```

-continued

```
Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Gly
            260


<210> SEQ ID NO 123
<211> LENGTH: 53
<212> TYPE: PRT
<213> ORGANISM: Homo sapiens

<400> SEQUENCE: 123

Asn Asp Ile Phe Leu Val Ala Val His Glu Leu Gly His Ala Leu Gly
1               5                   10                  15

Leu Glu His Ser Ser Asp Pro Ser Ala Ile Met Ala Pro Phe Tyr Gln
            20                  25                  30

Trp Met Asp Thr Glu Asn Phe Val Leu Pro Asn Asp Asp Arg Arg Gly
        35                  40                  45

Ile Gln Gln Leu Tyr
    50


<210> SEQ ID NO 124
<211> LENGTH: 2273
<212> TYPE: PRT
<213> ORGANISM: Homo sapiens

<400> SEQUENCE: 124

Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190
```

-continued

```
His Gly Val Pro Asp Leu Ala Leu Lys Asp Ile Ala Cys Ser Glu Ala
        195                 200                 205

Leu Leu Glu Arg Phe Ile Ile Phe Ser Gln Arg Arg Gly Ala Lys Thr
    210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                245                 250                 255

Leu Pro Thr Leu Leu Asp Ser Arg Ser Gln Gly Ile Asn Leu Arg Ser
            260                 265                 270

Trp Gly Gly Ile Leu Ser Asp Met Ser Pro Arg Ile Gln Glu Phe Ile
        275                 280                 285

His Arg Pro Ser Met Gln Asp Leu Leu Trp Val Thr Arg Pro Leu Met
    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Gly Ser Arg Val Leu Ser
                325                 330                 335

Phe Asn Trp Tyr Glu Asp Asn Asn Tyr Lys Ala Phe Leu Gly Ile Asp
            340                 345                 350

Ser Thr Arg Lys Asp Pro Ile Tyr Ser Tyr Asp Arg Arg Thr Thr Ser
        355                 360                 365

Phe Cys Asn Ala Leu Ile Gln Ser Leu Glu Ser Asn Pro Leu Thr Lys
    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
        435                 440                 445

Asn Met Ile Arg Asp Thr Leu Gly Asn Pro Thr Val Lys Asp Phe Leu
    450                 455                 460

Asn Arg Gln Leu Gly Glu Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
                485                 490                 495

Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
        515                 520                 525

Asn Asp Glu Thr Gln Leu Thr Gln Arg Ala Leu Ser Leu Leu Glu Glu
    530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
                565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
        595                 600                 605

Ala Tyr Leu Gln Asp Met Val Glu Gln Gly Ile Thr Arg Ser Gln Val
```

-continued

```
610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
                645                 650                 655

Ile Phe Met Val Leu Ala Trp Ile Tyr Ser Val Ser Met Thr Val Lys
            660                 665                 670

Ser Ile Val Leu Glu Lys Glu Leu Arg Leu Lys Glu Thr Leu Lys Asn
        675                 680                 685

Gln Gly Val Ser Asn Ala Val Ile Trp Cys Thr Trp Phe Leu Asp Ser
    690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
                725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
        755                 760                 765

Tyr Phe Thr Leu Tyr Leu Pro His Ile Leu Cys Phe Ala Trp Gln Asp
    770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
                805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
        835                 840                 845

Cys Tyr Gly Leu Leu Ala Trp Tyr Leu Asp Gln Val Phe Pro Gly Asp
    850                 855                 860

Tyr Gly Thr Pro Leu Pro Trp Tyr Phe Leu Leu Gln Glu Ser Tyr Trp
865                 870                 875                 880

Leu Ser Gly Glu Gly Cys Ser Thr Arg Glu Glu Arg Ala Leu Glu Lys
                885                 890                 895

Thr Glu Pro Leu Thr Glu Glu Thr Glu Asp Pro Glu His Pro Glu Gly
            900                 905                 910

Ile His Asp Ser Phe Phe Glu Arg Glu His Pro Gly Trp Val Pro Gly
        915                 920                 925

Val Cys Val Lys Asn Leu Val Lys Ile Phe Glu Pro Cys Gly Arg Pro
    930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
                965                 970                 975

Thr Gly Leu Leu Pro Pro Thr Ser Gly Thr Val Leu Val Gly Gly Arg
            980                 985                 990

Asp Ile Glu Thr Ser Leu Asp Ala  Val Arg Gln Ser Leu  Gly Met Cys
        995                 1000                1005

Pro Gln  His Asn Ile Leu Phe  His His Leu Thr Val  Ala Glu His
    1010                1015                1020

Met Leu  Phe Tyr Ala Gln Leu  Lys Gly Lys Ser Gln  Glu Glu Ala
    1025                1030                1035
```

-continued

Gln Leu Glu Met Glu Ala Met Leu Glu Asp Thr Gly Leu His His
1040 1045 1050

Lys Arg Asn Glu Glu Ala Gln Asp Leu Ser Gly Gly Met Gln Arg
1055 1060 1065

Lys Leu Ser Val Ala Ile Ala Phe Val Gly Asp Ala Lys Val Val
1070 1075 1080

Ile Leu Asp Glu Pro Thr Ser Gly Val Asp Pro Tyr Ser Arg Arg
1085 1090 1095

Ser Ile Trp Asp Leu Leu Leu Lys Tyr Arg Ser Gly Arg Thr Ile
1100 1105 1110

Ile Met Pro Thr His His Met Asp Glu Ala Asp His Gln Gly Asp
1115 1120 1125

Arg Ile Ala Ile Ile Ala Gln Gly Arg Leu Tyr Cys Ser Gly Thr
1130 1135 1140

Pro Leu Phe Leu Lys Asn Cys Phe Gly Thr Gly Leu Tyr Leu Thr
1145 1150 1155

Leu Val Arg Lys Met Lys Asn Ile Gln Ser Gln Arg Lys Gly Ser
1160 1165 1170

Glu Gly Thr Cys Ser Cys Ser Ser Lys Gly Phe Ser Thr Thr Cys
1175 1180 1185

Pro Ala His Val Asp Asp Leu Thr Pro Glu Gln Val Leu Asp Gly
1190 1195 1200

Asp Val Asn Glu Leu Met Asp Val Val Leu His His Val Pro Glu
1205 1210 1215

Ala Lys Leu Val Glu Cys Ile Gly Gln Glu Leu Ile Phe Leu Leu
1220 1225 1230

Pro Asn Lys Asn Phe Lys His Arg Ala Tyr Ala Ser Leu Phe Arg
1235 1240 1245

Glu Leu Glu Glu Thr Leu Ala Asp Leu Gly Leu Ser Ser Phe Gly
1250 1255 1260

Ile Ser Asp Thr Pro Leu Glu Glu Ile Phe Leu Lys Val Thr Glu
1265 1270 1275

Asp Ser Asp Ser Gly Pro Leu Phe Ala Gly Gly Ala Gln Gln Lys
1280 1285 1290

Arg Glu Asn Val Asn Pro Arg His Pro Cys Leu Gly Pro Arg Glu
1295 1300 1305

Lys Ala Gly Gln Thr Pro Gln Asp Ser Asn Val Cys Ser Pro Gly
1310 1315 1320

Ala Pro Ala Ala His Pro Glu Gly Gln Pro Pro Pro Glu Pro Glu
1325 1330 1335

Cys Pro Gly Pro Gln Leu Asn Thr Gly Thr Gln Leu Val Leu Gln
1340 1345 1350

His Val Gln Ala Leu Leu Val Lys Arg Phe Gln His Thr Ile Arg
1355 1360 1365

Ser His Lys Asp Phe Leu Ala Gln Ile Val Leu Pro Ala Thr Phe
1370 1375 1380

Val Phe Leu Ala Leu Met Leu Ser Ile Val Ile Leu Pro Phe Gly
1385 1390 1395

Glu Tyr Pro Ala Leu Thr Leu His Pro Trp Ile Tyr Gly Gln Gln
1400 1405 1410

Tyr Thr Phe Phe Ser Met Asp Glu Pro Gly Ser Glu Gln Phe Thr
1415 1420 1425

-continued

Val Leu Ala Asp Val Leu Leu Asn Lys Pro Gly Phe Gly Asn Arg
1430 1435 1440

Cys Leu Lys Glu Gly Trp Leu Pro Glu Tyr Pro Cys Gly Asn Ser
1445 1450 1455

Thr Pro Trp Lys Thr Pro Ser Val Ser Pro Asn Ile Thr Gln Leu
1460 1465 1470

Phe Gln Lys Gln Lys Trp Thr Gln Val Asn Pro Ser Pro Ser Cys
1475 1480 1485

Arg Cys Ser Thr Arg Glu Lys Leu Thr Met Leu Pro Glu Cys Pro
1490 1495 1500

Glu Gly Ala Gly Gly Leu Pro Pro Pro Gln Arg Thr Gln Arg Ser
1505 1510 1515

Thr Glu Ile Leu Gln Asp Leu Thr Asp Arg Asn Ile Ser Asp Phe
1520 1525 1530

Leu Val Lys Thr Tyr Pro Ala Leu Ile Arg Ser Ser Leu Lys Ser
1535 1540 1545

Lys Phe Trp Val Asn Glu Gln Arg Tyr Gly Gly Ile Ser Ile Gly
1550 1555 1560

Gly Lys Leu Pro Val Val Pro Ile Thr Gly Glu Ala Leu Val Gly
1565 1570 1575

Phe Leu Ser Asp Leu Gly Arg Ile Met Asn Val Ser Gly Gly Pro
1580 1585 1590

Ile Thr Arg Glu Ala Ser Lys Glu Ile Pro Asp Phe Leu Lys His
1595 1600 1605

Leu Glu Thr Glu Asp Asn Ile Lys Val Trp Phe Asn Asn Lys Gly
1610 1615 1620

Trp His Ala Leu Val Ser Phe Leu Asn Val Ala His Asn Ala Ile
1625 1630 1635

Leu Arg Ala Ser Leu Pro Lys Asp Arg Ser Pro Glu Glu Tyr Gly
1640 1645 1650

Ile Thr Val Ile Ser Gln Pro Leu Asn Leu Thr Lys Glu Gln Leu
1655 1660 1665

Ser Glu Ile Thr Val Leu Thr Thr Ser Val Asp Ala Val Val Ala
1670 1675 1680

Ile Cys Val Ile Phe Ser Met Ser Phe Val Pro Ala Ser Phe Val
1685 1690 1695

Leu Tyr Leu Ile Gln Glu Arg Val Asn Lys Ser Lys His Leu Gln
1700 1705 1710

Phe Ile Ser Gly Val Ser Pro Thr Thr Tyr Trp Val Thr Asn Phe
1715 1720 1725

Leu Trp Asp Ile Met Asn Tyr Ser Val Ser Ala Gly Leu Val Val
1730 1735 1740

Gly Ile Phe Ile Gly Phe Gln Lys Lys Ala Tyr Thr Ser Pro Glu
1745 1750 1755

Asn Leu Pro Ala Leu Val Ala Leu Leu Leu Leu Tyr Gly Trp Ala
1760 1765 1770

Val Ile Pro Met Met Tyr Pro Ala Ser Phe Leu Phe Asp Val Pro
1775 1780 1785

Ser Thr Ala Tyr Val Ala Leu Ser Cys Ala Asn Leu Phe Ile Gly
1790 1795 1800

Ile Asn Ser Ser Ala Ile Thr Phe Ile Leu Glu Leu Phe Asp Asn
1805 1810 1815

Asn Arg Thr Leu Leu Arg Phe Asn Ala Val Leu Arg Lys Leu Leu

-continued

```
    1820                1825                1830

Ile Val  Phe Pro His Phe Cys  Leu Gly Arg Gly Leu  Ile Asp Leu
    1835                1840                1845

Ala Leu  Ser Gln Ala Val Thr  Asp Val Tyr Ala Arg  Phe Gly Glu
    1850                1855                1860

Glu His  Ser Ala Asn Pro Phe  His Trp Asp Leu Ile  Gly Lys Asn
    1865                1870                1875

Leu Phe  Ala Met Val Val Glu  Gly Val Val Tyr Phe  Leu Leu Thr
    1880                1885                1890

Leu Leu  Val Gln Arg His Phe  Phe Leu Ser Gln Trp  Ile Ala Glu
    1895                1900                1905

Pro Thr  Lys Glu Pro Ile Val  Asp Glu Asp Asp Asp  Val Ala Glu
    1910                1915                1920

Glu Arg  Gln Arg Ile Ile Thr  Gly Gly Asn Lys Thr  Asp Ile Leu
    1925                1930                1935

Arg Leu  His Glu Leu Thr Lys  Ile Tyr Leu Gly Thr  Ser Ser Pro
    1940                1945                1950

Ala Val  Asp Arg Leu Cys Val  Gly Val Arg Pro Gly  Glu Cys Phe
    1955                1960                1965

Gly Leu  Leu Gly Val Asn Gly  Ala Gly Lys Thr Thr  Thr Phe Lys
    1970                1975                1980

Met Leu  Thr Gly Asp Thr Thr  Val Thr Ser Gly Asp  Ala Thr Val
    1985                1990                1995

Ala Gly  Lys Ser Ile Leu Thr  Asn Ile Ser Glu Val  His Gln Asn
    2000                2005                2010

Met Gly  Tyr Cys Pro Gln Phe  Asp Ala Ile Asp Glu  Leu Leu Thr
    2015                2020                2025

Gly Arg  Glu His Leu Tyr Leu  Tyr Ala Arg Leu Arg  Gly Val Pro
    2030                2035                2040

Ala Glu  Glu Ile Glu Lys Val  Ala Asn Trp Ser Ile  Lys Ser Leu
    2045                2050                2055

Gly Leu  Thr Val Tyr Ala Asp  Cys Leu Ala Gly Thr  Tyr Ser Gly
    2060                2065                2070

Gly Asn  Lys Arg Lys Leu Ser  Thr Ala Ile Ala Leu  Ile Gly Cys
    2075                2080                2085

Pro Pro  Leu Val Leu Leu Asp  Glu Pro Thr Thr Gly  Met Asp Pro
    2090                2095                2100

Gln Ala  Arg Arg Met Leu Trp  Asn Val Ile Val Ser  Ile Ile Arg
    2105                2110                2115

Lys Gly  Arg Ala Val Val Leu  Thr Ser His Ser Met  Glu Glu Cys
    2120                2125                2130

Glu Ala  Leu Cys Thr Arg Leu  Ala Ile Met Val Lys  Gly Ala Phe
    2135                2140                2145

Arg Cys  Met Gly Thr Ile Gln  His Leu Lys Ser Lys  Phe Gly Asp
    2150                2155                2160

Gly Tyr  Ile Val Thr Met Lys  Ile Lys Ser Pro Lys  Asp Asp Leu
    2165                2170                2175

Leu Pro  Asp Leu Asn Pro Val  Glu Gln Phe Phe Gln  Gly Asn Phe
    2180                2185                2190

Pro Gly  Ser Val Gln Arg Glu  Arg His Tyr Asn Met  Leu Gln Phe
    2195                2200                2205

Gln Val  Ser Ser Ser Ser Leu  Ala Arg Ile Phe Gln  Leu Leu Leu
    2210                2215                2220
```

-continued

```
Ser His  Lys Asp Ser Leu Leu  Ile Glu Glu Tyr Ser  Val Thr Gln
    2225                 2230                 2235

Thr Thr  Leu Asp Gln Val Phe  Val Asn Phe Ala Lys  Gln Gln Thr
    2240                 2245                 2250

Glu Ser  His Asp Leu Pro Leu  His Pro Arg Ala Ala  Gly Ala Ser
    2255                 2260                 2265

Arg Gln  Ala Gln Asp
    2270
```

<210> SEQ ID NO 125
<211> LENGTH: 317
<212> TYPE: PRT
<213> ORGANISM: Homo sapiens

<400> SEQUENCE: 125

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
```

-continued

```
305                 310                 315


<210> SEQ ID NO 126
<211> LENGTH: 374
<212> TYPE: PRT
<213> ORGANISM: Homo sapiens

<400> SEQUENCE: 126

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
            340                 345                 350

Gly Arg Gly Lys Gly Lys Ser Ile Gly Arg Ala Pro Glu Ala Ser Leu
        355                 360                 365
```

-continued

```
Gln Asp Lys Glu Gly Ala
    370


<210> SEQ ID NO 127
<211> LENGTH: 146
<212> TYPE: PRT
<213> ORGANISM: Homo sapiens

<400> SEQUENCE: 127

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
    130                 135                 140

Asp Ala
145


<210> SEQ ID NO 128
<211> LENGTH: 5622
<212> TYPE: PRT
<213> ORGANISM: Homo sapiens

<400> SEQUENCE: 128

Met Ile Ser Trp Glu Val Val His Thr Val Phe Leu Phe Ala Leu Leu
1               5                   10                  15

Tyr Ser Ser Leu Ala Gln Asp Ala Ser Pro Gln Ser Glu Ile Arg Ala
            20                  25                  30

Glu Glu Ile Pro Glu Gly Ala Ser Thr Leu Ala Phe Val Phe Asp Val
        35                  40                  45

Thr Gly Ser Met Tyr Asp Asp Leu Val Gln Val Ile Glu Gly Ala Ser
    50                  55                  60

Lys Ile Leu Glu Thr Ser Leu Lys Arg Pro Lys Arg Pro Leu Phe Asn
65                  70                  75                  80

Phe Ala Leu Val Pro Phe His Asp Pro Glu Ile Gly Pro Val Thr Ile
                85                  90                  95

Thr Thr Asp Pro Lys Lys Phe Gln Tyr Glu Leu Arg Glu Leu Tyr Val
            100                 105                 110

Gln Gly Gly Gly Asp Cys Pro Glu Met Ser Ile Gly Ala Ile Lys Ile
        115                 120                 125

Ala Leu Glu Ile Ser Leu Pro Gly Ser Phe Ile Tyr Val Phe Thr Asp
    130                 135                 140

Ala Arg Ser Lys Asp Tyr Arg Leu Thr His Glu Val Leu Gln Leu Ile
145                 150                 155                 160
```

-continued

```
Gln Gln Lys Gln Ser Gln Val Val Phe Val Leu Thr Gly Asp Cys Asp
                165                 170                 175

Asp Arg Thr His Ile Gly Tyr Lys Val Tyr Glu Glu Ile Ala Ser Thr
            180                 185                 190

Ser Ser Gly Gln Val Phe His Leu Asp Lys Lys Gln Val Asn Glu Val
        195                 200                 205

Leu Lys Trp Val Glu Glu Ala Val Gln Ala Ser Lys Val His Leu Leu
    210                 215                 220

Ser Thr Asp His Leu Glu Gln Ala Val Asn Thr Trp Arg Ile Pro Phe
225                 230                 235                 240

Asp Pro Ser Leu Lys Glu Val Thr Val Ser Leu Ser Gly Pro Ser Pro
                245                 250                 255

Met Ile Glu Ile Arg Asn Pro Leu Gly Lys Leu Ile Lys Lys Gly Phe
            260                 265                 270

Gly Leu His Glu Leu Leu Asn Ile His Asn Ser Ala Lys Val Val Asn
        275                 280                 285

Val Lys Glu Pro Glu Ala Gly Met Trp Thr Val Lys Thr Ser Ser Ser
    290                 295                 300

Gly Arg His Ser Val Arg Ile Thr Gly Leu Ser Thr Ile Asp Phe Arg
305                 310                 315                 320

Ala Gly Phe Ser Arg Lys Pro Thr Leu Asp Phe Lys Lys Thr Val Ser
                325                 330                 335

Arg Pro Val Gln Gly Ile Pro Thr Tyr Val Leu Leu Asn Thr Ser Gly
            340                 345                 350

Ile Ser Thr Pro Ala Arg Ile Asp Leu Leu Glu Leu Leu Ser Ile Ser
        355                 360                 365

Gly Ser Ser Leu Lys Thr Ile Pro Val Lys Tyr Tyr Pro His Arg Lys
    370                 375                 380

Pro Tyr Gly Ile Trp Asn Ile Ser Asp Phe Val Pro Pro Asn Glu Ala
385                 390                 395                 400

Phe Phe Leu Lys Val Thr Gly Tyr Asp Lys Asp Asp Tyr Leu Phe Gln
                405                 410                 415

Arg Val Ser Ser Val Ser Phe Ser Ser Ile Val Pro Asp Ala Pro Lys
            420                 425                 430

Val Thr Met Pro Glu Lys Thr Pro Gly Tyr Tyr Leu Gln Pro Gly Gln
        435                 440                 445

Ile Pro Cys Ser Val Asp Ser Leu Leu Pro Phe Thr Leu Ser Phe Val
    450                 455                 460

Arg Asn Gly Val Thr Leu Gly Val Asp Gln Tyr Leu Lys Glu Ser Ala
465                 470                 475                 480

Ser Val Asn Leu Asp Ile Ala Lys Val Thr Leu Ser Asp Glu Gly Phe
                485                 490                 495

Tyr Glu Cys Ile Ala Val Ser Ser Ala Gly Thr Gly Arg Ala Gln Thr
            500                 505                 510

Phe Phe Asp Val Ser Glu Pro Pro Pro Val Ile Gln Val Pro Asn Asn
        515                 520                 525

Val Thr Val Thr Pro Gly Glu Arg Ala Val Leu Thr Cys Leu Ile Ile
    530                 535                 540

Ser Ala Val Asp Tyr Asn Leu Thr Trp Gln Arg Asn Asp Arg Asp Val
545                 550                 555                 560

Arg Leu Ala Glu Pro Ala Arg Ile Arg Thr Leu Ala Asn Leu Ser Leu
                565                 570                 575

Glu Leu Lys Ser Val Lys Phe Asn Asp Ala Gly Glu Tyr His Cys Met
```

-continued

```
            580                 585                 590

Val Ser Ser Glu Gly Gly Ser Ser Ala Ala Ser Val Phe Leu Thr Val
        595                 600                 605

Gln Glu Pro Pro Lys Val Thr Val Met Pro Lys Asn Gln Ser Phe Thr
    610                 615                 620

Gly Gly Ser Glu Val Ser Ile Met Cys Ser Ala Thr Gly Tyr Pro Lys
625                 630                 635                 640

Pro Lys Ile Ala Trp Thr Val Asn Asp Met Phe Ile Val Gly Ser His
                645                 650                 655

Arg Tyr Arg Met Thr Ser Asp Gly Thr Leu Phe Ile Lys Asn Ala Ala
            660                 665                 670

Pro Lys Asp Ala Gly Ile Tyr Gly Cys Leu Ala Ser Asn Ser Ala Gly
        675                 680                 685

Thr Asp Lys Gln Asn Ser Thr Leu Arg Tyr Ile Glu Ala Pro Lys Leu
    690                 695                 700

Met Val Val Gln Ser Glu Leu Leu Val Ala Leu Gly Asp Ile Thr Val
705                 710                 715                 720

Met Glu Cys Lys Thr Ser Gly Ile Pro Pro Pro Gln Val Lys Trp Phe
                725                 730                 735

Lys Gly Asp Leu Glu Leu Arg Pro Ser Thr Phe Leu Ile Ile Asp Pro
            740                 745                 750

Leu Leu Gly Leu Leu Lys Ile Gln Glu Thr Gln Asp Leu Asp Ala Gly
        755                 760                 765

Asp Tyr Thr Cys Val Ala Ile Asn Glu Ala Gly Arg Ala Thr Gly Lys
    770                 775                 780

Ile Thr Leu Asp Val Gly Ser Pro Pro Val Phe Ile Gln Glu Pro Ala
785                 790                 795                 800

Asp Val Ser Met Glu Ile Gly Ser Asn Val Thr Leu Pro Cys Tyr Val
                805                 810                 815

Gln Gly Tyr Pro Glu Pro Thr Ile Lys Trp Arg Arg Leu Asp Asn Met
            820                 825                 830

Pro Ile Phe Ser Arg Pro Phe Ser Val Ser Ser Ile Ser Gln Leu Arg
        835                 840                 845

Thr Gly Ala Leu Phe Ile Leu Asn Leu Trp Ala Ser Asp Lys Gly Thr
    850                 855                 860

Tyr Ile Cys Glu Ala Glu Asn Gln Phe Gly Lys Ile Gln Ser Glu Thr
865                 870                 875                 880

Thr Val Thr Val Thr Gly Leu Val Ala Pro Leu Ile Gly Ile Ser Pro
                885                 890                 895

Ser Val Ala Asn Val Ile Glu Gly Gln Gln Leu Thr Leu Pro Cys Thr
            900                 905                 910

Leu Leu Ala Gly Asn Pro Ile Pro Glu Arg Arg Trp Ile Lys Asn Ser
        915                 920                 925

Ala Met Leu Leu Gln Asn Pro Tyr Ile Thr Val Arg Ser Asp Gly Ser
    930                 935                 940

Leu His Ile Glu Arg Val Gln Leu Gln Asp Gly Gly Glu Tyr Thr Cys
945                 950                 955                 960

Val Ala Ser Asn Val Ala Gly Thr Asn Asn Lys Thr Thr Ser Val Val
                965                 970                 975

Val His Val Leu Pro Thr Ile Gln His Gly Gln Gln Ile Leu Ser Thr
            980                 985                 990

Ile Glu Gly Ile Pro Val Thr Leu  Pro Cys Lys Ala Ser  Gly Asn Pro
        995                 1000                1005
```

-continued

```
Lys Pro  Ser Val Ile Trp Ser  Lys Lys Gly Glu Leu  Ile Ser Thr
    1010                 1015                 1020

Ser Ser  Ala Lys Phe Ser Ala  Gly Ala Asp Gly Ser  Leu Tyr Val
    1025                 1030                 1035

Val Ser  Pro Gly Gly Glu Glu  Ser Gly Glu Tyr Val  Cys Thr Ala
    1040                 1045                 1050

Thr Asn  Thr Ala Gly Tyr Ala  Lys Arg Lys Val Gln  Leu Thr Val
    1055                 1060                 1065

Tyr Val  Arg Pro Arg Val Phe  Gly Asp Gln Arg Gly  Leu Ser Gln
    1070                 1075                 1080

Asp Lys  Pro Val Glu Ile Ser  Val Leu Ala Gly Glu  Glu Val Thr
    1085                 1090                 1095

Leu Pro  Cys Glu Val Lys Ser  Leu Pro Pro Pro Ile  Ile Thr Trp
    1100                 1105                 1110

Ala Lys  Glu Thr Gln Leu Ile  Ser Pro Phe Ser Pro  Arg His Thr
    1115                 1120                 1125

Phe Leu  Pro Ser Gly Ser Met  Lys Ile Thr Glu Thr  Arg Thr Ser
    1130                 1135                 1140

Asp Ser  Gly Met Tyr Leu Cys  Val Ala Thr Asn Ile  Ala Gly Asn
    1145                 1150                 1155

Val Thr  Gln Ala Val Lys Leu  Asn Val His Val Pro  Pro Lys Ile
    1160                 1165                 1170

Gln Arg  Gly Pro Lys His Leu  Lys Val Gln Val Gly  Gln Arg Val
    1175                 1180                 1185

Asp Ile  Pro Cys Asn Ala Gln  Gly Thr Pro Leu Pro  Val Ile Thr
    1190                 1195                 1200

Trp Ser  Lys Gly Gly Ser Thr  Met Leu Val Asp Gly  Glu His His
    1205                 1210                 1215

Val Ser  Asn Pro Asp Gly Thr  Leu Ser Ile Asp Gln  Ala Thr Pro
    1220                 1225                 1230

Ser Asp  Ala Gly Ile Tyr Thr  Cys Val Ala Thr Asn  Ile Ala Gly
    1235                 1240                 1245

Thr Asp  Glu Thr Glu Ile Thr  Leu His Val Gln Glu  Pro Pro Thr
    1250                 1255                 1260

Val Glu  Asp Leu Glu Pro Pro  Tyr Asn Thr Thr Phe  Gln Glu Arg
    1265                 1270                 1275

Val Ala  Asn Gln Arg Ile Glu  Phe Pro Cys Pro Ala  Lys Gly Thr
    1280                 1285                 1290

Pro Lys  Pro Thr Ile Lys Trp  Leu His Asn Gly Arg  Glu Leu Thr
    1295                 1300                 1305

Gly Arg  Glu Pro Gly Ile Ser  Ile Leu Glu Asp Gly  Thr Leu Leu
    1310                 1315                 1320

Val Ile  Ala Ser Val Thr Pro  Tyr Asp Asn Gly Glu  Tyr Ile Cys
    1325                 1330                 1335

Val Ala  Val Asn Glu Ala Gly  Thr Thr Glu Arg Lys  Tyr Asn Leu
    1340                 1345                 1350

Lys Val  His Val Pro Pro Val  Ile Lys Asp Lys Glu  Gln Val Thr
    1355                 1360                 1365

Asn Val  Ser Val Leu Leu Asn  Gln Leu Thr Asn Leu  Phe Cys Glu
    1370                 1375                 1380

Val Glu  Gly Thr Pro Ser Pro  Ile Ile Met Trp Tyr  Lys Asp Asn
    1385                 1390                 1395
```

-continued

```
Val Gln  Val Thr Glu Ser Ser  Thr Ile Gln Thr Val  Asn Asn Gly
    1400                 1405                 1410

Lys Ile  Leu Lys Leu Phe Arg  Ala Thr Pro Glu Asp  Ala Gly Arg
    1415                 1420                 1425

Tyr Ser  Cys Lys Ala Ile Asn  Ile Ala Gly Thr Ser  Gln Lys Tyr
    1430                 1435                 1440

Phe Asn  Ile Asp Val Leu Val  Pro Pro Thr Ile Ile  Gly Thr Asn
    1445                 1450                 1455

Phe Pro  Asn Glu Val Ser Val  Val Leu Asn Arg Asp  Val Ala Leu
    1460                 1465                 1470

Glu Cys  Gln Val Lys Gly Thr  Pro Phe Pro Asp Ile  His Trp Phe
    1475                 1480                 1485

Lys Asp  Gly Lys Pro Leu Phe  Leu Gly Asp Pro Asn  Val Glu Leu
    1490                 1495                 1500

Leu Asp  Arg Gly Gln Val Leu  His Leu Lys Asn Ala  Arg Arg Asn
    1505                 1510                 1515

Asp Lys  Gly Arg Tyr Gln Cys  Thr Val Ser Asn Ala  Ala Gly Lys
    1520                 1525                 1530

Gln Ala  Lys Asp Ile Lys Leu  Thr Ile Tyr Ile Pro  Pro Ser Ile
    1535                 1540                 1545

Lys Gly  Gly Asn Val Thr Thr  Asp Ile Ser Val Leu  Ile Asn Ser
    1550                 1555                 1560

Leu Ile  Lys Leu Glu Cys Glu  Thr Arg Gly Leu Pro  Met Pro Ala
    1565                 1570                 1575

Ile Thr  Trp Tyr Lys Asp Gly  Gln Pro Ile Met Ser  Ser Ser Gln
    1580                 1585                 1590

Ala Leu  Tyr Ile Asp Lys Gly  Gln Tyr Leu His Ile  Pro Arg Ala
    1595                 1600                 1605

Gln Val  Ser Asp Ser Ala Thr  Tyr Thr Cys His Val  Ala Asn Val
    1610                 1615                 1620

Ala Gly  Thr Ala Glu Lys Ser  Phe His Val Asp Val  Tyr Val Pro
    1625                 1630                 1635

Pro Met  Ile Glu Gly Asn Leu  Ala Thr Pro Leu Asn  Lys Gln Val
    1640                 1645                 1650

Val Ile  Ala His Ser Leu Thr  Leu Glu Cys Lys Ala  Ala Gly Asn
    1655                 1660                 1665

Pro Ser  Pro Ile Leu Thr Trp  Leu Lys Asp Gly Val  Pro Val Lys
    1670                 1675                 1680

Ala Asn  Asp Asn Ile Arg Ile  Glu Ala Gly Gly Lys  Lys Leu Glu
    1685                 1690                 1695

Ile Met  Ser Ala Gln Glu Ile  Asp Arg Gly Gln Tyr  Ile Cys Val
    1700                 1705                 1710

Ala Thr  Ser Val Ala Gly Glu  Lys Glu Ile Lys Tyr  Glu Val Asp
    1715                 1720                 1725

Val Leu  Val Pro Pro Ala Ile  Glu Gly Gly Asp Glu  Thr Ser Tyr
    1730                 1735                 1740

Phe Ile  Val Met Val Asn Asn  Leu Leu Glu Leu Asp  Cys His Val
    1745                 1750                 1755

Thr Gly  Ser Pro Pro Pro Thr  Ile Met Trp Leu Lys  Asp Gly Gln
    1760                 1765                 1770

Leu Ile  Asp Glu Arg Asp Gly  Phe Lys Ile Leu Leu  Asn Gly Arg
    1775                 1780                 1785

Lys Leu  Val Ile Ala Gln Ala  Gln Val Ser Asn Thr  Gly Leu Tyr
```

-continued

```
    1790                1795                1800

Arg Cys  Met Ala Ala Asn Thr  Ala Gly Asp His Lys  Lys Glu Phe
    1805                1810                1815

Glu Val  Thr Val His Val Pro  Pro Thr Ile Lys Ser  Ser Gly Leu
    1820                1825                1830

Ser Glu  Arg Val Val Val Lys  Tyr Lys Pro Val Ala  Leu Gln Cys
    1835                1840                1845

Ile Ala  Asn Gly Ile Pro Asn  Pro Ser Ile Thr Trp  Leu Lys Asp
    1850                1855                1860

Asp Gln  Pro Val Asn Thr Ala  Gln Gly Asn Leu Lys  Ile Gln Ser
    1865                1870                1875

Ser Gly  Arg Val Leu Gln Ile  Ala Lys Thr Leu Leu  Glu Asp Ala
    1880                1885                1890

Gly Arg  Tyr Thr Cys Val Ala  Thr Asn Ala Ala Gly  Glu Thr Gln
    1895                1900                1905

Gln His  Ile Gln Leu His Val  His Glu Pro Pro Ser  Leu Glu Asp
    1910                1915                1920

Ala Gly  Lys Met Leu Asn Glu  Thr Val Leu Val Ser  Asn Pro Val
    1925                1930                1935

Gln Leu  Glu Cys Lys Ala Ala  Gly Asn Pro Val Pro  Val Ile Thr
    1940                1945                1950

Trp Tyr  Lys Asp Asn Arg Leu  Leu Ser Gly Ser Thr  Ser Met Thr
    1955                1960                1965

Phe Leu  Asn Arg Gly Gln Ile  Ile Asp Ile Glu Ser  Ala Gln Ile
    1970                1975                1980

Ser Asp  Ala Gly Ile Tyr Lys  Cys Val Ala Ile Asn  Ser Ala Gly
    1985                1990                1995

Ala Thr  Glu Leu Phe Tyr Ser  Leu Gln Val His Val  Ala Pro Ser
    2000                2005                2010

Ile Ser  Gly Ser Asn Asn Met  Val Ala Val Val Val  Asn Asn Pro
    2015                2020                2025

Val Arg  Leu Glu Cys Glu Ala  Arg Gly Ile Pro Ala  Pro Ser Leu
    2030                2035                2040

Thr Trp  Leu Lys Asp Gly Ser  Pro Val Ser Ser Phe  Ser Asn Gly
    2045                2050                2055

Leu Gln  Val Leu Ser Gly Gly  Arg Ile Leu Ala Leu  Thr Ser Ala
    2060                2065                2070

Gln Ile  Ser Asp Thr Gly Arg  Tyr Thr Cys Val Ala  Val Asn Ala
    2075                2080                2085

Ala Gly  Glu Lys Gln Arg Asp  Ile Asp Leu Arg Val  Tyr Val Pro
    2090                2095                2100

Pro Asn  Ile Met Gly Glu Glu  Gln Asn Val Ser Val  Leu Ile Ser
    2105                2110                2115

Gln Ala  Val Glu Leu Leu Cys  Gln Ser Asp Ala Ile  Pro Pro Pro
    2120                2125                2130

Thr Leu  Thr Trp Leu Lys Asp  Gly His Pro Leu Leu  Lys Lys Pro
    2135                2140                2145

Gly Leu  Ser Ile Ser Glu Asn  Arg Ser Val Leu Lys  Ile Glu Asp
    2150                2155                2160

Ala Gln  Val Gln Asp Thr Gly  Arg Tyr Thr Cys Glu  Ala Thr Asn
    2165                2170                2175

Val Ala  Gly Lys Thr Glu Lys  Lys Asn Tyr Asn Val  Asn Ile Trp
    2180                2185                2190
```

-continued

```
Val Pro  Pro Asn Ile Gly Gly  Ser Asp Glu Leu Thr  Gln Leu Thr
    2195                 2200                 2205

Val Ile  Glu Gly Asn Leu Ile  Ser Leu Leu Cys Glu  Ser Ser Gly
    2210                 2215                 2220

Ile Pro  Pro Pro Asn Leu Ile  Trp Lys Lys Lys Gly  Ser Pro Val
    2225                 2230                 2235

Leu Thr  Asp Ser Met Gly Arg  Val Arg Ile Ile Ala  Glu Lys Ser
    2240                 2245                 2250

Asp Ala  Ala Leu Tyr Ser Cys  Val Ala Ser Asn Val  Ala Gly Thr
    2255                 2260                 2265

Ala Lys  Lys Glu Tyr Asn Leu  Gln Val Tyr Ile Arg  Pro Thr Ile
    2270                 2275                 2280

Thr Asn  Ser Gly Ser His Pro  Thr Glu Ile Ile Val  Thr Arg Gly
    2285                 2290                 2295

Lys Ser  Ile Ser Leu Glu Cys  Glu Val Gln Gly Ile  Pro Pro Pro
    2300                 2305                 2310

Thr Val  Thr Trp Met Lys Asp  Gly His Pro Leu Ile  Lys Ala Lys
    2315                 2320                 2325

Gly Val  Glu Ile Leu Asp Glu  Gly His Ile Leu Gln  Leu Lys Asn
    2330                 2335                 2340

Ile His  Val Ser Asp Thr Gly  Arg Tyr Val Cys Val  Ala Val Asn
    2345                 2350                 2355

Val Ala  Gly Met Thr Asp Lys  Lys Tyr Asp Leu Ser  Val His Ala
    2360                 2365                 2370

Pro Pro  Ser Ile Ile Gly Asn  His Arg Ser Pro Glu  Asn Ile Ser
    2375                 2380                 2385

Val Val  Glu Lys Asn Ser Val  Ser Leu Thr Cys Glu  Ala Ser Gly
    2390                 2395                 2400

Ile Pro  Leu Pro Ser Ile Thr  Trp Phe Lys Asp Gly  Trp Pro Val
    2405                 2410                 2415

Ser Leu  Ser Asn Ser Val Arg  Ile Leu Ser Gly Gly  Arg Met Leu
    2420                 2425                 2430

Arg Leu  Met Gln Thr Thr Met  Glu Asp Ala Gly Gln  Tyr Thr Cys
    2435                 2440                 2445

Val Val  Arg Asn Ala Ala Gly  Glu Glu Arg Lys Ile  Phe Gly Leu
    2450                 2455                 2460

Ser Val  Leu Val Pro Pro His  Ile Val Gly Glu Asn  Thr Leu Glu
    2465                 2470                 2475

Asp Val  Lys Val Lys Glu Lys  Gln Ser Val Thr Leu  Thr Cys Glu
    2480                 2485                 2490

Val Thr  Gly Asn Pro Val Pro  Glu Ile Thr Trp His  Lys Asp Gly
    2495                 2500                 2505

Gln Pro  Leu Gln Glu Asp Glu  Ala His His Ile Ile  Ser Gly Gly
    2510                 2515                 2520

Arg Phe  Leu Gln Ile Thr Asn  Val Gln Val Pro His  Thr Gly Arg
    2525                 2530                 2535

Tyr Thr  Cys Leu Ala Ser Ser  Pro Ala Gly His Lys  Ser Arg Ser
    2540                 2545                 2550

Phe Ser  Leu Asn Val Phe Val  Ser Pro Thr Ile Ala  Gly Val Gly
    2555                 2560                 2565

Ser Asp  Gly Asn Pro Glu Asp  Val Thr Val Ile Leu  Asn Ser Pro
    2570                 2575                 2580
```

-continued

```
Thr Ser  Leu Val Cys Glu Ala  Tyr Ser Tyr Pro Pro  Ala Thr Ile
    2585                 2590                 2595

Thr Trp  Phe Lys Asp Gly Thr  Pro Leu Glu Ser Asn  Arg Asn Ile
    2600                 2605                 2610

Arg Ile  Leu Pro Gly Gly Arg  Thr Leu Gln Ile Leu  Asn Ala Gln
    2615                 2620                 2625

Glu Asp  Asn Ala Gly Arg Tyr  Ser Cys Val Ala Thr  Asn Glu Ala
    2630                 2635                 2640

Gly Glu  Met Ile Lys His Tyr  Glu Val Lys Val Tyr  Ile Pro Pro
    2645                 2650                 2655

Ile Ile  Asn Lys Gly Asp Leu  Trp Gly Pro Gly Leu  Ser Pro Lys
    2660                 2665                 2670

Glu Val  Lys Ile Lys Val Asn  Asn Thr Leu Thr Leu  Glu Cys Glu
    2675                 2680                 2685

Ala Tyr  Ala Ile Pro Ser Ala  Ser Leu Ser Trp Tyr  Lys Asp Gly
    2690                 2695                 2700

Gln Pro  Leu Lys Ser Asp Asp  His Val Asn Ile Ala  Ala Asn Gly
    2705                 2710                 2715

His Thr  Leu Gln Ile Lys Glu  Ala Gln Ile Ser Asp  Thr Gly Arg
    2720                 2725                 2730

Tyr Thr  Cys Val Ala Ser Asn  Ile Ala Gly Glu Asp  Glu Leu Asp
    2735                 2740                 2745

Phe Asp  Val Asn Ile Gln Val  Pro Pro Ser Phe Gln  Lys Leu Trp
    2750                 2755                 2760

Glu Ile  Gly Asn Met Leu Asp  Thr Gly Arg Asn Gly  Glu Ala Lys
    2765                 2770                 2775

Asp Val  Ile Ile Asn Asn Pro  Ile Ser Leu Tyr Cys  Glu Thr Asn
    2780                 2785                 2790

Ala Ala  Pro Pro Pro Thr Leu  Thr Trp Tyr Lys Asp  Gly His Pro
    2795                 2800                 2805

Leu Thr  Ser Ser Asp Lys Val  Leu Ile Leu Pro Gly  Gly Arg Val
    2810                 2815                 2820

Leu Gln  Ile Pro Arg Ala Lys  Val Glu Asp Ala Gly  Arg Tyr Thr
    2825                 2830                 2835

Cys Val  Ala Val Asn Glu Ala  Gly Glu Asp Ser Leu  Gln Tyr Asp
    2840                 2845                 2850

Val Arg  Val Leu Val Pro Pro  Ile Ile Lys Gly Ala  Asn Ser Asp
    2855                 2860                 2865

Leu Pro  Glu Glu Val Thr Val  Leu Val Asn Lys Ser  Ala Leu Ile
    2870                 2875                 2880

Glu Cys  Leu Ser Ser Gly Ser  Pro Ala Pro Arg Asn  Ser Trp Gln
    2885                 2890                 2895

Lys Asp  Gly Gln Pro Leu Leu  Glu Asp Asp His His  Lys Phe Leu
    2900                 2905                 2910

Ser Asn  Gly Arg Ile Leu Gln  Ile Leu Asn Thr Gln  Ile Thr Asp
    2915                 2920                 2925

Ile Gly  Arg Tyr Val Cys Val  Ala Glu Asn Thr Ala  Gly Ser Ala
    2930                 2935                 2940

Lys Lys  Tyr Phe Asn Leu Asn  Val His Val Pro Pro  Ser Val Ile
    2945                 2950                 2955

Gly Pro  Lys Ser Glu Asn Leu  Thr Val Val Val Asn  Asn Phe Ile
    2960                 2965                 2970

Ser Leu  Thr Cys Glu Val Ser  Gly Phe Pro Pro Pro  Asp Leu Ser
```

-continued

```
    2975                2980                2985

Trp Leu Lys Asn Lys Leu Asn Thr Asn Thr Leu Ile Val Pro Gly
    2990                2995                3000

Gly Arg Thr Leu Gln Ile Ile Arg Ala Lys Val Ser Asp Gly Gly
    3005                3010                3015

Glu Tyr Thr Cys Ile Ala Ile Asn Gln Ala Gly Glu Ser Lys Lys
    3020                3025                3030

Lys Phe Ser Leu Thr Val Tyr Val Pro Pro Ser Ile Lys Asp His
    3035                3040                3045

Asp Ser Glu Ser Leu Ser Val Val Asn Val Arg Glu Gly Thr Ser
    3050                3055                3060

Val Ser Leu Glu Cys Glu Ser Asn Ala Val Pro Pro Pro Val Ile
    3065                3070                3075

Thr Trp Tyr Lys Asn Gly Arg Met Ile Thr Glu Ser Thr His Val
    3080                3085                3090

Glu Ile Leu Ala Asp Gly Gln Met Leu His Ile Lys Lys Ala Glu
    3095                3100                3105

Val Ser Asp Thr Gly Gln Tyr Val Cys Arg Ala Ile Asn Val Ala
    3110                3115                3120

Gly Arg Asp Asp Lys Asn Phe His Leu Asn Val Tyr Val Pro Pro
    3125                3130                3135

Ser Ile Glu Gly Pro Glu Arg Glu Val Ile Val Glu Thr Ile Ser
    3140                3145                3150

Asn Pro Val Thr Leu Thr Cys Asp Ala Thr Gly Ile Pro Pro Pro
    3155                3160                3165

Thr Ile Ala Trp Leu Lys Asn His Lys Arg Ile Glu Asn Ser Asp
    3170                3175                3180

Ser Leu Glu Val Arg Ile Leu Ser Gly Gly Ser Lys Leu Gln Ile
    3185                3190                3195

Ala Arg Ser Gln His Ser Asp Ser Gly Asn Tyr Thr Cys Ile Ala
    3200                3205                3210

Ser Asn Met Glu Gly Lys Ala Gln Lys Tyr Tyr Phe Leu Ser Ile
    3215                3220                3225

Gln Val Pro Pro Ser Val Ala Gly Ala Glu Ile Pro Ser Asp Val
    3230                3235                3240

Ser Val Leu Leu Gly Glu Asn Val Glu Leu Val Cys Asn Ala Asn
    3245                3250                3255

Gly Ile Pro Thr Pro Leu Ile Gln Trp Leu Lys Asp Gly Lys Pro
    3260                3265                3270

Ile Ala Ser Gly Glu Thr Glu Arg Ile Arg Val Ser Ala Asn Gly
    3275                3280                3285

Ser Thr Leu Asn Ile Tyr Gly Ala Leu Thr Ser Asp Thr Gly Lys
    3290                3295                3300

Tyr Thr Cys Val Ala Thr Asn Pro Ala Gly Glu Glu Asp Arg Ile
    3305                3310                3315

Phe Asn Leu Asn Val Tyr Val Thr Pro Thr Ile Arg Gly Asn Lys
    3320                3325                3330

Asp Glu Ala Glu Lys Leu Met Thr Leu Val Asp Thr Ser Ile Asn
    3335                3340                3345

Ile Glu Cys Arg Ala Thr Gly Thr Pro Pro Pro Gln Ile Asn Trp
    3350                3355                3360

Leu Lys Asn Gly Leu Pro Leu Pro Leu Ser Ser His Ile Arg Leu
    3365                3370                3375
```

-continued

```
Leu Ala  Ala Gly Gln Val Ile  Arg Ile Val Arg Ala  Gln Val Ser
    3380                 3385                 3390

Asp Val  Ala Val Tyr Thr Cys  Val Ala Ser Asn Arg  Ala Gly Val
    3395                 3400                 3405

Asp Asn  Lys His Tyr Asn Leu  Gln Val Phe Ala Pro  Pro Asn Met
    3410                 3415                 3420

Asp Asn  Ser Met Gly Thr Glu  Glu Ile Thr Val Leu  Lys Gly Ser
    3425                 3430                 3435

Ser Thr  Ser Met Ala Cys Ile  Thr Asp Gly Thr Pro  Ala Pro Ser
    3440                 3445                 3450

Met Ala  Trp Leu Arg Asp Gly  Gln Pro Leu Gly Leu  Asp Ala His
    3455                 3460                 3465

Leu Thr  Val Ser Thr His Gly  Met Val Leu Gln Leu  Leu Lys Ala
    3470                 3475                 3480

Glu Thr  Glu Asp Ser Gly Lys  Tyr Thr Cys Ile Ala  Ser Asn Glu
    3485                 3490                 3495

Ala Gly  Glu Val Ser Lys His  Phe Ile Leu Lys Val  Leu Glu Pro
    3500                 3505                 3510

Pro His  Ile Asn Gly Ser Glu  Glu His Glu Glu Ile  Ser Val Ile
    3515                 3520                 3525

Val Asn  Asn Pro Leu Glu Leu  Thr Cys Ile Ala Ser  Gly Ile Pro
    3530                 3535                 3540

Ala Pro  Lys Met Thr Trp Met  Lys Asp Gly Arg Pro  Leu Pro Gln
    3545                 3550                 3555

Thr Asp  Gln Val Gln Thr Leu  Gly Gly Gly Glu Val  Leu Arg Ile
    3560                 3565                 3570

Ser Thr  Ala Gln Val Glu Asp  Thr Gly Arg Tyr Thr  Cys Leu Ala
    3575                 3580                 3585

Ser Ser  Pro Ala Gly Asp Asp  Asp Lys Glu Tyr Leu  Val Arg Val
    3590                 3595                 3600

His Val  Pro Pro Asn Ile Ala  Gly Thr Asp Glu Pro  Arg Asp Ile
    3605                 3610                 3615

Thr Val  Leu Arg Asn Arg Gln  Val Thr Leu Glu Cys  Lys Ser Asp
    3620                 3625                 3630

Ala Val  Pro Pro Pro Val Ile  Thr Trp Leu Arg Asn  Gly Glu Arg
    3635                 3640                 3645

Leu Gln  Ala Thr Pro Arg Val  Arg Ile Leu Ser Gly  Gly Arg Tyr
    3650                 3655                 3660

Leu Gln  Ile Asn Asn Ala Asp  Leu Gly Asp Thr Ala  Asn Tyr Thr
    3665                 3670                 3675

Cys Val  Ala Ser Asn Ile Ala  Gly Lys Thr Thr Arg  Glu Phe Ile
    3680                 3685                 3690

Leu Thr  Val Asn Val Pro Pro  Asn Ile Lys Gly Gly  Pro Gln Ser
    3695                 3700                 3705

Leu Val  Ile Leu Leu Asn Lys  Ser Thr Val Leu Glu  Cys Ile Ala
    3710                 3715                 3720

Glu Gly  Val Pro Thr Pro Arg  Ile Thr Trp Arg Lys  Asp Gly Ala
    3725                 3730                 3735

Val Leu  Ala Gly Asn His Ala  Arg Tyr Ser Ile Leu  Glu Asn Gly
    3740                 3745                 3750

Phe Leu  His Ile Gln Ser Ala  His Val Thr Asp Thr  Gly Arg Tyr
    3755                 3760                 3765
```

-continued

```
Leu Cys  Met Ala Thr Asn Ala  Ala Gly Thr Asp Arg  Arg Arg Ile
    3770                 3775                 3780

Asp Leu  Gln Val His Val Pro  Pro Ser Ile Ala Pro  Gly Pro Thr
    3785                 3790                 3795

Asn Met  Thr Val Ile Val Asn  Val Gln Thr Thr Leu  Ala Cys Glu
    3800                 3805                 3810

Ala Thr  Gly Ile Pro Lys Pro  Ser Ile Asn Trp Arg  Lys Asn Gly
    3815                 3820                 3825

His Leu  Leu Asn Val Asp Gln  Asn Gln Asn Ser Tyr  Arg Leu Leu
    3830                 3835                 3840

Ser Ser  Gly Ser Leu Val Ile  Ile Ser Pro Ser Val  Asp Asp Thr
    3845                 3850                 3855

Ala Thr  Tyr Glu Cys Thr Val  Thr Asn Gly Ala Gly  Asp Asp Lys
    3860                 3865                 3870

Arg Thr  Val Asp Leu Thr Val  Gln Val Pro Pro Ser  Ile Ala Asp
    3875                 3880                 3885

Glu Pro  Thr Asp Phe Leu Val  Thr Lys His Ala Pro  Ala Val Ile
    3890                 3895                 3900

Thr Cys  Thr Ala Ser Gly Val  Pro Phe Pro Ser Ile  His Trp Thr
    3905                 3910                 3915

Lys Asn  Gly Ile Arg Leu Leu  Pro Arg Gly Asp Gly  Tyr Arg Ile
    3920                 3925                 3930

Leu Ser  Ser Gly Ala Ile Glu  Ile Leu Ala Thr Gln  Leu Asn His
    3935                 3940                 3945

Ala Gly  Arg Tyr Thr Cys Val  Ala Arg Asn Ala Ala  Gly Ser Ala
    3950                 3955                 3960

His Arg  His Val Thr Leu His  Val His Glu Pro Pro  Val Ile Gln
    3965                 3970                 3975

Pro Gln  Pro Ser Glu Leu His  Val Ile Leu Asn Asn  Pro Ile Leu
    3980                 3985                 3990

Leu Pro  Cys Glu Ala Thr Gly  Thr Pro Ser Pro Phe  Ile Thr Trp
    3995                 4000                 4005

Gln Lys  Glu Gly Ile Asn Val  Asn Thr Ser Gly Arg  Asn His Ala
    4010                 4015                 4020

Val Leu  Pro Ser Gly Gly Leu  Gln Ile Ser Arg Ala  Val Arg Glu
    4025                 4030                 4035

Asp Ala  Gly Thr Tyr Met Cys  Val Ala Gln Asn Pro  Ala Gly Thr
    4040                 4045                 4050

Ala Leu  Gly Lys Ile Lys Leu  Asn Val Gln Val Pro  Pro Val Ile
    4055                 4060                 4065

Ser Pro  His Leu Lys Glu Tyr  Val Ile Ala Val Asp  Lys Pro Ile
    4070                 4075                 4080

Thr Leu  Ser Cys Glu Ala Asp  Gly Leu Pro Pro Pro  Asp Ile Thr
    4085                 4090                 4095

Trp His  Lys Asp Gly Arg Ala  Ile Val Glu Ser Ile  Arg Gln Arg
    4100                 4105                 4110

Val Leu  Ser Ser Gly Ser Leu  Gln Ile Ala Phe Val  Gln Pro Gly
    4115                 4120                 4125

Asp Ala  Gly His Tyr Thr Cys  Met Ala Ala Asn Val  Ala Gly Ser
    4130                 4135                 4140

Ser Ser  Thr Ser Thr Lys Leu  Thr Val His Val Pro  Pro Arg Ile
    4145                 4150                 4155

Arg Ser  Thr Glu Gly His Tyr  Thr Val Asn Glu Asn  Ser Gln Ala
```

-continued

```
    4160                4165                4170

Ile Leu  Pro Cys Val Ala Asp  Gly Ile Pro Thr Pro  Ala Ile Asn
    4175                4180                4185

Trp Lys  Lys Asp Asn Val Leu  Leu Ala Asn Leu Leu  Gly Lys Tyr
    4190                4195                4200

Thr Ala  Glu Pro Tyr Gly Glu  Leu Ile Leu Glu Asn  Val Val Leu
    4205                4210                4215

Glu Asp  Ser Gly Phe Tyr Thr  Cys Val Ala Asn Asn  Ala Ala Gly
    4220                4225                4230

Glu Asp  Thr His Thr Val Ser  Leu Thr Val His Val  Leu Pro Thr
    4235                4240                4245

Phe Thr  Glu Leu Pro Gly Asp  Val Ser Leu Asn Lys  Gly Glu Gln
    4250                4255                4260

Leu Arg  Leu Ser Cys Lys Ala  Thr Gly Ile Pro Leu  Pro Lys Leu
    4265                4270                4275

Thr Trp  Thr Phe Asn Asn Asn  Ile Ile Pro Ala His  Phe Asp Ser
    4280                4285                4290

Val Asn  Gly His Ser Glu Leu  Val Ile Glu Arg Val  Ser Lys Glu
    4295                4300                4305

Asp Ser  Gly Thr Tyr Val Cys  Thr Ala Glu Asn Ser  Val Gly Phe
    4310                4315                4320

Val Lys  Ala Ile Gly Phe Val  Tyr Val Lys Glu Pro  Pro Val Phe
    4325                4330                4335

Lys Gly  Asp Tyr Pro Ser Asn  Trp Ile Glu Pro Leu  Gly Gly Asn
    4340                4345                4350

Ala Ile  Leu Asn Cys Glu Val  Lys Gly Asp Pro Thr  Pro Thr Ile
    4355                4360                4365

Gln Trp  Asn Arg Lys Gly Val  Asp Ile Glu Ile Ser  His Arg Ile
    4370                4375                4380

Arg Gln  Leu Gly Asn Gly Ser  Leu Ala Ile Tyr Gly  Thr Val Asn
    4385                4390                4395

Glu Asp  Ala Gly Asp Tyr Thr  Cys Val Ala Thr Asn  Glu Ala Gly
    4400                4405                4410

Val Val  Glu Arg Ser Met Ser  Leu Thr Leu Gln Ser  Pro Pro Ile
    4415                4420                4425

Ile Thr  Leu Glu Pro Val Glu  Thr Val Ile Asn Ala  Gly Gly Lys
    4430                4435                4440

Ile Ile  Leu Asn Cys Gln Ala  Thr Gly Glu Pro Gln  Pro Thr Ile
    4445                4450                4455

Thr Trp  Ser Arg Gln Gly His  Ser Ile Ser Trp Asp  Asp Arg Val
    4460                4465                4470

Asn Val  Leu Ser Asn Asn Ser  Leu Tyr Ile Ala Asp  Ala Gln Lys
    4475                4480                4485

Glu Asp  Thr Ser Glu Phe Glu  Cys Val Ala Arg Asn  Leu Met Gly
    4490                4495                4500

Ser Val  Leu Val Arg Val Pro  Val Ile Val Gln Val  His Gly Gly
    4505                4510                4515

Phe Ser  Gln Trp Ser Ala Trp  Arg Ala Cys Ser Val  Thr Cys Gly
    4520                4525                4530

Lys Gly  Ile Gln Lys Arg Ser  Arg Leu Cys Asn Gln  Pro Leu Pro
    4535                4540                4545

Ala Asn  Gly Gly Lys Pro Cys  Gln Gly Ser Asp Leu  Glu Met Arg
    4550                4555                4560
```

-continued

```
Asn Cys Gln Asn Lys Pro Cys Pro Val Asp Gly Ser Trp Ser Glu
    4565                4570                4575

Trp Ser Leu Trp Glu Glu Cys Thr Arg Ser Cys Gly Arg Gly Asn
    4580                4585                4590

Gln Thr Arg Thr Arg Thr Cys Asn Asn Pro Ser Val Gln His Gly
    4595                4600                4605

Gly Arg Pro Cys Glu Gly Asn Ala Val Glu Ile Ile Met Cys Asn
    4610                4615                4620

Ile Arg Pro Cys Pro Val His Gly Ala Trp Ser Ala Trp Gln Pro
    4625                4630                4635

Trp Gly Thr Cys Ser Glu Ser Cys Gly Lys Gly Thr Gln Thr Arg
    4640                4645                4650

Ala Arg Leu Cys Asn Asn Pro Pro Pro Ala Phe Gly Gly Ser Tyr
    4655                4660                4665

Cys Asp Gly Ala Glu Thr Gln Met Gln Val Cys Asn Glu Arg Asn
    4670                4675                4680

Cys Pro Ile His Gly Lys Trp Ala Thr Trp Ala Ser Trp Ser Ala
    4685                4690                4695

Cys Ser Val Ser Cys Gly Gly Gly Ala Arg Gln Arg Thr Arg Gly
    4700                4705                4710

Cys Ser Asp Pro Val Pro Gln Tyr Gly Gly Arg Lys Cys Glu Gly
    4715                4720                4725

Ser Asp Val Gln Ser Asp Phe Cys Asn Ser Asp Pro Cys Pro Thr
    4730                4735                4740

His Gly Asn Trp Ser Pro Trp Ser Gly Trp Gly Thr Cys Ser Arg
    4745                4750                4755

Thr Cys Asn Gly Gly Gln Met Arg Arg Tyr Arg Thr Cys Asp Asn
    4760                4765                4770

Pro Pro Pro Ser Asn Gly Gly Arg Ala Cys Gly Gly Pro Asp Ser
    4775                4780                4785

Gln Ile Gln Arg Cys Asn Thr Asp Met Cys Pro Val Asp Gly Ser
    4790                4795                4800

Trp Gly Ser Trp His Ser Trp Ser Gln Cys Ser Ala Ser Cys Gly
    4805                4810                4815

Gly Gly Glu Lys Thr Arg Lys Arg Leu Cys Asp His Pro Val Pro
    4820                4825                4830

Val Lys Gly Gly Arg Pro Cys Pro Gly Asp Thr Thr Gln Val Thr
    4835                4840                4845

Arg Cys Asn Val Gln Ala Cys Pro Gly Gly Pro Gln Arg Ala Arg
    4850                4855                4860

Gly Ser Val Ile Gly Asn Ile Asn Asp Val Glu Phe Gly Ile Ala
    4865                4870                4875

Phe Leu Asn Ala Thr Ile Thr Asp Ser Pro Asn Ser Asp Thr Arg
    4880                4885                4890

Ile Ile Arg Ala Lys Ile Thr Asn Val Pro Arg Ser Leu Gly Ser
    4895                4900                4905

Ala Met Arg Lys Ile Val Ser Ile Leu Asn Pro Ile Tyr Trp Thr
    4910                4915                4920

Thr Ala Lys Glu Ile Gly Glu Ala Val Asn Gly Phe Thr Leu Thr
    4925                4930                4935

Asn Ala Val Phe Lys Arg Glu Thr Gln Val Glu Phe Ala Thr Gly
    4940                4945                4950
```

-continued

```
Glu Ile  Leu Gln Met Ser His  Ile Ala Arg Gly Leu  Asp Ser Asp
    4955                 4960                 4965

Gly Ser  Leu Leu Leu Asp Ile  Val Val Ser Gly Tyr  Val Leu Gln
    4970                 4975                 4980

Leu Gln  Ser Pro Ala Glu Val  Thr Val Lys Asp Tyr  Thr Glu Asp
    4985                 4990                 4995

Tyr Ile  Gln Thr Gly Pro Gly  Gln Leu Tyr Ala Tyr  Ser Thr Arg
    5000                 5005                 5010

Leu Phe  Thr Ile Asp Gly Ile  Ser Ile Pro Tyr Thr  Trp Asn His
    5015                 5020                 5025

Thr Val  Phe Tyr Asp Gln Ala  Gln Gly Arg Met Pro  Phe Leu Val
    5030                 5035                 5040

Glu Thr  Leu His Ala Ser Ser  Val Glu Ser Asp Tyr  Asn Gln Ile
    5045                 5050                 5055

Glu Glu  Thr Leu Gly Phe Lys  Ile His Ala Ser Ile  Ser Lys Gly
    5060                 5065                 5070

Asp Arg  Ser Asn Gln Cys Pro  Ser Gly Phe Thr Leu  Asp Ser Val
    5075                 5080                 5085

Gly Pro  Phe Cys Ala Asp Glu  Asp Glu Cys Ala Ala  Gly Asn Pro
    5090                 5095                 5100

Cys Ser  His Ser Cys His Asn  Ala Met Gly Thr Tyr  Tyr Cys Ser
    5105                 5110                 5115

Cys Pro  Lys Gly Leu Thr Ile  Ala Ala Asp Gly Arg  Thr Cys Gln
    5120                 5125                 5130

Asp Ile  Asp Glu Cys Ala Leu  Gly Arg His Thr Cys  His Ala Gly
    5135                 5140                 5145

Gln Asp  Cys Asp Asn Thr Ile  Gly Ser Tyr Arg Cys  Val Val Arg
    5150                 5155                 5160

Cys Gly  Ser Gly Phe Arg Arg  Thr Ser Asp Gly Leu  Ser Cys Gln
    5165                 5170                 5175

Asp Ile  Asn Glu Cys Gln Glu  Ser Ser Pro Cys His  Gln Arg Cys
    5180                 5185                 5190

Phe Asn  Ala Ile Gly Ser Phe  His Cys Gly Cys Glu  Pro Gly Tyr
    5195                 5200                 5205

Gln Leu  Lys Gly Arg Lys Cys  Met Asp Val Asn Glu  Cys Arg Gln
    5210                 5215                 5220

Asn Val  Cys Arg Pro Asp Gln  His Cys Lys Asn Thr  Arg Gly Gly
    5225                 5230                 5235

Tyr Lys  Cys Ile Asp Leu Cys  Pro Asn Gly Met Thr  Lys Ala Glu
    5240                 5245                 5250

Asn Gly  Thr Cys Ile Asp Ile  Asp Glu Cys Lys Asp  Gly Thr His
    5255                 5260                 5265

Gln Cys  Arg Tyr Asn Gln Ile  Cys Glu Asn Thr Arg  Gly Ser Tyr
    5270                 5275                 5280

Arg Cys  Val Cys Pro Arg Gly  Tyr Arg Ser Gln Gly  Val Gly Arg
    5285                 5290                 5295

Pro Cys  Met Asp Ile Asn Glu  Cys Glu Gln Val Pro  Lys Pro Cys
    5300                 5305                 5310

Ala His  Gln Cys Ser Asn Thr  Pro Gly Ser Phe Lys  Cys Ile Cys
    5315                 5320                 5325

Pro Pro  Gly Gln His Leu Leu  Gly Asp Gly Lys Ser  Cys Ala Gly
    5330                 5335                 5340

Leu Glu  Arg Leu Pro Asn Tyr  Gly Thr Gln Tyr Ser  Ser Tyr Asn
```

-continued

```
    5345                5350                5355

Leu Ala  Arg Phe Ser Pro Val  Arg Asn Asn Tyr Gln  Pro Gln Gln
    5360                5365                5370

His Tyr  Arg Gln Tyr Ser His  Leu Tyr Ser Ser Tyr  Ser Glu Tyr
    5375                5380                5385

Arg Asn  Ser Arg Thr Ser Leu  Ser Arg Thr Arg Arg  Thr Ile Arg
    5390                5395                5400

Lys Thr  Cys Pro Glu Gly Ser  Glu Ala Ser His Asp  Thr Cys Val
    5405                5410                5415

Asp Ile  Asp Glu Cys Glu Asn  Thr Asp Ala Cys Gln  His Glu Cys
    5420                5425                5430

Lys Asn  Thr Phe Gly Ser Tyr  Gln Cys Ile Cys Pro  Pro Gly Tyr
    5435                5440                5445

Gln Leu  Thr His Asn Gly Lys  Thr Cys Gln Asp Ile  Asp Glu Cys
    5450                5455                5460

Leu Glu  Gln Asn Val His Cys  Gly Pro Asn Arg Met  Cys Phe Asn
    5465                5470                5475

Met Arg  Gly Ser Tyr Gln Cys  Ile Asp Thr Pro Cys  Pro Pro Asn
    5480                5485                5490

Tyr Gln  Arg Asp Pro Val Ser  Gly Phe Cys Leu Lys  Asn Cys Pro
    5495                5500                5505

Pro Asn  Asp Leu Glu Cys Ala  Leu Ser Pro Tyr Ala  Leu Glu Tyr
    5510                5515                5520

Lys Leu  Val Ser Leu Pro Phe  Gly Ile Ala Thr Asn  Gln Asp Leu
    5525                5530                5535

Ile Arg  Leu Val Ala Tyr Thr  Gln Asp Gly Val Met  His Pro Arg
    5540                5545                5550

Thr Thr  Phe Leu Met Val Asp  Glu Glu Gln Thr Val  Pro Phe Ala
    5555                5560                5565

Leu Arg  Asp Glu Asn Leu Lys  Gly Val Val Tyr Thr  Thr Arg Pro
    5570                5575                5580

Leu Arg  Glu Ala Glu Thr Tyr  Arg Met Arg Val Arg  Ala Ser Ser
    5585                5590                5595

Tyr Ser  Ala Asn Gly Thr Ile  Glu Tyr Gln Thr Thr  Phe Ile Val
    5600                5605                5610

Tyr Ile  Ala Val Ser Ala Tyr  Pro Tyr
    5615                5620


<210> SEQ ID NO 129
<211> LENGTH: 222
<212> TYPE: PRT
<213> ORGANISM: Homo sapiens

<400> SEQUENCE: 129

Met Leu Ser Arg Ala Val Cys Gly Thr Ser Arg Gln Leu Pro Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80
```

-continued

```
Gln Ile Ala Leu Gln Pro Ala Leu Lys Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Leu Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220


<210> SEQ ID NO 130
<211> LENGTH: 99
<212> TYPE: PRT
<213> ORGANISM: Homo sapiens

<400> SEQUENCE: 130

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr


<210> SEQ ID NO 131
<211> LENGTH: 355
<212> TYPE: PRT
<213> ORGANISM: Homo sapiens

<400> SEQUENCE: 131

Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Leu Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
```

-continued

```
                85                  90                  95
Val Leu Glu Leu Gly Ile Thr Gly Ser Lys Phe Asp Val Ser Ser Phe
            100                 105                 110
Asn Pro His Gly Ile Ser Thr Phe Thr Asp Glu Asp Asn Ala Met Tyr
        115                 120                 125
Leu Leu Val Val Asn His Pro Asp Ala Lys Ser Thr Val Glu Leu Phe
    130                 135                 140
Lys Phe Gln Glu Glu Glu Lys Ser Leu Leu His Leu Lys Thr Ile Arg
145                 150                 155                 160
His Lys Leu Leu Pro Asn Leu Asn Asp Ile Val Ala Val Gly Pro Glu
                165                 170                 175
His Phe Tyr Gly Thr Asn Asp His Tyr Phe Leu Asp Pro Tyr Leu Gln
            180                 185                 190
Ser Trp Glu Met Tyr Leu Gly Leu Ala Trp Ser Tyr Val Val Tyr Tyr
        195                 200                 205
Ser Pro Ser Glu Val Arg Val Val Ala Glu Gly Phe Asp Phe Ala Asn
    210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asn Thr Leu Val Asp Asn Ile Ser
            260                 265                 270
Val Asp Pro Glu Thr Gly Asp Leu Trp Val Gly Cys His Pro Asn Gly
        275                 280                 285
Met Lys Ile Phe Phe Tyr Asp Ser Glu Asn Pro Pro Ala Ser Glu Val
    290                 295                 300
Leu Arg Ile Gln Asn Ile Leu Thr Glu Glu Pro Lys Val Thr Gln Val
305                 310                 315                 320
Tyr Ala Glu Asn Gly Thr Val Leu Gln Gly Ser Thr Val Ala Ser Val
                325                 330                 335
Tyr Lys Gly Lys Leu Leu Ile Gly Thr Val Phe His Lys Ala Leu Tyr
            340                 345                 350
Cys Glu Leu
        355
```

METHODS AND COMPOSITIONS FOR DETECTING AND TREATING RETINAL DISEASES

BACKGROUND OF THE INVENTION

Age-related macular degeneration (AMD) is the number one cause of blindness for the elderly population over 60 years of age. It is a devastating disease that destroys central vision in the affected individuals, robbing them of their ability to perform activities necessary for everyday life such as reading and driving (Bressler et al., 1988; Evans, 2001; Gottlieb, 2002). In one study, the prevalence of AMD in persons 75 or older has been reported to be 7.8% (Klein et al., 1992).

AMD is a slow, progressive disease that involves cells of the outer retinal layers (including photoreceptors and the retinal pigment epithelial (RPE) cells that support the photoreceptors), as well as cells in the adjacent vascular layer of the eye known as the choroid. Macular degeneration is characterized by the breakdown of the macula, a small portion of the central retina (about 2 mm in diameter) responsible for high-acuity vision. Late-onset macular degeneration (i.e., AMD) is generally defined as either "dry" or "wet." The wet ("exudative") neovascular form of AMD affects approximately 10% of those with the disease, and is characterized by abnormal blood vessels growing from the choriocapillaris through the RPE, typically resulting in hemorrhage, exudation, scarring, and/or serous retinal detachment. Approximately 90% of patients with AMD have the non-neovascular dry form, characterized by atrophy of the RPE and loss of macular photoreceptors.

One of the clinical hallmarks of AMD is the presence of deposits of debris-like material, termed "drusen," that accumulate on Bruch's membrane, a multilayered composite of extracellular matrix components separating the RPE (the outermost layer of the retina) from the underlying choroid. Drusen can be observed by funduscopic eye examination. These deposits have been extensively characterized in microscopic studies of donor eyes from patients with AMD (Sarks, et al., 1988). The deposits observed in the living eye upon clinical examination are classified as either soft drusen or hard drusen, according to several criteria including relative size, abundance, and shape of the deposits (reviewed, for example, in Abdelsalam et al., 1999). Histochemical and immunocytochemical studies have shown that drusen contain a variety of lipids, polysaccharides, glycosaminoglycans and proteins (Abdelsalam et al., 1999; Hageman et al., 1999, 2001).

There is presently no cure for AMD. Several types of treatments are available, with laser photocoagulation of abnormal vessels in the wet form of the disease being the standard (Gottlieb, 2002; Algvere and Seregard, 2002). This treatment is limited by the fact that only well-delineated neovascular lesions can be treated in this way and that 50% of patients will suffer recurrence of the leakage from the vessels (Fine et al., 2000). Because of the energy of the laser required for this treatment, the photoreceptors in the treated area will also die, and the patient will also often suffer central blindness immediately after the treatment. New neovascular lesions will eventually develop, requiring repeated treatments.

Photodynamic therapy, which combines low energy laser activation with a photosensitive agent, has been a valuable addition to the laser treatment approach (Bressler, 2001). In this method, a photosensitive agent, i.e., verteporfin is used which has an affinity for abnormal new blood vessels. Selective targeting of these vessels can be activated by nonthermal laser to produce reactive oxygen species which can destroy the abnormal vessels. In a study group, only 33% of those receiving photodynamic therapy with verteporfin had substantial loss of vision, compared to 61% of those who did not receive verteporfin. The treatment, however, was only beneficial for patients with classic choroidal neovascular membranes. The full long-term benefit of this new treatment modality has yet to be established. Despite this advance, however, the treatment does not prevent the subsequent formation of new neovascular lesions.

Other available treatments for the wet form of AMD include submacular surgery and external-beam radiation therapy. Those under study include retinal translocation and inhibition of vascular endothelial growth factor (Algvere and Seregard, 2002). For prevention of progression to advanced AMD, treatment with antioxidants, including vitamins C and E, β-carotene, and zinc, was shown to be helpful, and prophylactic laser treatment is under study (Gottlieb, 2002).

Despite the above-described advances, it is recognized that current treatment for AMD is mostly palliative (Algvere and Seregard, 2002). None of the available treatments attacks the fundamental cause of the disease, which is unknown. The disease therefore can continue to progress following treatment, with re-development of neovascularization and destruction of the macula. Accordingly, there remains a compelling need to understand the molecular mechanism of this disease, so that therapeutic treatment or cure can be directed at its root cause.

It is well recognized that genetic factors play an important role in the etiology of AMD. For example, it has been reported that people with a family history of AMD and siblings of AMD patients have a higher risk of developing AMD (Evans, 2001). Monozygotic twins have shown a higher concordance rate of clinical features of AMD compared to dizygotic twins (Klein et al., 1994). Another study found all monozygotic twins affected with AMD to be concordant for AMD while only 42% of dizygotic twins were concordant (Meyers et al., 1995). Accordingly, one major approach to understanding AMD etiology is to look for genes involved in AMD. For example, approaches such as linkage analysis in large families, allele sharing analysis among sib pairs, and association studies in populations have been used in attempts to identify genes associated with AMD (Guymer, 2001). Linkage to chromosomal region 1q was reported in a large AMD family (Klein et al., 1998). Results of an allele sharing analysis did not yield any new candidate genes (Weeks et al., 2000). An association of a mutation in hemicentin-1 has been reported in a familial form of age-related macular degeneration mapping to human chromosome 1q in a large family (Schultz et al., 2003).

Another genetic strategy for AMD is to test genes causing other forms of inherited macular degenerations as putative causative genes ("candidate genes") for AMD. Several macular diseases with a clearly hereditary pattern of inheritance (so-called "Mendelian macular degenerations") have been described that resemble AMD in phenotype. Examples of these diseases include Sorsby's fundus dystrophy, Stargardt's disease, Best disease, and Doyne's honeycomb retinal dystrophy (Guymer, 2001). Causative genes for these diseases have been analyzed as candidate genes for AMD. To date however, none of them has clearly demonstrated a causal relationship with AMD. For example, the ATP-binding cassette transporter gene (ABCR) was found to be the pathogenic gene for recessive Stargardt's disease (Hutchinson et al., 1997). ABCR was proposed as a candidate gene for AMD, and in one study, 16% of patients with AMD were initially shown to have mutations in this gene (Allikmets et al., 1997). This conclusion, however, has been challenged (Stone et al., 1998).

The most likely reason for the failure to find AMD genes through classical genetic approaches such as chromosomal mapping, genetic linkage analysis, and candidate gene analysis, is that AMD is a "multigene," or "complex" genetic disease. Complex genetic diseases are those diseases believed to be caused by changes in multiple genes. Such diseases characteristically demonstrate a complex pattern of inheritance (Heiba et al., 1994; Klein et al., 1994). In the case of AMD, a disease of old age, it is generally thought that the course of the disease is influenced not only by the combined effects of the above-described multiple genetic factors, but is further affected by certain environmental risk factors.

A second broad approach aimed at discovering causative genes in AMD has been hypothesis-based research aimed at elucidating the mechanism of the disease, with the goal of secondarily identifying the genes involved in the mechanism. Numerous hypotheses regarding the pathogenic mechanism of AMD have been proposed and tested, resulting in a voluminous literature on this subject.

Oxidative damage has been one major theme as a proposed mechanism for AMD (Winkler et al., 1999; Evans, 2001; Husain et al., 2002). The retina is known to have an extremely high consumption of oxygen, and the photoreceptors and RPE are in a very oxygen-rich environment. The RPE is situated immediately adjacent to the choriocapillaris, a rich capillary plexus coursing with highly oxygenated blood. The retina is a light-sensitive organ in which photoactivated events are constantly occurring during times of light exposure, resulting inter alia in the production of reactive oxygen species. In general support of the oxidative damage hypothesis, antioxidants tested in clinical studies have been reported to have a moderate beneficial effect of reducing progression to severe AMD (Hyman and Neborsky, 2002), although the results of several studies are conflicting (Flood et al., 2002). Smoking, which can reduce plasma levels of antioxidants, has been associated with increased risk of AMD (Mitchell et al., 2002). Adding support to the oxidative damage theory is a recent proteomic analysis of drusen, which demonstrated the presence in these deposits of several oxidation-modified products (Crabb et al., 2002).

It has been proposed that dysfunction in the RPE is central to the pathogenesis of AMD and can lead to drusen formation (Hogan, 1972). The earliest known sign of RPE dysfunction is accumulation of lipofuscin, which may lead to the characteristic thickening of Bruch's membrane, formation of drusen, and choroidal neovascularization observed in the wet form of AMD (Gass et al., 1985; Sarks et al., 1988; Green, 1999). Lipofuscin is composed of oxidized, polymeric molecules derived mostly from phagocytosed membranes of photoreceoptor outer segments (OS) (Katz, 1989; Kennedy et al., 1995). OS membranes are known to be rich in polyunsaturated fatty acids, which are an excellent substrate for peroxidation (Katz, 1989). It is believed that these molecules cannot be degraded and therefore begin to accumulate in the RPE cells as lipofuscin. At least one component of lipofuscin, i.e., the fluorophore A2E, a pyridinium bisretinoid, has been demonstrated to be toxic, causing membrane destabilization (De and Sakmar, 2002), and inhibition of cytochrome c oxidase and apoptosis in cultured porcine and human RPE cells (Shaban et al., 2002). Thus, A2E and lipofuscin accumulation in the RPE is thought to be directly related to dysfunction and demise of these cells with aging.

The processes of oxidative damage, lipofuscin accumulation, and drusen formation are not limited to AMD, but rather occur to some extent in all individuals with advancing age. Accordingly, a fundamental question that remains unanswered is why these processes are more advanced in some people than others, leading to AMD. Progress in developing new therapies targeting the root cause of AMD will require much greater knowledge of specific gene targets involved in the key cellular metabolic pathways in photoreceptors, RPE and choroidal cells that contribute to the observed pathology.

SUMMARY OF THE INVENTION

The invention provides novel methods and compositions for screening and treating retinal degenerative conditions, including age-related macular degeneration (AMD), as well as animal models useful for testing therapeutic compounds and methods. The invention is the product of a gene discovery strategy resulting in isolation of genes showing differential expression 1) in AMD-affected vs. normal eye tissues and 2) during the process of phagocytosis of outer segments (OS) by RPE cells. OS phagocytosis is a critical function of the RPE cells, involving a complex multi-step process, the byproducts of which contribute to generation of reactive oxygen species and lipofuscin accumulation in the RPE cells.

Using a novel expression cloning strategy termed CHANGE (for Comparative Hybridization ANalysis of Gene Expression) at least 200 AMD-related genes and at least 60 phagocytosis-related genes expressed in RPE cells were isolated. Five previously uncharacterized genes were identified by this strategy and demonstrated to be related to AMD and/or RPE phagocytosis. The nucleic acid sequences of cDNAs encoding the products of these genes are listed herein as SEQ ID NOS:1, 4, 5, 12, and 17.

A subset of six genes, termed "AMD/phagogenes," or "AMDP genes" are further described herein that fit the dual criteria of relatedness to AMD and to RPE phagocytosis. Three of these genes, i.e., prostaglandin D2 synthase (SEQ ID NO:2), matrix metalloproteinase, membrane-type 1 (MT1-MMP) (SEQ ID NO:15), and unknown RPE-expressed cDNA AMDP-3 (SEQ ID NO:17) all demonstrate up-regulation in AMD. AMDP genes down-regulated in AMD include casein kinase 1 epsilon (SEQ ID NO:9), ferritin heavy polypeptide 1 (SEQ ID NO:10), and SWI/SNF related/OSA-1 nuclear protein (SEQ ID NO:16).

Other genes previously not known to be functionally related to RPE phagocytosis are disclosed herein, including unknown PHG-1 (SEQ ID NO:1), myelin basic protein (SEQ ID NO:3), unknown PHG-4 (SEQ ID NO:4), unknown PHG-5 (SEQ ID NO:5), peanut-like2/septin 4 (SEQ ID NO:6), coactosin-like 1 (SEQ ID NO:7), clusterin (SEQ ID NO:8), metargidin (SEQ ID NO:11), unknown PHG-13 (SEQ ID NO:12), retinaldehyde binding protein 1 (SEQ ID NO:13), and actin gamma 1 (SEQ ID NO:14).

An exemplary AMDP gene discovered by the above strategy is the membrane-type matrix metalloproteinase 1 (MT1-MMP) (SEQ ID NO:15). MT1-MMP is a gene encoding a protease involved in the remodeling of extracellular matrix, for example by specifically activating pro-gelatinase A. Gelatinase A is the major metalloproteinase responsible for specific cleavage of type IV collagen, the main structural component of basement membranes. MT1-MMP also shows activity against other extracellular matrix components.

It has been demonstrated that MT1-MMP is a highly attractive therapeutic target for screening and treating AMD and other retinal conditions, based on the following findings:

1) MT1-MMP is upregulated in the RPE and photoreceptors in the eyes of patients with AMD, in a monkey model of AMD, and in the RCS rat, a model of retinal degeneration involving a defect in OS phagocytosis by the RPE;
2) MT1-MMP is directly involved in the mechanism of phagocytosis by RPE cells;
3) the progress of retinal degeneration in the RCS rat is significantly reduced by blocking activated MT1-MMP present in the subretinal space with an anti-MT1-MMP antibody;
4) a synonymous polymorphism of MT1-MMP (i.e., P259P) that could produce a splice variant of the mRNA resulting in a truncated protein, and a missense polymorphism of MT1-MMP (i.e., D273N) affecting the catalytic domain of the protein are found with higher frequency in the DNA of patients with AMD (54.8% vs. 31.6%) and familial maculopathies (68.2% vs. 31.6%).

Based on the foregoing discoveries, it is an object of the invention to provide a method for delaying or reversing a retinal or choroidal degenerative disease or condition in a subject. The method includes contacting a retinal or chorídal cell of a subject having, or at risk of developing, a retinal or choroidal degenerative disease or condition with an agent that modulates the expression or activity of an AMDP-related or phagocytosis-related gene. The AMDP-related or phagocytosis-related gene can be human unknown PHG-1; prostaglandin D2 synthase; myelin basic protein; human unknown PHG-4; human unknown PHG-5; human peanut-like 2/septin 4; coactosin-like 1; clusterin; casein kinase 1 epsilon; ferritin heavy polypeptide 1; metargidin; human unknown PHG-13; retinaldehyde binding protein 1; actin gamma 1; matrix metalloproteinase, membrane-associated 1 (MT1-MMP); SWI/SNF related/OSA-1 nuclear protein; and human unknown AMDP-3. The foregoing AMDP-related or phagocytosis-related genes include, respectively, the nucleotide sequences identified herein as SEQ ID NOS:1, 2, 3, 4, 5, 6, 7, 8, 9, 10, 11, 12, 13, 14, 15, 16, and 17.

Preferred genes targeted for modulation of expression or activity are prostaglandin D2 synthase, MT1-MMP and unknown gene AMDP-3, shown herein to be up-regulated in AMD. In a particularly preferred embodiment, the agent is directed against a MT1-MMP nucleic acid or protein. The retinal or choroidal degenerative disease or condition can be AMD. The method can be used to treat a subject suffering from AMD, or at risk of developing AMD.

The method can delay the retinal or choroidal degenerative disease or condition, or it can reverse the disease or condition.

The cell type to be contacted in the practice of the method can be a photoreceptor, an RPE cell or a Muller cell, or a cell type of the choroid, including an endothelial cell, a smooth muscle cell, a leukocyte, a macrophage, a melanocyte or a fibroblast.

In a preferred embodiment of the method, in which the AMDP-related or phagocytosis-related gene is MT1-MMP, the MT1-MMP may be located within the cell or in an extracellular matrix, such as an interphotoreceptor matrix.

In some embodiments of the method, the agent down-regulates expression of a nucleic acid or amino acid sequence of an AMDP-related or phagocytosis-related gene. In preferred embodiments, the targeted genes include MT1-MMP, prostaglandin D2 synthase and AMDP-3, which genes are shown herein to be over-expressed in AMD. The agent may be an oligonucleotide, for example a ribozyme, an antisense RNA, an interfering RNA (RNAi) molecule, or a triple helix forming molecule.

The agent may also be an antibody that specifically binds to a MT1-MMP, prostaglandin D2 synthase or AMDP-3 protein or peptide. Preferably the antibody can neutralize at least one biological activity of the protein or peptide. For example, an antibody against MT1-MMP can neutralize activation of a progelatinase A, or degradation of an extracellular matrix component.

In another embodiment, the agent that down-regulates expression of MT1-MMP, prostaglandin D2 synthase or AMDP-3 can be a small molecule.

It is a further object of the invention to provide a method of determining risk of a subject of developing a retinal or choroidal degenerative disease or condition. The method includes screening a nucleic acid sequence of the subject for the presence of at least one polymorphism in at least one phagocytosis-related or AMDP-related gene, wherein the presence of a polymorphism indicates that the subject is at higher risk for developing a retinal degenerative disorder than a subject without the polymorphism.

The phagocytosis-related genes can include, but are not limited to, unknown PHG-1, prostaglandin D2 synthase, myelin basic protein, unknown PHG-4, unknown PHG-5, peanut-like 2/septin 4, coactosin-like 1, clusterin, casein kinase 1 epsilon, ferritin heavy polypeptide 1, metargidin, unknown PHG-13, retinaldehyde binding protein 1, actin gamma 1, membrane type metalloprotinase 1 (MT1-MMP), SWI/SNF related/OSA-1 nuclear protein, and unknown AMDP-3. Nucleic acids encoding these phagocytosis-related gene products include, respectively, cDNA sequences listed herein as SEQ ID NOS:1-17.

The AMDP-related genes to be screened in the method can include, but are not limited to, prostaglandin D2 synthase, casein kinase 1 epsilon, ferritin heavy polypeptide 1, SWI/SNF related/OSA-1 nuclear protein, and AMDP-3. Nucleic acids encoding these AMDP-related gene products include, respectively, cDNA sequences listed herein as SEQ ID NOS:2, 9, 10, 16 and 17.

The polymorphisms screened in the method can be within an intronic, exonic or promoter region of the gene of interest.

In a preferred embodiment of the screening method, the gene of interest is MT1-MMP. The polymorphism can be within a region of the human MT1-MMP gene that can be amplified by PCR using amplimer pairs having nucleic acid sequences selected from the following groups: SEQ ID NOS:18 and 19; 20 and 21; 22 and 23; 24 and 25; 26 and 27; 28 and 29; 30 and 31; 32 and 33; 34 and 35; 36 and 37; 38 and 39; 40 and 41; 42 and 43; 44 and 45; 46 and 47; 48 and 49; 50 and 51; 52 and 53; 54 and 55; 56 and 57; and 57 and 58.

In a particularly preferred embodiment of the method, the polymorphism is within a 285 bp fragment of exon 5 of the human MT1-MMP gene. Within this region, the polymorphisms can include a D273N missense polymorphism and a P259P synonymous polymorphism.

It is also an object of the invention to provide a method of treating a retinal or choroidal degenerative disease or condition in a subject. The method includes contacting a retinal or choroidal cell of the subject with a vector that includes a nucleic acid encoding an agent that down-regulates or inhibits expresion of a phagocytosis-related or AMDP-related mRNA or protein. The agent included in the vector can be an antisense RNA, a ribozyme, or an interfering RNA (RNAi) molecule. In preferred embodiments, the phagocytosis-related or AMDP-related genes targeted for down-regulation are prostaglandin D2 synthase, MT1-

MMP, and AMDP-3, comprising respectively the nucleic acid sequences shown herein as SEQ ID NOS:2, 15 and 17.

In another aspect, the invention provides a method of treating a retinal or choridal degenerative disease or condition using a vector to deliver a desired form of a phagocytosis-related or AMDP-related gene product to a subject in need thereof. The vector can include a nucleic acid encoding either a wild type or polymorphic variant of a phagocytosis-related or AMDP-related gene.

Yet another embodiment of the invention is a composition for prevention or treatment of a retinal or choroidal degenerative disease or condition in a subject comprising an agent that blocks the expression or activity of a phagocytosis-related or AMDP-related gene. In some embodiments, the agent can be an antisense RNA, a ribozyme, or an interfering RNA (RNAi) molecule. The agent can also be an antibody or a small molecule.

Also within the invention are compositions for prevention or treatment of a retinal or choroidal degenerative disease or condition in a subject comprising a vector. In various embodiments, the vectors can include a nucleic acid encoding an agent that down-regulates or inhibits expression of a phagocytosis-related or AMDP-related mRNA or protein, or a nucleic acid that encodes a wild type or polymorphic variant of a phagocytosis-related or AMDP-related protein. In preferred embodiments, the phagocytosis-related or AMDP-related genes include MT1-MMP, prostaglandin D2 synthase and AMDP-3. In particularly preferred embodiments, the gene is MT1-MMP.

The invention further provides several embodiments of nonhuman transgenic animals useful, for example, as models of AMD and other retinal degenerative conditions. Preferably, the transgenic animal is a mammal, more preferably a rodent, and most preferably a mouse. In one embodiment, a transgenic animal includes an isolated nucleic acid construct that causes at least one cell type of the animal to over-express a phagocytosis-related or AMDP-related gene. The phagocytosis-related or AMDP-related gene is preferably MT1-MMP, prostaglandin D2 synthase, or AMDP-3. Preferred versions of the transgenic animals are engineered to overexpress the phagocytosis-related or AMDP-related gene product in particular cell types, including retinal cell types selected from photoreceptors, RPE cells and Muller cells, and choroidal cell types including endothelial cells, smooth muscle cells, leukocytes, macrophages, melanocytes and fibroblasts. In some embodiments, the gene of interest is conditionally over-expressed.

Another preferred embodiment of an animal model of AMD/retinal degeneration is a nonhuman transgenic animal including an isolated nucleic acid construct that causes at least one cell type of the animal to express a polymorphic variant of a phagocytosis-related or AMDP-related nucleic acid and/or protein. In preferred embodiments, the nucleic acid and/or protein is MT1-MMP, prostaglandin D2 synthase, or AMDP-3. The polymorphic variant can be increased in incidence in a population of humans with AMD, compared to a normal control population.

Yet another embodiment is a nonhuman polytransgenic animal including at least a first isolated nucleic acid construct and at least a second isolated nucleic acid construct, the first construct causing at least one cell type of the animal to express a polymorphic variant of a first gene correlated with increased incidence of AMD, and the second nucleic acid construct causing at least one cell type of the animal to express a polymorphic variant of a second gene correlated with increased incidence of AMD, or havingan association with RPE phagocytosis.

In preferred embodiments of the polytransgenic animals, the first gene is MT1-MMP and the second gene is selected from ABCR, apolipoprotein E, C—C chemokine receptor-2, cystatin C, hemicentin/FIBL-6, manganese superoxide dismutase, C—C chemokine ligand/monocyte chemoattractant protein 1, and paraoxonase.

In other preferred embodiments of the polytransgenic models, the first gene is MT1-MMP and the second gene is a phagocytosis-related or AMDP-related gene selected from human unknown PHG-1, prostaglandin D2 synthase, myelin basic protein, human unknown PHG-4, human unknown PHG-5, human peanut-like 2/septin 4, coactosin-like 1, clusterin, casein kinase 1 epsilon, ferritin heavy polypeptide 1, metargidin, human unknown PHG-13, retinaldehyde binding protein 1, actin gamma 1, SWI/SNF related/OSA-1 nuclear protein, and human unknown AMDP-3.

Particularly preferred embodiments of the transgenic animals of the invention are mice, which provide the advantage of a relatively short life span, making them more suitable for study of age-related diseases than other longer-lived animal models such as monkeys.

In yet another aspect, the invention provides isolated nucleic acids encoding previously uncharacterized gene products shown herein to be phagocytosis-related and/or AMDP-related proteins. The nucleic acids encoding these proteins include nucleic acid sequences comprising SEQ ID NOS:1, 4, 5, 12, and 17.

The invention further provides a gene array including a plurality of isolated oligonucleotide sequences, said sequences being positioned within an intronic, exonic or promoter sequence of a native human AMD-related or phagocytosis-related gene. The genes represented by the oligonucleotide sequences in the array encode cDNAs comprising nucleic acid sequences shown herein as SEQ ID NOS:1-17 and SEQ ID NOS:62-69.

In preferred embodiments of the gene array, at least one gene is MT1-MMP and the oligonucleotide sequences include a P259P or a D273N polymorphic variant of the MT1-MMP coding sequence. These variants of MT1-MMP are shown herein to be increased in frequency in a population of patients with AMD and other macular degenerative conditions, relative to their frequency in a population of normal control subjects.

The gene array can further include at least one oligonucleotide sequence comprising at least one polymorphic variant of one or more AMD-related genes besides MT1-MMP. The polymorphic variant sequences can include: ABCR (D217N; G1961E), manganese superoxide dismutase (V47A), apolipoprotein E (C130, R176C and C130R, R176), cystatin C (A25T) and paraoxonase (Q192R, L54M).

The gene arrays of the invention are useful, for example, for screening DNA samples from subjects to determine the distribution of polymorphic variants of a plurality of AMD-related and/or phagocytosis-related genes in the subject's DNA. In keeping with the multi-gene (complex disease) etiology of AMD, it is contemplated that information pertaining to the distribution of combinations of particular polymorphic variants of AMD-related or phagocytosis-related genes in a subject's DNA can be used to predict the likelihood that the subject is at greater risk of developing a retinal disorder such as AMD than is a subject lacking said combination of particular polymorphic variants of AMD-related or phagocytosis-related genes.

The gene arrays of the invention, tailored to AMD and related disorders, can provide a convenient and relatively inexpensive means of testing polymorphic variants of a plurality of genes known to be related to AMD and related disorders.

These and other objects of the invention are set forth in more detail in the description and examples below, which are intended to illustrate the invention but not limit the scope thereof.

BRIEF DESCRIPTION OF THE DRAWINGS

The drawings form part of the present specification and are included to further demonstrate certain aspects of the present invention. The invention may be better understood by reference to one or more of the following drawings in combination with the detailed description of specific embodiments presented herein.

FIG. 14 shows the nucleic acid sequence of a 285 bp PCR product including exon 5 of human MT1-MMP. The positions of codons 259 and 273 are underlined. Bases showing changes in polymorphisms P259P and D273N found in AMD and macular degeneration patients are indicated in boldface.

DETAILED DESCRIPTION OF THE INVENTION

Figure 1B:
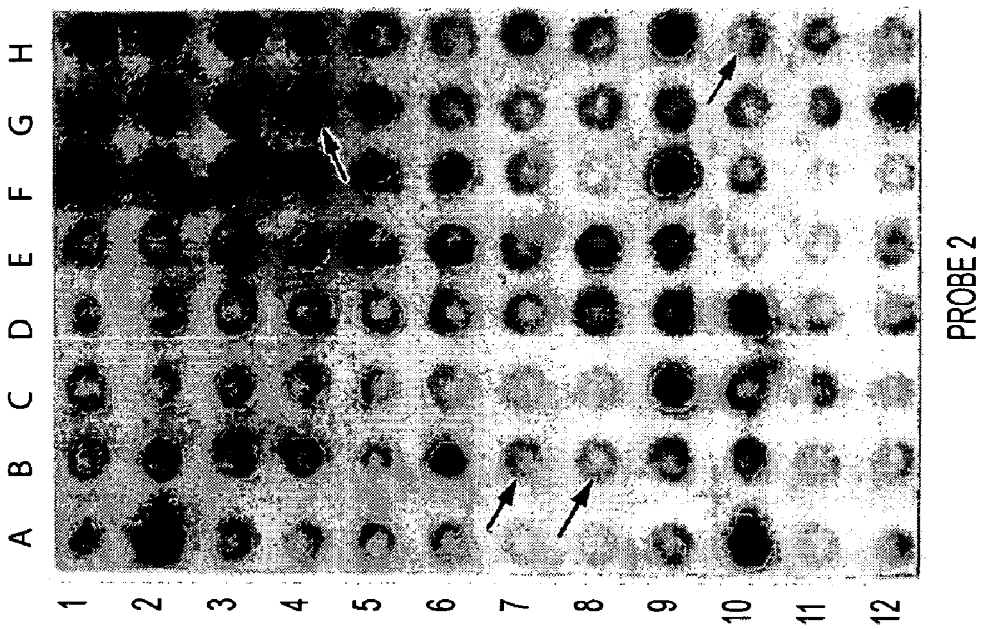
FIG. 1 is a photograph showing duplicate CHANGE array panels, each containing 96 genes (spots) hybridized with "+" and "−" probes (Probes 1 and 2), according to an embodiment of the invention. Up and down arrows indicate genes showing increased or decreased expression, respectively, upon hybridization with Probe 1 vs. Probe 2.

Based on the foregoing discoveries, the invention provides novel genes related to AMD and/or phagocytosis by RPE cells, methods and compositions for detecting and treating AMD and other retinal degenerative conditions, and animal models based on phagocytosis-related and/or AMDP-related genes useful, inter alia, for testing therapeutic compounds and treatment protocols for AMD. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, for example, in Innis et al., PCR Protocols: A Guide to Methods and Applications, Academic Press: San Diego, 1990. Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (for example, preparation of antigen-specific antibodies, immunoprecipitation, and immunoblotting) are described, for example, in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, for example, Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Phagocytosis-Related Genes Isolated by CHANGE

Studies leading to the invention were performed to identify genes involved in OS phagocytosis by RPE cells that, when perturbed, could result in stress and dysfunction in the RPE. Such stresses could lead to one or more undesirable changes associated with macular, retinal or choroidal diseases, such as enhanced lipofuscin accumulation, drusen formation, or formation of neovascular membranes. The gene discoveries described herein were based on the premise that dysfunction in phagocytosis by the RPE is a key factor leading to such AMD-related changes. RPE cells perform the crucial function of sustaining the homeostasis of the photoreceptors. This demanding task includes inter alia a daily process of phagocytosis and digestion of OS membranes which are renewed and shed daily from the tips of the OS of the photoreceptors (Young and Bok, 1969). As further described below, the phagocytic process includes the steps of binding, ingestion and digestion of OS membranes. Under normal circumstances, RPE cells are non-dividing cells. Thus, throughout the lifetime of an individual, the daily process of OS phagocytosis represents not only an enormous metabolic load on these cells, but also contributes to the accumulation within these cells of undigested material, particularly lipofuscin, a complex amalgam of cellular waste products including toxic photoreceptor-derived materials such as A2E.

Accordingly, in one aspect, the invention provides nucleic acid and protein sequences of genes previously unknown to be functionally related to the process of phagocytosis by RPE cells. Prior to the invention, there had not been a systematic search for genes involved in the mechanism of OS phagocytosis by RPE cells, herein also designated "phagocytosis-related genes," or "phagogenes," abbreviated to "PHG." Consistent with the knowledge that AMD is a complex, multi-gene disease, and that RPE phagocytosis is a multi-step cellular process necessarily involving many different gene products, the inventors sought to identify phagocytosis-related genes based on the realization that subtle changes, such as polymorphisms, in the DNA sequences of one or more phagocytosis-related genes, or a polymorphism in a phagocytosis-related gene in combination with a polymorphism in another gene, are likely to cooperate to produce the phenotype observed in AMD.

Figure 4:
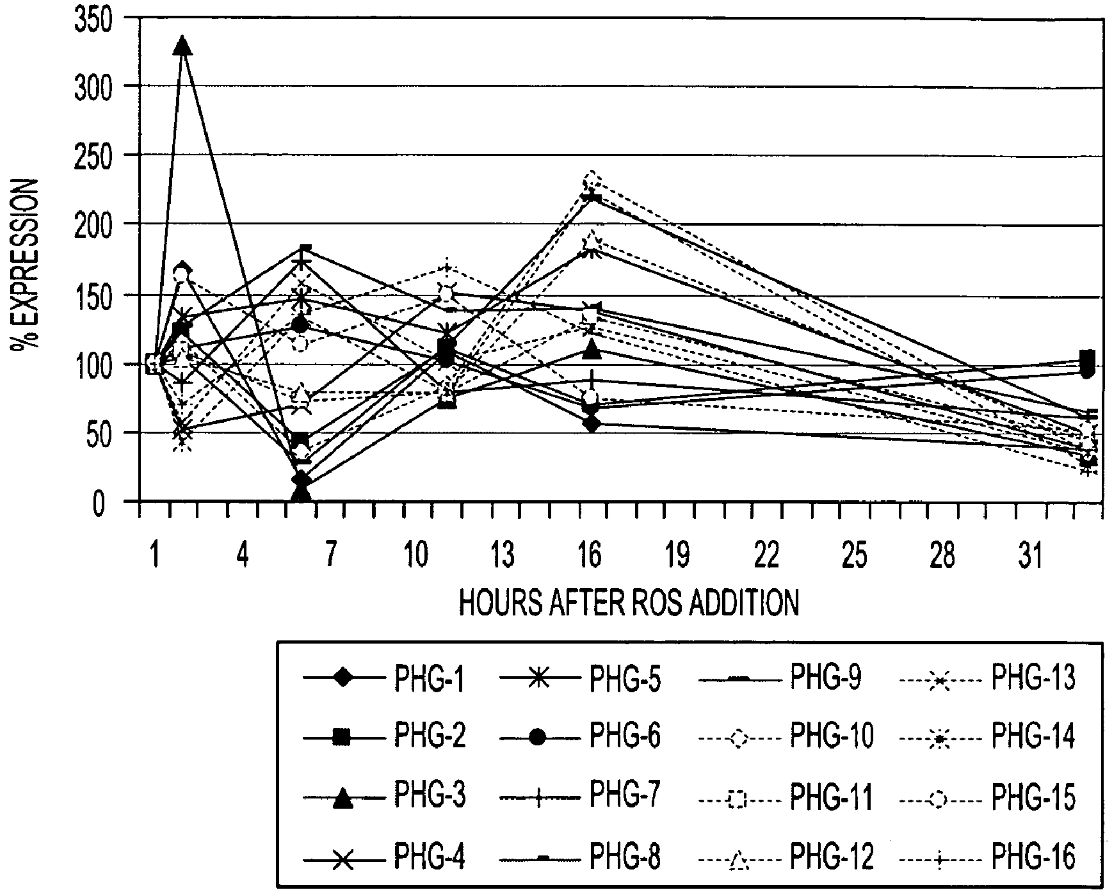
FIG. 4 is a graph showing the mRNA expression profiles of 16 phagocytosis-related genes ("phagogenes") expressed by RPE cells, discovered by CHANGE, according to an embodiment of the invention. Expression levels of phagogenes fluctuate in RPE cells at selected times during the course of ROS phagocytosis in vitro. Identities of the phagogenes (PHG-1-16) are provided in Table 1, infra.

To obtain genes of interest by differential expression, as further described in the examples below, a custom expression profiling strategy was developed, termed CHANGE (for Comparative Hybridization ANalysis of Gene Expression). The CHANGE array included approximately 10,000 genes expressed in the RPE, arrayed in panels each comprising 96 cDNAs. (See FIG. 1.) To obtain phagogenes, the CHANGE array of RPE-expressed genes was screened with pairs of "+/−OS" hybridization probes made from total RNA expressed in a phagocytic RPE cell line during OS phagocytosis in vitro (+OS probe) and in control cells without feeding of OS (−OS probe). Genes in the array were selected for further analysis based upon a showing of altered (i.e., increased or decreased) expression during OS phagocytosis, evidenced by a changed hybridization signal upon hybridization with the +OS vs. −OS probes, as indicated by arrows in FIG. 1. Of the approximately 10,000 genes screened, about 60 putative phagocytosis-related genes were identified on the basis of altered gene expression detected by CHANGE. Of these, 16 genes demonstrating very pronounced change in hybridization intensity upon phagocytic challenge (i.e., screening with +/−OS probes) were randomly selected for further study and confirmation of their functional relationship to RPE phagocytosis. Table 1 provides a listing of the above-described phagogenes with subsequently confirmed association with OS phagocytosis by RPE cells. These genes are further described in Example 2, infra. See also FIG. 4 showing mRNA expression profiles of these genes during phagocytosis of OS by RPE cells in vitro.

TABLE 1

Human Phagocytosis-related Genes Isolated by CHANGE

| NAME | CLONE NUMBER | NUCLEIC ACID SEQ ID NO. | AMINOACID SEQ ID NO(S) | IDENTITY |
|---|---|---|---|---|
| PHG-1 | 6-29 | 1 | 70–78 | Unknown |
| PHG-2 | 33-25 | 2 | 79 | Prostaglandin D2 synthase |
| PHG-3 | 33-74 | 3 | 80 | Myelin basic protein |
| PHG-4 | 43-16 | 4 | 81–83 | Unknown |
| PHG-5 | 45-88 | 5 | 84 | Unknown |
| PHG-6 | 53-7 | 6 | 85 | Peanut-like 2/septin 4 |
| PHG-7 | 55-26 | 7 | 86 | Coactosin-like 1 |
| PHG-8 | 55-28 | 8 | 87 | Clusterin |
| PHG-9 | 57-29 | 9 | 88 | Casein kinase 1 epsilon |
| PHG-10 | 57-29 | 9 | 88 | Casein kinase 1 epsilon (duplicate) |
| PHG-11 | 73-51 | 10 | 89 | Ferritin heavy polypeptide 1 |
| PHG-12 | 74-39 | 11 | 90 | Metargidin |
| PHG-13 | 78-70a | 12 | 91–97 | Unknown |
| PHG-14 | 78-70c | 13 | 98 | Retinaldehyde binding protein 1 |
| PHG-15 | 80-31 | 14 | 99 | Actin gamma 1 |
| PHG-16 | 91-40 | 15 | 100 | Matrix metalloproteinase, membrane-associated 1 (MT1-MMP) |

AMDP-Related Genes Isolated by CHANGE

In another aspect, the invention provides nucleic acid and protein sequences of genes previously unknown to be associated with AMD. To obtain AMD-related genes, the CHANGE array of 10,000 RPE-expressed genes was iteratively screened, as described above, using other pairs of "+/−" probes. The +/− probes used to identify AMD-related genes were made from total RNA extracted from the RPE/choroid of AMD-affected and unaffected human donor eyes, and from age-matched normal and affected eyes from a monkey model of AMD. Genes in the array were selected for further analysis based upon a showing of differential (i.e., increased or decreased) expression in AMD relative to aged normal control eyes. Based on the criterion of altered gene expression detected by CHANGE, approximately 200 AMD-related genes were identified.

To identify AMD-related phagogenes ("AMDP genes"), the data from the above-described two CHANGE screenings were compared, to identify a subset of RPE genes differentially expressed both in OS phagocytosis by RPE cells and in AMD. As described above, the phagocytosis CHANGE screening yielded approximately 60 phagogenes and the putative AMD-related genes numbered approximately 200. Initial comparison of the two databases yielded a subset of 6 genes showing changed expression in both phagocytosis and AMD (Table 2). These genes are herein designated "AMD-related phagogenes" or "AMD/phagogenes," abbreviated to "AMDP."

TABLE 2

AMD-Related Phagogenes ("AMDP" Genes) Isolated by Iterative CHANGE Analysis

| NAME | CLONE NUMBER | NUCLEIC ACID SEQ ID NO. | AMINOACID SEQ ID NO(S) | IDENTITY |
|---|---|---|---|---|
| AMDP-1 | 33-25 | 2 | 79 | Prostaglandin D2 synthase |
| AMDP-2 | 37-14 | 16 | 101 | SWI/SNF related/OSA-1 nuclear protein |
| AMDP-3 | 47-94 | 17 | 102–120 | Unknown |
| AMDP-4 | 57-29 | 9 | 88 | Casein kinase 1 epsilon |
| AMDP-5 | 73-51 | 10 | 89 | Ferritin heavy polypeptide 1 |
| AMDP-6 | 91-40 | 15 | 100 | Matrix metalloproteinase, membrane associated 1 (MT1-MMP) |

Of the above listed genes, the CHANGE hybridization analysis indicated that mRNAs for genes AMDP-1, 3, and 6 were expressed at higher levels in AMD eyes than in controls, whereas the expression levels of genes AMDP-2, 4 and 5 were lower in AMD eyes than in controls. AMDP genes are further described in Example 3, infra.

Nucleic Acids Encoding Phagocytosis-Related and/or AMDP-Related Gene Products and Polymorphic Variants thereof As described above, the invention provides nucleic acid and amino acid sequences relating to genes discovered by a differential cloning strategy (CHANGE) to exhibit altered expression during RPE phagocytosis and/or in AMD. In one aspect, the invention provides novel purified nucleic acids (polynuoleotides) isolated by this strategy. Previously unknown nucleic acids of the invention include nucleic acid sequences identified herein as PHG-1 (SEQ ID NO:1); PHG-4 (SEQ ID NO:4); PHG-5 (SEQ ID NO:5); PHG-13 (SEQ ID NO:12); and AMDP-3 (SEQ ID NO:17). These nucleic acids encode, respectively, polypeptides having the amino acid sequences identified herein as SEQ ID NOS:70-78, 81-83, 84, 91-97, and 102-120.

The invention also encompasses use of characterized nucleic acids and polypeptides previously unknown to be related to RPE phagocytosis and/or AMD. The relationship of the previously characterized genes to phagocytosis and AMD was discovered on the basis of changed expression during RPE phagocytosis and/or in AMD patients. Nucleic acids of the latter group include prostaglandin D2 synthase (SEQ ID NO:2), myelin basic protein (SEQ ID NO:3), peanut-like 2/septin 4 (SEQ ID NO:6); coactosin-like 1 (SEQ ID NO:7); clusterin (SEQ ID NO:8); casein kinase 1 epsilon (SEQ ID NO:9); ferritin heavy polypeptide 1 (SEQ ID NO:10); metargidin (SEQ ID NO:11); retinaldehyde binding protein 1 (SEQ ID NO:13); actin gamma 1 (SEQ ID NO:14); matrix metalloproteinase, membrane associated 1 (SEQ ID NO: 15); and SWI/SNF related/OSA-1 nuclear protein (SEQ ID NO:16).

Nucleic acid molecules of the present invention can be in the form of RNA or in the form of DNA (for example, cDNA, genomic DNA, and synthetic DNA). Preferred nucleic acid molecules of the invention are the respective native polynucleotides, including the nucleotide sequences shown herein as SEQ ID NOS:1, 2, 3, 4, 5, 6, 7, 8, 9, 10, 11, 12, 13, 14, 15, 16 and 17.

The coding sequences which encode native phagocytosis-related and/or AMDP-related genes may be identical to the those of nucleotide sequences shown in SEQ ID NOS:1-17. They may also be different coding sequences which, as a result of the redundancy or degeneracy of the genetic code, encode the same polypeptides as the polynucleotides of SEQ ID NOS:1-17. Other nucleic acid molecules within the invention are variants of SEQ ID NOS:1-17 such as those that encode fragments, analogs and derivatives of the phagocytosis-related and AMDP-related genes described herein. Such variants may be, for example, naturally occurring allelic variants of native phagocytosis-related and AMDP-related genes, homologs of native phagocytosis-related and/or AMDP-related genes, splice variants, or non-naturally occurring variants of phagocytosis-related and/or AMDP-related genes. These variants have a nucleotide sequence that differs from the corresponding native SEQ ID NOS:1-7 in one or more bases. For example, the nucleotide sequence of such variants can feature a deletion, addition, or substitution of one or more nucleotides of native phagocytosis-related and/or AMDP-related genes.

In some applications, variant nucleic acid molecules encode polypeptides that substantially maintain a phagocytosis-related and/or AMDP-related functional activity. For other applications, variant nucleic acid molecules encode polypeptides that lack or feature a significant reduction in a phagocytosis-related and/or AMDP-related gene functional activity. Where it is desired to retain a functional activity of a native phagocytosis-related and/or AMDP-related gene, preferred variant nucleic acids feature silent or conservative nucleotide changes.

In other applications, variant phagocytosis-related and/or AMDP-related polypeptides displaying substantial changes in one or more functional activities of native phagocytosis-related and/or AMDP-related genes can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, for example, serine or threonine, by a hydrophobic residue, for example, leucine, isoleucine, phenylalanine, valine or alanine; (b) a cysteine or proline by any other residue; (c) a residue having an electropositive side chain, for example, lysine, arginine, or histidine, by an electronegative residue, for example, glutamine or asparagine; or (d) a residue having a bulky side chain, for example, phenylalanine, by one not having a side chain, for example, glycine.

Naturally occurring allelic variants of native phagocytosis-related and/or AMDP-related genes within the invention are nucleic acids that have at least 75% (for example, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native phagocytosis-related and/or AMDP-related genes, and encode polypeptides having at least one functional activity in common with native phagocytosis-related and/or AMDP-related genes. Homologs of native phagocytosis-related and/or AMDP-related genes within the invention are nucleic acids isolated from non-human species that have at least 75% (for example, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native phagocytosis-related and/or AMDP-related genes, and encode polypeptides having at least one functional activity in common with native phagocytosis-related and/or AMDP-related genes.

Naturally occurring allelic variants of phagocytosis-related and/or AMDP-related genes and homologs of phagocytosis-related and/or AMDP-related genes can be isolated by screening for a native functional activity of a phagocytosis-related and/or AMDP-related gene (for example, activation of progelatinase A, in the case MT1-MMP) using techniques known in the art. The nucleotide sequence of such homologs and allelic variants can be determined by conventional DNA sequencing methods. Alternatively, public or non-proprietary nucleic acid databases can be searched to identify other nucleic acid molecules having a high percent (for example, 70, 80, 90%, 95% or more) sequence identity to a native phagocytosis-related and/or AMDP-related gene.

Non-naturally occurring variants of phagocytosis-related and/or AMDP-related genes are nucleic acids that do not occur in nature (for example, are made by the hand of man), have at least 75% (for example, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native phagocytosis-related and/or AMDP-related genes and encode polypeptides having at least one functional activity in common with native phagocytosis-related and/or AMDP-related genes. Examples of non-naturally occurring phagocytosis-related and/or AMDP-related nucleic acids are those that encode a fragment of a phagocytosis-related and/or AMDP-related protein, those that hybridize to a native phagocytosis-related and/or AMDP-related gene, or a complement of a native phagocytosis-related and/or AMDP-related genes under stringent conditions, those that share at least 65% sequence identity with a native phagocytosis-related and/or AMDP-related gene, or a complement of a native phagocytosis-related and/or AMDP-related gene, and those that encode a phagocytosis-related and/or AMDP-related gene fusion protein.

Nucleic acids encoding fragments of phagocytosis-related and/or AMDP-related genes within the invention are those that encode, for example, 2, 5, 10, 25, 50, 100, 150, 200, 250, 300, or more amino acid residues of the respective phagocytosis-related and/or AMDP-related proteins. Shorter oligonucleotides (for example, those of 6, 12, 20, 30, 50, 100, 125, 150 or 200 bases in length) that encode or hybridize with nucleic acids that encode fragments of phagocytosis-related and/or AMDP-related genes can be used as probes, primers, or antisense molecules. Longer polynucleotides (for example, those of 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 or more bases, such as 4000, 5000, 6000, 7000, 8000, and 9000 bases) that encode or hybridize with nucleic acids that encode fragments of phagocytosis-related and/or AMDP-related genes can be used in place of native phagocytosis-related and/or AMDP-related genes in applications where it is desired to modulate a functional activity of native phagocytosis-related and/or AMDP-related gene. Nucleic acids encoding fragments of phagocytosis-related and/or AMDP-related genes can be made by enzymatic digestion (for example, using a restriction enzyme) or chemical degradation of full length sequences of phagocytosis-related and/or AMDP-related genes, or variants thereof.

Nucleic acids that hybridize under stringent conditions to the nucleic acid of SEQ ID NOS:1, 4, 5, 12 and 17 or the complement of SEQ ID NOS:1, 4, 5, 12 and 17 are also within the invention. For example, such nucleic acids can be those that hybridize to SEQ ID NOS:1, 4, 5, 12 and 17 or the complement of SEQ ID NOS:1, 4, 5, 12 and 17 under low stringency conditions, moderate stringency conditions, or high stringency conditions. Preferred such nucleic acids are those having a nucleotide sequence that is the complement of all or a portion of SEQ ID NOS:1, 4, 5, 12 or 17. Other variants of SEQ ID NOS:1, 4, 5, 12 and 17 within the invention are polynucleotides that share at least 65% (for example, 65, 70, 75, 80, 85, 90, 91, 92, 93, 94, 95, 96, 97, 98, and 99%) sequence identity to SEQ ID NOS:1, 4, 5, 12 and 17 or the complement of SEQ ID NOS:1, 4, 5, 12 and 17. Nucleic acids that hybridize under stringent conditions or share at least 65% sequence identity with SEQ ID NOS:1, 4, 5, 12 and 17 or the complement of SEQ ID NOS:1, 4, 5, 12 and 17 can be obtained by techniques known in the art.

Nucleic acid molecules encoding fusion proteins of phagocytosis-related and/or AMDP-related genes, for example those encoded by nucleic acids described herein as SEQ ID NOS:1-17, are also within the invention. Such nucleic acids can be made by preparing a construct (for example, an expression vector) that expresses a phagocytosis-related and/or AMDP-related fusion protein when introduced into a suitable host. For example, such a construct can be made by ligating a first polynucleotide encoding a phagocytosis-related and/or AMDP-related protein, for example MT1-MMP, filsed in frame with a second polynucleotide encoding another protein such that expression of the construct in a suitable expression system yields a fusion protein.

The invention encompasses labeled nucleic acid probes capable of hybridizing to a nucleic acid encoding a phagocytosis-related and/or AMDP-related polypeptide, as described above. The nucleic acid molecules of the invention allow those skilled in the art to construct nucleotide probes for use in the detection of nucleic acid sequences of the invention in biological materials. The probe may be used in hybridization to detect a phagocytosis-related and/or AMDP-related gene. The technique generally involves contacting and incubating nucleic acids (for example mRNA molecules) obtained from a sample from a patient or other cellular source with a probe of the present invention under conditions favorable for the specific annealing of the probes to complementary sequences in the nucleic acids. After incubation, the non-annealed nucleic acids are removed, and the presence of nucleic acids that have hybridized to the probe, if any, are detected.

The detection of nucleic acid molecules of the invention may involve the amplification of specific gene sequences using an amplification method (for example PCR), followed by the analysis of the amplified molecules using techniques known to those skilled in the art. Suitable primers can be routinely designed by one of skill in the art. For example, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 60° C. to 72° C.

Hybridization and amplification techniques described herein may be used to assay qualitative and quantitative aspects of phagocytosis-related and/or AMDP-related gene expression. For example, RNA may be isolated from a cell type or tissue known to express a phagocytosis-related and/or AMDP-related gene, for example genes having SEQ ID NOS:1-17, and tested utilizing the hybridization (for example, standard Northern analyses) or PCR techniques referred to herein. The techniques may be used, for example, to detect differences in transcript size that may be due to normal or abnormal alternative splicing. The techniques may be used to detect quantitative differences between levels of full length and/or alternatively spliced transcripts detected in normal individuals relative to those individuals exhibiting symptoms of a disease. The primers and probes may be used in the above-described methods in situ, i.e., directly on tissue sections (fixed and/or frozen) of patient tissue obtained from biopsies, resections or eyebank eyes. Particular uses of the probes and primers of the invention are further described in the examples below.

Genetic Screening of Phagocytosis-Related and/or AMD-Related Nucleic Acids

In another aspect, the invention provides a method for determining the risk of a subject of developing a retinal or choroidal disease or degenerative condition. As used herein, a "retinal or choroidal disease or degenerative condition" includes but is not limited to any condition of the retina or choroid of the eye which results in injury or death of photoreceptors, RPE cells or other cell types of the retina, or injury, death or abnormal proliferation of choroidal cell types including but not limited to endothelial cells, melanocytes, smooth muscle cells, fibroblasts, lymphocytes, neutrophils, eosinophils, megokaryocytes, monocytes, macrophages and mast cells.

Degenerative conditions affecting the retina and/or choroid include age-related and other maculopathies, including but not limited to age-related macular degeneration (AMD), hereditary and early onset forms of macular degeneration ("familial AMD") such as Stargardt's disease/fundus flavimaculatus, Best disease/vitelliform dystrophy, congenital diffuse drusen/Doyne's honeycomb dystrophy, pattern dystrophies, Sorsby's macular dystrophy, juxtafoveal telangiectasia, choroidal atrophy, dominant drusen, crystalline drusen, annular macular dystrophy, occult choroidal neovascular membrane, choroideremia, idiopathic bulls-eye maculopathies, gyrate atrophy and the various forms of hereditary retinitis pigmentosa conditions. Other diseases or degenerative conditions of the retina and choroid include toxic maculopathies, for example, drug-induced maculopathies such as plaquenil toxicity, retinal disorders including retinal detachment, photic retinopathies, retinopathies induced by surgery, toxic retinopathies, retinopathy of prematurity, viral retinopathies such as CMV or HIV retinopathy related to AIDS, uveitis, ischemic retinopathies due to venous or arterial occlusion or other vascular disorders, retinopathies due to trauma or penetrating lesions of the eye, peripheral vitreoretinopathy, and cancers affecting the eye such as retinoblastoma and choriodal melanoma.

The method for determining risk involves screening a nucleic acid of a subject for the presence of polymorphisms in AMD-related or phagocytosis-related genes, wherein the presence of a polymorphism indicates that the subject is at higher risk for developing a retinal or choroidal disease or degenerative disorder than a control subject without the polymorphism. As used herein, a "normal" or "wild type"

nucleotide is a base located at a particular position in a subject's DNA that is known to be the predominant base at that position in the general population. A "polymorphism," "polymorphic variant," or "polymorphic base or nucleotide," is a naturally occurring base change that occurs at lower frequency in the general population than the base representing the "wild type." A "polymorphism" as used herein can include a base change recognized as a "mutation."

A phagocytosis-related and/or AMDP-related nucleic acid of the invention, either alone or in combination with one or more other nucleic acids, may be used in hybridization, amplification and screening assays of biological samples to detect abnormalities, including point mutations, insertions, deletions, and chromosomal rearrangements. Genetic screening methods are well known in the art of molecular medicine. For example, using genomic DNA, direct sequencing, single stranded conformational polymorphism analyses, heteroduplex analysis, denaturing gradient gel electrophoresis, chemical mismatch cleavage, and oligonucleotide hybridization (including hybridization to oligonucleotides in a gene array) may be utilized. In general, a genomic DNA sample is obtained from a subject, for example from the subject's peripheral blood, or from a biological sample prepared from donated tissue such as an eyebank eye. The DNA is used for amplification of specific gene sequences, for example a particular exonic, intronic or promoter sequence of interest. To detect the presence of polymorphisms in a subject's DNA, single strand conformation polymorphism (SSCP) analysis, heteroduplex analysis, and automated versions thereof can be used, followed by DNA sequence analysis to determine the particular base change(s). These methods are also useful for confirming reported polymorphisms, for example those available in the Human Genome Single Nucleotide Polymorphism (SNP) database.

The invention provides methods for screening a subject for polymorphic variants of genes related to RPE phagocytosis and/or AMD. In one preferred method, pairs of sense and antisense primers (amplimers) are designed based on the nucleic acid sequence of a gene of interest and are used to amplify one or more exons, introns or promoter sequences within the gene. One preferred group of genes useful for screening for mutations and polymorphisms in patients with AMD and other macular diseases includes previously unknown genes shown herein to be correlated with phagocytosis and/or AMD, the cDNA sequences of which are identified herein as SEQ ID NOS:1, 4, 5, 12, and 17. Other preferred genes, also disclosed herein to be related to phagocytosis and/or AMD, have nucleic acid (cDNA) sequences described herein as SEQ ID NOS:2, 3, 6, 7, 8, 9, 10, 11, 13, 14, 15, and 16. (See Tables 1 and 2, supra.) As shown herein, an exemplary gene related to AMD and phagocytosis is MT1-MMP (SEQ ID NO:15). Any amplimers suitable for amplifying an exonic, intronic or promoter sequence of a phagocytosis-related and/or AMDP-related genes disclosed herein can be designed by those of skill in the art of molecular biology and used to screen DNA samples for mutations and/or polymorphisms. As an example, specific amplimer pairs, suitable for amplification of Exons 1-10, introns 1-9 and promoter regions of the human MT1-MMP gene are disclosed in Table 3 below.

The nucleic acids of the invention can also be used for screening of multiple genes in an array. Oligonucleotides or longer fragments derived from any of the nucleic acid molecules of the invention may be used as targets in a gene array such as a microarray. The gene targets in the array can include, for example, nucleic acids derived from any combination of phagocytosis-related and/or AMDP-related genes disclosed herein (i.e., SEQ ID NOS: 1-17) and any previously described nucleic acids, for example those previously associated with RPE phagocytosis and/or AMD, including but not limited to those derived from sequences identified herein as SEQ ID NOS:62-69. The oligonucleotide sequences included in the array can be derived from sequences positioned within an intronic, exonic or promoter sequence of the native human gene of interest. Preferably the arrays include oligonucleotide sequences encompassing all known polymorphic variants of the genes of interest. Particularly preferred custom arrays, suitable for example for sceening the DNA of patients with eye diseases such as AMD, include all known polymorphic variants of genes shown to exhibit particular polymorphic variants with increased incidence in populations of patients with AMD and related disorders, relative to control populations of normal subjects. For a listing of genes with previously reported polymorphisms or mutations correlated with AMD, see Table 5, infra. Accordingly, genes suitable for inclusion in a custom array of the invention useful for AMD screening, and the relevant polymorphic variants thereof showing increased incidence in AMD (in parentheses) can include, but are not limited to: MT1-MMP (P259P; D273N); ABCR (D217N; G1961E); manganese superoxide dismutase (V47A); apolipoprotein E (C130, R176C and C130R, R176); cystatin C (A25T) and paraoxonase (Q192R, L54M).

The gene arrays of the invention can be used, for example, to simultaneously monitor the expression levels of large numbers of genes, and to identify genetic variants, mutations, and polymorphisms in a plurality of genes. The information derived from the analysis of the hybridization of patient DNA samples to the array can be used, for example, to determine gene function, to understand the genetic basis of a disorder, to diagnose or predict the likelihood of developing a disorder, or to develop and monitor the activities of therapeutic agents. The preparation, use, and analysis of gene arrays, including microarrays are well known to persons skilled in the art. (See, for example, Brennan, T. M. et al. (1995) U.S. Pat. No. 5,474,796; Schena, et al. (1996) Proc. Natl. Acad. Sci. 93:10614-10619; Baldeschweiler et al. (1995), PCT Application WO95/251116; Shalon, D. et al. (I 995) PCT application WO95/35505; Heller, R. A. et al. (1997) Proc. Natl. Acad. Sci. 94:2150-2155; and Heller, M. J. et al. (1997) U.S. Pat. No. 5,605,662 and Cronin, M. et al. (2003) U.S. Pat. No. 6,632,605.

Agents that Modulate Expression or Activity of Phagocytosis-Related and AMDP-Related Gene Products In another aspect, the invention provides agents that modulate expression levels of mRNA or protein of phagocytosis-related and/or AMDP-related genes. Preferred genes/proteins to be targeted for down-regulation are those showing increased expression in AMD and related disorders, including, as demonstrated herein, prostaglandin D2 synthase, PD2S (respective nucleic acid and amino acid sequences: SEQ ID NOS:2 and 79), MT1-MMP (SEQ ID NOS:15 and 100) and AMDP-3 (SEQ ID NOS:17 and 102-120). Preferred geneslproteins to be targeted for up-regulation are those showing decreased expression in AMD and related disorders, including, as demonstrated herein, SWI/SNF related OSA-1 nuclear protein (SEQ ID NOS:16 and 101), casein kinase 1 epsilon (SEQ ID NOS:9 and 88) and ferritin heavy polypeptide 1 (SEQ ID NOS:10 and 89).

The AMDP-related and/or phagocytosis-related mRNA or protein can be the native, i.e., "wild-type" mRNA or protein, for example native MT1-MMP. In other embodiments, a polymorphic variant of an AMD-related or phagocytosis-related gene is targeted, for example one which results in an altered function of the expressed mRNA or protein. The altered mRNA or protein is inhibited while leaving expression of the wild type mRNA or protein intact.

The inhibitory agents used for down-regulation of expression can include, for example, antisense RNA molecules, ribozymes, small interfering RNA (RNAi) molecules and triple helix structures. Preferred embodiments of such agents are directed against PD2S (SEQ ID NO:2), MT1-MMP (SEQ ID NO:15) and AMDP-3 (SEQ ID NO:17), or variants thereof. The inhibitory agents can also include antibody molecules that selectively bind to an over-expressed phagocytosis-related and/or AMDP-related protein, such as PD2S, MT1-MMP or AMDP-3.

Antisense nucleic acid molecules within the invention are those that specifically hybridize (for example bind) under cellular conditions to cellular mRNA and/or genomic DNA encoding a phagocytosis-related and/or AMDP-related protein in a manner that inhibits expression of the phagocytosis-related and/or AMDP-related protein, for example, by inhibiting transcription and/or translation. The binding may be by conventional base pair complementarity, or, for example, in the case of binding to DNA duplexes, through specific interactions in the major groove of the double helix. Methods for design of antisense molecules are well known to those of skill in the art. General approaches to constructing oligomers useful in antisense therapy have been reviewed, for example, by Van der Krol et al. (1988) Biotechniques 6:958-976; Stein et al. (1988) Cancer Res 48:2659-2668; and Narayanan, R. and Aktar, S. (1996): Antisense therapy. Curr. Opin. Oncol. 8(6):509-15. As non-limiting examples, antisense oligonucleotides may be targeted to hybridize to the following regions: mRNA cap region; translation initiation site; translational termination site; transcription initiation site; transcription termination site; polyadenylation signal; 3' untranslated region; 5' untranslated region; 5' coding region; mid coding region; and 3' coding region.

An antisense construct can be delivered, for example, as an expression plasmid which when transcribed in the cell produces RNA which is complementary to at least a unique portion of the cellular mRNA which encodes a phagocytosis-related and/or AMDP-related gene product. Alternatively, the antisense construct can take the form of an oligonucleotide probe generated ex vivo which, when introduced into a phagocytosis-related or AMDP-related gene expressing cell, causes selective inhibition of expression of the corresponding gene by hybridizing with an mRNA and/or genomic sequence coding for the phagocytosis-related or AMDP-related gene. Such oligonucleotide probes are preferably modified oligonucleotides that are resistant to endogenous nucleases, for example exonucleases and/or endonucleases, and are therefore stable in vivo. Exemplary nucleic acid molecules for use as antisense oligonucleotides are phosphoramidate, phosphothioate and methylphosphonate analogs of DNA (see, for example, U.S. Pat. Nos. 5,176,996; 5,264,564; and 5,256,775). With respect to antisense DNA, oligodeoxyribonucleotides derived from the translation initiation site, for example, between the −10 and +10 regions of a phagocytosis-related or AMDP-related gene encoding nucleotide sequence, are preferred.

Antisense approaches involve the design of oligonucleotides (either DNA or RNA) that are complementary to a phagocytosis-related and/or AMDP-related mRNA. The antisense oligonucleotides will bind to mRNA transcripts of the phagocytosis-related or AMDP-related gene and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Oligonucleotides that are complementary to the 5' end of the message, for example, the 5' untranslated sequence up to and including the AUG initiation codon, in general work most efficiently at inhibiting translation. However, sequences complementary to the 3' untranslated sequences of mRNAs have been shown to be effective at inhibiting translation of mRNAs as well. (See, for example, Wagner, R. (1994) Nature 372:333.) Therefore, oligonucleotides complementary to either the 5' or 3' untranslated non-coding regions of a phagocytosis-related or AMDP-related gene could be used in an antisense approach to inhibit translation of endogenous mRNA of a phagocytosis-related or AMDP-related gene. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of the mRNA of a phagocytosis-related or AMDP-related gene, antisense nucleic acids should be at least six nucleotides in length, and are preferably less than about 100 and more preferably less than about 50, 25, 17 or 10 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is preferred that the control oligonucleotide is of approximately the same length as the test oligonucleotide, and that the nucleotide sequence of the control oligonucleotide differs from that of the antisense sequence by no more than is necessary to prevent specific hybridization to the target sequence. It is also preferred that these studies compare levels of the target RNA or protein with that of an internal control RNA or protein.

Antisense oligonucleotides of the invention may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxyethyl)uracil, 5-carboxymethylaminomethyl-2-thiouridine, 5-carboxymethylaminomethyluracil, dihydrouricil, beta-D-galactosylqueosine, inosine, N6-isopentenyladenine, 1-methylguanine, 1-methylinosine, 2,2-idimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

Antisense oligonucleotides of the invention may also comprise at least one modified sugar moiety selected from the group including but not limited to arabinose, 2-fluoroarabinose, xylulose, and hexose, and may additionally include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Oligonucleotides of the invention may be synthesized by standard methods known in the art, for example, by use of an automated DNA synthesizer. As examples, phosphorothioate oligonucleotides may be synthesized by the method of Stein et al. (1988) Nucl. Acids Res. 16:3209), and methylphosphonate oligonucleotides can be prepared, for example, by use of controlled pore glass polymer supports (Sarin et al. (1988) Proc. Natl. Acad. Sci. U.S.A. 85:7448-7451).

The antisense molecules can be delivered into cells that express phagocytosis-related or AMDP-related genes in vivo. A number of methods have been developed for delivering antisense DNA or RNA into cells and are well known in the art. Because it is often difficult to achieve intracellular concentrations of the antisense sufficient to suppress translation of endogenous mRNAs, a preferred approach utilizes a recombinant DNA construct in which the antisense oligonucleotide is placed under the control of a strong promoter. The use of such a construct to transfect target cells in a subject preferably will result in the transcription of single-stranded RNAs that will hybridize with endogenous transcripts encoding the gene products of interest in sufficient amounts to prevent translation of the respective mRNAs. For example, a vector can be introduced in vivo such that it is taken up by a cell and directs the transcription of an antisense RNA. Such a vector can remain episomal or can become chromosomally integrated, as long as it can be transcribed to produce the desired antisense RNA. Such vectors can be constructed by recombinant DNA technology methods standard in the art and are further described below. Vectors can be plasmid, viral, or others known in the art, used for replication and expression in mammalian cells.

Expression of the sequence encoding the antisense RNA can be by any promoter known in the art to act in mammalian, and preferably human cells. Such promoters can be inducible or constitutive. Such promoters can include, but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), and the regulatory sequences of the metallothionein gene (Brinster et al., 1982, Nature 296:39-42). Promoters useful for tissue- or cell-specific expression, for example in photoreceptors, RPE cells, or choroidal cell types such as endothelial cells or melanocytes, are also known in the art, and are further described in Example 7 below.

A ribozyme is another preferred embodiment of an agent that can down-regulate expression of a phagocytosis-related and/or AMDP-related gene product. Ribozyme molecules are designed to catalytically cleave a transcript of a gene of interest, preventing its translation into a polypeptide. (See, for example, Sarver et al. (1990) Science 247:1222-1225 and U.S. Pat. No. 5,093,246). In general, ribozymes catalyze site-specific cleavage or ligation of phosphodiester bonds in RNA. While various forms of ribozymes that cleave mRNA at site-specific recognition sequences can be used to destroy phagocytosis-related or AMDP-related mRNAs, the use of hammerhead ribozymes is preferred. Hammerhead and hairpin ribozymes are RNA molecules that act by base pairing with complementary RNA target sequences, and carrying out cleavage reactions at particular sites. In the case of the hammerhead, the ribozyme cleaves after UX dinucleotides, where X can be any ribonucleotide except guanosine, although the rate of cleavage is highest if X is cytosine. The catalytic efficiency is further affected by the nucleotide preceding the uridine. In practice, NUX triplets (typically GUC, CUC or UUC) are required in the target mRNA. Such targets are used to design an antisense RNA of approximately 12 or 13 nucleotides surrounding that site, but skipping the C, which does not form a conventional base pair with the ribozyme.

Synthetic hammerhead ribozymes can be engineered to selectively bind and cleave a complementary mRNA molecule, then release the fragments, repeating the process with the efficiency of a protein enzyme. This can represent a significant advantage over, for example, antisense oligonucleotides which are not catalytic, but rather are stoichiometric, forming a 1:1 complex with target sequences. The hammerhead ribozymes of the invention can be designed in a 6-4-5 stem-loop-stem configuration, or any other configuration suitable for the purpose. In general, because the chemical cleavage step is rapid and the release step is rate-limiting, speed and specificity are enhanced if the hybridizing "arms" of the ribozyme (helices I and III) are relatively short, for example, about 5 or 6 nucleotides. Suitability of the design of a particular configuration can be determined empirically, using various assays known to those of skill in the art.

The construction and production of hammerhead ribozymes is well known in the art and is described more fully, for example, in Haseloff and Gerlach (1988) Nature 334:585-591. There are numerous potential hammerhead ribozyme cleavage sites within the nucleotide sequences of native phagocytosis-related or AMDP-related genes, for example, those encoded by SEQ ID NOS:1-17. Preferably the ribozyme is engineered so that the cleavage recognition site is located near the 5' end of the phagocytosis-related or AMDP-related mRNA, in order to increase efficiency and minimize the intracellular accumulation of non-functional mRNA transcripts. Ribozymes within the invention can be delivered to a cell using a vector as described below.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (see, for example, Zaug et al., (1984), Science, 224:574-578; Been and Cech, (1986), Cell, 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the mRNAs specific for the peptides and proteins of interest of the current invention.

Yet another preferred agent within the invention is an RNA-mediated interference (RNAi) molecule that down-regulates expression of a phagocytosis-related and/or AMDP-related gene. The RNAi mechanism involves the use of double-stranded RNA (dsRNA) to trigger the silencing of genes highly homologous in sequence to the dsRNA. RNAi is an evolutionarily conserved phenomenon common to such diverse organisms as plants, nematodes (*Caenorhabditis*

*elegans*), fruit flies (*Drosophila*), amphibians, and mammals. It is thought to have evolved to protect the genome against invasion by mobile genetic elements such as transposons and viruses. In a multistep process, active small interfering RNA (siRNA) molecules are generated in vivo through the action of an RNase III endonuclease, termed Dicer. The resulting 21-to 23-nucleotide siRNA molecules mediate degradation of the complementary homologous RNA (Zamore et al., 2000; Grishok et al., 2000).

Non-naturally occurring RNAi molecules can be synthesized by methods known in the art and used advantageously to silence the expression of genes of interest. In mammalian cells, dsRNAs longer than 30 nucleotides are known to activate an antiviral response, leading to the nonspecific degradation of RNA transcripts and a general shutdown of host cell protein translation. However, gene-specific suppression in mammalian cells can be achieved by in vitro-synthesized siRNAs that are about 21 nucleotides in length, these molecules being long enough to induce gene-specific suppression, but short enough to evade the host interferon response (Elbashir, S. M. et al., 2001). Those of skill in the art will recognize that computer programs are available for the design of RNAi molecules directed against specific mRNA target sequences.

Small inhibitory RNA molecules act by binding to a protein complex within the cell, termed an RNA-induced silencing complex (RISC), which contains a helicase activity and an endonuclease activity. The helicase activity unwinds the two strands of RNA molecules, allowing the antisense strand of the siRNA to bind to the targeted RNA molecule (Zamore, 2002; Vickers et al., 2003). The endonuclease activity hydrolyzes the target RNA at the site where the antisense strand is bound.

RNAi strategies can be successfully combined with vector-based approaches to achieve synthesis in transfected cells of small RNAs from a DNA template under the control, for example, of an RNA polymerase III (Pol III) promoter. Use of Pol III provides the advantage of directing the synthesis of small, non-coding transcripts whose 3' ends are defined by termination within a stretch of 4-5 thymidines (Ts). These properties make it possible to use DNA templates to synthesize, in vivo, small RNAs with structural features close to those found to be required for active siRNAs synthesized in vitro. Using such templates, small RNAs targeting selected mRNAs of interest have been expressed in transfected cells, and shown to be able to efficiently and specifically inhibit the synthesis of the corresponding proteins (Sui et al., 2002).

For suppression of dominant gain-of-function mutations, or undesirable polymorphic variants of mRNAs of phagocytosis-related and/or AMDP-related genes which may differ from the wild type sequences by only a single base change (for example one of the AMD-associated variants of MT1-MMP, described herein), it may be desirable to selectively silence expression of the abnormal mRNA while permitting expression of the normal allele. A highly advantageous feature of the RNAi technology is the ability to selectively silence a mutation with single-nucleotide specificity. The feasibility of this approach has been demonstrated using RNAi to suppress the expression of a mutant allele of the Cu, Zn superoxide dismutase (SOD1) gene causing amyotrophic lateral sclerosis (ALS), while leaving expression of the normal allele intact (Ding et al., 2003).

The effectiveness of RNAi administration in vivo has been recently demonstrated in several mouse models of autoimmune hepatitis. Fas-mediated apoptosis is implicated in a broad spectrum of liver diseases. The in vivo silencing effect of siRNA duplexes targeting the Fas gene (also known as Tnfrsf6) encoding the Fas receptor was shown to protect mice from liver failure and fibrosis in these models. Intravenous injection of Fas siRNA specifically reduced Fas mRNA levels and expression of Fas protein in mouse hepatocytes, and the effects persisted without diminution for 10 days. In a fulminant hepatitis induced by injecting agonistic Fas-specific antibody, 82% of mice treated with siRNA that effectively silenced Fas survived for 10 days of observation, whereas all control mice died within 3 days (Song et al., 2003). A similar RNAi-based strategy is envisioned be useful in targeting or down-regulating abnormal or over-expressed genes in AMD patients.

Alternatively, expression of phagocytosis-related and/or AMDP-related genes can be reduced by targeting deoxyribonucleotide sequences complementary to regulatory regions of the phagocytosis-related or AMDP-related gene (i.e., the phagocytosis-related or AMDP-related gene promoters and/or enhancers) to form triple helical structures that prevent transcription of the phagocytosis-related or AMDP-related gene in target cells. (See generally, Helene, C. (1991) Anticancer Drug Des. 6(6):569-84; Helene, C., et al. (1992) Ann. N.Y. Acad. Sci. 660:27-36; and Maher, L. J. (1992) Bioassays 14(12):807-15). Nucleic acid molecules to be used in triple helix formation for the inhibition of transcription are preferably single-stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues is located on a single strand of the targeted duplex, resulting in CGC triplets across the three strands in the triplex. Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA, ribozyme, RNAi and triple helix molecules of the invention may be prepared by any method known in the art for the synthesis of such molecules. These include techniques for chemically synthesizing oligodeoxyribonucleotides and oligoribonucleotides well known in the art, such as for example solid phase phosphoramide chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be used.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone, as described above.

Other embodiments of agents that can down-regulate expression or neutralize the biological activity of the phagocytosis-relateci and/or AMDP-related genes of the invention are based on proteins. An example of a protein that can modulate expression and/or neutralize a biological function of a phagocytosis-related and/or AMDP-related gene product is an antibody that specifically binds a phagocytosis-related and/or AMDP-related polypeptide or peptide. Preferred polypeptides, for which mRNA levels are shown herein to be elevated in AMD, include those encoded by nucleic adds having SEQ ID NOS:2, 15 and 17, i.e., polypeptides having amino acid sequences respectively identified herein as SEQ ID NOS:79, 100, and 102-120. The antibodies of the invention can be used to interfere with the interaction of a phagocytosis-related an-or AMDP-related protein with one or more molecules that bind or otherwise interact with the phagocytosis-related and/or AMDP-related protein. For instance, an antibody directed against MT1-MMP protein is thought to neutralize the ability of this protein to activate progelatinase A. The results of a study described herein using an antibody directed against MT1-MMP showed delay of retinal degeneration in a rat model of RPE-based disease characterized by over-expression of MT1-MMP. Accordingly, inhibition of excessive production of MT1-MMP in the interphotoreceptor matrix using an anti-MT1-MMP antibody might be used in the eyes of patients with AMD to reduce destruction of The matrix and improve phagocytosis.

The proteins encoded by the nucleic acids of the invention (for example SEQ ID NOS:1-17, or immunogenic fragments or analogs thereof, and most preferably those encoded by nucleic acids found to be up-regulated in AMD (i.e., SEQ ID NOS:2, 15 and 17) can be used to raise antibodies useful in the invention. Such proteins can be produced by purification from cells/tissues, recombinant techniques or chemical synthesis well known to those of skill in the art. Antibodies for use in the invention can include polyclonal antibodies, monoclonal antibodies, single chain antibodies, Fab fragments, $F(ab')_2$ fragments, and molecules produced using a Fab expression library. See, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra; U.S. Pat. Nos. 4,376,110, 4,704,692, and 4,946,778; Kosbor et al., Immunology Today 4:72, 1983; Cole et al., Proc. Natl. Acad. Sci. USA 80:2026, 1983; Cole et al., "Monoclonal Antibodies and Cancer Therapy," Alan R. Liss, Inc., pp. 77-96, 1983; and Huse et al., Science 246:1275, 1989.

Other protein-based agents that can modulate expression or activity of a phagocytosis-related and/or AMDP-related protein include variants of phagocytosis-related and/or AMDP-related proteins that can compete with the corresponding native proteins for binding ligands, for example naturally occurring ligands that bind prostaglandin D2 synthase (SEQ ID NO:2), MT1-MMP (SEQ ID NO:15) and unknown gene AMDP-3 (SEQ ID NO:17). Such protein variants can be generated through various techniques known in the art. For example, a phagocytosis-related and/or AMDP-related protein variant can be made by mutagenesis, such as by introducing discrete point mutation(s), or by truncation. The mutation(s) can give rise to a phagocytosis-related and/or AMDP-related protein variant having substantially the same, or merely a subset of the functional activity of a native phagocytosis-related and/or AMDP-related protein. Alternatively, antagonistic forms of the protein can be generated which are able to inhibit the function of the naturally occurring form of the protein, such as by competitively binding to another molecule that interacts with a phagocytosis-related and/or AMDP-related protein. In addition, agonistic (or superagonistic) forms of the protein may be generated that constitutively express one or more phagocytosis-related and/or AMDP-related protein functional activities. Other variants of phagocytosis-related and/or AMDP-related proteins that can be generated include those that are resistant to proteolytic cleavage, as for example, due to mutations which alter protease target sequences. Whether a change in the amino acid sequence of a peptide results in a phagocytosis-related and/or AMDP-related protein variant having one or more functional activities of a native phagocytosis-related and/or AMDP-related protein can be readily determined by testing the variant for a native phagocytosis-related and/or AMDP-related gene protein functional activity (for example, binding a receptor or other ligand, or inducing a cellular response such as phagocytosis).

Another agent that can modulate expression or activity of a phagocytosis-related and/or AMDP-related gene product is a non-peptide mimetic or a chemically modified form of a phagocytosis-related and/or AMDP-related gene product that disrupts binding of a phagocytosis-related and/or AMDP-related protein to other proteins or molecules with which the native phagocytosis-related and/or AMDP-related gene product interacts. See, for example, Freidinger et al., in Peptides: Chemistry and Biology, G. R. Marshall ed., ESCOM Publisher: Leiden, Netherlands, 1988). Examples of such molecules include azepine (for example, see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1:1231), and beta-amino alcohols (Gordon et al. (1985) Biochem. Biophys. Res. Commun. 126:419; and Dann et al. (1986) Biochem. Biophys. Res. Commun. 134:71).

A phagocytosis-related and/or AMDP-related protein may also be chemically modified to create a protein derivative by forming covalent or aggregate conjugates with other chemical moieties, such as glycosyl groups, lipids, phosphate, acetyl groups and the like. Covalent derivatives of phagocytosis-related and/or AMDP-related proteins can be prepared by linking the chemical moieties to functional groups on amino acid side chains of the protein or at the N-terminus or at the C-terminus of the polypeptide.

Yet other embodiments of agents that can modulate expression or activity of a phagocytosis-related or AMDP-related gene are small molecules. Small molecules from a wide range of chemical classes can interfere with the activity of a phagocytosis-related and/or AMDP-related protein, for example by binding to the protein and inactivating its activity, or alternatively by binding to a target of the phagocytosis-related and/or AMDP-related protein, thereby interfering with the interaction of the protein with its target. Depending upon the nature of the gene/protein of interest, inhibitory small molecules can be designed to achieve various purposes, such as 1) to occupy a binding site for a substrate or target interacting protein, 2) to bind to the phagocytosis and/or AMDP related protein so as to change its 3-dimensional conformation, thereby inhibiting its activity, or 3) to bind to a target molecule of the phago/AMDP protein, thereby inhibiting interaction of the protein with its normal target. For example, small molecule inhibitors of MT1-MMP protein (SEQ ID NO:100) are known, such as polyphenols extractable from green tea (i.e., Epigallocatechin 3-O-gallate (EGCG), (−)-epigallocatechin 3,5-di-O-gallate, and epitheaflagallin 3-O-gallate) that have potent and distinct inhibitory activity against this protein (Oku N. et al., Biol Pharm Bull. September (2003);26(9):1235-8). Other classes of inhibitors of metalloproteinases in general are disclosed, for example, in Beckett, R. et al. (2001), U.S. Pat. No. 6,310,084.

Gene Therapy for AMD and Other Retinal Degenerative Conditions Based on Phagocytosis-Related and AMD-Related Genes In another aspect, the present invention provides for the delivery of natural or synthetic nucleic acids encoding phagocytosis-related and/or AMDP-related genes, or agents that modulate expression or activity of these genes. "Gene therapy" can be defined as the treatment of inherited or acquired diseases by the introduction and expression of genetic information in cells. Methods and compositions involving gene therapy vectors are described herein. Such techniques are generally known in the art and are described in methodology references such as Viral Vectors, eds. Yakov Gluzman and Stephen H. Hughes, Cold Spring Harbor Laboratory Press, Cold Spring Harbor, N.Y., 1988; Retroviruses, Cold Spring Harbor Laboratory Press, Plainview, N.Y., 2000; Gene Therapy Protocols (Methods in Molecular Medicine), ed. Jeffrey R. Morgan, Humana Press, Totawa, N.J., 2001.

In the various embodiments, the nucleic acids according to the invention are incorporated into recombinant nucleic acid constructs, typically DNA constructs, capable of introduction into and replication in a host cell. Such a construct preferably is a vector that includes a replication system and sequences that are capable of transcription and translation of a polypeptide-encoding sequence in a given host cell. For the present invention, conventional compositions and methods for preparing and using vectors and host cells can be employed, as described, for example, in Sambrook et al., supra, or Ausubel et al., supra.

Vectors useful in the practice of the invention comprise various types according to the purpose of the gene therapeutic approach. Some embodiments are vectors that include a nucleic acid encoding an agent that modulates (for example, down-regulates) expression of an AMDP-related or phagocytosis-related mRNA or protein. Other embodiments of the vectors include a wild-type or desirable polymorphic variant of a phagocytosis-related and/or AMDP-related gene of the invention. In various versions of the vectors of the former type, expression can be down-regulated by expressing, for example, an antisense RNA, ribozyme, RNAi molecule or triple helix molecule directed against an over-expressed mRNA, for example that of PD2S (SEQ ID NO:2), MT1-MMP (SEQ ID NO:15), or AMDP-3 (SEQ ID NO:17).

Other embodiments of the vectors direct expression of a desired polymorphic form of an AMDP-related or phagocytosis-related gene, either a wild-type, or a variant form. For example, in one embodiment the nucleic acid encodes a normal (wild-type) form of MT1-MMP (for example, SEQ ID NO:15). Delivery of a wild type form can be useful, for example, for subjects who do not express the normal variant, but rather are homozygous for an undesirable polymorphic form (such as a D273N missense polymorphism of MT1-MMP described herein), or are heterozygous for two different undesirable allelic forms (for example, a D273N missense polymorphism and a P259P synonomous/splice variant polymorphism).

Natural or synthetic nucleic acids according to the present invention, including cDNAs, antisense, ribozyme and RNAi molecules can be incorporated into recombinant nucleic acid constructs, typically DNA constructs, capable of introduction into and replication in a host cell. For the present invention, conventional compositions and methods for preparing and using vectors and host cells can be employed, as described, for example, in Sambrook et al., supra, or Ausubel et al., supra. As used herein, an "expression vector" is a vector which (due to the presence of appropriate transcriptional and/or translational control sequences) is capable of expressing a DNA (encoding cDNA, antisense, ribozyme, or RNAi) molecule which has been cloned into the vector and of thereby producing an RNA or polypeptide/protein. Expression of the cloned sequences occurs when the expression vector is introduced into an appropriate host cell.

The precise nature of regulatory regions needed for gene expression may vary from organism to organism, and according to the nature of the cloned sequence and purpose for expressing the sequence in a cell, but in general these elements include a promoter which directs the initiation of RNA transcription. Such regions may include those 5'non-coding sequences involved with initiation of transcription, such as a TATA box. The promoter may be constitutive or regulatable. Constitutive promoters are those which cause an operably linked gene to be expressed essentially at all times. Regulatable promoters are those which can be activated or deactivated. Regulatable promoters include inducible promoters, which are usually "off," but which may be induced to turn "on," and "repressible" promoters, which are usually "on," but which may be turned "off." Many different regulators are known, including temperature, hormones, heavy metals, and regulatory proteins. These distinctions are not absolute; a constitutive promoter may be regulatable to some degree.

The promoter may be a "ubiquitous" promoter active in essentially all cells of the host organism, for example, the beta-actin or optomegalovirus promoters, or it may be a promoter whose expression is more or less specific to the target cell or tissue. Promoters suitable for cell-specific (for example, photoreceptor-specific, RPE-specific, and melanocyte-specific) expression in the eye, and inducible promoters used to initiate transgene expression in transgenic animals at specific ages are described in examples below.

A number of vectors suitable for stable transformation of animal cells or for the establishment of transgenic animals are known. See, for example, Pouwels et al., Cloning Vectors: A Laboratory Manual, 1985, Supp. 1987. Typically, animal expression vectors include (1) one or more cloned animal genes under the transcriptional control of 5' and 3' regulatory sequences and (2) a dominant selectable marker. Such animal expression vectors may also contain, if desired, a promoter regulatory region (for example, a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal. Animal expression vectors within the invention preferably contain a selectable marker gene used to identify the cells that have become transformed. Suitable selectable marker genes for animal systems include genes encoding enzymes that produce antibiotic resistance (for example, those conferring resistance to hygromycin, kanamycin, bleomycin, G418, or streptomycin).

An example of a useful promoter which could be used to express a gene according to the invention is a cytomegalovirus (CMV) immediate early promoter (CMV IE) (Xu et al., Gene 272: 149-156, 2001). These promoters confer high levels of expression in most animal tissues, and are generally not dependent on the particular encoded proteins to be expressed. As an example, in most tissues of transgenic animals, the CMV IE promoter is a strong promoter. Examples of other promoters that are of use in the invention include SV40 early promoter, Rous sarcoma virus promoter, adenovirus major late promoter (MLP), Herpes Simplex Virus promoter, Mouse mammary tumor virus LTR promoter, HIV long terminal repeat (LTR) promoter, beta actin promoter (Genbank # K00790), or murine metallothionein promoter (Stratagene San Diego Calif.). Synthetic promoters, hybrid promoters, and the like are also useful in the invention and are known in the art.

Animal expression vectors may also include RNA processing signals such as introns, which have been shown to increase gene expression (Yu et al. (2002) 81: 155-163 and Gough et al. (2001) Immunology 103: 351-361). The location of the RNA splice sequences can influence the level of transgene expression in animals. In view of this fact, an intron may be positioned upstream or downstream of a phagocytosis-related or AMDP-related polypeptide-encoding sequence in the transgene to modulate levels of gene expression. Expression vectors within the invention may also include regulatory control regions which are generally present in the 5' regions of animal genes. Additionally, a 3' terminator region may be included in the expression vector to increase stability of the mRNA. See, for example, Jacobson et al. (1996) Annu. Rev. Biochem. 65:693-739; and Rajagopalan et al., (1997) Prog. Nucleic Acid Res. Mol. Biol. 56:257-286.

Adenovirus vectors have been shown to be capable of highly efficient gene expression in target cells and allow for a large coding capacity of heterologous DNA. "Heterologous DNA" in this context may be defined as any nucleotide sequence or gene which is not native to the adenovirus. Methods for use of recombinant adenoviruses as gene therapy vectors are discussed, for example, in W. C. Russell, Journal of General Virology 81:2573-2604, 2000, and Bramson et al., Curr. Opin. Biotechnol. 6:590-595, 1995.

A preferred form of recombinant adenovirus is a "gutless," "high-capacity," or "helper-dependent" adenovirus vector which has all viral coding sequences deleted, and contains the viral inverted terminal repeats (ITRs), therapeutic gene (including a natural or synthetic nucleic acid encoding a phagocytosis-related or AMDP-related gene, or an agent that modulates expression of a phagocytosis-related or AMDP-related gene, up to 28-32 kb) and the viral DNA packaging sequence. Variants of such recombinant adenovirus vectors such as vectors containing tissue-specific enhancers and promoters operably linked to a natural or synthetic nucleic acids encoding a phagocytosis-related or AMDP-related gene, or agent that modulates expression of such genes are also within the invention. More than one promoter can be present in a vector. Accordingly, more than one heterologous gene can be expressed by a vector.

The viral vectors of the present invention can also include Adeno-Associated Virus (AAV) vectors. AAV exhibits a high transduction efficiency of target cells and can integrate into the host genome in a site-specific manner. Methods for use of recombinant AAV vectors are discussed, for example, in Tal, J., J. Biomed. Sci. 7:279-291, 2000 and Monahan and Samulski, Gene Therapy 7:24-30, 2000. For cell-specific targeting, a preferred AAV vector comprises a pair of AAV inverted terminal repeats which flank at least one cassette containing a promoter which directs cell-specific (for example, photoreceptor, RPE, or melanocyte) expression, operably linked to the gene of interest. Using this vector, the DNA sequence of the AAV vector, including the ITRs, the promoter and natural or synthetic nucleic acid encoding a phagocytosis-related or AMDP-related genes, or agent that modulate expression of such a gene may be integrated into the host genome.

Another preferred vector for use in the invention is a herpes simplex virus (HSV) vector. Methods for use of HSV vectors are discussed, for example, in Cotter and Robertson, Curr. Opin. Mol. Ther. 1:633-644, 1999. HSV vectors, deleted of one or more immediate early genes (IE), are advantageously non-cytotoxic, persist in a state similar to latency in the host cell, and afford efficient host cell transduction. Recombinant HSV vectors allow for approximately 30 kb of coding capacity. A preferred HSV vector is engineered from HSV type I, deleted of the IE genes. HSV amplicon vectors may also be used according to the invention. Typically, HSV amplicon vectors are approximately 15 kb in length, possess a viral origin of replication and packaging sequences. More than one promoter can be present in the vector. Accordingly, more than one heterologous gene can be expressed by the vector. Further, the vector can comprise a sequence which encodes a signal peptide or other moiety which facilitates the secretion of the gene product from the host cell.

Viral vectors of the present invention may also include replication-defective lentiviral vectors, including HIV. Methods for use of lentiviral vectors are discussed, for example, in Vigna and Naldini, J. Gene Med. 5:308-316, 2000 and Miyoshi et al., J. Virol. 72:8150-8157, 1998. Lentiviral vectors are capable of infecting both dividing and non-dividing cells and of efficiently transducing epithelial tissues of humans. Lentiviral vectors according to the invention may be derived from human and non-human (including SIV) lentiviruses. These vectors may include the viral LTRs, primer binding site, polypurine tract, att sites and an encapsidation site. The lentiviral vector may be packaged into any suitable lentiviral capsid. The substitution of one particle protein by one from a different virus is referred to as "pseudotyping." The vector capsid may contain viral envelope proteins from other viruses, including Murine Leukemia Virus (MLV) or Vesicular Stomatitis Virus (VSV). The use of the VSV G-protein yields a high vector titer and results in greater stability of the vector virus particles. More than one promoter can be present in the lentiviral vector. Accordingly, more than one heterologous gene can be expressed by the vector.

The invention also provides for use of retroviral vectors, including Murine Leukemia Virus-based vectors. Methods for use of retrovirus-based vectors are discussed, for example, in Hu and Pathak, Pharmacol. Rev. 52:493-511, 2000 and Fong et al., Crit. Rev. Ther. Drug Carrier Syst. 17:1-60, 2000. Retroviral vectors according to the invention may contain up to 8 kb of heterologous (therapeutic) DNA, in place of the viral genes. Heterologous may be defined in this context as any nucleotide sequence or gene which is not native to the retrovirus. The heterologous DNA may include a tissue- or cell-specific promoter, as described above, and a phagocytosis-related and/or AMDP-related gene. The retroviral particle may be pseudotyped, and may contain a viral envelope glycoprotein from another virus, in place of the native retroviral glycoprotein. The retroviral vector of the present invention may integrate into the genome of the host cell. More than one promoter can be present in the retroviral vector. Accordingly, more than one heterologous gene can be expressed by the vector.

To combine advantageous properties of two viral vector systems, hybrid viral vectors may be used to deliver a phagocytosis-related or AMDP-related gene or an agent that modulate expression of such a gene, to a target tissue. Standard techniques for the construction of hybrid vectors are well known to those skilled in the art. Such techniques can be found, for example, in Sambrook, et al., In Molecular Cloning: A Laboratory Manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless," "helper-dependent," or "high-capacity" adenoviral vector. Adenovirus/AAV hybrid vectors are discussed, for example, in Lieber et al., J. Virol. 73:9314-, 1999. Retroviral/adenovirus hybrid vectors are discussed, for example, in Zheng et al., Nature Biotechnol. 18:176-186, 2000. Retroviral genomes contained within an adenovirus may integrate within the host cell genome and effect stable transgene expression. More than one promoter can be present in the hybrid viral vector. Accordingly, more than one heterologous gene can be expressed by the vector.

In accordance with the present invention, other nucleotide sequence elements which facilitate expression of a phagocytosis-related or AMDP-related gene, or agent that modulate expression or activity of such a gene, and cloning of the vector are further contemplated. The presence of enhancers upstream of the promoter, or terminators downstream of the coding region, for example, can facilitate expression.

Several non-viral methods are known for introducing a phagocytosis-related and/or AMDP-related nucleic acid, or an agent that modulates expression or activity of such a nucleic acid in a cell. For a review of non-viral methods, see, for example, Nishikawa and Huang, Human Gene Ther. 12:861-870, 2001. Various techniques employing plasmid DNA for the introduction into a cell of a phagocytosis-related and/or AMDP-related nucleic acid, or an agent that modulates expression of a phagocytosis-related and/or AMDP-related nucleic acid expressed within a cell are provided for according to the invention. Such techniques are generally known in the art and are described in references such as Ilan, Y., Curr. Opin. Mol. Ther. 1:116-120 (1999); and Wolff, J. A., Neuromuscular Disord. 7:314-318 (1997).

Methods involving physical techniques for the introduction into a host cell of a phagocytosis-related and/or AMDP-related nucleic acid, or an agent that modulates expression of such a nucleic acid in a cell can be adapted for use in the present invention. Cell electropermeabilization (also termed cell electroporation) may be employed for delivery of the selected nucleic acid into cells. This technique is discussed in Preat, V., Ann. Pharm. Fr. 59:239-244 (2001), and involves the application of pulsed electric fields to cells to enhance cell permeability, resulting in exogenous polynucleotide transit across the cytoplasmic membrane. Alternatively, the particle bombardment method of gene transfer involves an Accell device (gene gun) to accelerate DNA-coated microscopic gold particles into target tissue. This methodology is described, for example, in Yang et al., Mol. Med. Today 2:476-481 (1996); and Davidson et al., Rev. Wound Repair Regen. 6:452-459 (2000).

For construction of embodiments of the invention that are transgenic animals, several standard methods are known for introduction of recombinant genetic material into oocytes for the generation of a transgenic animal. Examples of such methods include: 1) particle delivery systems (see for example, Novakovic S et al. (1999) J Exp Clin Cancer Res 18:531-6; Tanigawa et al. (2000) Cancer Immunol Immunother 48:635-43); 2) microinjection protocols (see, for example, Krisher et al. (1994) Transgenic Res. 3: 226-231; Robinett C C and Dunaway M (1999), Modeling transcriptional regulation using microinjection into *Xenopus oocytes*. In: Methods: A Companion to Methods in Enzymology 17: 151-160; or Pinkert C A and Trounce I A (2002), Methods 26:348-57); (3) polyethylene glycol (PEG) procedures (see for example, Meyer O et al. (1998) J. Biol. Chem. 273: 15621-7; or Park et al. (2002) Bioconj Chem, 13: 232-239); (4) liposome-mediated DNA uptake (see, for example, Hofland H E J and Sullivan S M (1997) J. Liposome Res. 7: 187-205; or Hui S W et al. (1996) Biophys. J. 71:590-599); and (5) electroporation protocols, desribed above.

Synthetic gene transfer molecules according to the invention can be designed to form multimolecular aggregates with plasmid DNA (harboring sequences encoding a phagocytosis-related and/or AMDP-related nucleic acid, or an agent that modulates expression or activity of such a nucleic acid in a cell, operably linked to a promoter) and to bind the resulting particles to a target cell surface in such a way as to trigger endocytosis and endosomal membrane disruption. Polymeric DNA-binding cations (including polylysine, protamine, and cationized albumin) can be linked to cell-targeting ligands to trigger receptor-mediated endocytosis. Methods involving polymeric DNA-binding cations are reviewed, for example, in Guy et al., Mol. Biotechnol. 3:237-248 (1995); and Garnett, M. C., Crit. Rev. Ther. Drug Carrier Syst. 16:147-207 (1999).

Cationic amphiphiles, including lipopolyamines and cationic lipids, may provide receptor-independent gene transfer into target cells of phagocytosis-related and/or AMDP-related nucleic acids, or nucleic acids encoding an agent that modulates expression or activity of a phagocytosis-related and/or AMDP-related gene. Preformed cationic liposomes or cationic lipids may be mixed with plasmid DNA to generate cell transfecting complexes. Methods involving cationic lipid formulations are reviewed, for example, in Felgner et al., Ann. N.Y. Acad. Sci. 772:126-139 (1995); and Lasic and Templeton, Adv. Drug Delivery Rev. 20:221-266 (1996). Suitable methods can also include use of cationic liposomes as agents for introducing DNA or protein into cells. For therapeutic gene delivery, DNA may also be coupled to an amphipathic cationic peptide (Fominaya et al., J. Gene Med. 2:455-464, 2000).

Methods that involve both viral and non-viral based components may be used according to the invention. An Epstein Barr Virus (EBV) based plasmid for therapeutic gene delivery is described in Cui et al., Gene Therapy 8:1508-1513, 2001. A method involving a DNA/ligand/polycationic adjunct coupled to an adenovirus is described in Curiel, D. T., Nat. Immun. 13:141-164 (1994).

Protein transduction offers an alternative to gene therapy for the delivery of therapeutic proteins into target cells, and methods of protein transduction are within the scope of the invention. Protein transduction is the internalization of proteins into a host cell from the external environment. The internalization process relies on a protein or peptide which is able to penetrate the cell membrane. The transducing property of such a protein or peptide can be conferred upon proteins (phagocytosis-related and/or AMDP-related proteins, for example) which are expressed as fusion proteins. Commonly used protein transduction vehicles include the antennapedia peptide, the HIV TAT protein transduction domain and the herpes simplex virus VP22 protein. Such vehicles are reviewed, for example, in Ford et al., Gene Ther. 8:1-4 (2001).

Nucleic acids of the present invention may be expressed for any suitable length of time within the host cell, including transient expression and stable, long-term expression. In a preferred embodiment, a phagocytosis-related and/or AMDP-related nucleic acid, or an agent that modulates expression or activity of such a nucleic acid in a cell will be expressed in therapeutic amounts for a suitable and defined length of time. Methods of delivery that achieve either transient or long-term expression of a transgene are described herein. Episomally replicating vectors typically are maintained at intermediate to high copy number in the cell, which contributes to high levels of inserted DNA. Some vectors persist as episomes, and such vectors may behave as autonomous units replicating in the host independent of the host chromosome. DNA delivered via a plasmid or viral-based vector, including adenovirus, for example, exists in an episomal state within the host cell and is expressed in a transient manner.

Vectors according to the invention may contain nucleotide sequence elements which facilitate integration of DNA into host chromosomes. Integration is well tolerated by most transduced cells, and is preferred to ensure stability of newly introduced genetic information into a cell. Integration of a vector including a phagocytosis-related and/or AMDP-related nucleic acid, or a nucleic acid encoding an agent that modulates expression or activity of a phagocytosis-related and/or AMDP-related gene product in a cell may occur in a random or site-specific manner. Viral-based vectors that allow for integration into the host genome include those derived from AAV, retroviruses, and some AAV/adenovirus hybrids.

The compositions comprising nucleic acid molecules (including gene therapy vectors) of the invention may be administered to a mammalian subject by any suitable technique. For example, various techniques are known using viral vectors for the introduction of a natural or synthetic nucleic acid encoding a phagocytosis-related or AMDP-related gene, or in another aspect, an agent that modulates expression or activity of a natural or synthetic nucleic acid encoding a phagocytosis-related or AMDP-related gene. Viruses are naturally evolved vehicles which efficiently deliver their genes into host cells and therefore are desirable vector systems for the delivery of therapeutic genes. Preferred viral vectors exhibit low toxicity to the host cell and produce therapeutic quantities of the natural or synthetic nucleic acid encoding a phagocytosis-related or AMDP-related gene, or agent that modulates expression or activity of such a gene, for example in a tissue-specific manner. For delivery of the vectors of the invention to the eye, various approaches are known to those of skill in the art, including intraocular injection.

Association of MT1-MMP with AMD and Other Retinal Degenerations.

Some embodiments of the invention are methods of screening, animals models of retinal degeneration and treatment methods based on matrix metalloproteinase, membrane type 1 (MT1-MMP) (SEQ ID NO:15). Among the AMDP genes listed above, one gene, i.e., MT1-MMP, (herein also designated PHG-16 and AMDP-6), was initially selected for further evaluation as a candidate target for AMD therapy. As shown in the examples below, results of various confirmatory analyses clearly demonstrated that MT1-MMP is a phagogene, as evidenced by: 1) a diurnal pattern of expression, peaking in the early morning, the time of maximal OS shedding and phagoctytosis in vivo (FIG. 7); 2) localization to the tips of the OS in rat and human eyes (FIGS. 8, 9); and 3) inhibition of OS phagocytosis by an antibody to MT1-MMP, both in vitro (FIG. 10) and in vivo, following subretinal injection into rat eyes (FIG. 11).

A relationship of MT1-MMP with AMD was demonstrated by: 1) correlation of a graded increase in mRNA expression with severity of AMD-related changes in human donor eyes (FIGS. 12 and 13); 2) enhanced immunolocalization of MT1-MMP antibody in the interphotoreceptor matrix in a monkey model of AMD; and 3) increased incidence of a missense polymorphism (i.e., D273N) in the catalytic domain of MT1-MMP in human macular degenerative diseases including AMD, and increased incidence in AMD and macular degeneration patients of a synonymous polymorphism in MT1-MMP (i.e., P259P). (See Table 4 in Example 5, infra.)

Additional studies of MT1-MMP provided evidence that overexpression of this gene is a common feature of at least one form of hereditary retinal degeneration besides AMD in which the primary etiology is in the RPE, i.e., that of the Royal College of Surgeons (RCS) rat. The RCS rat is a well known animal model of inherited retinal degeneration in which photoreceptor degeneration is due to a phagocytic defect in the RPE cells (Bok and Hall, 1971). The causative gene in this model is a mutated MERTK (D'Cruz et al. 2000). In studies described herein, MT1-MMP is shown to be overexpressed in the retina and RPE of the mutant RCS rat. Significantly, following injection of an anti-MT1-MMP antibody (2 μl volume) into the subretinal space of 7-day old RCS rats, the rate of photoreceptor degeneration relative to controls, is markedly slowed in anti-MT1-MMP antibody-injected animals observed at 30 and 60 days of age, whereas control antibodies or sham injection have no effect (FIG. 14). These results provide evidence that an agent directed against MT1-MMP protein present in the outer retina, for example within the interphotoreceptor matrix in the subretinal space, can provide a beneficial effect, such as slowing or reversing a retinal degenerative condition.

Previously recognized functions of MT1-MMP, which is expressed on invasive tumor cells, include an ability to activate progelatinase A, and to digest various ECM components (Sato et al., 1994; Cao et al., 1995; Pei and Weiss, 1996). Based on the discoveries described herein, it is now apparent that this gene provides an attractive new candidate gene to target therapeutically for AMD and other retinal and choroidal degenerative diseases.

Animal Models of AMD Based on Phagocytosis-Related and/or AMDP-Related Genes

In another aspect, the invention includes nonhuman transgenic animals (for example, mice) suitable for use as animal models of AMD and other degenerative conditions of the retina and choroid. Heretofore, testing of therapeutic compounds and treatment methods for AMD has been impeded by the lack of suitably short-lived animal models of the disease in which aging changes are practical to follow. Based on the discovery of overexpression of at least three AMD/phagogenes, i.e., PD2S (SEQ ID NO: 2), MT1-MMP (SEQ ID NO:15) and AMDP-3 (SEQ ID NO:17) in AMD eyes, and demonstration of overexpression of the MT1-MMP mRNA and protein in the retinas of humans with AMD, monkeys with AMD, and RCS rats with inherited retinal degeneration, the invention provides as preferred embodiments transgenic animals that overexpress at least one of PD2S, MT1-MMP and AMDP-3.

Some of the transgenic models are engineered to conditionally overexpress the transgene only upon addition of an exogenous stimulus, such as doxycycline. Thus, the onset of transgene expression can be controlled in these animals by administration of doxycycline. As an example, transgene expression can be triggered at a particular time of life, such as after completion of postnatal development of the retina (occurring at around 30 days of age in a mouse). The feature of inducible expression is particularly advantageous with a gene such as MT1-MMP, which if overexpressed during the embryonic or early postnatal periods might be predicted to result in developmental abnormalities in the animals. Other transgenic embodiments selectively overexpress a transgene, such as MT1-MMP, PD2S or AMDP-3 in particular cell types, for example in photoreceptors, RPE cells, or cell types of the choroid.

Yet other preferred embodiments of animal models of AMD/retinal and/or choroidal degenerations combine polymorphic variants of AMDP-related or phagocytosis-related genes, including those discovered and described herein. These models reflect the complex genetic inheritance pattern of AMD. A single genetic defect, such as a polymorphism present in MT1-MMP, may be unable to cause a disease in isolation. However, certain combinations of polymorphic variants of several genes, appropriate environmental factors, and the passage of time are likely to contribute jointly to dysfunction sufficient to tip the scale, the end result being AMD or another form of retinal, macular or choroidal degeneration. For example, other AMDP genes are likely to cooperate with polymorphic variants of MT1-MMP to produce the full spectrum of AMD.

Accordingly, some embodiments of the transgenic animal models of AMD and other retinal and choroidal degenerations express polymorphic variants of one or more genes with involvement in AMD and/or phagocytosis by RPE cells. Various preferred embodiments are polytransgenic models expressing MT1-MMP variants, for example in combination with polymorphic variants of one or more other AMD-related genes, including those AMDP genes disclosed herein (for example, genes having the wild type cDNA sequences shown herein as SEQ ID NOS: 2, 9,10, 16, 17), and AMD-related genes having polymorphic variants previously described to be correlated with AMD (for example, SEQ ID NOS:62, 63, 64, 65, 66, 67, 68, and 69). In other preferred embodiments of the polytransgenic models, polymorphic variants of MT1-MMP are expressed in combination with polymorphic variants of other phagocytosis-related genes (for example, genes having the wild type cDNA sequences shown herein as SEQ ID NOS:1, 2, 3, 4, 5, 6, 7, 8, 9, 10, 11, 12, 13 and 14).

EXAMPLES

The present invention is further illustrated by the following specific examples, which should not be construed as limiting the scope or content of the invention in any way.

Example 1

Research Tools for Isolation of Phagocytosis-Related and AMD-Related Genes

Described below are research tools developed during the course of the invention, including: 1) a simple and affordable method of simultaneously gauging expression in a large number of genes by hybridization; and 2) tools for identification of phagocytosis-related genes, based on a phagocytic RPE cell line and a vital assay of phagocytosis.

CHANGE Array System

Figure 1A:
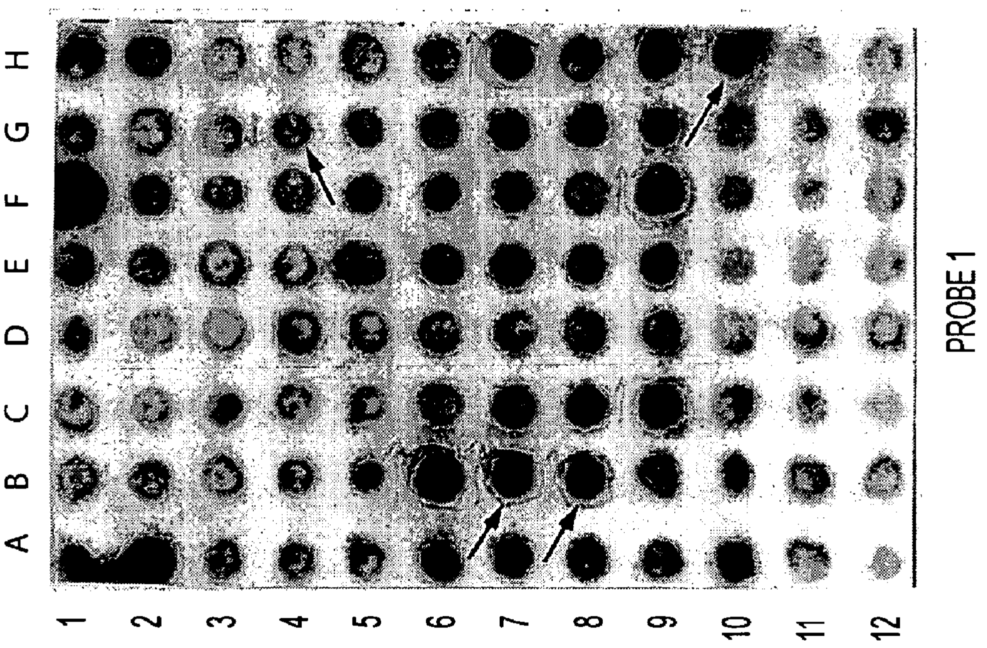
Figure 2A:
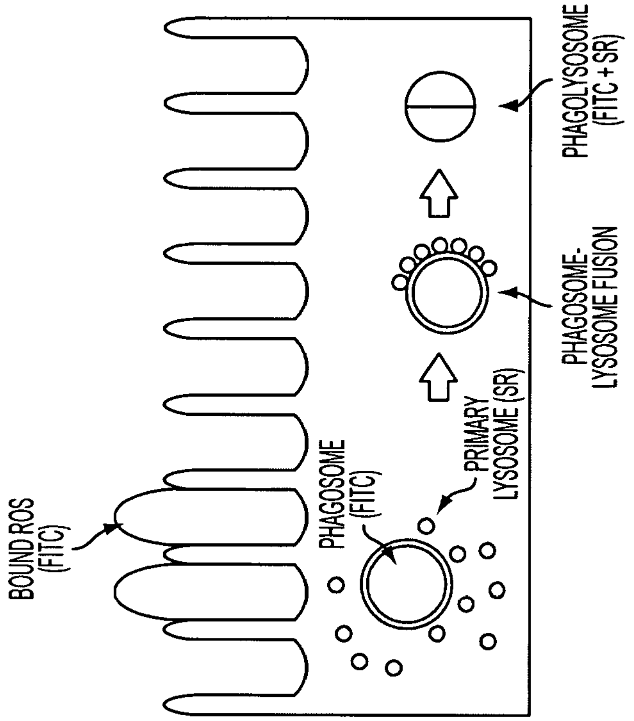
FIG. 2 (upper panel) shows a schematic drawing of a vital assay of rod outer segment (ROS) phagocytosis by cultured RPE cells. The lower panel shows black and white photographs of living BPEI-1 RPE cells undergoing phagocytosis after ROS feeding, according to an embodiment of the invention. When observed by fluorescence microscopy, lysosomes in the RPE cells appear red due to sulforhodamine (SR) staining and FITC-stained ROS appear green. During successive stages of phagocytosis, ROS are bound to the cell surfaces, then ingested by the RPE cells, first becoming phagosomes and then phagolysosomes (distinguishable by yellow-orange fluorescence) upon fusion with lysosomes.
Figure 2B:
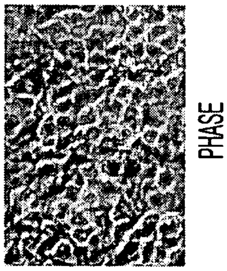
Figure 2C:
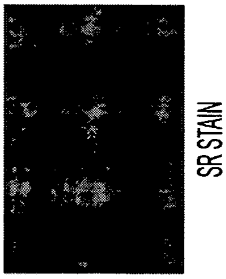
Figure 2D:
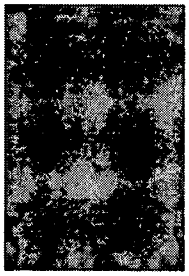
Figure 2E:

Referring to FIG. 1, a macroarray technique termed Comparative Hybridization Analysis of Gene Expression (CHANGE) was developed. λgt11 cDNA libraries were constructed using techniques well known to those of skill in the art of molecular biology, from rat RPE/choroid RNA and human retinal RNA. Rat RNA used for the library was obtained from the RPE/choroid of animals approximately 2-3 months of age, raised in cyclic light (12 h light:12 hr dark), and sacrificed at various times throughout the diurnal cycle. Approximately ten thousand clones from the libraries were individually picked, amplified on plates, and transferred to blots as arrays.

Total RNA from rat and human sources was used as a global expression hybridization probe, following conversion into cDNA, amplification by PCR, and testing to confirm its usefulness for detecting expression of specific genes on the arrays.

Preliminary comparison of expression of a number of genes by CHANGE and Northern blot analysis confirmed the accuracy and demonstrated that a difference in mRNA expression as small as about 15-20% could be detected using the CHANGE method. It was apparent that the ability to readily perform iterative analysis with a combination of biologically related probes (for example, probes related on the basis of function, phenomenon, or pathology) was a very powerful aspect of this strategy.

Phagocytosis Gene Discovery Tools

A preferred approach to identifying genes relevant to RPE phagocytosis in vivo is to analyze RPE gene expression in an in vitro system that performs the function of outer segment (OS) phagocytosis in a synchronous manner, as it occurs in vivo. In rodents and other mammals, shedding and phagocytosis of OS follows a circadian rhythm. Peak shedding by the photoreceptors and ingestion on a massive scale by the RPE cells is known to occur over a period of several hours beginning just before light onset (LaVail, 1976). To successfully identify phagogenes on the basis of differential expression in cultured RPE cells during the course of OS phagocytosis, it is preferable that the kinetics of the phagocytic process be uniform across the cultures, inter alia, to minimize "noise" from cells showing asynchronous phagocytosis with respect to their neighbors. Primary RPE cultures are generally unsuitable for this purpose, due to the marked phenotypic heterogeneity of RPE cells within primary cultures, and the corresponding heterogeneity in kinetics of phagocytosis displayed by cells of different phenotypes (McLaren, 1996).

The problem of heterogeneity can be circumvented by using an immortal RPE cell line that, like the RPE in vivo, demonstrates cobblestone morphology in culture, and is able to phagocytose fed OS with synchronous binding and ingestion. Methods for producing and maintaining immortal RPE cell lines from rodent and human sources are well known in the art. An exemplary cell line exhibiting the desired phagocytic characteristics is the BPEI-1 RPE cell line (McLaren et al., 1993b). BPEI-1 cultures were shown to follow the same kinetics of OS phagocytosis as "type 1" primary RPE cells, which most closely resemble RPE in vivo (McLaren et al., 1993a; McLaren, 1996). Use of such cell lines for isolation of phagocytosis-related genes is preferably carried out in large-scale phagocytosis assays having sufficient cells to yield RNA amounts (about 10-30 μg) needed for both probe preparation and Northern blotting. Accordingly, cells of a suitable RPE cell line, such as BPEI-1, are plated at high density (for example with approximately $10^6$ cells per well in 6-well multi-well plates), and cultured for 1-2 days, for example in media as previously described (McLaren et al., 1993c; McLaren, 1996).

Figure 3:
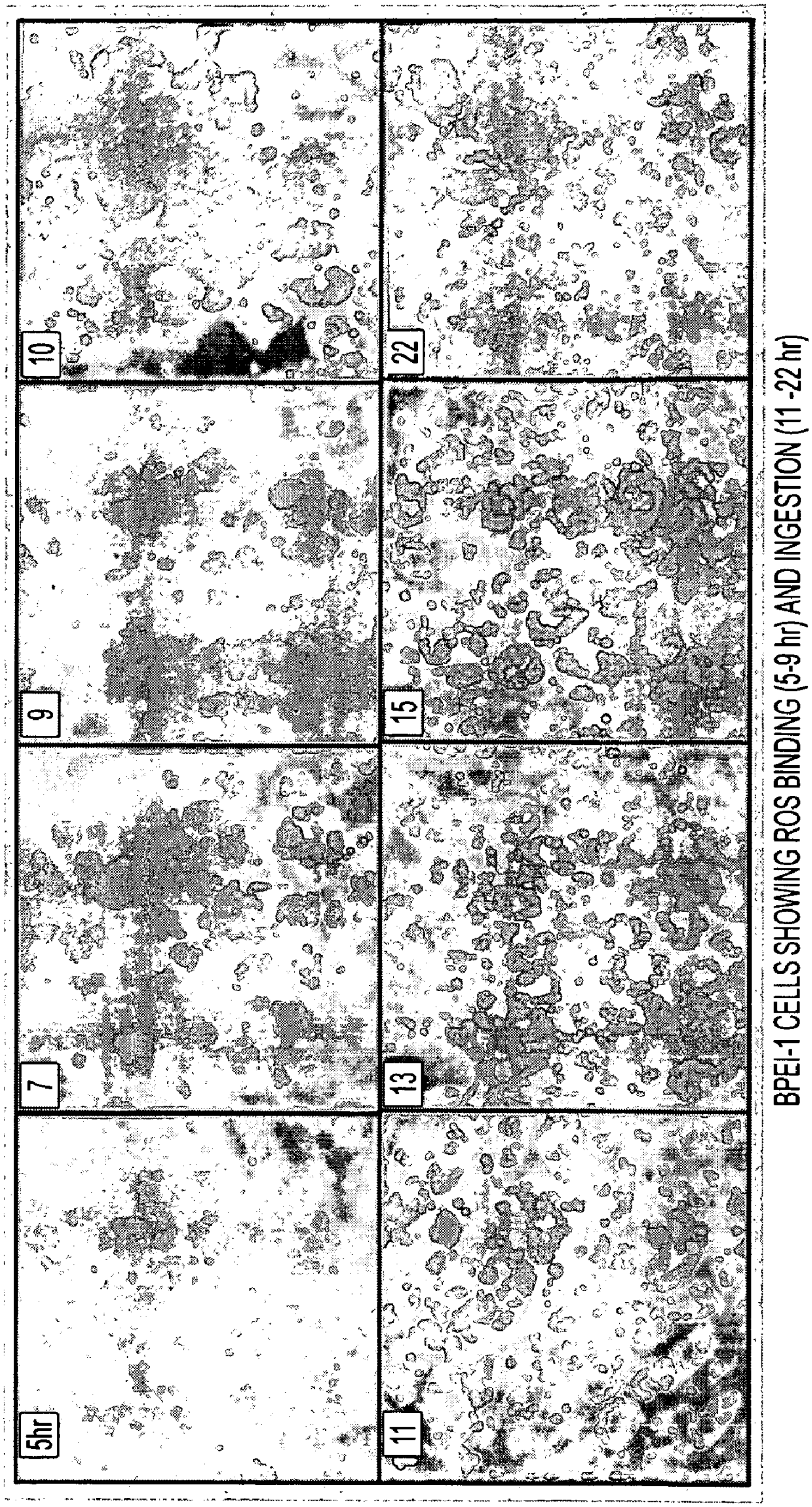
FIG. 3 is a series of photographs showing different stages of ROS phagocytosis viewed in large scale cultures of living BPEI-1 RPE cells at the indicated times after feeding with FITC-ROS, according to an embodiment of the invention. The upper four panels show massive binding of ROS to the cell surfaces during the first 9-10 hours after feeding. The lower four panels show synchronous ROS ingestion and formation of phagolysosomes, starting approximately 11 hours after feeding with ROS.

For preparation of probes for the CHANGE analysis representing specific stages of phagocytosis ("stage-specific" probes), it is advantageous to be able to follow the course of OS phagocytosis in living RPE cell cultures, to permit isolation of RNA at specific, documented, stages of the phagocytic process. To facilitate this, any suitable vital assay of OS phagocytosis can be used, for example, a double fluorescent assay previously described by McLaren et al. (1993c). Referring to FIG. 2, in this assay the lysosomes in the RPE cells are vitally stained with sulforhodamine. (red fluorescence), and OS fed to the cells are prelabeled with fluorescein (FITC) (green fluorescence). The assay allows all stages of the phagocytic process (i.e., OS binding, ingestion, and digestion) to be followed by fluorescent microscopy in living cultures. FIG. 3 shows different stages of synchronous binding, ingestion and intracellular processing of OS typically observed in cultures of living BPEI-1 cells at various times after feeding the cells with FITC-stained OS.

Isolation of Phagogenes Using CHANGE

To isolate phagogenes expressed at different stages of phagocytosis, stage-specific probes are prepared from total RNA extracted from the RPE cell cultures at various times (for example, 0, 1, 6, 12, 18, and 30 hours) after OS feeding, and at the same time points from control cultures not fed with OS. Following preparation of "+/−OS" phagocytosis probes by reverse transcription of the total RNA, pairs of such probes are used in a CHANGE analysis to screen a gene array, for example an array of approximately 10,000 RPE-expressed genes as disclosed herein, to identify those genes differentially expressed during OS phagocytosis by the RPE cells. Genes showing changes in expression during OS phagocytosis are subsequently identified by DNA sequence analysis using standard techniques and compared with sequences in databases such as GenBank.

Example 2

Isolation and Confirmation of Phagocytosis-Related Genes Expressed in RPE Cells

This example describes the isolation of genes showing changed expression during RPE phagocytosis, using the above-described methods.

From CHANGE analyses using "+/−OS" probes to screen arrays containing approximately 10,000 RPE-derived cDNAs, approximately 60 putative differentially expressed genes were initially obtained. Further detailed analyses, including confirmation of differential expression by Northern blot analysis, provided an initial subset of 16 confirmed phagocytosis-related genes selected for further investigation. Table 1 supra provides a listing of the identities and sequence listing notations (i.e., nucleic acids: SEQ ID NOS. 1-15 and amino acids: SEQ ID NOS:71-101) of confirmed phagogenes isolated as described herein by the CHANGE technique.

Detailed analysis of expression patterns of these genes during phagocytosis in vitro was examined in Northern blots of RNA extracted from BPEI cultures at various times after feeding the cells with OS. The particular stages of phagocytosis were observed in the living cells and documented photographically immediately prior to RNA extraction. As seen in FIG. 4, expression patterns of the 16 phagogenes were clustered into distinct groups that demonstrated peaks of expression at different times in the phagocytic process: i.e., early, early-mid, mid-late, and late.

Example 3

Isolation and Confirmation of RPE-Expressed Genes Exhibiting Differential Expression in AMD Described herein are procedures used for isolation of putative AMD genes by CHANGE, and methods for confirming their relationship to AMD.

A similar approach to that described in Example 2 utilized the CHANGE technique to identify genes related to AMD, based on the assumption that genes playing a role in the pathogenesis of AMD show changes in expression during the course of the disease. Human donor eyes were obtained from a local eye bank. Generally, eyes were accepted that were enucleated within 3 hours of death and were available for processing within 12 hours. Regardless of time of death and time elapsed until processing, the actual quality of the tissue was assessed by several criteria, including appearance on gross examination, microscopic assessment of tissue sections, and the quantity and quality of the RNA obtained, as assessed by Northern blot analysis and RT-PCR.

Figure 5A:
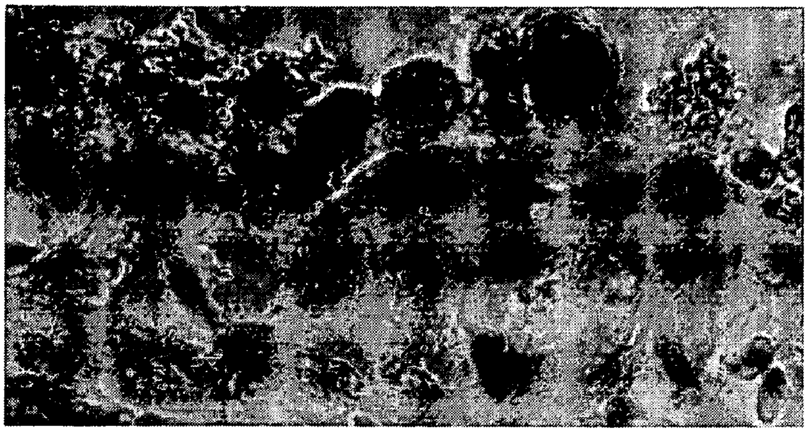
FIG. 5 is three photographs showing the grading system used to classify human donor eyes for AMD-related changes in the retina, according to an embodiment of the invention. Grades shown: 0-+1, minimal thickening of the Bruch's membrane; +2-+3, multiple small to mid size drusen, with thickened Bruch's membrane; +3-+4, large coalescing drusen.
Figure 5B:
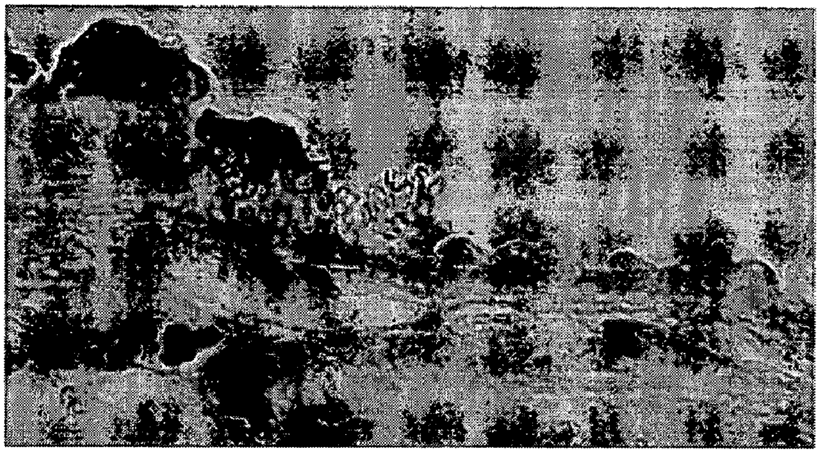
Figure 5C:
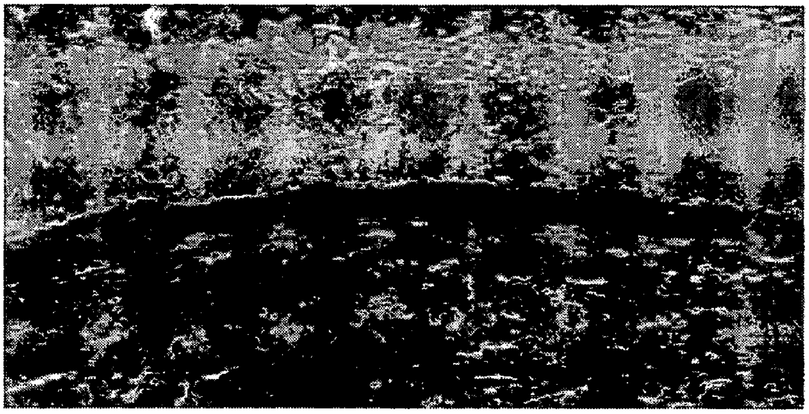

Referring to FIG. 5, each eye was graded microscopically for AMD-related changes, on a scale of increasing severity of AMD changes from 0 to +5, in a strip of retina/choroid, approximately 3-4 mm wide, running from periphery to periphery and passing through the optic nerve head and the macula. In assigning a grade to each eye, several morphological criteria were taken into account, including: 1) degree of thickening of Bruch's membrane; 2) number, size, and location of any drusen; 3) presence or absence of neovascularization or choridal neovascular (CNV) membranes; and 4) RPE/photoreceptor atrophy, if any. RNA, DNA, and protein were isolated from the retina and RPE/choroid of each eye.

To prepare "+AMD" probes, total RNA was extracted from RPE/choroids of human donor eyes and pooled from multiple eyes with +3 to +5 (moderate to severe) AMD changes. Pooled RNAs from RPE/choroids of age-matched, unaffected eyes were used to prepare "−AMD" control probes. The +/− probes were used to identify differentially expressed genes by CHANGE, as described above. Approximately 200 RPE-expressed genes were initially identified that showed differential expression in subjects with AMD, compared to unaffected individuals.

To then obtain a subset of phagocytosis-related genes differentially expressed in AMD (i.e., "AMDP genes"), the results of the CHANGE screening for phagocytosis-related genes (Example 2 above) and the CHANGE screening for AMD-related genes (this example) were compared, to identify those RPE genes on the CHANGE panels demonstrating differential expression in both phagocytosis and AMD. The results of this analysis yielded an initial subset of 6 genes fitting both criteria, i.e., prostaglandin D2 synthase (SEQ ID NO:2), casein kinase epsilon 1 (SEQ ID NO:9), ferritin heavy polypeptide 1 (SEQ ID NO:10), MT1-MMP (SEQ ID NO:15), SWI/SNF related/OSA-1 nuclear protein (SEQ ID NO:16) and human unknown cDNA AMDP-3 (SEQ ID NO:17). (See also Table 2 supra.)

Example 4

Isolation and Characterization of MT1-MMP as an AMD-Related and Phagocytosis-Related (AMDP) Gene This example describes the identification of MT1-MMP (SEQ ID NO:15), an exemplary gene found by CHANGE to be differentially expressed in both phagocytosis and in AMD (i.e., an "AMD-related phagogene," or "AMDP gene"), and results of studies confirming that MT1-MMP is a phagogene and is upregulated in AMD eyes.

To identify genes related to both AMD and OS phagocytosis, the results of the two CHANGE analyses were compared as described above. Among the candidate genes differentially expressed in both screens, clone 91-40 stood out, as being a relatively new type of metalloproteinase, i.e., MT1-MMP (Sato et al., 1994) having functions that would reasonably fulfill the requirements of a gene with suspected involvement in AMD. These functions include a role in OS phagocytosis (as disclosed herein) as well as activation of progelatinase A and degradative activity against various extracellular matrix components (Sato et al., 1994; Cao et al., 1995; Pei and Weiss, 1996).

Figure 6A:
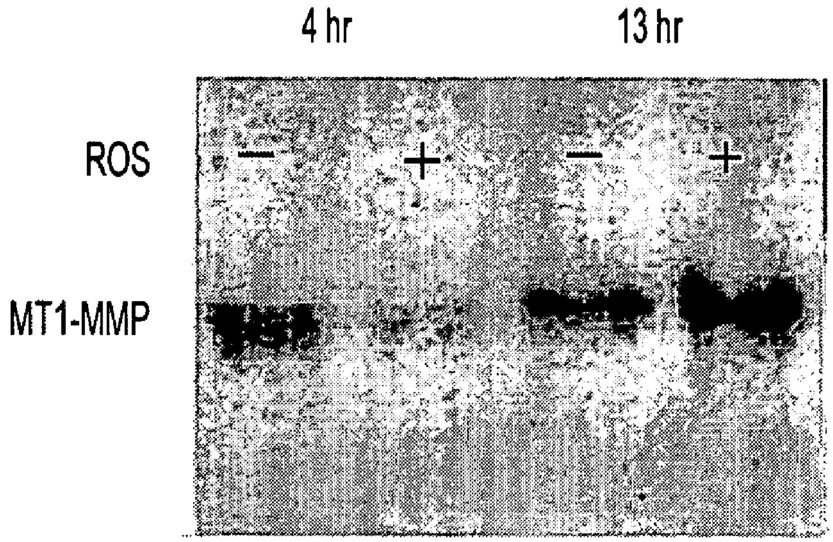
FIG. 6 is a two Northern blots and a graph showing expression of MT1-MMP and actin mRNA during phagocytosis by cultured RPE cells at 4 and 13 hours after ROS feeding. Decreased expression at 4 hours and increased expression at 13 hours is seen, confirming results obtained by CHANGE. The amount of RNA present in each lane is estimated by actin hybridization, used to normalize the MT1-MMP hybridization signal.
Figure 6B:
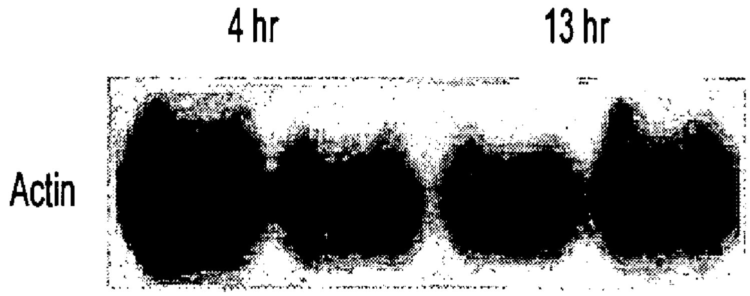
Figure 6C:
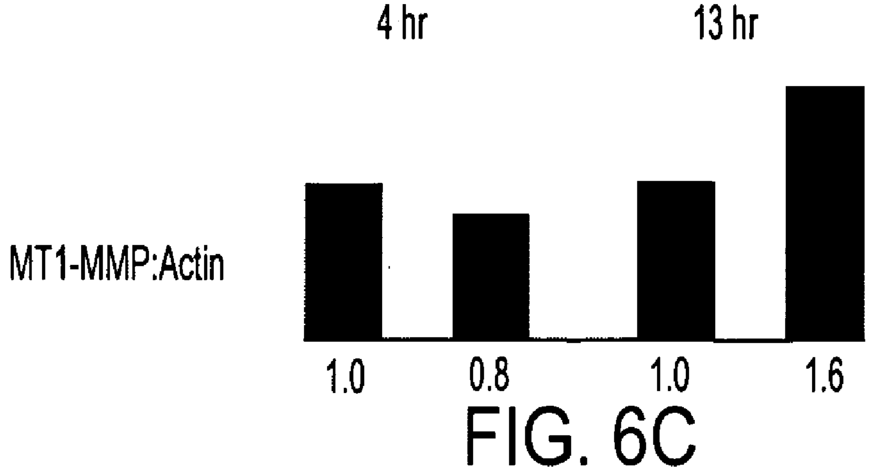
Figure 7:
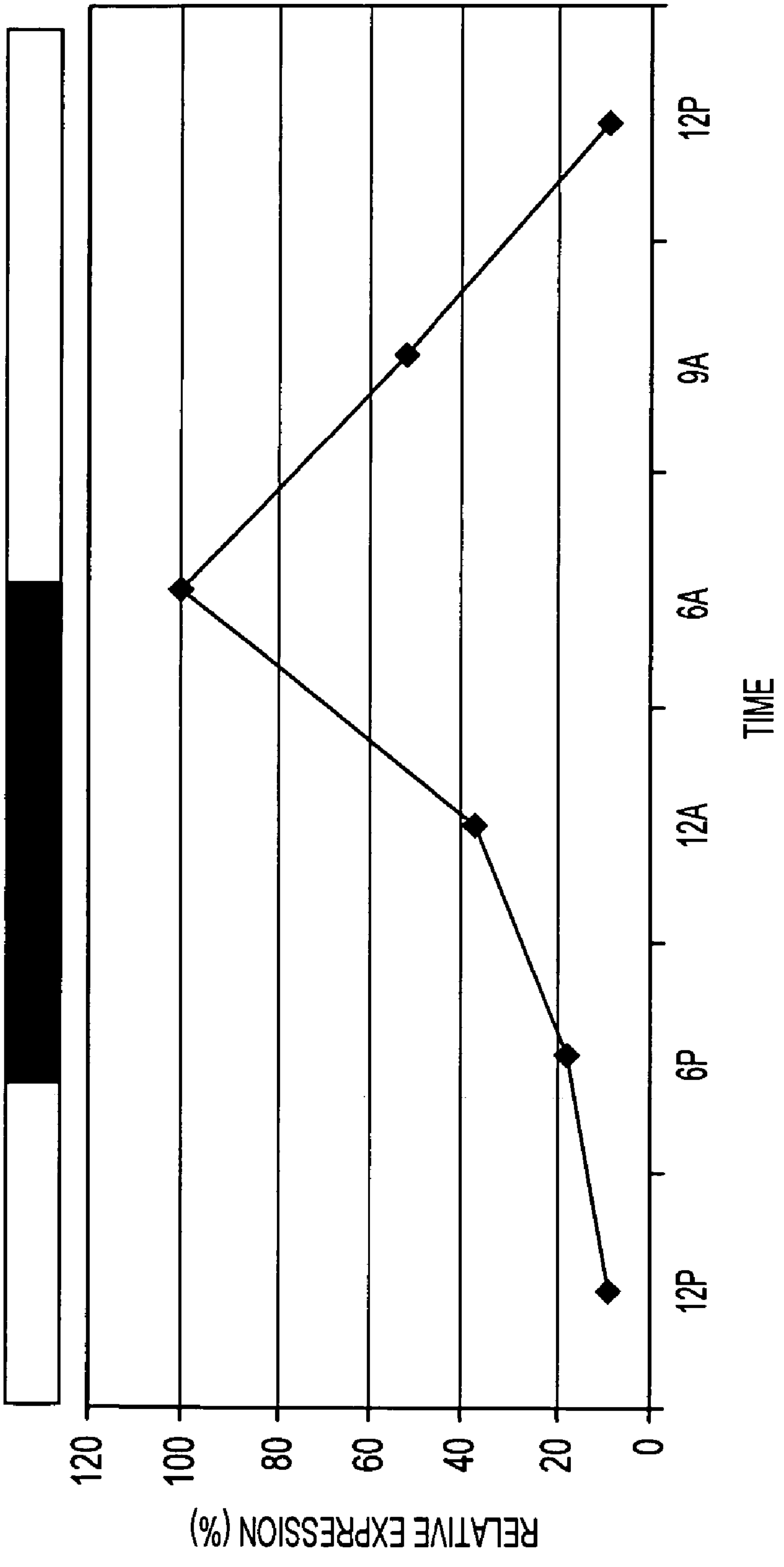
FIG. 7 is a graph showing a fluctuating (diurnal) pattern of expression of MT1-MMP mRNA in the normal rat retina, according to an embodiment of the invention. The highest level of MT1-MMP expression occurs at 6 AM, approximately 1-2 hours before the time of maximal shedding and phagocytosis of the photoreceptor (OS) in vivo.

Northern blot analysis of expression of MT1-MMP in various tissues demonstrated highest levels of expression in the RPE, choroid, and retina, followed by lung and adrenal. The putative designation of MT1-MMP as a phagogene was based on its differential expression detected by CHANGE during OS phagocytosis in vitro. For functional confirmation, the pattern of expression of this gene was examined by Northern blot analysis in an independent assay of OS phagocytosis. Referring to FIG. 6, the result confirmed the increase in MT1-MMP expression at 13 hours after the initiation of phagocytosis, the same time of increase detected by CHANGE. The involvement of MT1-MMP in diurnally controlled OS phagocytosis in vivo was strongly supported by the further finding that expression of MT1-MMP mRNA, in both RPE and retina, follows a diurnal pattern with a peak at 6 AM, approximately 1-2 hours prior to the time of maximal shedding and phagocytosis of OS in vivo (FIG. 7).

Figures 8A, 8B, 8C, 8D, 8E, 8F, 8G, 8H:
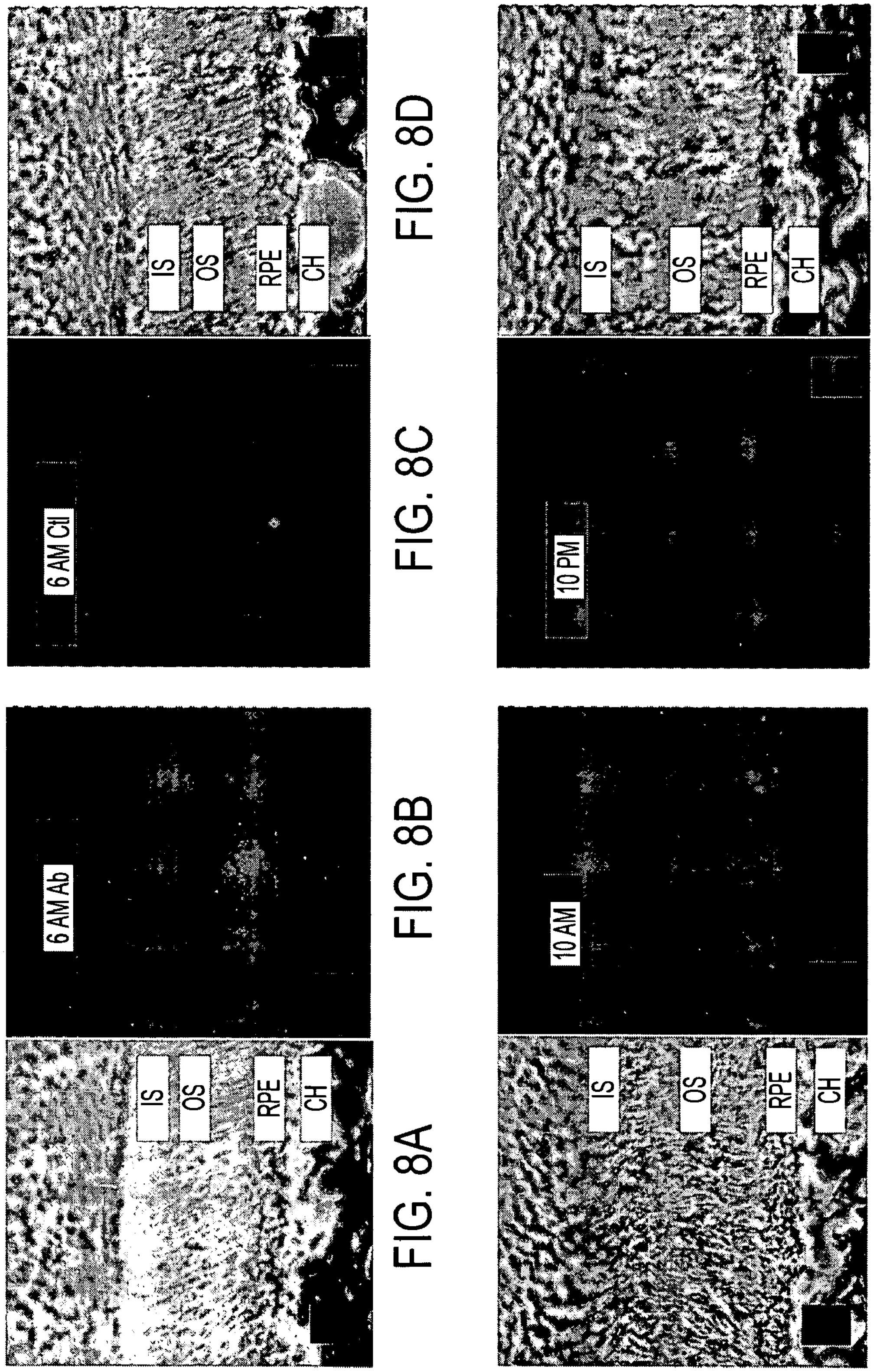
FIG. 8 is eight photomicrographs (phase contrast and fluorescence) showing immunofluorescent staining of normal rat retina fixed at various times of day and immunostained with an anti-MT1-MMP antibody, according to an embodiment of the invention. Diurnal variation is seen in the immunofluorescence level of MT1-MMP protein present in the OS and RPE, with the highest level of signal observed at 6 AM, less at 10 AM, and no signal at 10 PM, consistent with the diurnal pattern of MT1-MMP mRNA expression levels shown in FIG. 7.
Figure 9:
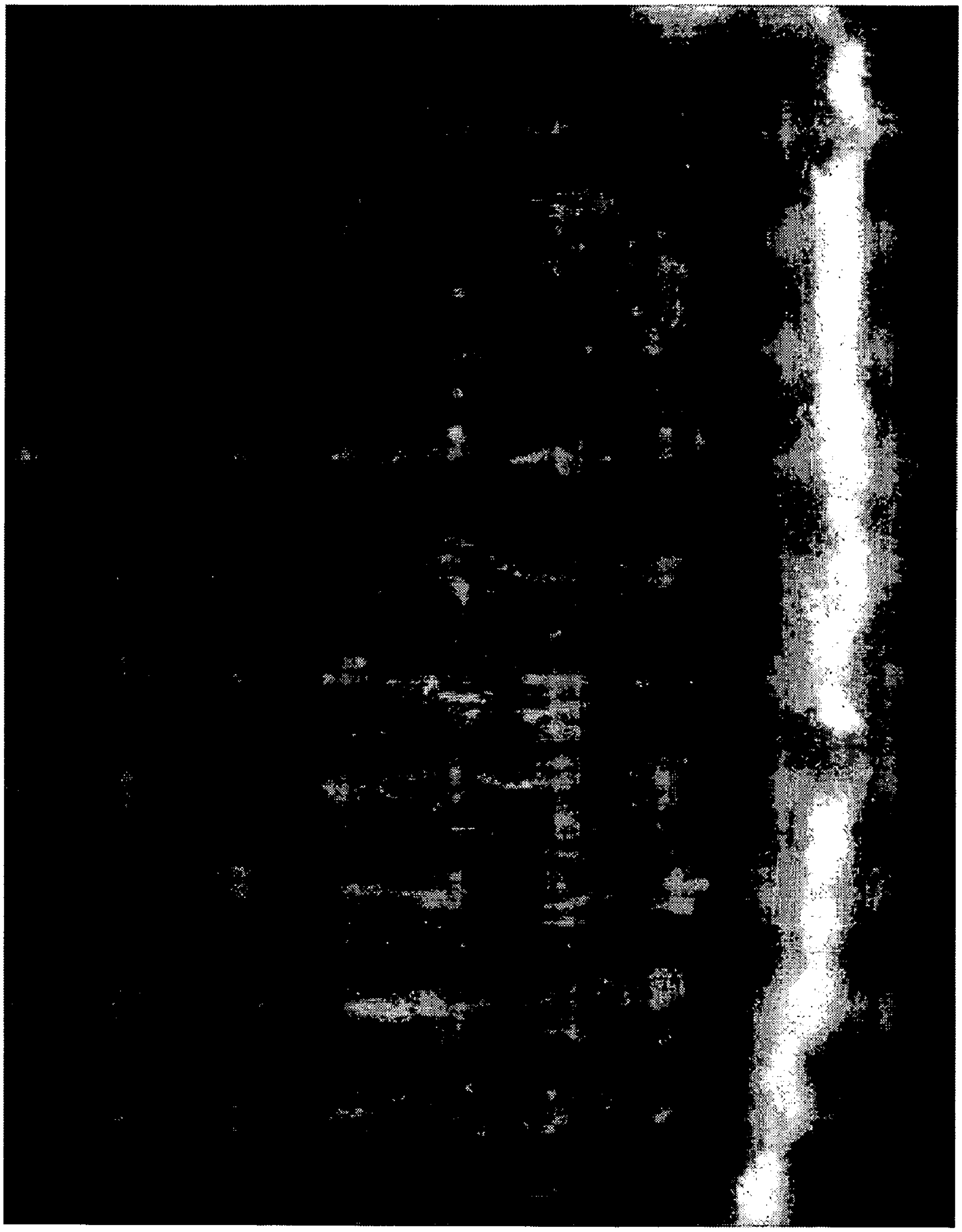
FIG. 9 is a fluorescence micrograph of a section of human retina stained with anti-MT1-MMP antibody, showing localization of the MT1-MMP protein in the OS of rod and cone photoreceptors and in phagosomes within the RPE cells, according to an embodiment of the invention.

Referring now to FIG. 8, immunofluorescent localization of MT1-MMP in the rat retina at several time points throughout the diurnal cycle demonstrated the strongest signal in the photoreceptor OS and RPE in retinas fixed at 6 AM. Immunolocalization of MT1-MMP protein in the human retina demonstrated signal in the tips of the rod, and especially cone, outer segments, consistent with activity at the interface between the photoreceptor OS membranes and the RPE apical processes, where it may be playing a role in preparing the OS tips for shedding and phagocytosis by the RPE (FIG. 9).

Figure 10C:
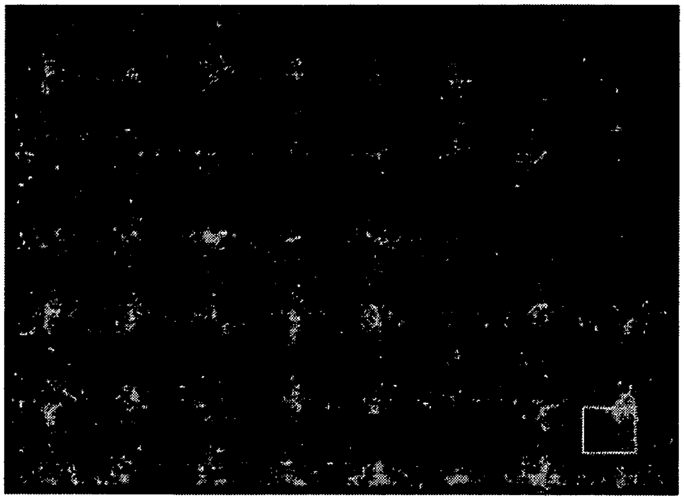
FIG. 10(A-C) is three fluorescence micrographs showing the effect of anti-MT1-MMP antibody on ROS phagocytosis by RPE cells in culture, according to an embodiment of the invention. Ingestion of the fed ROS (fluorescence) is evident in the cytoplasm in control cells not incubated with antibody (B) and in cells incubated with an unrelated (X-arrestin) antibody (C), whereas ROS binding and phagocytosis does not occur in cells incubated with anti-MT1-MMP antibody prior to feeding with ROS (A).
Figure 10B:
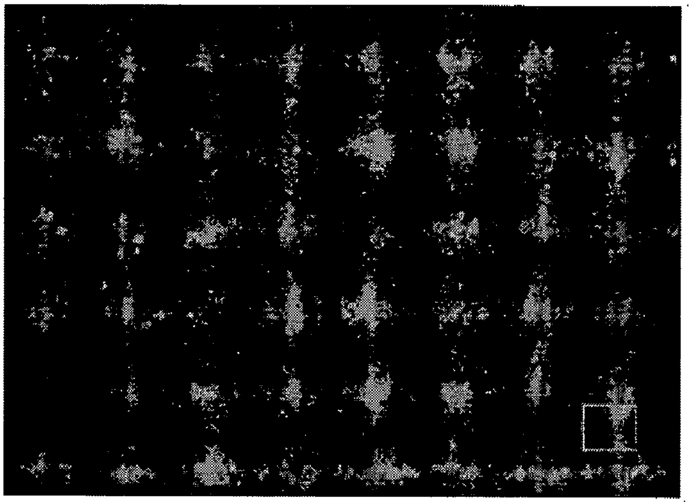
Figure 10A:
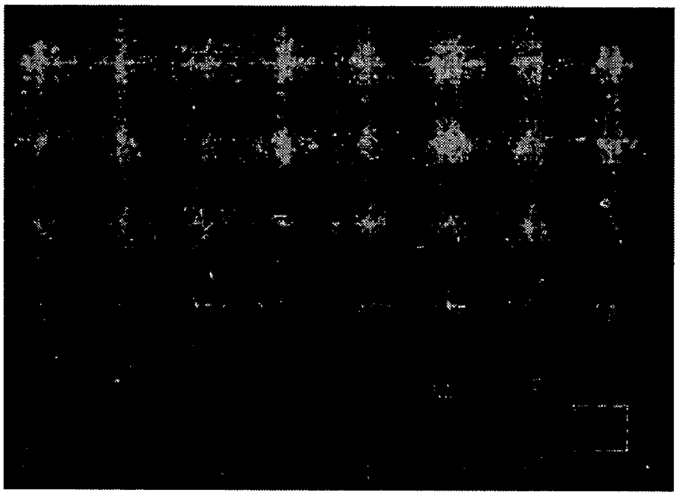
Figure 11A:
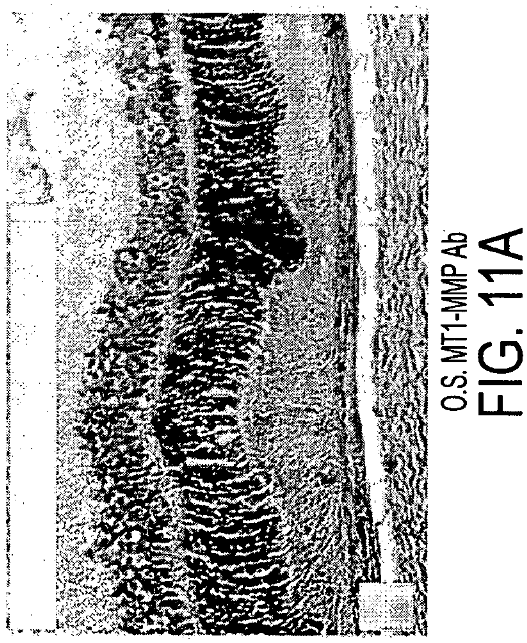
FIG. 11(A-D) is four micrographs of H&E stained paraffin sections of normal rat retina showing the effect of subretinal injection of anti-MT1-MMP antibody on the structure of the outer retina. Pronounced lengthening and abnormal orientation of the OS, consistent with inhibited OS phagocytosis, is observed in the anti-MT1-MMP antibody injected left eye, O.S. (A, B). In contrast, retinal architecture is normal in the uninjected right eye (O.D.) of the same animal (C). Subretinal injection of an unrelated (X-arrestin) antibody has no effect (D).
Figure 11B:
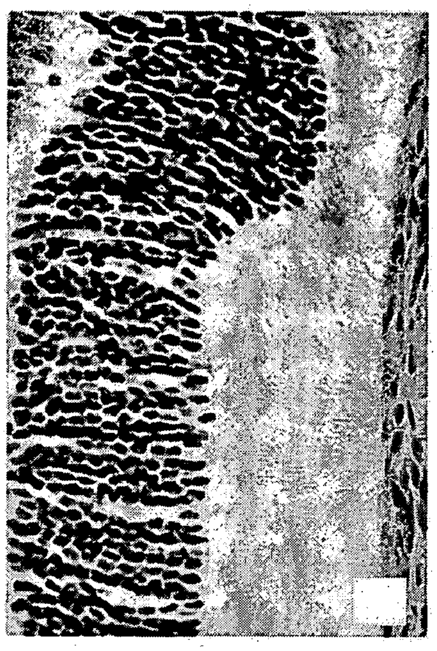
Figure 11C:
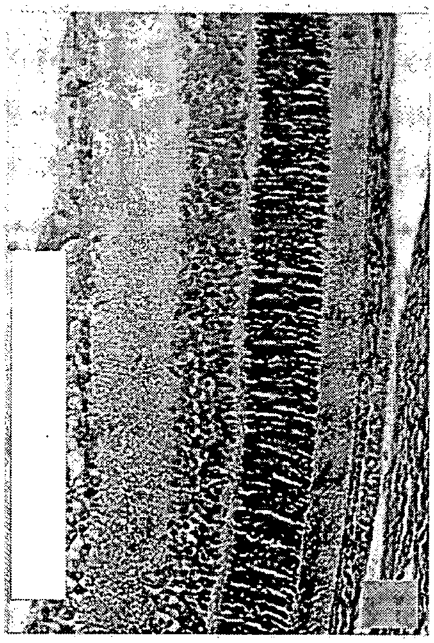
Figure 11D:
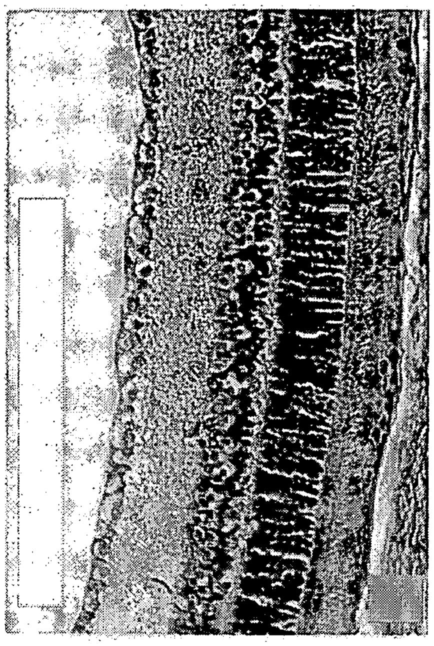

To obtain functional confirmation of the involvement of MT1-MMP in OS phagocytosis, an antibody against MT1-MMP (Chemicon International, Temecula, Calif.) was tested for its ability to inhibit OS phagocytosis by BPEI-1 cells in vitro. As seen in FIG. 10, the results clearly demonstrated inhibition of OS phagocytosis by this antibody, but not by an irrelevant (X-arrestin) antibody, confirming the functional requirement of MT1-MMP for the process of OS phagocytosis. Furthermore, in an in vivo functional assay, subretinal injection of the MT1-MMP antibody, but not X-arrestin antibody, into normal rat eyes resulted in marked structural disorganization and lengthening of the OS four days later, consistent with interference with the daily phagocytic process (FIGS. 11A, B). Thus, abundant evidence pointed to the involvement of MT1-MMP in OS phagocytosis by RPE cells.

Figures 12A, 12B, 12C, 12D:
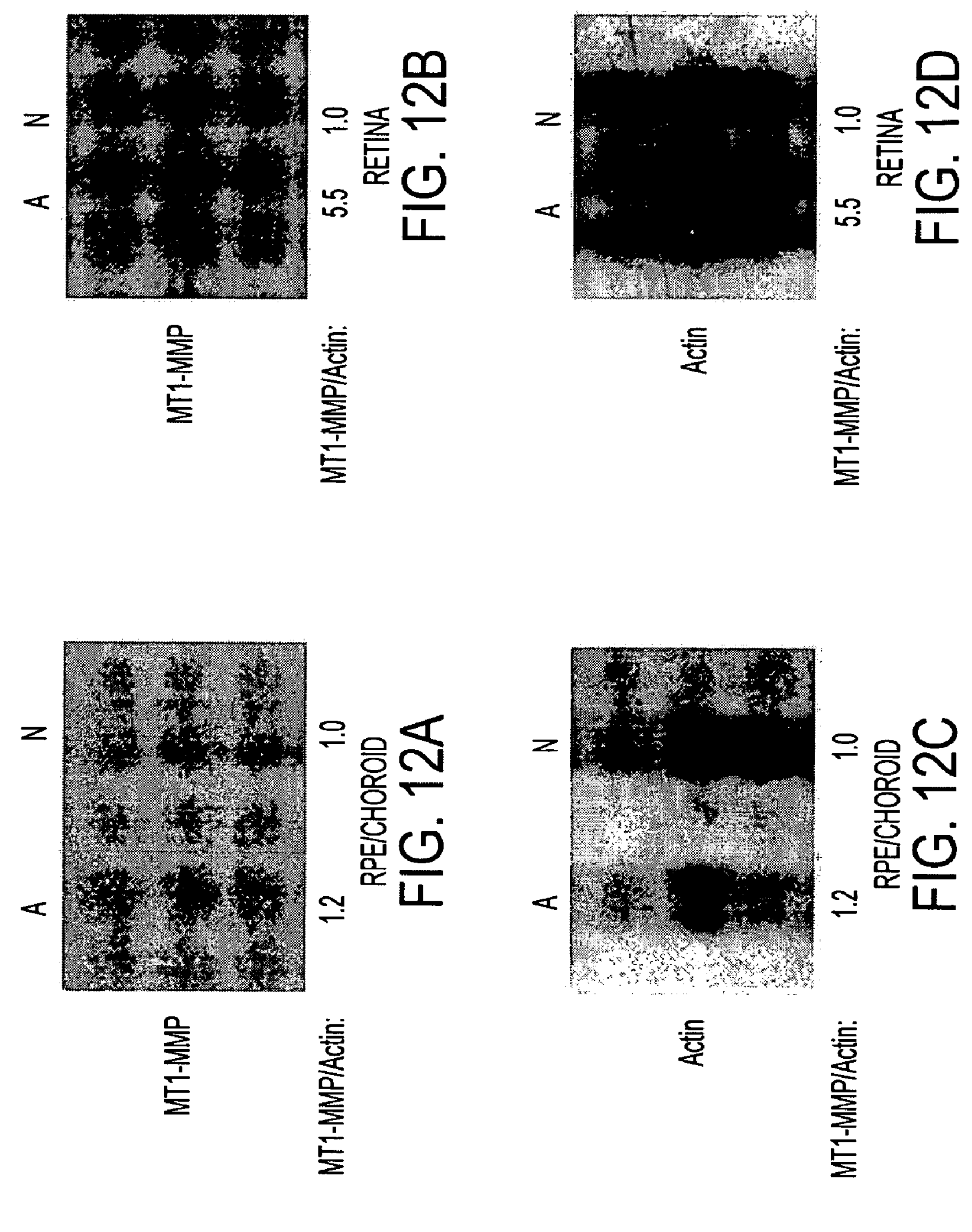
FIG. 12 shows Northern blot analysis of MT1-MMP mRNA expression levels in the RPE/choroid and retina of a subject affected with AMD (A) compared to a normal control subject (N). A 5.5-fold increase in the level of MT1-MMP mRNA is seen in the affected retina, with a 1.2-fold increase in the RPE/choroid of this subject. The Northern blot hybridization signals are normalized with respect to the amount of RNA present in each lane using actin hybridization as a reference.
Figure 13:
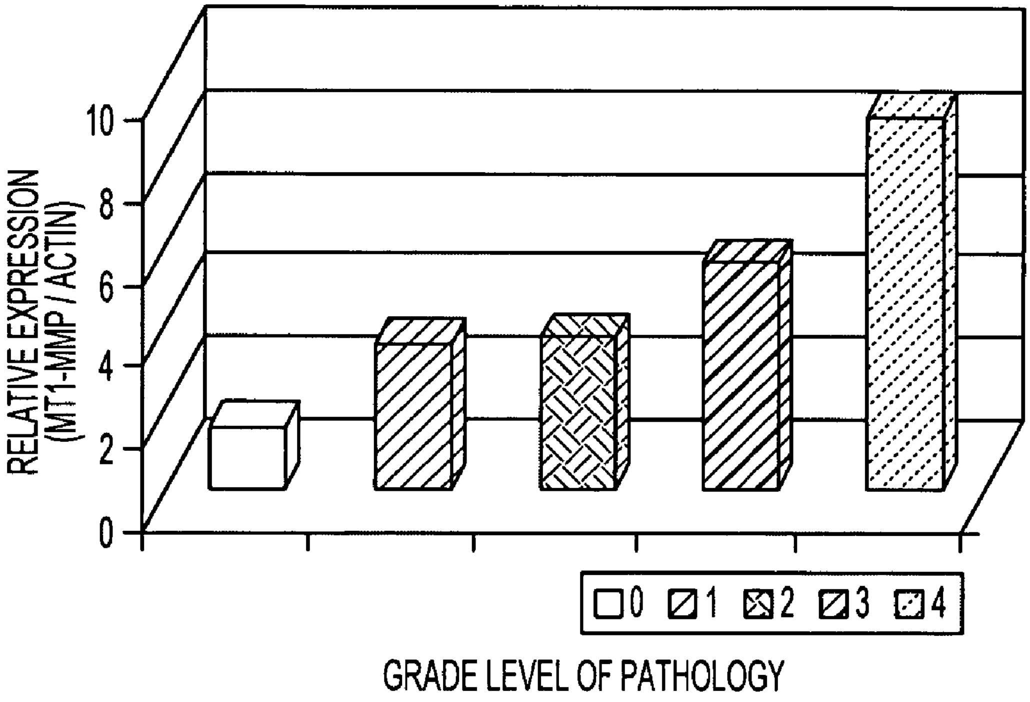
FIG. 13 is a graph showing a positive correlation of level of expression of MT1-MMP mRNA with increasing severity of AMD-related pathology (grade 0-+4 changes) in retinas of subjects affected with AMD.

MT1-MMP was also identified as a putative AMD gene by CHANGE on the basis of differential expression in AMD (i.e., an increase). The expression of this gene was examined independently by Northern blot analysis of RNAs from the RPE/choroid and retina of AMD-affected and normal human donor eyes. The result confirmed the increase and showed a greater increase in the retina than in the RPE (FIG. 12). As shown in FIG. 13, when a series of RNA samples from eyes with varying severity of AMD-related changes was tested, a positive correlation of increased expression of MT1-MMP in the retina was observed with increasing pathology in the eye (FIG. 13). This result strongly supported a possible role for this gene in the pathogenesis of AMD. Further, when tested in a monkey model of AMD that also showed increased expression of MT1-MMP by Northern analysis, MT1-MMP was found to be localized in the interphotoreceptor matrix (IPM) among highly disorganized OS.

Because MT1-MMP had been discovered to play a role in diurnally regulated OS phagocytosis, the inventors next tested whether the increased expression in AMD occurred at the time of maximal shedding and phagocytosis. The increase in MT1-MMP expression seen in the human eyes with AMD changes did not support this possibility, as the increase was present in eyes obtained at many different times of day after death. A plausible explanation for this result is that there may be dysregulation of MT1-MMP expression, which normally should peak only at approximately 6 AM, but in AMD may be highly active at other times as well. The functional consequence of dysregulation of MT1-MMP expression to the tightly controlled diurnal processes of OS shedding and phagocytosis could be profoundly deleterious over time.

Example 5

Genetic Screening of MT1-MMP in Subjects with AMD and Macular Degenerative Conditions This example describes methods for genetic analysis of MT1-MMP in AMD and macular degeneration patients and normal control populations, and results showing discovery of MT1-MMP polymorphisms correlated with macular degenerations including AMD.

Peripheral blood was collected from elderly patients affected with AMD and other macular diseases, and aged normal patients. DNA was extracted from the white blood cells. DNA was also extracted from the retina and RPE/choroid of donor eyes from a local eye bank. The degree of pathology in the donor eyes was recorded in fundus photographs and graded microscopically using the criteria described in Example 3. To enable screening for polymorphisms in MT1-MMP, all 10 exons of human MT1-MMP were determined from the published mouse gene structure (Apte et al. 1997), and amplified by PCR using human exon-specific amplimers (i.e, SEQ ID NOS:18-37) shown in Table 3 below.

TABLE 3

DNA Primers (Amplimers) for Amplifying Exons, Introns and Promoter Sequences of Human MT1-MMP.

| | | |
|---|---|---|
| **Exon 1:** | | |
| SEQ ID NO:18 | 9140ex1s | 5'-GCCTACCGAAGACAAAGGCG-3' |
| SEQ ID NO:19 | 9140ex1a | 5'-TAGAGGCTGTCCCCTAGGAG-3' |
| **Exon 2:** | | |
| SEQ ID NO:20 | 9140ex2s | 5'-AGAGGCACCCTATGGGCCAG-3' |
| SEQ ID NO:21 | 9140ex2a | 5'-CATCTCTGGCGCTGGCATTG-3' |
| **Exon 3:** | | |
| SEQ ID NO:22 | 9140ex3s | 5'-GCACTGATCCCAATCCTCGC-3' |
| SEQ ID NO:23 | 9140ex3a | 5'-CCCTGCATAAGCACAATGGG-3' |
| **Exon 4:** | | |
| SEQ ID NO:24 | 9140ex4s | 5'-GGGAAGGAGAATGTTGCCCC-3' |
| SEQ ID NO:25 | 9140ex4a | 5'-GAGGAGGGAACCACCCCTAC-3' |
| **Exon 5:** | | |
| SEQ ID NO:26: | 9140ex5s | 5'-GGGAGGCTGAGGGAAGGGAC-3' |
| SEQ ID NO:27 | 9140ex5a | 5'-GGGGAAATGCGTAGACCAGG-3' |
| **Exon 6:** | | |
| SEQ ID NO:28 | 9140ex6s | 5'-CCCGCCTCCTCCTAAGTCTG-3' |
| SEQ ID NO:29 | 9140ex6a | 5'-CAGCATGAGCCACCATGCCC-3' |
| **Exon 7:** | | |
| SEQ ID NO:30 | 9140ex7s | 5'-GAACCAGAGACCTAGGCCGC-3' |
| SEQ ID NO:31 | 9140ex7a | 5'-CAGCTCCTCTAGGGAGACCC-3' |
| **Exon 8:** | | |
| SEQ ID NO:32 | 9140ex8s | 5'-CTAGAGCCTAAGTTGAACCC-3' |
| SEQ ID NO:33 | 9140ex8a | 5'-GTGGTGGTGGTTTATGAGGG-3' |
| **Exon 9:** | | |
| SEQ ID NO:34 | 9140ex9s | 5'-TAGGACATGCCCATGTCCGC-3' |
| SEQ ID NO:35 | 9140ex9a | 5'-TCCGCTCTTCCTCAACTCCC-3' |
| **Exon 10:** | | |
| SEQ ID NO:36 | 9140ex10s | 5'-CTCTTTGGGTCTTCCCTTCC-3' |
| SEQ ID NO:37 | 9140ex10s | 5'-CTCTTTGGGTCTTCCCTTCC-3' |
| **Intron 1:** | | |
| SEQ ID NO:38 | 9140int1s | 5'CTCGGCTCGGCCCAAAGCAG 3' |
| SEQ ID NO:39 | 9140int1a | 5'GTAGGTCCCCGGGAGGCAGG 3' |

TABLE 3-continued

DNA Primers (Amplimers) for Amplifying Exons, Introns and Promoter Sequences of Human MT1-MMP.

| | | |
|---|---|---|
| **Intron 2:** | | |
| SEQ ID NO:40 | 9140int2s | 5'GTTTTACGGCTTGCAAGTAAC 3' |
| SEQ ID NO:41 | 9140int2a | 5'CCAAACTTGTCTGGAACACC 3' |
| **Intron 3:** | | |
| SEQ ID NO:42 | 9140int3s | 5'CCAGGGTCTCAAATGGCAAC 3' |
| SEQ ID NO:43 | 9140int3a | 5'ATGTGGCATACTCGCCCACC 3' |
| **Intron 4:** | | |
| SEQ ID NO:44 | 9140int4s | 5'CTCTGCCGAGCCTTGGACTG 3' |
| SEQ ID NO:45 | 9140int4a | 5'GCATGGCCCAGCTCGTGCAC 3' |
| **Intron 5:** | | |
| SEQ ID NO:46 | 9140int5s | 5'TGCCCGATGATGACCGCCGG 3' |
| SEQ ID NO:47 | 9140int5a | 5'GGGTTGAGGGGGCATCTTGG 3' |
| **Intron 6:** | | |
| SEQ ID NO:48 | 9140int6s | 5'CACCGTGGCCATGCTCCGAG 3' |
| SEQ ID NO:49 | 9140int6a | 5'CCATCACTTGGTTATTCCTC 3' |
| **Intron 7:** | | |
| SEQ ID NO:50 | 9140int7s | 5'CCTACGAGAGGAAGGATGGC 3' |
| SEQ ID NO:51 | 9140int7a | 5'GGTTCCAGGGACGCCTCATC 3' |
| **Intron 8:** | | |
| SEQ ID NO:52 | 9140int8s | 5'GGATGCCCAATGGAAAGACC 3' |
| SEQ ID NO:53 | 9140int8a | 5'CGCTATCCACTGCCCTGAGC 3' |
| **Intron 9:** | | |
| SEQ ID NO:54 | 9140int9s | 5'GGGATCCCTGAGTCTCCCAG 3' |
| SEQ ID NO:55 | 9140int9a | 5'TGTTGAATTTCCAGTATTTG 3' |
| **Promoter 1 (-1 to -480):** | | |
| SEQ ID NO:56 | 9140pro5s-1 | 5'-TATTAGTAAACTGGCCCTTC-3' |
| SEQ ID NO:57 | 9140pro3a | 5'-ATCTTTCTTCTGCTTAGTCG-3' |
| **Promoter 2 (-1 to -790):** | | |
| SEQ ID NO:58 | 9140pro5s-2 | 5'-TAGAGGTGGAACTAAACCCC-3' |
| SEQ ID NO:57 | 9140pro3a | 5'-ATCTTTCTTCTGCTTAGTCG-3' |

Figure 15A:
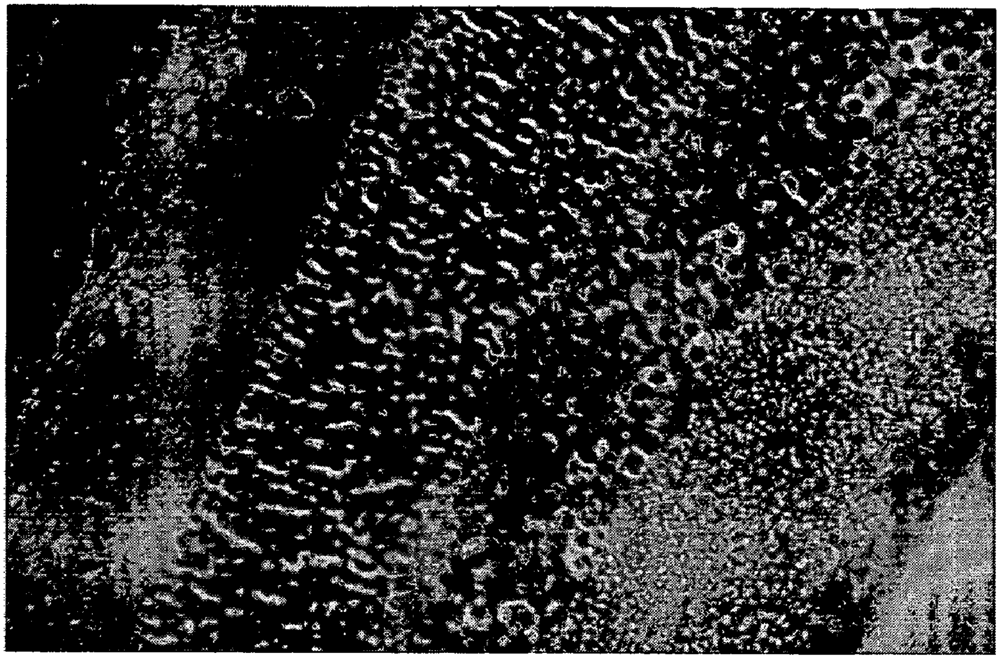
FIG. 15 is two micrographs showing a delay in inherited retinal degeneration in an RCS rat injected subretinally on postnatal day 7 with an anti-MT1-MMP antibody and fixed at 30 days of age. The delay in retinal degeneration is evidenced by the greater number of photoreceptor nuclei (approximately double) remaining in the outer nuclear layer of the retina of the injected eye (A), compared to a comparable mid-central region in the uninjected control eye of the same animal (B).
Figure 15B:
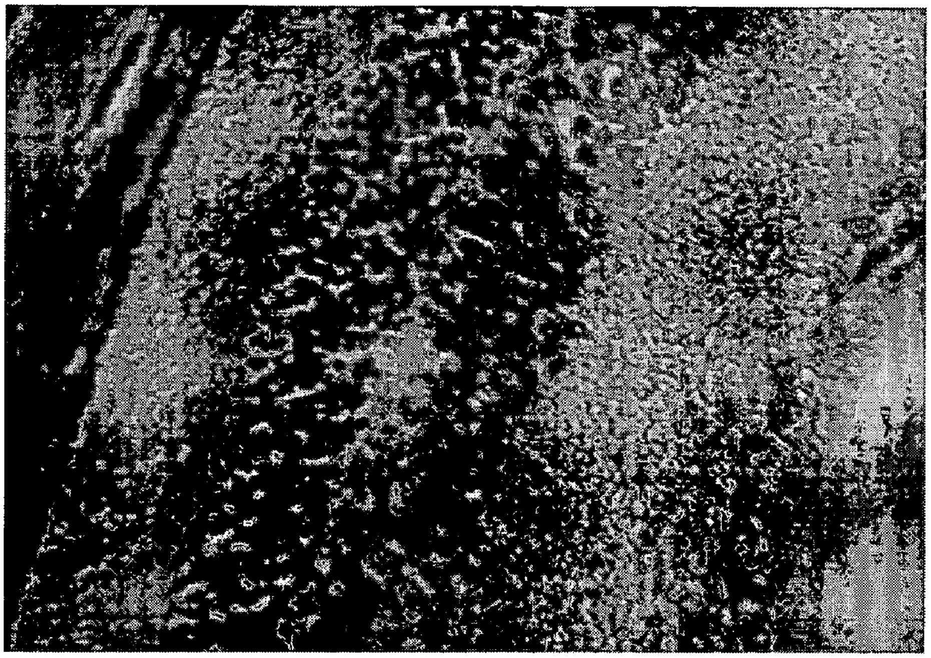

As an example, exon 5 of the human MT1-MMP gene was amplified by PCR using amplimers having the nucleic acid sequences shown herein as SEQ ID NOS:26 and 27, to obtain a 285 bp wild type PCR product having the DNA sequence (SEQ ID NO:59) shown in FIG. 15. A suitable PCR amplification protocol to obtain this product was the following: 3 minutes at 95° C., 30 cycles of 1 minute at 95° C., 30 seconds at 62° C., 30 seconds at 72° C., and 5 minutes at 72° C. The 285 bp PCR product was purified by gel electrophoresis and extraction, and subjected to DNA sequencing.

Using the amplimers shown in Table 3, the MT1-MMP gene was screened for mutations and polymorphisms in DNA from patients affected with AMD and familial macular diseases, and unaffected control subjects. Screening was performed using DNA obtained from three groups of macular degeneration subjects: 1) 56 clinically documented AMD patients seen in a local clinic; 2) 22 sporadic and familial macular degeneration patients seen in ophthalmic genetics clinics; and 3) eyes from 6 eye bank donors, the eyes showing a range of +2-+5 AMD-related changes. Clinical disease diagnoses in the familiar macular disease group of patients included familial macular dystrophy, vitelliform macular dystrophy, juxtafoveal telangiectasia, dominant drusen, crystalline drusen, annular macular dystrophy, and choroidal atrophy.

Results of screening the DNA from normal and macular degeneration-affected patients revealed a "hotspot" containing several polymorphic variants within exon 5 of MT1-MMP. A first variant was identified i.e., a synonymous polymorphism herein designated P259P, that differed between a C and G nucleotide (i.e., CCC Proline vs. CCG Proline) within codon 259 in the MT1-MMP cDNA sequence. The P259P variant base was at the $143^{rd}$ base position in the 285 bp exon 5 fragment shown in FIG. 14. Referring to FIG. 14, the position of codon 259 is indicated by underlining, and the position of the P259P polymorphic variant base is indicated in boldface. The wild type DNA sequence for the human MT1-MMP exon 5 product obtained by PCR using the above-indicated primer pair is listed herein as SEQ ID NO:59, and the exon 5 sequence containing the P259P variant is listed as SEQ ID NO:60.

Analysis of potential splice donor (GT) and splice acceptor (AG) sites in the human MT1-MMP gene sequence revealed that the P259P polymorphism could give rise to a splice variant of the mRNA for MT1-MMP. Normal splicing to remove introns from the wild type gene sequence results in a 582 amino acid full length MT1-MMP protein product (SEQ ID NO:100) including 53 amino acids encoded by exon 5 (shown herein as SEQ ID NO:121). By contrast, the P259P variant could create a new splice donor site in codon 259 that jumps to an alternate acceptor site.

Referring again to FIG. 14, a second variant was identified, herein designated D273N, which is a missense polymorphism in MT1-MMP codon 273 that differs between a G and A nucleotide (GAT Aspartic acid vs. AAT Asparagine). This polymorphism is located at the $183^{rd}$ base position within the 285 bp exon 5 fragment (codon 273 underlined, and variant base boldfaced in FIG. 14). The D273N missense variant changes the wild type, charged amino acid (i.e., aspartic acid) to an uncharged amino acid (i.e., asparagine). The nucleic acid sequence of the human MT1-MMP exon 5 product obtained by PCR in subjects having the D273N polymorphism is listed herein as SEQ ID NO:61, and the corresponding predicted variant protein product from exon 5 is listed as SEQ ID NO:123.

Referring now to Table 4, results of the MT1-MMP screening analysis for the P259P synonymous polymorphism showed a frequency of 27.4% of this variant in all patients with macular disease, as opposed to 10.5% frequency in the normal population.

TABLE 4

Frequency of Polymorphic Variants of MT1-MMP in Macular Diseases.

| Polymorphic variant | P259P Synonymous | D273N Missense | P259P or D273N |
|---|---|---|---|
| Normal subjects | 10.5% | 21.1% | 31.6% |
| All macular disease subjects | 27.4% | 31% | 58.3% |
| AMD | 25.8% | 29% | 54.8% |
| Familial maculopathies | 31.8% | 36.4% | 68.2% |
| Macular disease subjects Homozygous for variant | 0% | 4.8% | |

A higher frequency of the D273N missense polymorphism (i.e., 31%) was also found in all macular diseases, compared to unaffected individuals (21.1%). The total number of subjects having one of the two polymorphic variants of MT1-MMP, as opposed to the wild type base at the respective positions, was higher in the macular disease subjects (58.3%) than in the normal population (31%; p=0.043).

Separate analysis of AMD, as opposed to familial macular diseases, revealed increased frequencies of the polymorphic variants of MT1-MMP in both AMD and familial forms of macular degenerations (Table 4). In AMD subjects, the frequency of finding one of the two polymorphic variants of MT1-MMP was 54.8%, whereas this frequency was 31.6% in the general population. In subjects with familial maculopathies, this percentage was even higher (68.2%; p=0.029). These results strongly indicate that the presence of polymorphic variants of MT1-MMP are correlated with increased risk of developing a maculopathy, including AMD. Of note, 4.8% of the macular disease subjects, but none of the controls, were homozygous for the D273N missense polymorphism (Table 4).

Example 6

Delay of Retinal Degeneration by an Agent that Binds MT1-MMP Polypeptide

This example describes studies demonstrating slowing of the rate of an inherited retinal degeneration in an animal (rat) model, using an agent that neutralizes MT1-MMP protein.

As described in Example 4 above, MT1-MMP was found to be overexpressed in human eyes with AMD, in a monkey model of AMD, and in the RCS rat, an animal model of an RPE-based inherited retinal degeneration. The mutant phenotype in the RCS rat, due to a mutation in the MERTK gene, is characterized by a defect in the ingestion phase of phagocytosis by the RPE cells. In separate studies, MT1-MMP was again isolated in a CHANGE analysis wherein +/− probes were prepared from retinal RNA of mutant and age-matched control RCS rats. Northern blot analysis of MT1-MMP expression in the RCS rat retina revealed that expression of MT1-MMP mRNA increased as the retinal degeneration progressed in this model. This result suggests that MT1-MMP may play a common role in the pathogenesis of multiple forms of retinal degeneration, particularly those based on a defect thought to affect primarily the RPE cells.

To test the functional involvement of MT1-MMP in the pathogenesis of the retinal degeneration in the RCS rat, a 2 μl volume, (as supplied by the manufacturer), of an antibody against MT1-MMP (Chemicon, Temecula, Calif.), was injected subretinally into the eyes of immature (7 day) RCS rats. The course of the retinal degeneration was followed for the subsequent two months. Referring to FIG. 15, the results showed a remarkable delay of up to a 50% in the retinal degeneration, as determined by the thickness of the outer nuclear layer, observed at 1 month post-injection. Sham injection, or injection of an unrelated (i.e., X-arrestin) antibody did not produce this effect. This result further reinforces the involvement of MT1-MMP in the pathogenesis of retinal degenerations, making it an attractive therapeutic target for retinal degenerative conditions involving overexpression of MT1-MMP.

Example 7

Animal Models of AMD that Overexpress Genes Upregulated in AMD

Studies of the pathogenesis of AMD are impeded by a lack of appropriate and practical animal models useful, for example, for testing candidate therapeutic compounds and approaches. This example describes the construction of animal models of AMD in mice that over-express genes demonstrated herein to be upregulated in AMD. In preferred embodiments, the over-expressed genes are prostaglandin D2 synthase (PD2S), MT1-MMP, and AMDP-3, comprising respective cDNA sequences identified herein as SEQ ID NOs:2, 15, and 17. In some embodiments, the genes are conditionally over-expressed, and in some versions, only in photoreceptors, RPE cells, and/or choroidal cells of the animals.

As described in examples above, overexpression or overactivity of MT1-MMP is observed in human and monkey eyes with AMD and in RCS rats with an RPE-based inherited retinal degeneration. To model the overexpression phenotype in a small laboratory rodent such as a mouse, transgenic mice overexpressing, for example, MT1-MMP are constructed. A particularly preferred embodiment is a transgenic mouse model featuring conditional overexpression of MT1-MMP in the fully-developed, and aged retinas of these animals, which advantageously avoids deleterious effects that could result from overexpression of MT1-MMP during the embryonic or early postnatal stages of development.

For constructing an animal model that conditionally overexpresses MT1-MMP, a conditional expression system can be used, such as the Tet Gene Expression System (BD Biosciences, Palo Alto, Calif.). Over-expression of a transgene 1000-fold or more within hours of activation with doxycycline has been reported using this system (Gossen et al., 1995). Conditional expression systems are advantageous for temporal control of gene expression, such as the overexpression of MT1-MMP, to cause the expression of the MT1-MMP transgene to begin at a selected time in the life of the animal, for example only in adults with a fully developed retina.

Transgenic mice are constructed using techniques well known to those of skill in the art, that over-express, for example, a human or a mouse MT1-MMP. Any suitable overexpression system can be used. In embodiments using the Tet system, a transgenic mouse is constructed that expresses a chimeric tetracycline-regulated transactivator rtTA (Tet-On) from a suitable promoter and a second transgene containing, for example, a human or mouse MT1-MMP cDNA connected to a Tet Response Element-silent promoter which responds to the transactivator. Administration of doxycycline to a double transgenic mouse thus constructed results in overexpression of the transgene, for example, MT1-MMP, through activation of the transactivator by doxycycline, and subsequent binding and activation of the silent promoter.

In some embodiments of transgenic mice overexpressing genes of interest such as PD2S, MT1-MMP and AMDP-3, expression of the transgene is limited to selected cell or tissue types. As is well known in the art of molecular biology, the cellular site of transgene expression can be controlled by selection of tissue- or cell-specific promoters. Accordingly, in one preferred embodiment, a transgenic model overexpresses a MT1-MMP transgene in a photoreceptor-specific manner. An exemplary promoter for this purpose is a bovine rhodopsin promoter (Zack et al., 1991), shown, for example, to be suitable for photoreceptor-specific expression of HRG4 (UNC119), in a transgenic mouse model (Kobayashi et al., 2000). Other embodiments of the transgenic mice selectively overexpress transgenes, such as MT1-MMP, PD2S or AMDP-3, in RPE cells. RPE cell-specific expression is directed, for example, by an RPE-specific promoter such as one derived from promoter regions of the genes encoding RPE65 (Boulanger et al., 2000) or cellular retinaldehyde binding protein (Kennedy et al., 1998). Yet other embodiments are engineered to selectively express the transgenes in cell types of the choroid, for example in endothelial cells using an endothelial cell specific promoter (Cho et al., 2003), or in melanocytes and RPE cells using a promoter that drives expression of tyrosinase in pigmented cell types (Giraldo et al., 2003).

Transgenic mice are constructed by oocyte injection of a transgene-containing vector using techniques well known to those of skill in the art of molecular biology. (See, for example, Kobayashi et al., 2000). The overexpression of the selected transgene is confirmed in the appropriate tissues or cells of the transgenic animals (for example in the retina, or specifically in photoreceptors or RPE cells, or in one or more choroidal cell types) using techniques well known in the art and demonstrated in examples above, such as by Northern analysis or RT-PCR using appropriate probes or primers specific for the transgene, by Western blot analysis of proteins with an appropriate antibody, and by various immunolocalization techniques.

Pathology developing in the transgenic animals, for example in the retinas and/or RPE/choroid of these animals, is assessed by numerous known techniques, including, for example, examination of the retina by funduscopy, electroretinographic (ERG) testing, and light and electron microscopy at selected intervals throughout the lifetime of the animals, before and after activation of the transgene by administration of doxycycline, for example at 5, 10, 15, 20, 25 and 30 days of age, (with administration of doxycline at age 30 days), and at 1, 2, 5, 10, 20, 30, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680 and 700 days after activation with doxycycline. AMD-related pathology, such as lipofuscin accumulation, Bruch's membrane thickening, basal laminar and linear deposits, drusen formation, neovascularization, CNV membrane formation, photoreceptor/RPE atrophy or choroidal atrophy is monitored by standard techniques well known in the art.

Example 8

Animal Models of AMD that Express Polymorphic Variants of Phagocytosis-Related and/or AMD-Related Genes This example describes the construction of mouse models of AMD and other retinal degenerations that express one or more polymorphic variants of a phagocytosis-related or AMD-related gene.

As shown above, certain polymorphic variants of genes, including MT1-MMP, are found at higher frequency in the DNA of patients with AMD. To model the human conditions, transgenic mouse models expressing polymorphic and wild-type human genes, for example MT1-MMP, are constructed as follows. First, the baseline status of the mouse MT1-MMP gene is preferably determined. For example, it has been determined that the wild-type amino acid residue located at the position of the D273N polymorphism in the human MT1-MMP DNA sequence is conserved in the human and mouse. A polymorphism at this residue has not been demonstrated in the mouse (Mouse Genome Project). Presence of the wild type residue is confirmed in the mice used for transgenic construction, by tail biopsy, DNA isolation, and genotyping.

To construct polymorphic and control (wild type) transgenic mouse models, expressing respectively, polymorphic and wild type variants of a human gene of interest, such as MT1-MMP, cDNAs containing human polymorphic variants and wild-type MT1-MMP residues are connected to a promoter sequence suitable for driving expression of the transgene in a desired tissue or cell. For expression of the transgene throughout the body, an exemplary promoter sequence is, for example, a 385 bp human MT1-MMP promoter sequence, prepared by PCR amplification from human genomic DNA and previously determined to drive robust expression of the gene (Lohi et al., 2000). To aid identification of the transgene, in some embodiments the MT1-MMP gene is expressed as a green fluorescent protein (GFP) fusion protein, using a suitable vector construct, such as a BioSignal vector (InVitrogen, Carlsbad, Calif.). Other embodiments selectively express the transgene in particular tissues or cell types, driven by tissue- or cell type-specific promoters as described above.

Transgenic mice are constructed by oocyte injection of the vector using known techniques. Expression of the human polymorphic and wild type variants, for example of MT1-MMP, is confirmed in the transgenics, such as by RT-PCR with allele-specific primers and, in versions expressing GFP fusion proteins, by analysis of GFP expression, for example by fluorescence microscopy, Western blotting analysis, or immunodetection. The transgenics are analyzed for the presence of AMD-related pathologies as described in Example 7 above.

Other embodiments of the animal models of AMD and other retinal degenerations are polytransgenic mice expressing polymorphic variants of at least two genes having a known association with AMD. In preferred embodiments, the animals express a polymorphic variant of MT1-MMP in combination with at least one other polymorphic gene variant showing a correlation with phagocytosis and/or AMD.

The polytransgenic versions of the animal models are based on the complex, multi-gene theory of AMD, which assumes that subtle mutations in a number of genes, commonly referred to as "polymorphisms," cooperate to cause, or create a susceptibility to, a disease. Accordingly, the full phenotype of AMD is likely to require the cooperation of at least two, and perhaps many, etiologic genes with the appropriate combination of polymorphisms. The causative genes may tip the scale toward development of AMD by contributing either "collectively" (for example, if related by a common function, such as involvement in the pathway of OS phagocytosis), or "cumulatively," for example, if unrelated by function, but each involved in a separate aspect of the pathogenic process leading to AMD.

A preferred embodiment of a polytransgenic model of AMD is a polytransgenic animal that co-expresses a first polymorphic variant of MT1-MMP and at least a second polymorphic variant of at least one other phagocytosis-related and/or AMD-related gene. Any other second or more gene showing a polymorphic variant correlated with AMD can be combined with any polymorphic variant of MT1-MMP. Genes presently reported to have variants correlated with AMD are listed in Table 5.

TABLE 5

Genes with Reported Polymorphisms or Mutations Correlated with AMD

| GENE | NUCLEIC ACID SEQ ID NO: | AMINO ACID SEQ ID NO: | REFERENCE |
|---|---|---|---|
| ABCR | 62 | 124 | Allikmets et al., 1997 |
| Apolipoprotein E | 63 | 125 | Klaver et al. 1998; Simonelli et al. 2001 |
| C—C chemokine receptor-2 | 64 | 126 | Ambati et al. 2003 |
| Cystatin C | 65 | 127 | Zurdel et al. 2002 |
| Hemicentin/FIBL-6 | 66 | 128 | Schultz et al. 2003 |
| Manganese superoxide dismutase | 67 | 129 | Kimura et al. 2000 |
| C—C chemokine ligand/monocyte chemoattractant protein 1 | 68 | 130 | Ambati et al. 2003 |
| Paraoxonase | 69 | 131 | Ikeda et al. 2001 |

Accordingly, in one form of the preferred embodiments, a polymorphic form of MT1-MMP is combined with a polymorphic form of at least one other gene, including ABCR, apolipoprotein E, C—C chemokine receptor-2, cystatin C, hemicentin/FIBL-6, manganese superoxide dismutase, C—C chemokine ligand/monocyte chemoattractant protein 1, and paraoxonase.

Similarly, a polytransgenic model reflecting the "collective" etiology theory of AMD combines polymorphic variants of genes with known involvement in the mechanism of an important function (for example OS phagocytosis) with polymorphic variants of MT1-MMP (a demonstrated phagocytosis-related gene as disclosed herein; wild type cDNA sequence: SEQ ID NO:15; wild type amino acid sequence: SEQ ID NO:100). Such genes include, for example, polymorphic variants of phagocytosis-related genes PHG-1 to PHG-15 (SEQ ID NOS:1-14) and AMDP-2 and 3 (SEQ ID NOS:16 and 17), disclosed herein (see Tables 1 and 2, supra).

For construction of the models, DNA containing the reported polymorphic variant(s) of a selected gene is first isolated using appropriate amplimers from DNA of patients with AMD and unaffected, age-matched individuals (for example, as described for MT1-MMP in Example 5 above), and is used to confirm the presence of the reported polymorphisms, for example, in ABCR (i.e., D2177N, G1961E); manganese superoxide dismutase (i.e., V47A); apolipoprotein E (i.e., epsilon2); cystatin C (i.e., A and B allele, including the Ala to Thr change); and paraoxonase (i.e., Q192R, L54M). Genotyping and mutational analyses are carried out using established methods (see for example, Mashima et al., 1994). The association of the polymorphism with AMD is confirmed and the statistical significance of any detected correlations with AMD is determined, for example by a chi-square test. For those polymorphic genes showing an association with AMD, their co-occurrence with a polymorphism in MT1-MMP is then confirmed.

Trangenic mice expressing a polymorphic variant of a selected gene, for example AMDP-3, are first constructed as generally described above. To construct polytransgenic models, transgenic mice expressing a polymorphic variant of the first gene of interest, for example, MT1-MMP, are crossed with transgenic mice expressing a polymorphic variant of a second phagocytosis/AMD-related gene of interest, such as AMDP-3. Expression of the various transgenes is confirmed in tissues of interest, for example the retina, RPE or choroid, by standard techniques known in the art, such as allele-specific RT-PCR of RNA and/or immunodetection of the polymorphic transgene protein of interest, for example by using antibodies specific for a particular polymorphic form of the protein. Alternatively, in embodiments in which a specific tag protein sequence is attached to the transgene protein, identification of the tag sequence is used to facilitate identification of the transgenic polymorphic variant protein and to distinguish it from the wild-type form. The polytransgenic mouse is analyzed for evidence of AMD-related changes as described above.

LITERATURE CITED

References cited herein are listed below for convenience and are hereby incorporated by reference in their entirety.

Abdelsalam, A., Del Priore, L. & Zarbin, M. A. Drusen in age-related macular degeneration: pathogenesis, natural course, and laser photocoagulation-induced regression. *Surv. Ophthalmol.* 1999; 44:1-29.

Algvere P V, Seregard S. Age-related maculopathy: pathogenetic features and new treatment modalities. Acta Ophthalmol Scand. April 2002; 80(2):136-43.

Allikmets R, Shroyer N F, Singh N, Seddon J M, Lewis R A, Bernstein P S, Peiffer A, abriskie N A, Li Y, Hutchinson A, Dean M, Lupski J R, Leppert M. Mutation of the Stargardt disease gene (ABCR) in age-related macular degeneration. Science. Sep. 19, 1997; 277(5333):1805-7.

Ambati J, Anand A, Fernandez S, Sakurai E, Lynn B C, Kuziel W A, Rollins B J and Ambati B K. An animal model of age-related macular degeneration in senescent Ccl-2 or Ccr-2 deficient mice. Nature Med. Oct. 19, 2003 [Epub ahead of print].

Apte S S, Fukai N, Beier D R, Olsen B R. The matrix metalloproteinase-14 (MMP-14) gene is structurally distinct from other MMP genes and is co-expressed with the TIMP-2 gene during mouse embryogenesis. J Biol Chem. Oct. 10, 1997; 272(41):25511-7.

Berglin L, Sarman S, van der Ploeg I, Steen B, Ming Y, Itohara S, Seregard S, Kvanta A. Reduced choroidal neovascular membrane formation in matrix metalloproteinase-2-deficient mice. Invest Ophthalmol Vis Sci. January 2003; 44(1):403-8.

Boulanger A, Liu S, Henningsgaard A A, Yu S, Redmond T M. The upstream region of the Rpe65 gene confers retinal pigment epithelium-specific expression in vivo and in vitro and contains critical octamer and E-box binding sites. J Biol Chem. Oct. 6, 2000; 275(40):31274-82.

Bok, D and Hall M O. The role of the pigment epithelium in the etiology of inherited retinal dystrophy in the rat. J Cell Biol. June 1971; 49(3):664-82.

Boyle D, Tien L F, Cooper N G, Shepherd V, McLaughlin B J. A mannose receptor is involved in retinal phagocytosis. Invest Ophthalmol Vis Sci. April 1991; 32(5):1464-70.

Bressler N M, Bressler S B, Fine S L. Age-related macular degeneration. Surv Ophthalmol May-June 1988; 32(6): 375-413

Bressler N M; Treatment of Age-Related Macular Degeneration with Photodynamic Therapy (TAP) Study Group. Photodynamic therapy of subfoveal choroidal neovascularization in age-related macular degeneration with verteporfin: two-year results of 2 randomized clinical trials-tap report 2. Arch Ophthalmol. February 2001; 119(2):198-207.

Cao J, Sato H, Takino T, Seiki M. The C-terminal region of membrane type matrix metalloproteinase is a functional transmembrane domain required for pro-gelatinase A activation. J Biol Chem. Jan. 13, 1995; 270(2):801-5.

Cho J, Lim W, Jang S, Lee Y. Development of an efficient endothelial cell specific vector using promoter and 5' untranslated sequences from the human preproendothelin-1 gene. Exp Mol Med. Aug. 31, 2003; 35(4):269-74.

Crabb J W, Miyagi M, Gu X, Shadrach K, West K A, Sakaguchi H, Kamei M, Hasan A, Yan L, Rayborn M E, Salomon R G, Hollyfield J G. Drusen proteome analysis: an approach to the etiology of age-related macular degeneration. Proc Natl Acad Sci USA. Nov. 12, 2002; 99(23): 14682-7.

D'Cruz P M, Yasumura D, Weir J, Matthes M T, Abderrahim H, LaVail M M, Vollrath D. Mutation of the receptor tyrosine kinase gene Mertk in the retinal dystrophic RCS rat. Hum Mol Genet. Mar. 1, 2000; 9(4):645-51.

De S, Sakmar T P. Interaction of A2E with model membranes. Implications to the pathogenesis of age-related macular degeneration. J Gen Physiol. August 2002; 120 (2):147-57.

Ding H, Schwarz D S, Keene A, Affar el B, Fenton L, Xia X, Shi Y, Zamore P D, Xu Z. Selective silencing by RNAi of a dominant allele that causes amyotrophic lateral sclerosis. Cell. August 2003; 2(4):209-17.

Elbashir S M, Lendeckel W, Tuschl T. RNA interference is mediated by 21- and 22-nucleotide RNAs. Genes Dev. Jan. 15, 2001; 15(2):188-200.

Evans, J. R. Risk factors for age-related macular degeneration. Prog. Retin. Eye. Res. 20, 227-253, 2001.

Fine S L, Berger J W, Maguire M G, Ho A C. Age-related macular degeneration. N Engl J Med. Feb. 17, 2000; 342(7):483-92.

Flood V, Smith W, Wang J J, Manzi F, Webb K, Mitchell P. Dietary antioxidant intake and incidence of early age-related maculopathy: the Blue Mountains Eye Study. Ophthalmology. December 2002; 109(12):2272-8.

Gass J D, Jallow S, Davis B. Adult vitelliform macular detachment occurring in patients with basal laminar drusen. Am J Ophthalmol. Apr. 15, 1985; 99(4):445-59.

Gossen M, Freundlieb S, Bender G, Muller G, Hillen W, Bujard H. Transcriptional activation by tetracyclines in mammalian cells. Science. Jun. 23, 1995; 268(5218): 1766-9.

Giraldo P, Regales L, Lavado A, Tovar V, Garcia-Diaz A, Jimenez E, Montoliu L. IL-22 The mouse tyrosinase gene: structural and functional studies in transgenic mice. Pigment Cell Res. October 2003; 16(5):582.

Gottlieb J L. Age-related macular degeneration. JAMA Nov. 13, 2002; 288(18):2233-6

Green W R. Histopathology of age-related macular degeneration. Mol Vis. Nov. 3, 1999; 5:27.

Grishok A, Tabara H, Mello CC. Genetic requirements for inheritance of RNAi in *C. elegans*. Science. Mar. 31, 2000; 287(5462):2494-7.

Guymer R. The genetics of age-related macular degeneration. Clin Exp Optom. July 2001; 84(4):182-189.

Hageman G S, Mullins R F, Russell S R, Johnson L V, Anderson D H. Vitronectin is a constituent of ocular drusen and the vitronectin gene is expressed in human retinal pigmented epithelial cells. FASEB J. March 1999; 13(3):477-84.

Hageman, G. S., Luthert, P. J. , Chong, N. H. V., Johnson, L. V., Anderson, D. H. & Mullins, R. F. An integrated hypothesis that considers drusen as biomarkers of immune-mediated processes at the RPE-Bruch's membrane interface in aging and age-related macular degeneration. *Prog. Retinal Eye Res.* 2001; 20:705-732.

Heiba I M, Elston R C, Klein B E, Klein R. Sibling correlations and segregation analysis of age-related maculopathy: the Beaver Dam Eye Study. Genet Epidemiol. 1994; 11(1):51-67.

Hogan M J. Role of the retinal pigment epithelium in macular disease. Trans Am Acad Ophthalmol Otolaryngol. January-February 1972; 76(1):64-80.

Husain D, Ambati B, Adamis A P, Miller J W. Mechanisms of age-related macular degeneration. Ophthalmol Clin North Am. March 2002; 15(1):87-91.

Hutchinson A, Dean M, Lupski J R, Leppert M. Mutation of the Stargardt disease gene (ABCR) in age-related macular degeneration. Science. Sep. 19, 1997; 277(5333):1805-7.

Hyman L, Neborsky R. Risk factors for age-related macular degeneration: an update. Curr Opin Ophthalmol. June 2002; 13(3):171-5.

Ikeda T, Obayashi H, Hasegawa G, Nakamura N, Yoshikawa T, Imamura Y, Koizumi K, Kinoshita S. Paraoxonase gene polymorphisms and plasma oxidized low-density lipoprotein level as possible risk factors for exudative age-related macular degeneration. Am J Ophthalmol. August 2001; 132(2):191-5.

Katz M L. Incomplete proteolysis may contribute to lipofuscin accumulation in the retinal pigment epithelium. Adv Exp Med Biol. 1989; 266:109-16.

Kennedy C J, Rakoczy P E, Constable I J. Lipofuscin of the retinal pigment epithelium: a review. Eye. 1995; 9 (Pt 6):763-71.

Kennedy B N, Goldflam S, Chang M A, Campochiaro P, Davis A A, Zack D J, Crabb J W. Transcriptional regulation of cellular retinaldehyde-binding protein in the retinal pigment epithelium. A role for the photoreceptor consensus element. J Biol Chem. Mar. 6, 1998; 273(10):5591-8.

Kimura K, Isashiki Y, Sonoda S, Kakiuchi-Matsumoto T, Ohba N. Genetic association of manganese superoxide dismutase with exudative age-related macular degeneration. Am J Ophthalmol. December 2000; 130(6):769-73.

Klaver C C, Kliffen M, van Duijn C M, Hofman A, Cruts M, Grobbee D E, van Broeckhoven C, de Jong P T. Genetic association of apolipoprotein E with age-related macular degeneration. Am J Hum Genet. July 1998; 63(1):200-6.

Klein R, Klein B E, Linton K L. Prevalence of age-related maculopathy. The Beaver Dam Eye Study. Ophthalmology. June 1992; 99(6):933-43.

Klein M L, Mauldin W M, Stoumbos V D. Heredity and age-related macular degeneration. Observations in monozygotic twins. Arch Ophthalmol. July 1994; 112(7): 932-7.

Klein M L, Schultz D W, Edwards A, Matise T C, Rust K, Berselli C B, Trzupek K, Weleber R G, Ott J, Wirtz M K, Acott T S. Age-related macular degeneration. Clinical features in a large family and linkage to chromosome 1q. Arch Ophthalmol. August 1998; 116(8):1082-8.

Kobayashi A, Higashide T, Hamasaki D, Kubota S, Sakuma H, An W, Fujimaki T, McLaren M J, Weleber R G, Inana G. HRG4 (UNC119) mutation found in cone-rod dystrophy causes retinal degeneration in a transgenic model. Invest Ophthalmol Vis Sci. October 2000; 41(11):3268-77.

LaVail M M. Rod outer segment disk shedding in rat retina: relationship to cyclic lighting. Science. Dec. 3, 1976; 194(4269):1071-4.

Lin H, Clegg D O. Integrin alphavbeta5 participates in the binding of photoreceptor rod outer segments during phagocytosis by cultured human retinal pigment epithelium. Invest Ophthalmol Vis Sci. August 1998; 39(9): 1703-12.

Lohi J, Lehti K, Valtanen H, Parks W C, Keski-Oja J. Structural analysis and promoter characterization of the human membrane-type matrix metalloproteinase-1 (MT1-MMP) gene. Gene. 242(1-2):75-86, Jan. 25, 2000.

Mashima Y, Shiono T, Inana G. Rapid and efficient molecular analysis of gyrate atrophy using denaturing gradient gel electrophoresis. Invest Ophthalmol Vis Sci. March 1994; 35(3):1065-70.

McLaren M J, Holderby M, Inana G. Phagocytosis of ROS by immortal rat RPE cell lines. Invest Ophthalmol Vis Sci 34:A817, 1993a.

McLaren M J, Sasabe T, Li C Y, Brown M E, Inana G. Spontaneously arising immortal cell line of rat retinal pigmented epithelial cells. Exp Cell Res. February 1993b; 204(2):311-20.

McLaren M J, Sasabe T, Li C Y, Brown M E, Inana G. Double fluorescent vital assay of phagocytosis by cultured retinal pigment epithelial cells. Invest Ophthalmol Vis Sci. February 1993c; 34(2):317-26.

McLaren M J. Kinetics of rod outer segment phagocytosis by cultured retinal pigment epithelial cells. Relationship to cell morphology. Invest Ophthalmol Vis Sci. June 1996; 37(7):1213-24.

Meyers S M, Greene T, Gutman F A. A twin study of age-related macular degeneration. Am J Ophthalmol. December 1995; 120(6):757-66.

Miceli M V, Newsome D A, Tate D J Jr. Vitronectin is responsible for serum-stimulated uptake of rod outer segments by cultured retinal pigment epithelial cells. Invest Ophthalmol Vis Sci. July 1997; 38(8):1588-97.

Mitchell P, Wang J J, Smith W, Leeder S R. Smoking and the 5-year incidence of age-related maculopathy: the Blue Mountains Eye Study. Arch Ophthalmol. October 2002; 120(10):1357-63.

Oku N, Matsukawa M, Yamakawa S, Asai T, Yahara S, Hashimoto F, Akizawa T. Inhibitory effect of green tea polyphenols on membrane-type 1 matrix metalloproteinase, MT1-MMP. Biol Pharm Bull. September 2003; 26(9):1235-8.

Pei D, Weiss S J. Transmembrane-deletion mutants of the membrane-type matrix metalloproteinase-1 process progelatinase A and express intrinsic matrix-degrading activity. J Biol Chem. Apr. 12, 1996; 271(15):9135-40.

Sarks J P, Sarks S H, Killingsworth M C. Evolution of geographic atrophy of the retinal pigment epithelium. Eye. 1988; 2 (Pt 5):552-77.

Sato H, Takino T, Okada Y, Cao J, Shinagawa A, Yamamoto E, Seiki M. A matrix metalloproteinase expressed on the surface of invasive tumour cells. Nature. July 7, 1994; 370(6484):61-5.

Schultz D W, Klein, M L, Humpert A J, Luzier C W, Persun V, /schain M, Mahan A, Runckel C, Cassera M, Vittal V, Doyle T M, Martin T M, Weleber R, Francis P J and Acott T S. Analysis of the ARMD1 locus: evidence that a mutation in hemicentin-1 is associated with age-related macular degeneration in a large family. *Human Molecular Genetics* Advance Access, published online Oct. 21, 2003.

Shaban H, Borras C, Vina J, Richter C. Phosphatidylglycerol potently protects human retinal pigment epithelial cells against apoptosis induced by A2E, a compound suspected to cause age-related macula degeneration. Exp Eye Res. July 2002; 75(1):99-108.

Simonelli F, Margaglione M, Testa F, Cappucci G, Manitto M P, Brancato R, Rinaldi E. Apolipoprotein E polymorphisms in age-related macular degeneration in an Italian population. Ophthalmic Res. November-December 2001; 33(6):325-8.

Song E, Lee S K, Wang J, Ince N, Ouyang N, Min J, Chen J, Shankar P, Lieberman J. RNA interference targeting Fas protects mice from fulminant hepatitis. Nat Med. March 2003; 9(3):347-51. Epub Feb. 10, 2003

Stone E M, Webster A R, Vandenburgh K, Streb L M, Hockey R R, Lotery A J, Sheffield V C. Allelic variation in ABCR associated with Stargardt disease but not age-related Sui G, Soohoo C, Affar el B, Gay F, Shi Y, Forrester W C, Shi Y. A DNA vector-based RNAi technology to suppress gene expression in mammalian cells. ProcNatl Acad Sci USA. Apr. 16, 2002; 99(8):5515-20.

Vickers T A, Koo S, Bennett C F, Crooke S T, Dean N M, Baker B F. Efficient reduction of target RNAs by small interfering RNA and RNase H-dependent antisense agents. A comparative analysis. J Biol Chem. Feb. 28, 2003; 278(9):7108-18. Epub Dec. 23, 2002.

Weeks D E, Conley Y P, Mah T S, Paul T O, Morse L, Ngo-Chang J, Dailey J P, Ferrell R E, Gorin M B. A full genome scan for age-related maculopathy. Hum Mol Genet. May 22, 2000; 9(9):1329-49.

Winkler B S, Boulton M E, Gottsch J D, Sternberg P. Oxidative damage and age-related macular degeneration. Mol Vis. Nov. 3, 1999; 5:32.

Young R W, Bok D. Participation of the retinal pigment epithelium in the rod outer segment renewal process. J Cell Biol. August 1969; 42(2):392-403.

Zack D J, Bennett J, Wang Y, Davenport C, Klaunberg B, Gearhart J, Nathans J. Unusual topography of bovine rhodopsin promoter-lacZ fusion gene expression in transgenic mouse retinas. Neuron. February 1991; 6(2):187-99.

Zamore P D. Ancient pathways programmed by small RNAs. Science. May 17, 2002; 296(5571):1265-9.

Zurdel J, Finckh U, Menzer G, Nitsch R M, Richard G. CST3 genotype associated with exudative age related macular degeneration. Br J Ophthalmol. February 2002; 86(2):214-9.

What is claimed is:

1. A method for treating a subject having age-related macular degeneration (AMD), comprising contacting a retinal or choroidal cell in said subject with an antibody that specifically binds to a matrix metalloproteinase membrane-associated 1 (MT1-MMP) protein.

2. The method of claim 1, wherein said antibody decreases the activation of progelatinase A or degradation of extracellular matrix.

3. The method of claim 1 wherein said MT1-MMP protein is human MT1-MMP, encoded by the nucleic acid sequence set forth in SEQ ID NO:15, or a polymorphic variant thereof.

4. The method of claim 1, wherein said antibody is selected from the group consisting of a polyclonal antibody, a monoclonal antibody, a single chain antibody and an Fab fragment.

5. The method of claim 1, wherein said cell is a photoreceptor, an RPE cell, a Muller cell, or a cell type of the choroid selected from the group consisting of an endothelial cell, a smooth muscle cell, a leukocyte, a macrophage, a melanocyte and a fibroblast.

6. The method of claim 5, wherein said MT1-MMP protein is located in an extracellular matrix.

7. The method of claim 6, wherein said extracellular matrix is an interphotoreceptor matrix.

* * * * *